US010876149B2

(12) United States Patent
Becker

(10) Patent No.: US 10,876,149 B2
(45) Date of Patent: Dec. 29, 2020

(54) COMPOSITIONS AND METHODS FOR THE DETECTION OF NUCLEIC ACIDS

(71) Applicant: Prominex, Inc., San Diego, CA (US)

(72) Inventor: Michael McClellan Becker, San Diego, CA (US)

(73) Assignee: Prominex, Inc., San Diego, CA (US)

( * ) Notice: Subject to any disclaimer, the term of this patent is extended or adjusted under 35 U.S.C. 154(b) by 30 days.

(21) Appl. No.: 15/521,093

(22) PCT Filed: Oct. 22, 2015

(86) PCT No.: PCT/US2015/056993
§ 371 (c)(1),
(2) Date: Apr. 21, 2017

(87) PCT Pub. No.: WO2016/065192
PCT Pub. Date: Apr. 28, 2016

(65) Prior Publication Data
US 2017/0356031 A1 Dec. 14, 2017

Related U.S. Application Data

(60) Provisional application No. 62/067,255, filed on Oct. 22, 2014, provisional application No. 62/081,954, filed on Nov. 19, 2014.

(51) Int. Cl.
C12Q 1/68 (2018.01)
C12Q 1/6823 (2018.01)
C12Q 1/6834 (2018.01)
C12P 19/30 (2006.01)
C12Q 1/6837 (2018.01)
C12Q 1/6818 (2018.01)

(52) U.S. Cl.
CPC ............ C12Q 1/6823 (2013.01); C12P 19/30 (2013.01); C12Q 1/6818 (2013.01); C12Q 1/6834 (2013.01); C12Q 1/6837 (2013.01); C12Y 301/30002 (2013.01)

(58) Field of Classification Search
None
See application file for complete search history.

(56) References Cited

U.S. PATENT DOCUMENTS

| | | | | |
|---|---|---|---|---|
| 7,435,794 | B2 * | 10/2008 | Lukyanov | C07K 16/40 435/18 |
| 2003/0165963 | A1 | 9/2003 | Dattagupta | |
| 2004/0175737 | A1 | 9/2004 | Olson et al. | |
| 2005/0164204 | A1 | 7/2005 | Reed | |
| 2005/0164216 | A1 | 7/2005 | Lukyanov et al. | |
| 2011/0294674 | A1 | 12/2011 | Cheung et al. | |
| 2012/0052502 | A1 | 3/2012 | Li | |
| 2013/0274135 | A1 * | 10/2013 | Zhang | C12Q 1/6832 506/9 |
| 2014/0322761 | A1 | 10/2014 | Nakamura et al. | |

FOREIGN PATENT DOCUMENTS

WO   WO-99/01570 A2   1/1999
WO   WO-2014/071029 A1   5/2014

OTHER PUBLICATIONS

Evrogen Research Products (Available on the Internet, copy retrieved Feb. 15, 2016) (2003)).*
Anisimova et al., "Isolation, characterization and molecular cloning of duplex-specific nuclease from the hepatopancreas of the Kamchatka crab," BMC Biochem. 9:14 (2008) (12 pages).
Castelnuovo et al., "Role of histone modifications and early termination in pervasive transcription and antisense-mediated gene silencing in yeast," Nucleic Acids Res. 42(7):4348-62 (2014).
Communication pursuant to Article 94(3) EPC for European Patent Application No. 15852414.0 dated Feb. 7, 2019 (5 pages).
Degliangeli et al., "Absolute and direct microRNA quantification using DNA-gold nanoparticle probes," J Am Chem Soc. 136(6):2264-7 (2014).
Deng et al., "A highly sensitive and selective homogenous assay for profiling microRNA expression," Biosens Bioelectron. 54:650-5 (2014).
Extended European Search Report for European Patent Application No. 15852414.0 dated Mar. 21, 2018 (8 pages).
International Preliminary Report on Patentability for International Application No. PCT/US2017/029903 dated Oct. 30, 2018 (20 pages).
International Preliminary Report on Patentability for International Patent Application No. PCT/US2015/056993 dated Apr. 25, 2017 (14 pages).
International Search Report and Written Opinion for International Application No. PCT/US2017/029903, dated Aug. 7, 2017 (26 pages).
International Search Report for International Patent Application No. PCT/US2015/056993 dated Feb. 26, 2016 (5 pages).

(Continued)

Primary Examiner — James Martinell
(74) Attorney, Agent, or Firm — Clark & Elbing LLP

(57) ABSTRACT

The present invention provides methods for detecting a target nucleic acid in a sample by, for example, incubating the target nucleic acid with a detection probe containing a nucleic acid sequence complementary to at least a portion of the target nucleic acid and a nuclease enzyme that specifically cleaves double-stranded nucleic acids. Hybridization between the detection probe and the target nucleic acid thereby leads to cleavage of the detection probe, releasing a portion of the probe attached to a detectable agent. The portions of the digested probes attached to the detectable agent can be separated from unbound probe and detected in order to determine the presence of the target nucleic acid in the sample. Thus, the invention enables rapid and accurate analysis of a sample for the presence of desired nucleic acid biomarkers.

11 Claims, 97 Drawing Sheets
Specification includes a Sequence Listing.

(56) References Cited

OTHER PUBLICATIONS

Miller et al., "A new method for stranded whole transcriptome RNA-seq," Methods 63(2):126-134 (2013). (18 pages).
Qiu et al., "Duplex-specific nuclease-mediated bioanalysis," Trends Biotechnol. 33(3):180-8 (2015).
Written Opinion of the International Searching Authority for International Patent Application No. PCT/US2015/056993 dated Feb. 26, 2016 (13 pages).

\* cited by examiner

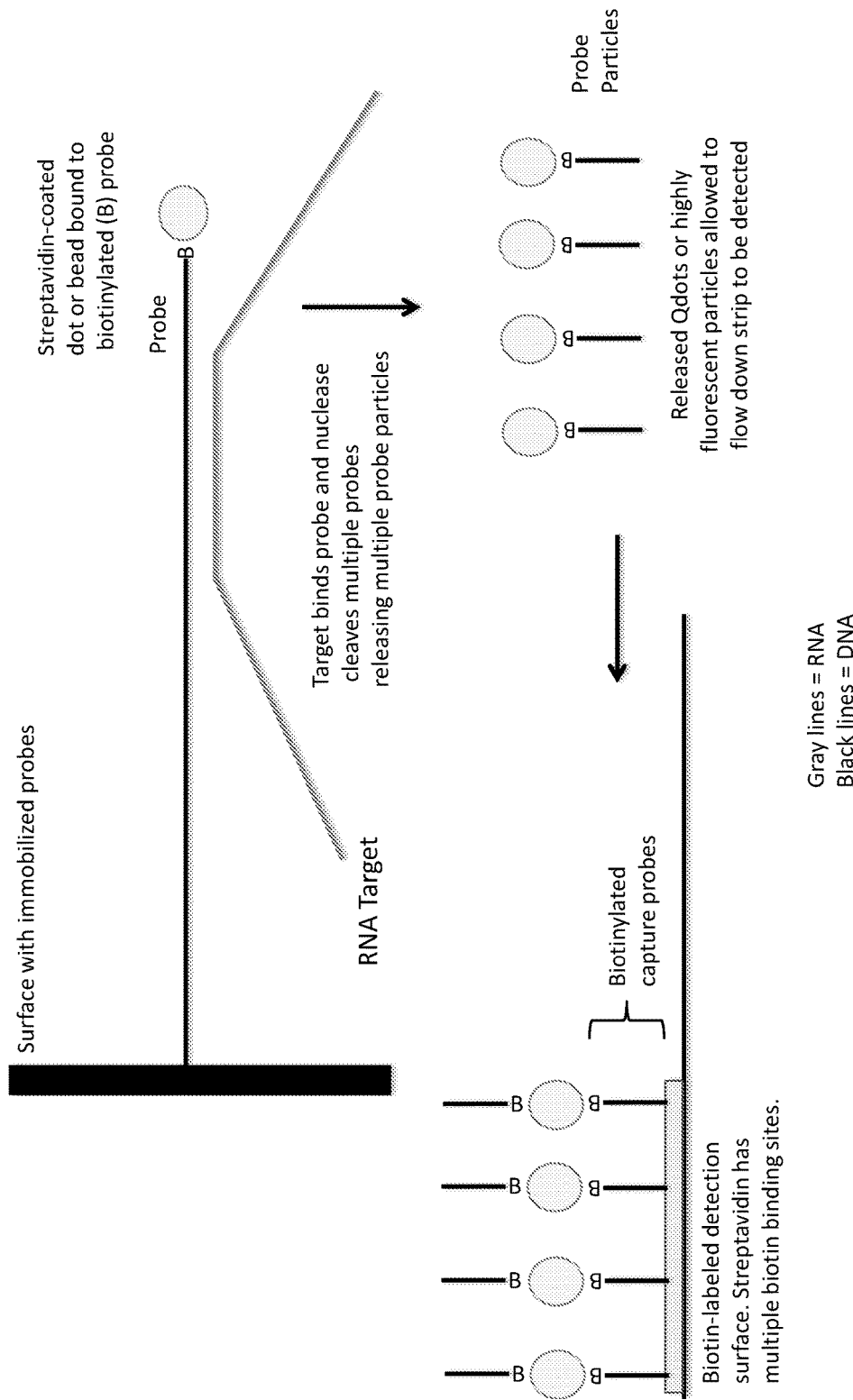
Fig. 1  Detection of RNA targets using a DSN and a detection probe immobilized on a surface

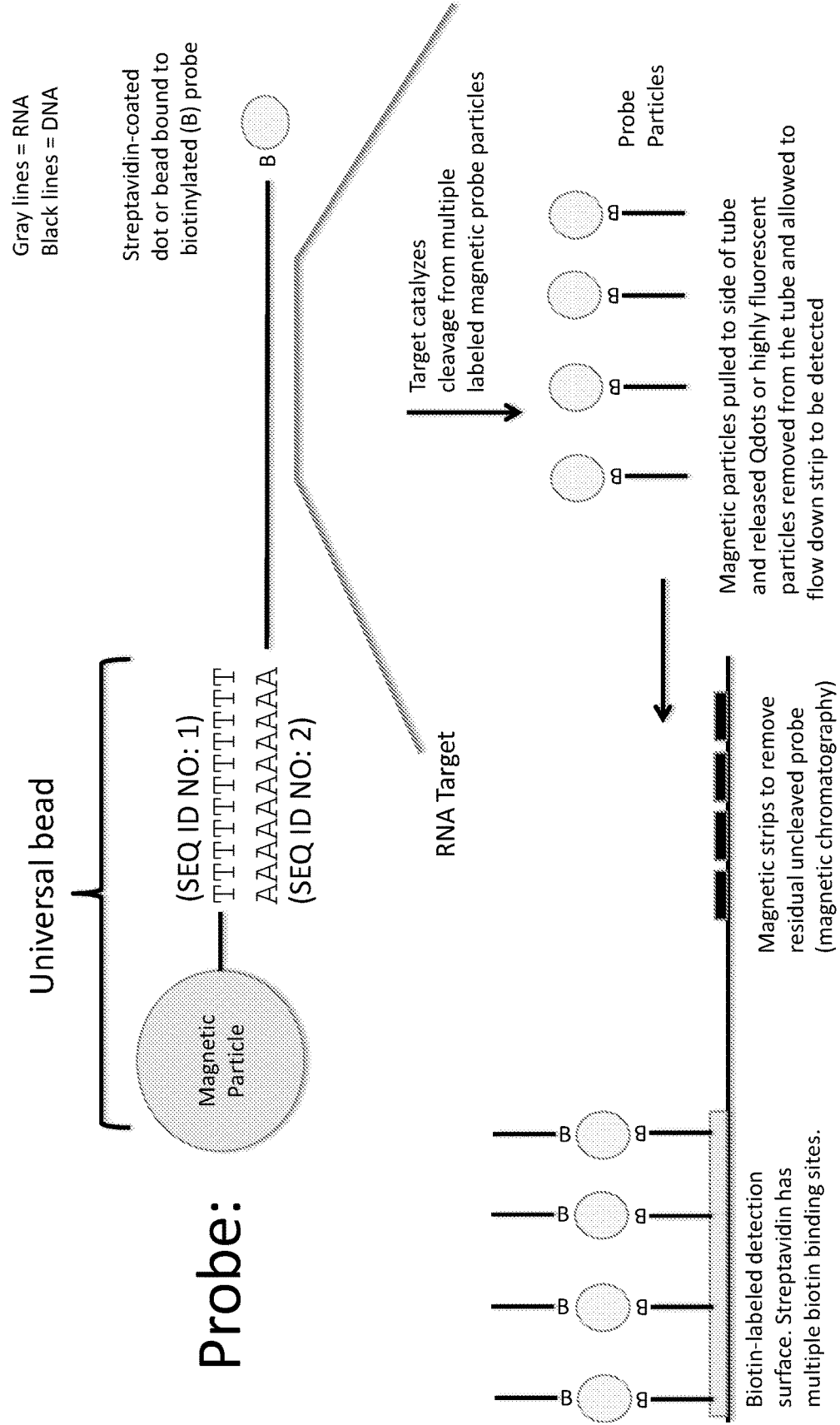

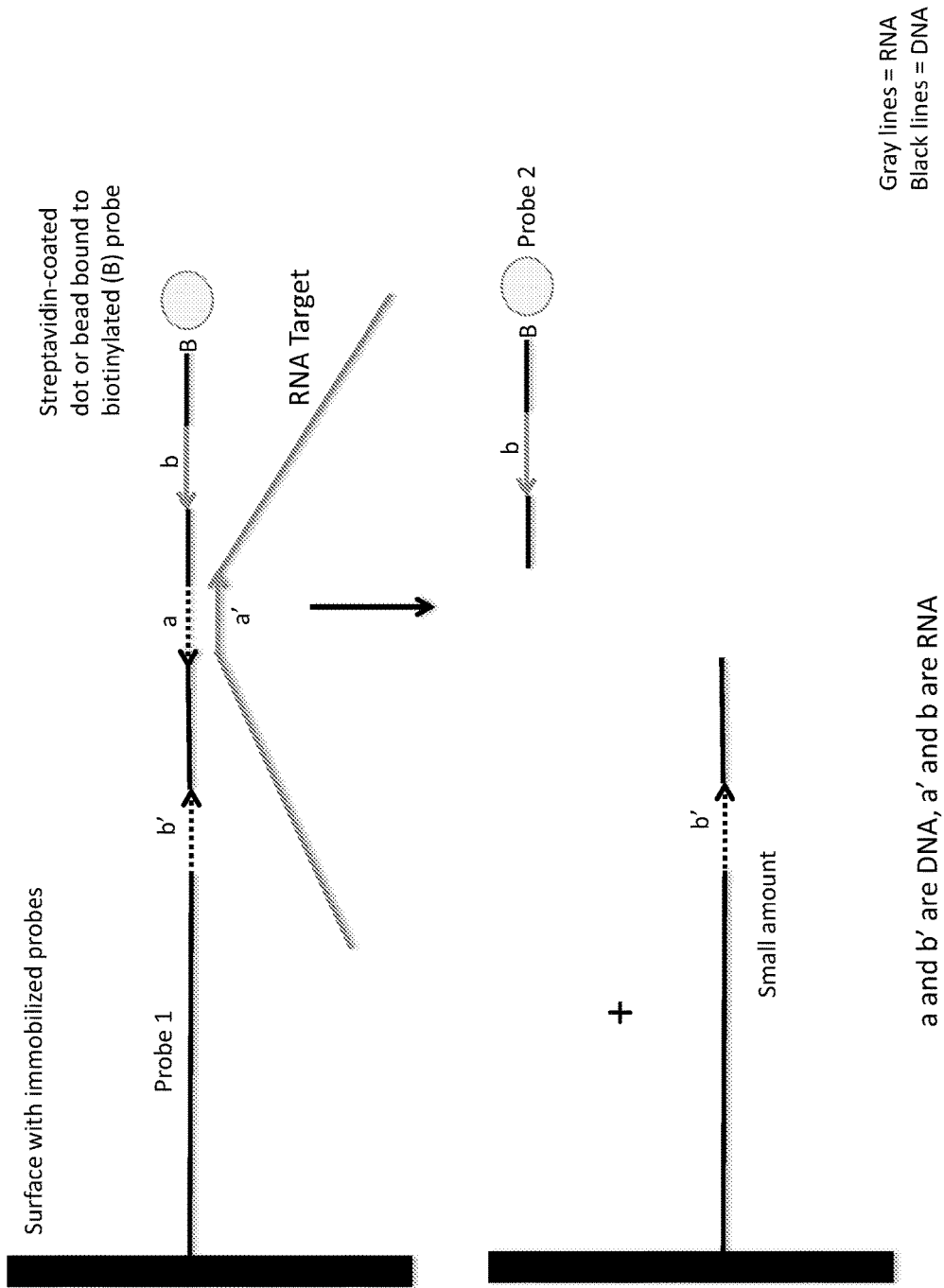

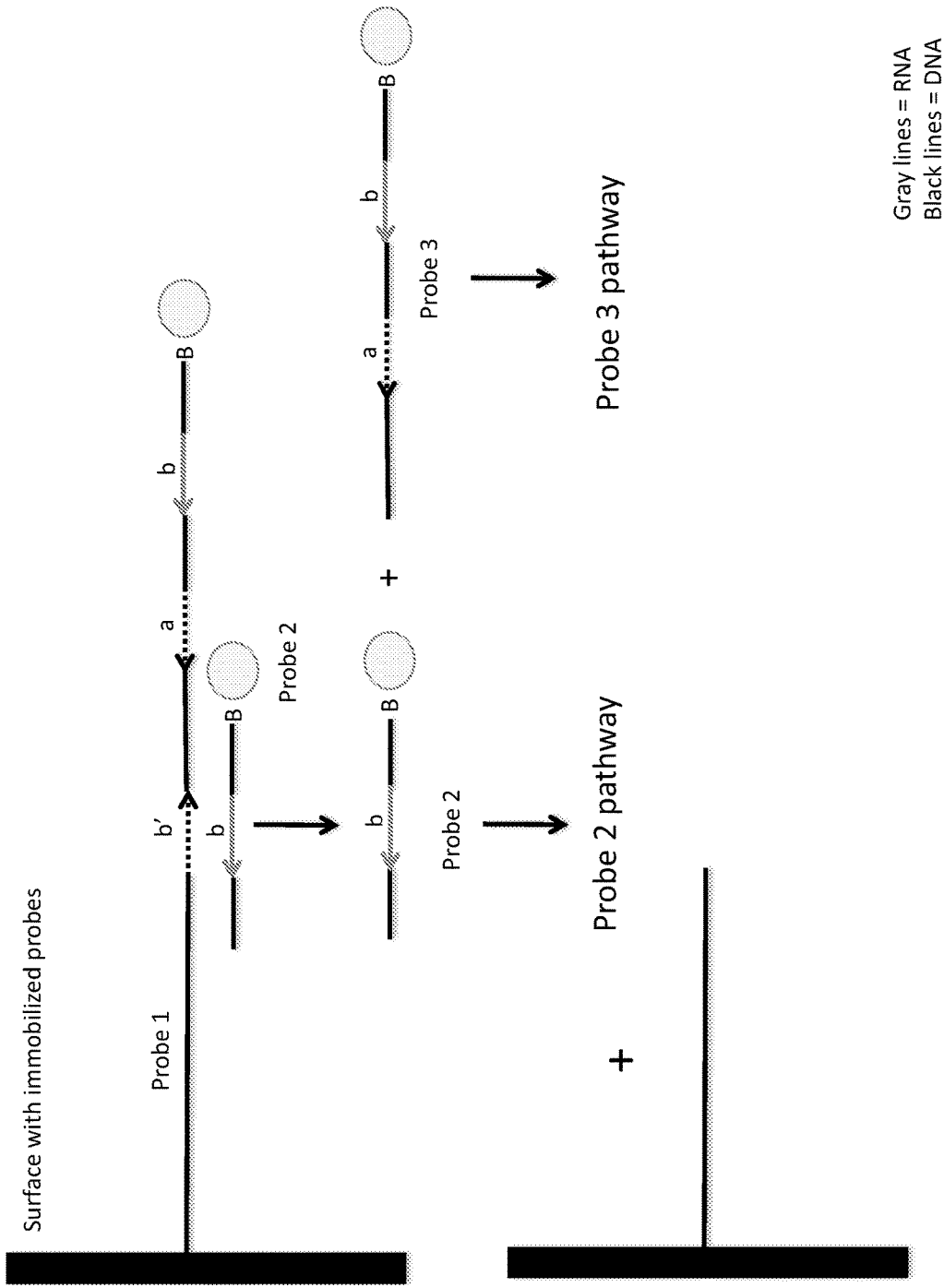

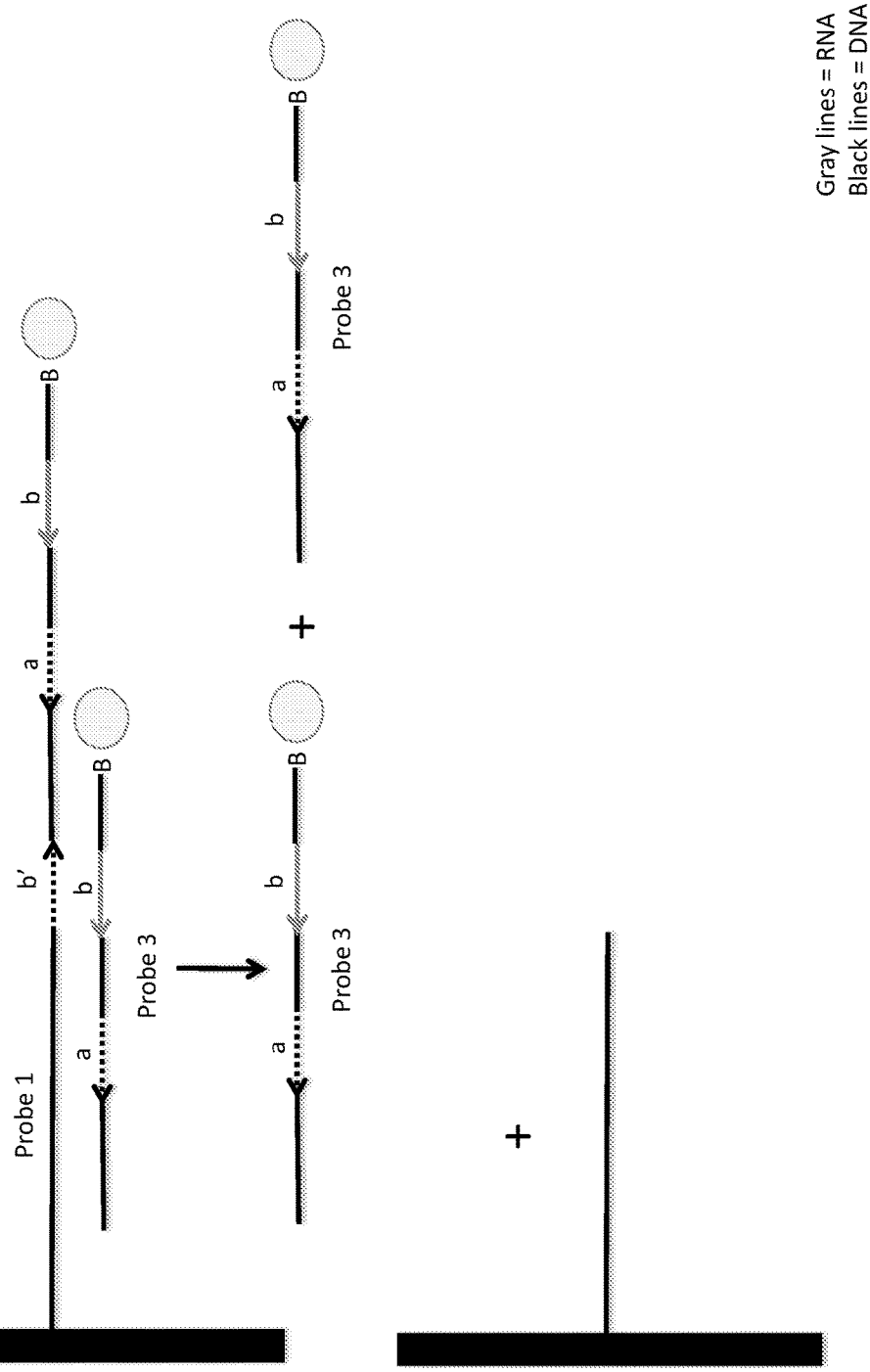

Fig. 6

Overall Amplification

- Overall reaction scheme
  - 1T + 1P1 = 1P2 + 1T
  - 1P2 + 1P1 = 1P2 + 1P3
  - 1P3 + 1P1 = 2P3
  - 1P3 + 1T = 1P2 + 1T (minor reaction)

- Consider what happens in time
  - Assume each basic reaction takes time = t
    - 1T + 1P1 = 1P2 + 1T    at time point = 1t
      - Total = 1P2 + 1T
    - 1P2 + 1P1 = 1P2 +1P3   at time point = 2t
    - 1T + 1P1 = 1P2 + 1T
      - Total = 2P2 + 1P3 +1T
    - 2P2 + 2P1 = 2P2 + 2P3   at time point = 3t
    - 1P3 + 1P1 = 2P3
    - 1T + 1P1 = 1P2 + 1T
      - Total = 3P2 + 4P3 + 1T
    - 3P2 + 3P1 = 3P2 + 3P3   at time point = 4t
    - 4P3 + 4P1 = 8P3
    - 1T + 1P1 = 1P2 + 1T
      - Total = 4P2 + 11P3 + 1T

- Overall: 0,1,4,11,26,....

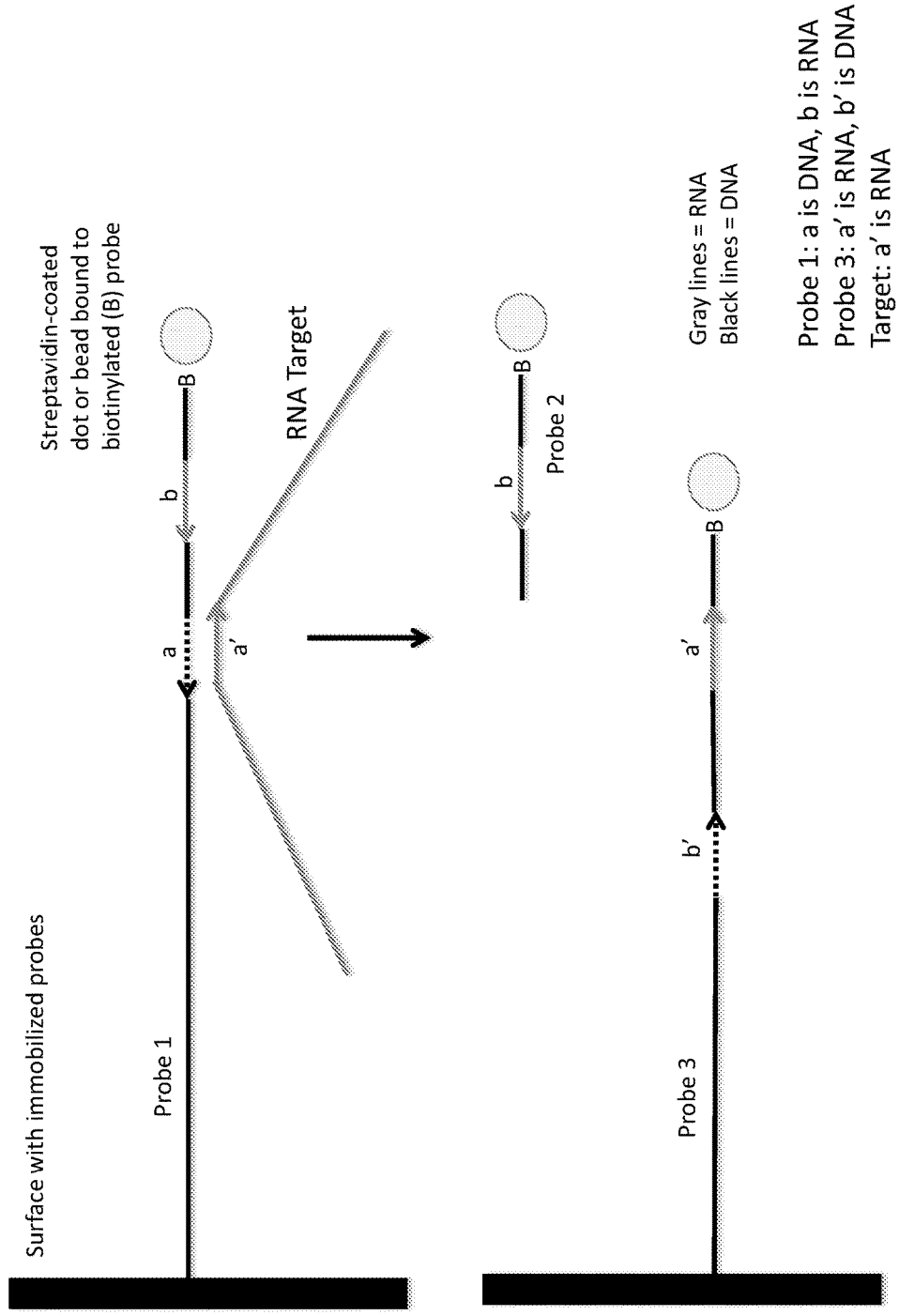
Fig. 8 Exponential DSA of RNA with multiple probes

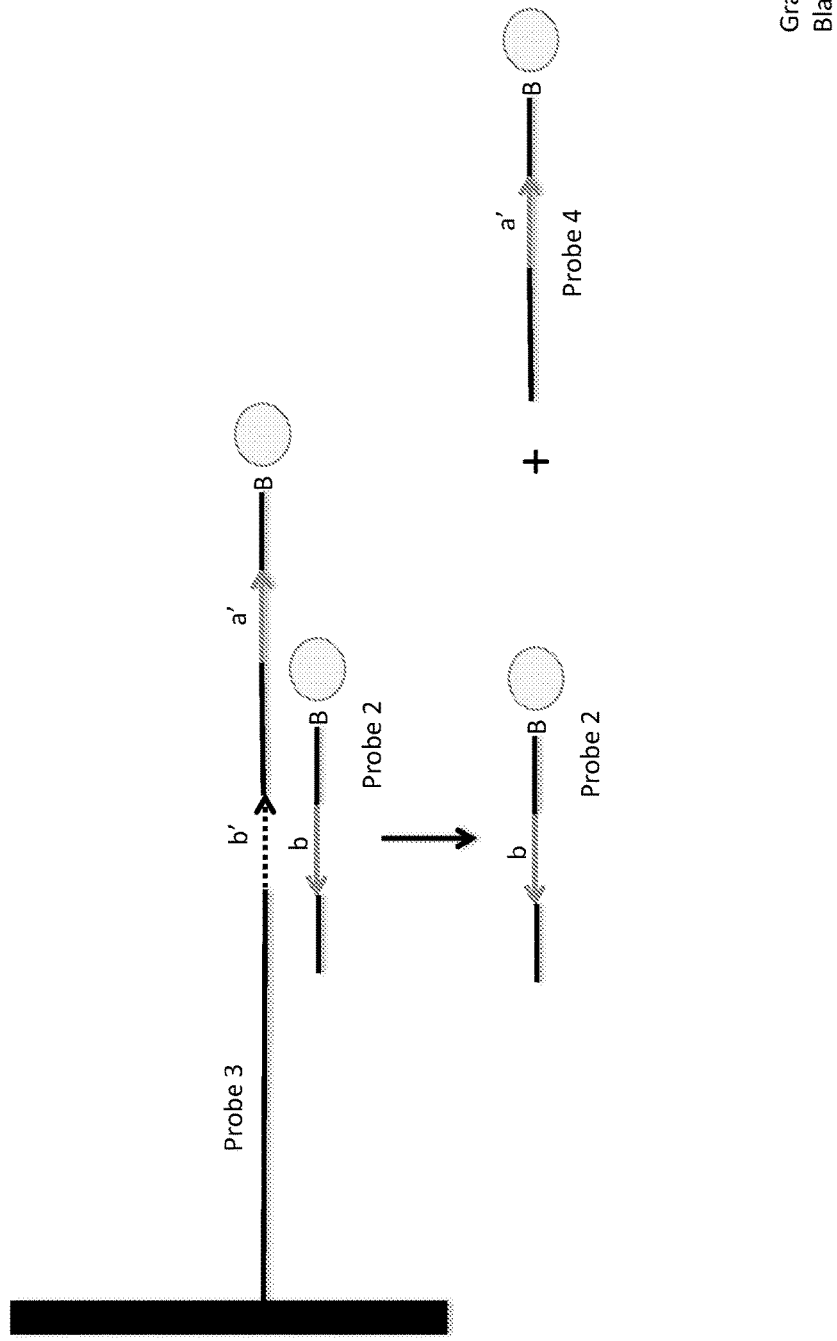
Fig. 9A  Exponential DSA of RNA with multiple probes

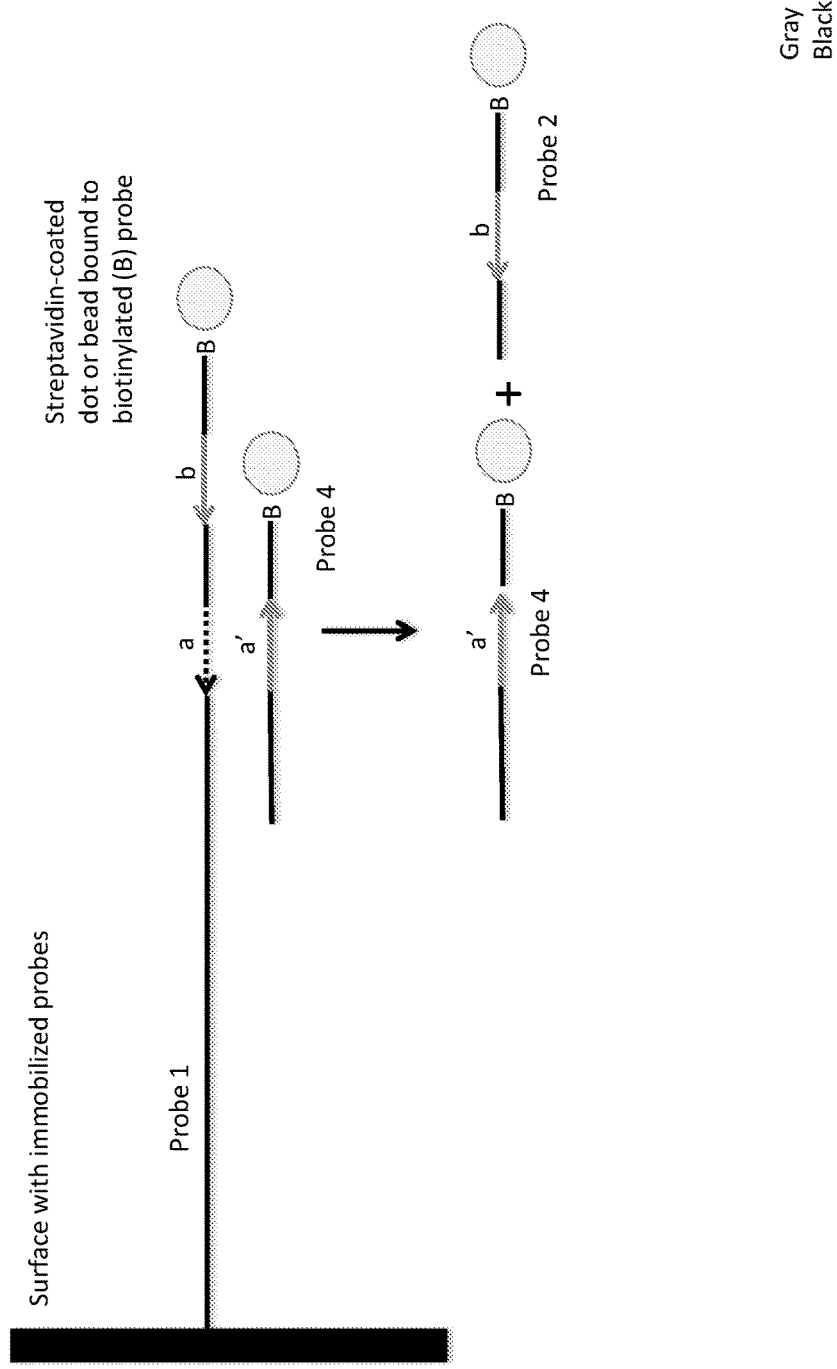

Fig. 10A

Overall Amplification

- Overall reaction scheme
  - 1T + 1P1 = <u>1P2</u> + 1T
  - <u>1P2</u> + 1P3 = <u>1P2</u> + 1P4
  - <u>1P4</u> + 1P1 = <u>1P4</u> + 1P2

- Consider what happens in time
  - Assume each basic reaction takes time = t
    - 1T + 1P1 = 1P2 + 1T    at time point = 1t (first step)
      - Total = 1P2 + 1T
    - 1T + 1P1 = 1P2 + 1T    at time point = 2t (first step repeats)
    - 1P2 + 1P3 = 1P2 + 1P4    Progeny reaction
      - Total: 2P2 + 1P4 + 1T
    - 1T + 1P1 = 1P2 + 1T    at time point = 3t (first step repeats)
    - 2P2 + 2P3 = 2P2 + 2P4
    - 1P4 + 1P1 = 1P4 + 1P2
      - Total: 4P2 + 3P4 + 1T

Fig. 10B

Overall Amplification

- 1T + 1P1 = 1P2 + 1T    at time point = 4t (first step repeats)
- 4P2 + 4P3 = 4P2 + 4P4
- 3P4 + 3P1 = 3P4 + 3P2
  – Total: 8P2 + 7P4
- 1T + 1P1 = 1P2 + 1T    at time point = 5t (first step repeats)
- 8P2 + 8P3 = 8P2 + 8P4
- 7P4 + 7P1 = 7P4 + 7P2
  – Total: 16P2 +15P4

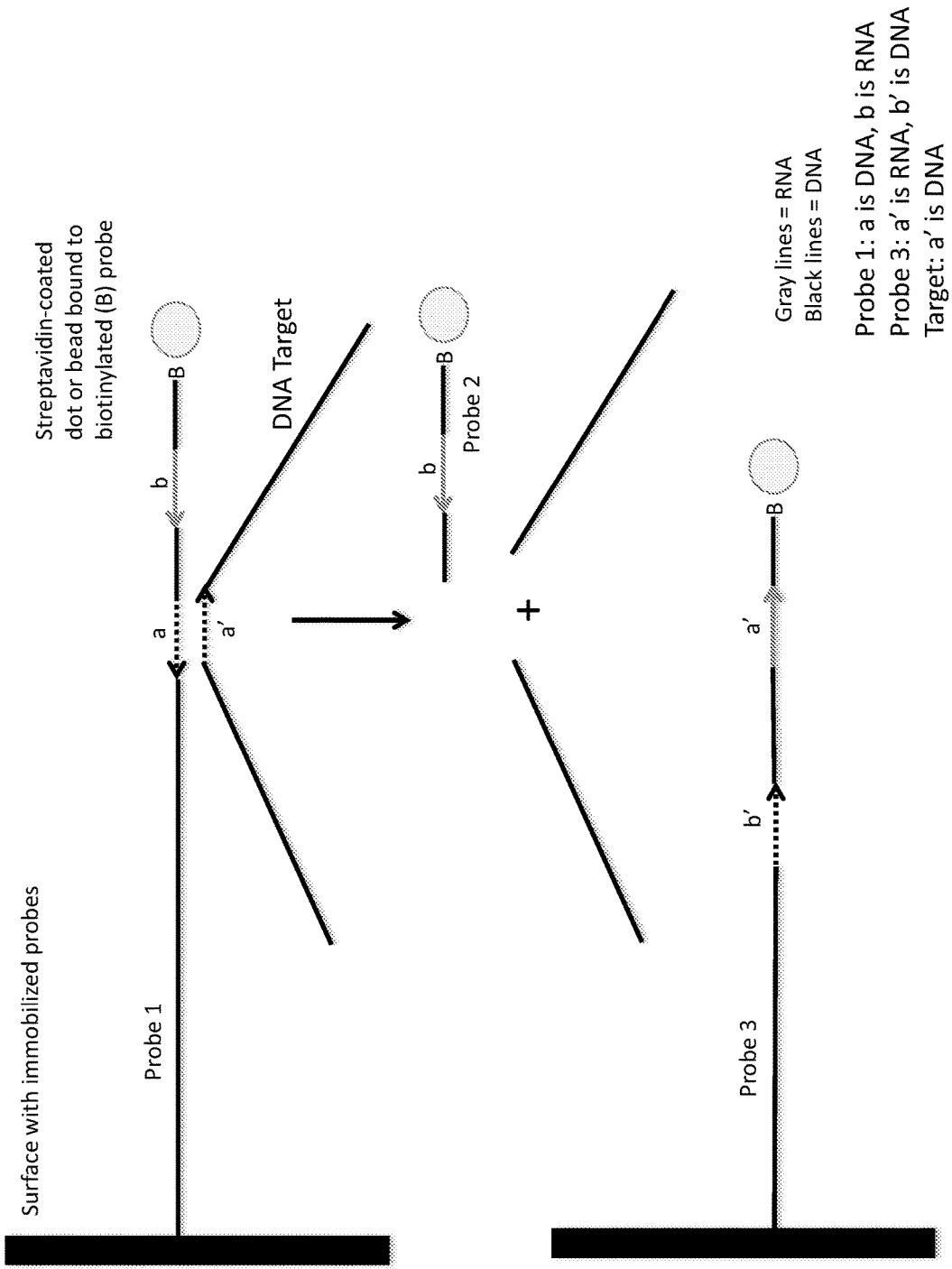

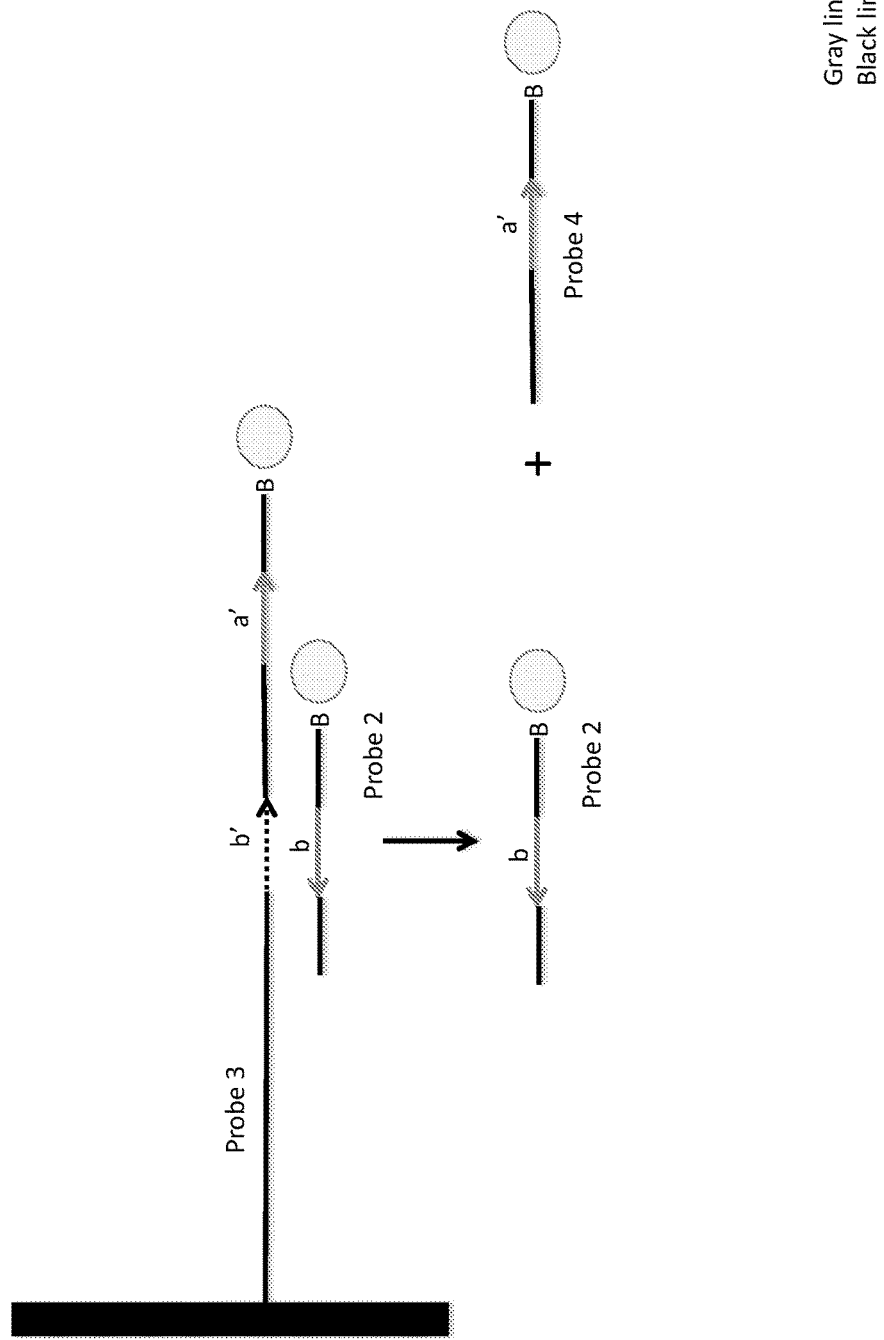
Fig. 12  Exponential DSA of DNA by multiple probes

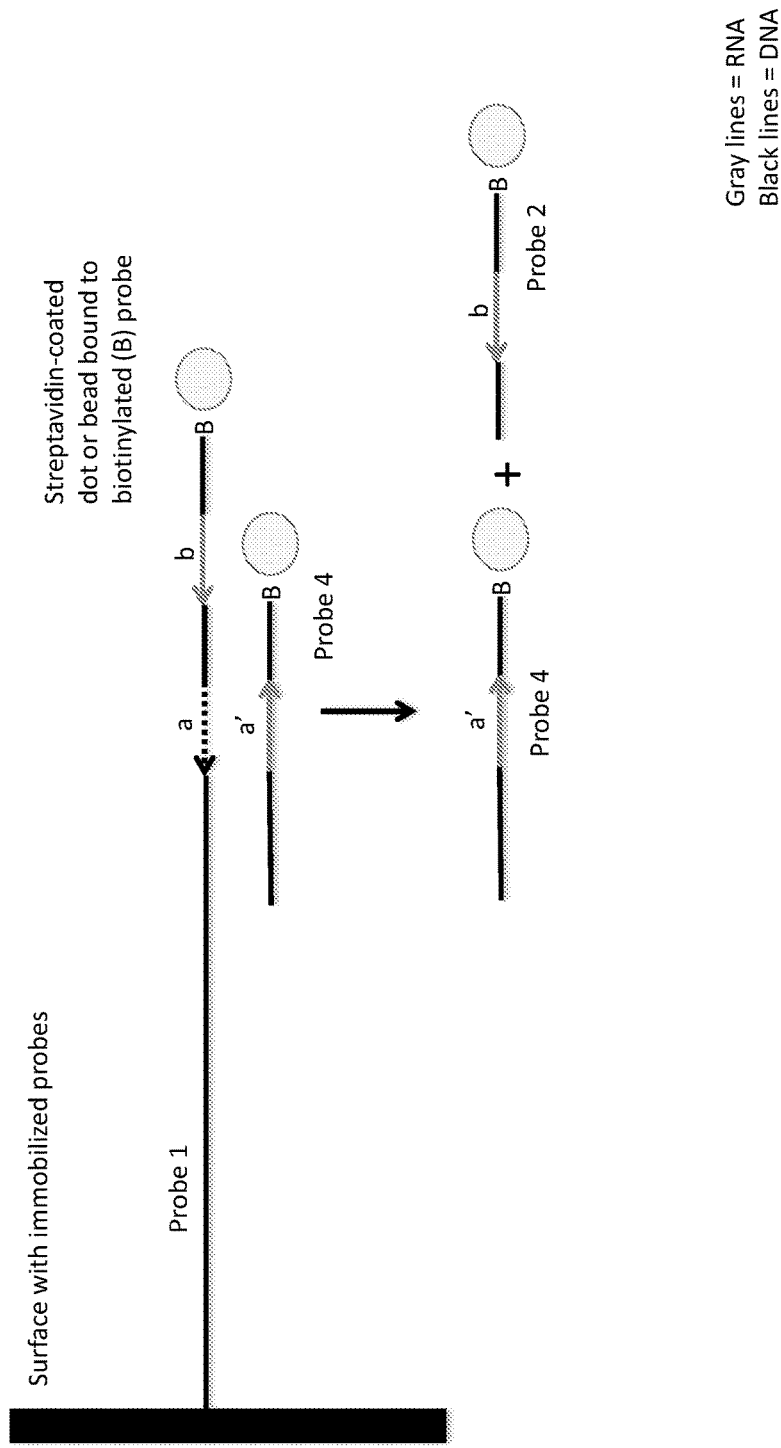
Fig. 13 Exponential DSA of DNA by multiple probes

Fig. 14

Overall Amplification

- Overall reaction scheme
  - 1T + 1 P1 = <u>1 P2</u>
  - 1P2 + 1P3 = <u>1P2</u> + 1P4
  - 1P4 + 1P1 = <u>1P4</u> + 1P2
    - Total: 2P2 + 1P4
  - 2P2 + 2P3 = <u>2P2</u> + 2P4
  - 1P4 + 1P1 = <u>1P4</u> + 1P2
    - Total: 3P2 + 3P4
  - 3P2 + 3P3 = <u>3P2</u> + 3P4
  - 3P4 + 3P1 = <u>3P4</u> + 3P2
    - Total: 6P2 + 6P4
  - 6P2 + 6P3 = <u>6P2</u> + 6P4
  - 6P4 + 6P1 = <u>6P4</u> + 6P2
    - Total: 12P2 + 12P4

Fig. 17

Overall Amplification

- Overall reaction scheme
  - 1T + 1P1 = 1P2
  - 1P2 + 1P1 = 2P2
- Consider what happens in time
  - Assume each basic reaction takes time = t
    - 1T + 1P1 = 1P2     at time point = 1t
      - Total = 1P2
    - 1P2 + 1P1 = 2P2    at time point = 2t
      - Total = 2P2
    - 2P2 + 2P1 = 4P2    at time point = 3t
      - Total = 4P2
    - Overall: 1,2,4,8,16,32......

Fig. 20

Overall Amplification

- Overall reaction scheme
  - 1T + 1P1 = 1P2 + 1T
  - 1P2 + 1P1 = 2P2
- Consider what happens in time
  - Assume each basic reaction takes time = t
    - 1T + 1P1 = 1P2 + 1T      at time point = 1t
      - Total = 1P2 + 1T
    - 1P2 + 1P1 = 2P2
    - 1T + 1P1 = 1P2 + 1T      at time point = 2t
      - Total = 3P2 + 1T
    - 3P2 + 3P1 = 6P2
    - 1T + 1P1 = 1P2 + 1T      at time point = 3t
      - Total = 7P2 + 1T
    - Overall: 1,3,7,15,31......

Fig. 22 Linear DSA of DNA with a single probe

Fig. 23

Overall Amplification

- Overall reaction scheme
  - 1T + 1P1 = <u>1P2</u>
  - 1P2 + 1P1 = <u>1P2 + 1P3</u>

- Consider what happens in time
  - Assume each basic reaction takes time = t
    - 1T + 1P1 = 1P2                      at time point = 1t
      - Total = 1P2
    - 1P2 + 1P1 = 1P2 + P3                at time point = 2t
      - Total = 1P2 + 1P3
    - 1P2 + 1P1 = 1P2 + 1P3               at time point = 3t
      - Total = 1P2 + 2P3
    - 1P2 + 1P1 = 1P2 + 1P3               at time point = 4t
      - Total = 1P2 + 3P3

Overall: 1,2,3,4,5,6......

Fig. 26    Overall Amplification

- Overall reaction scheme
  - 1T + 1P1 = 1P2 + 1T
  - 1P2 + 1P1 = 1P2 + 1P3
- Consider what happens in time
  - Assume each basic reaction takes time = t
    - 1T + 1P1 = 1P2 + 1T     at time point = 1t (first step)
      - Total = 1P2 + 1T
    - 1T + 1 P1 = 1P2 + 1T     at time point = 2t (first step repeats)
      - And
    - 1P2 + 1P1 =1P2 + 1P3     Progeny reaction
      - Total = 2P2 + 1P3 + 1T
    - 1T + 1 P1 = 1P2 + 1T     at time point = 3t (first step repeats)
      - And
    - 2P2 + 2P1 =2P2 + 2P3     Progeny reaction
      - Total = 3P2 + 3P3 + 1T

Fig. 27
Overall Amplification

- 1T + 1 P1 = 1P2 + 1T          at time point = 4t (first step repeats)
  – And
- 3P2 + 3P1 = 3P2 + 3P3          Progeny reaction
  – Total = 4P2 + 6P3 + 1T
- 1T + 1 P1 = 1P2 + 1T          at time point = 5t (first step repeats)
  – And
- 4P2 + 4P1 = 4P2 + 4P3          Progeny reaction
  – Total = 5P2 + 10P3 + 1T
- PCR: 1,2,4,8,16,32,64,128,256,512
- Cleavage: 1,3,6,10,15,21,28,36,45,55

Fig. 28

Overall Amplification for Exponential DSA of RNA using a single probe

- Overall reaction scheme
  - 1T + 1P1 = <u>1P2</u> + 1T
  - <u>1P2</u> + 1P1 = <u>2P2</u>
  - <u>2P2</u> + 2P1 = <u>4P2</u>
  - <u>4P2</u> + 4P1 = <u>8P2</u>

- Consider what happens in time
  - Assume each basic reaction takes time = t
    - 1T + 1P1 = <u>1P2</u> + 1T         at time point = 1t (first step)
      - Total = <u>1P2</u> + 1T
    - 1T + 1 P1 = <u>1P2</u> + 1T        at time point = 2t (first step repeats)
      - And
    - <u>1P2</u> + 1P1 =<u>2P2</u>            Progeny reaction
      - Total = <u>3P2</u> + 1T

Fig. 29

Overall Amplification for
Exponential DSA of RNA using a single probe

- 1T + 1 P1 = 1P2 + 1T    at time point = 3t (first step repeats)
  - And
  - 3P2 + 3P1 = 6P2                        Progeny reaction
  - Total = 7P2 + 1T
- 1T + 1 P1 = 1P2 + 1T    at time point = 4t (first step repeats)
  - 7P2 + 7P1 = 14P2                       Progeny reaction
  - Total = 15P2 + 1T
- PCR: 1,2,4,8,16,32
- Cleavage: 1,3,7,15,31,63
  - The time for each cleavage reaction could be shorter than the corresponding time for PCR (denature, hybridize, cool).

Fig. 31 Exponential DSA of RNA with RNA block

Fig. 32

Overall Amplification

- Overall reaction scheme
  - 1T + 1P1 = 1P2 + 1T
  - 1P2 + 1P1 = 2P2
- Consider what happens in time
  - Assume each basic reaction takes time = t
    - 1T + 1P1 = 1P2 + 1T    at time point = 1t
      - Total = 1P2 + 1T
    - 1P2 + 1P1 = 2P2
    - 1T + 1P1 = 1P2 + 1T    at time point = 2t
      - Total = 3P2 + 1T
    - 3P2 + 3P1 = 6P2
    - 1T + 1P1 = 1P2 + 1T    at time point = 3t
      - Total = 7P2 + 1T
    - Overall: 1,3,7,15,31.....

Fig. 35

Overall Amplification

- Overall reaction scheme
  - 1T + 1P1 = 1P2
  - 1P2 + 1P1 = 1P2 + 1P3
- Consider what happens in time
  - Assume each basic reaction takes time = t
    - 1T + 1P1 = 1P2                    at time point = 1t
      - Total = 1P2
    - 1P2 + 1P1 =1P2 + P3               at time point = 2t
      - Total = 1P2 + 1P3
    - 1P2 + 1P1 = 1P2 + 1P3             at time point = 3t
      - Total = 1P2 + 2P3
    - 1P2 + 1P1 = 1P2 + 1P3             at time point = 4t
      - Total = 1P2 + 3P3
    - Overall: 1,2,3,4,5,6......

Fig. 36 Exponential DSA of DNA with RNA block

Fig. 37 Exponential DSA of DNA with RNA block

Fig. 38

Overall Amplification

- Overall reaction scheme
  - 1T + 1P1 = 1P2
  - 1P2 + 1P1 = 2P2
- Consider what happens in time
  - Assume each basic reaction takes time = t
    - 1T + 1P1 = 1P2    at time point = 1t
      - Total = 1P2
    - 1P2 + 1P1 = 2P2    at time point = 2t
      - Total = 2P2
    - 2P2 + 2P1 = 4P2    at time point = 3t
      - Total = 4P2
    - Overall: 1,2,4,8,16,32.....

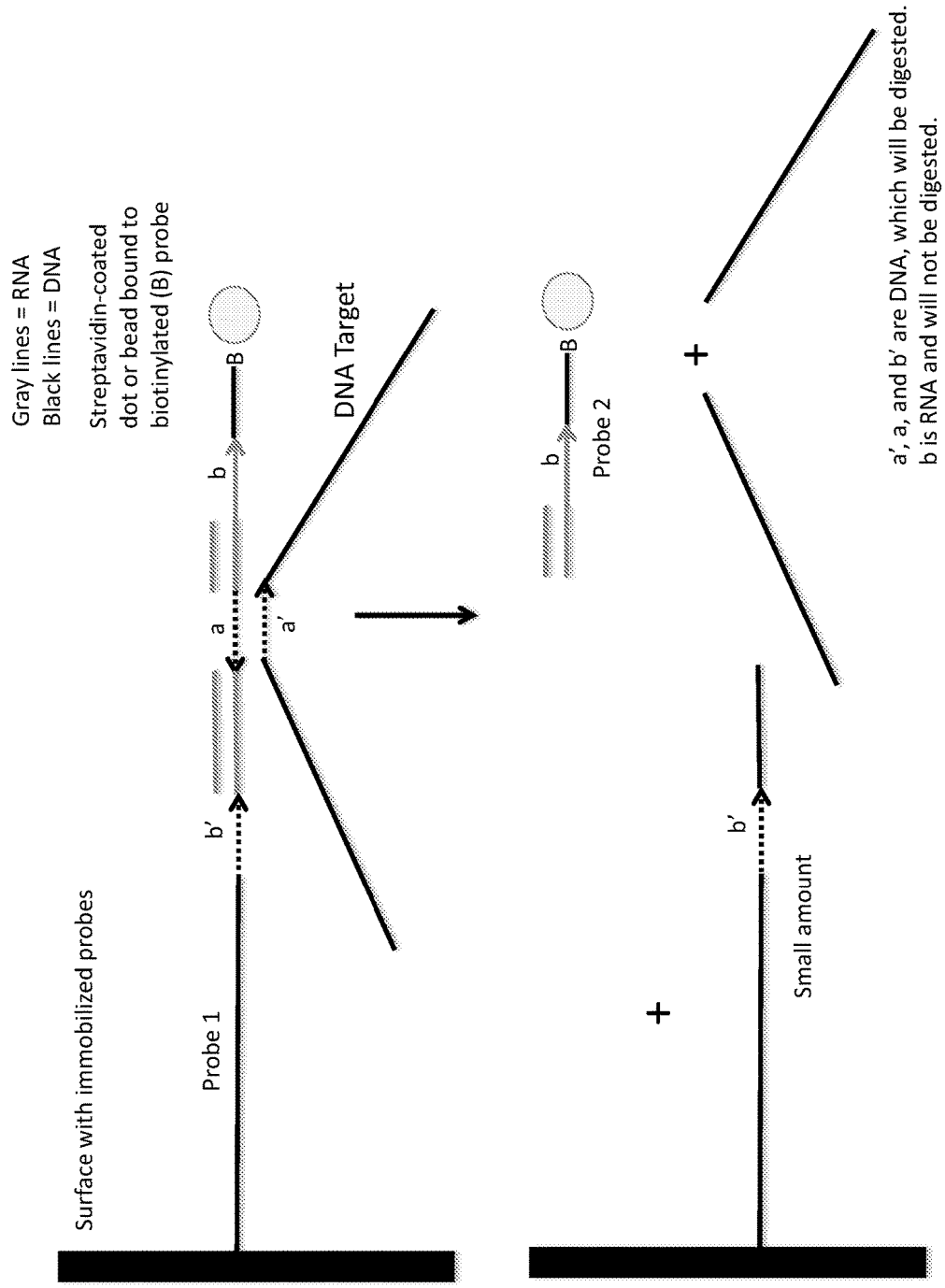
Fig. 43 Exponential DSA of DNA using a probe with two RNA blocks

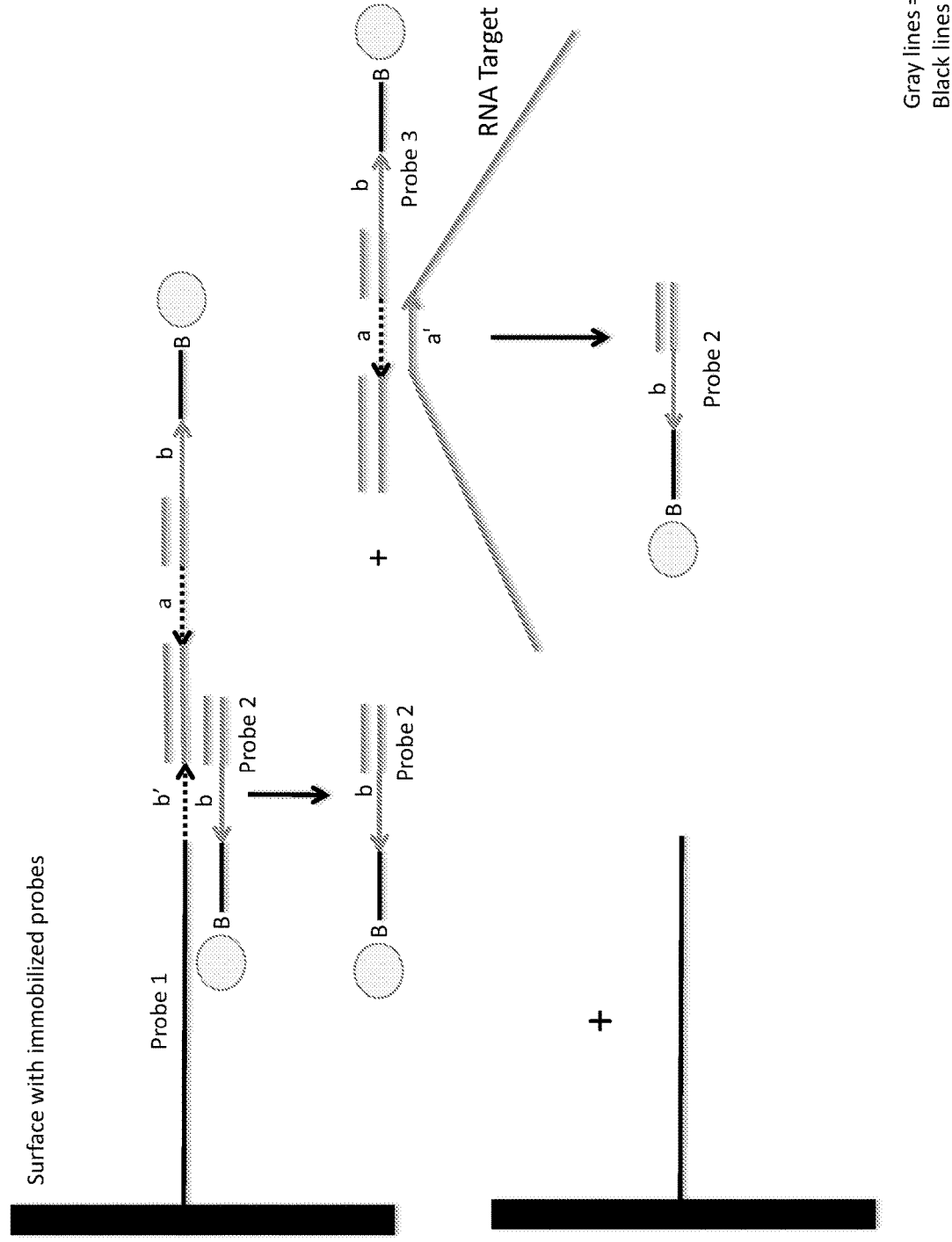
Fig. 44 RNA Target DSA of Released Probes

Fig. 45A    Overall Amplification (RNA target)

- Overall reaction scheme
  - 1T + 1P1 = 1P2 + 1T
  - 1P2 + 1P1 = 1P2 + 1P3
  - 1P3 + 1P1 = 2P3
  - 1P3 + 1T = 1P2 + 1T (minor reaction)

- Consider what happens in time
  - Assume each basic reaction takes time = t
    - 1T + 1P1 = 1P2 + 1T      at time point = 1t
      - Total = 1P2 + 1T
    - 1P2 + 1P1 = 1P2 +1P3     at time point = 2t
    - 1T + 1P1 = 1P2 + 1T
      - Total = 2P2 + 1P3 +1T
    - 2P2 + 2P1 = 2P2 + 2P3    at time point = 3t
    - 1P3 + 1P1 = 2P3
    - 1T + 1P1 = 1P2 + 1T
      - Total = 3P2 + 4P3 + 1T
    - 3P2 + 3P1 = 3P2 + 3P3    at time point = 4t
    - 4P3 + 4P1 = 8P3
    - 1T + 1P1 = 1P2 + 1T
      - Total = 4P2 + 11P3 + 1T
  - Overall: 0, 1, 4, 11, 26, ....

Fig. 45B  Overall Amplification (DNA target)

- Overall reaction scheme
  - 1 T + 1 P1 = 1 P2
  - 1 P2 + 1 P1 = 1 P2 + 1 P3
  - 1 P3 + 1 P1 = 2 P3

- Consider what happens in time
  - Assume each basic reaction takes time = t
    - 1T + 1P1 = 1P2     at time point = 1t
      - Total = 1P2
    - 1P2 + 1P1 = 1P2 +1P3     at time point = 2t
      - Total = 1P2 + 1P3
    - 1P2 + 1P1 = 1P2 + 1P3     at time point = 3t
    - 1P3 + 1P1 = 2P3
      - Total = 1P2 + 3P3
    - 1P2 + 1P1 = 1P2 + 1P3     at time point = 4t
    - 3P2 + 3P1 = 6P3
      - *Total: 1P2 + 7P3*
  - Overall: 0,1,3,7,15,31......

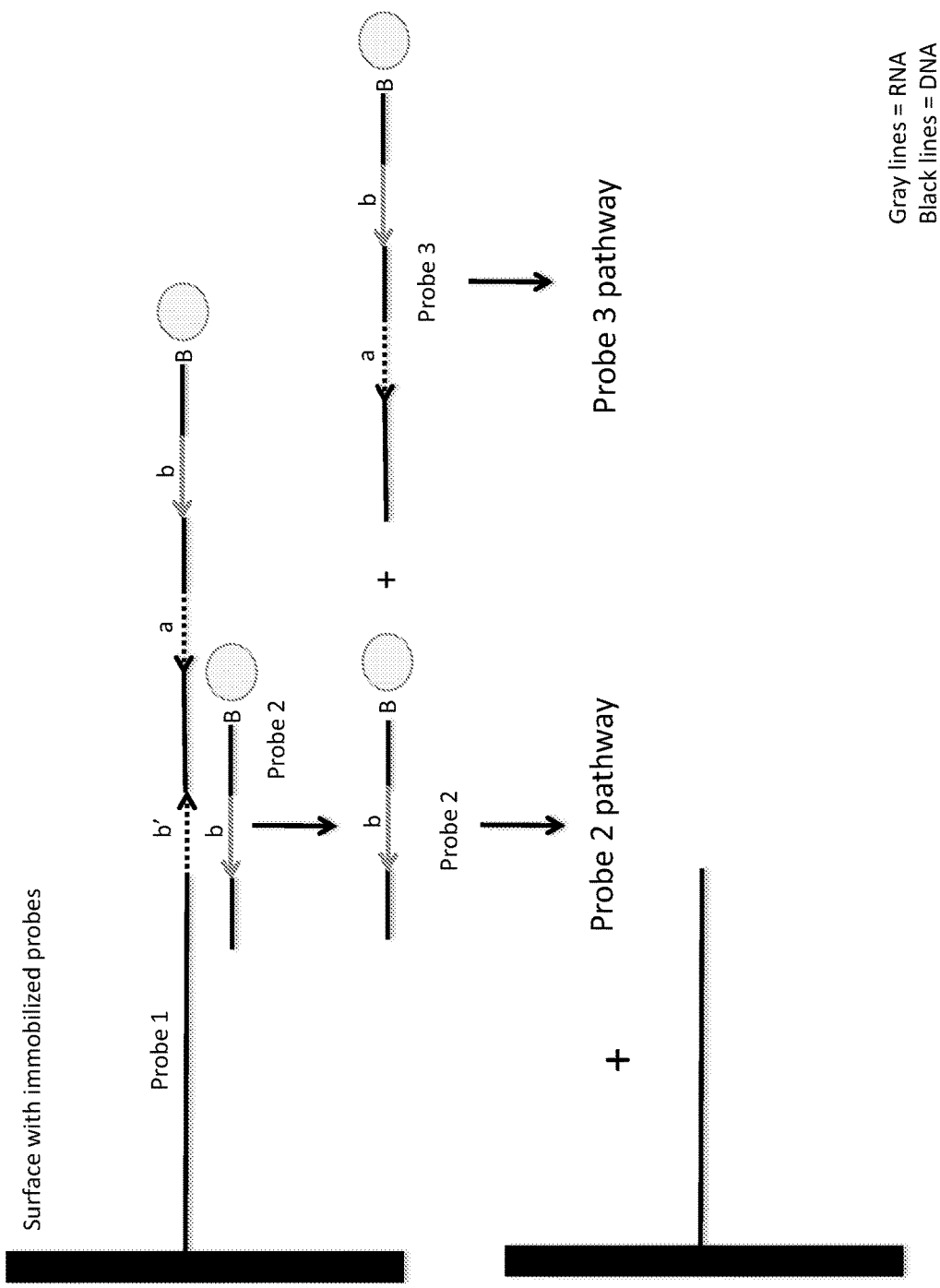

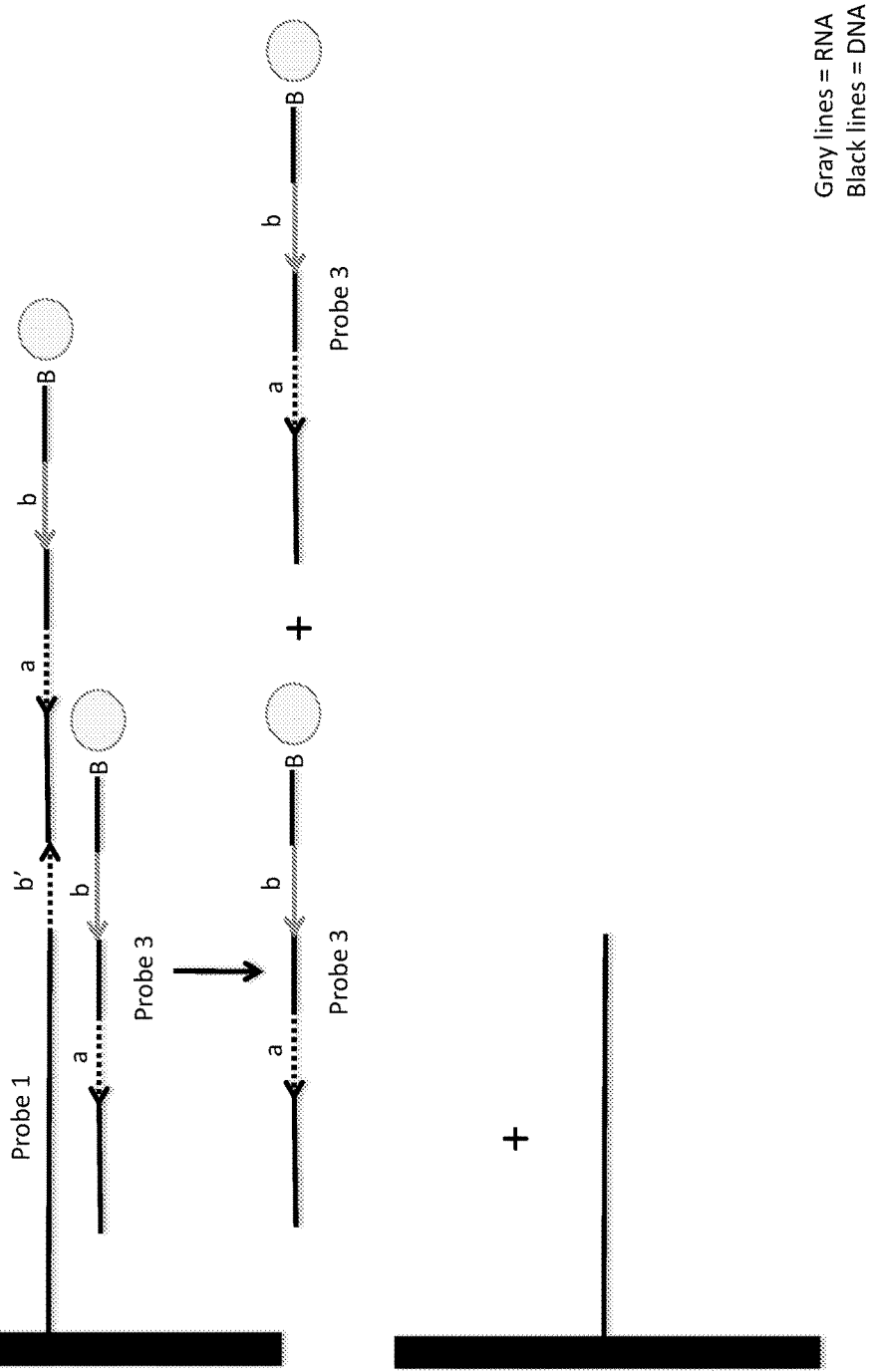
Fig. 48 Exponential DSA of DNA using probe with two cleavage sites

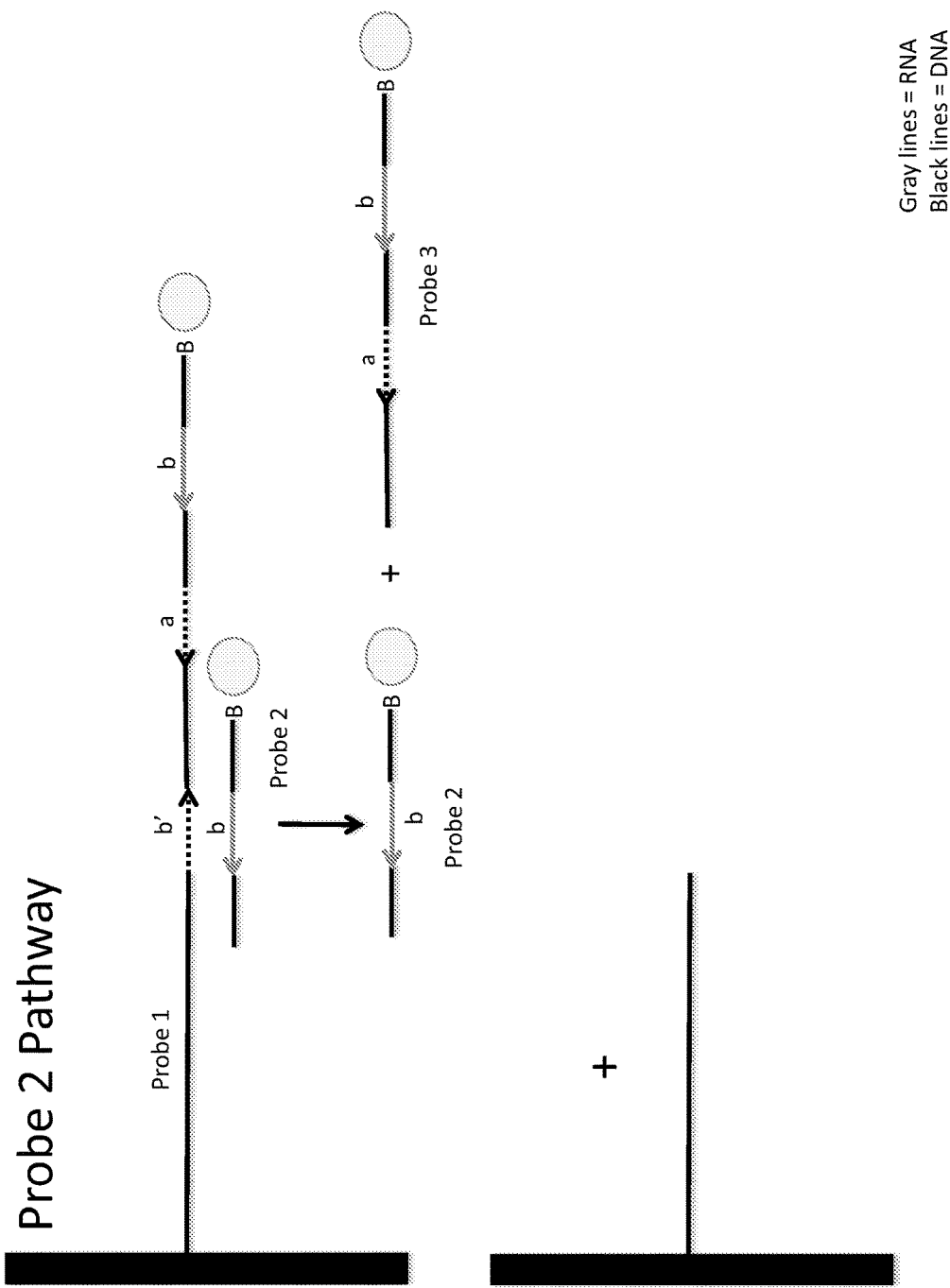

Fig. 50     Overall Amplification

- Overall reaction scheme
  - 1 T + 1 P1 = 1 P2
  - 1P2 + 1P1 = 1P2 + 1P3
  - 1P3 + 1P1 = 2P3

- Consider what happens in time
  - Assume each basic reaction takes time = t
    - 1T + 1P1 = 1P2                              at time point = 1t
      - Total = 1P2
    - 1P2 + 1P1 = 1P2 +1P3                        at time point = 2t
      - Total = 1P2 + 1P3
    - 1P2 + 1P1 = 1P2 + 1P3
    - 1P3 + 1P1 = 2P3                             at time point = 3t
      - Total = 1P2 + 3P3
    - 1P2 + 1P1 = 1P2 + 1P3
    - 3P2 + 3P1 = 6P3                             at time point = 4t
      - Total: 1P2 + 7P3
    - Overall: 0,1,3,7,15,31......

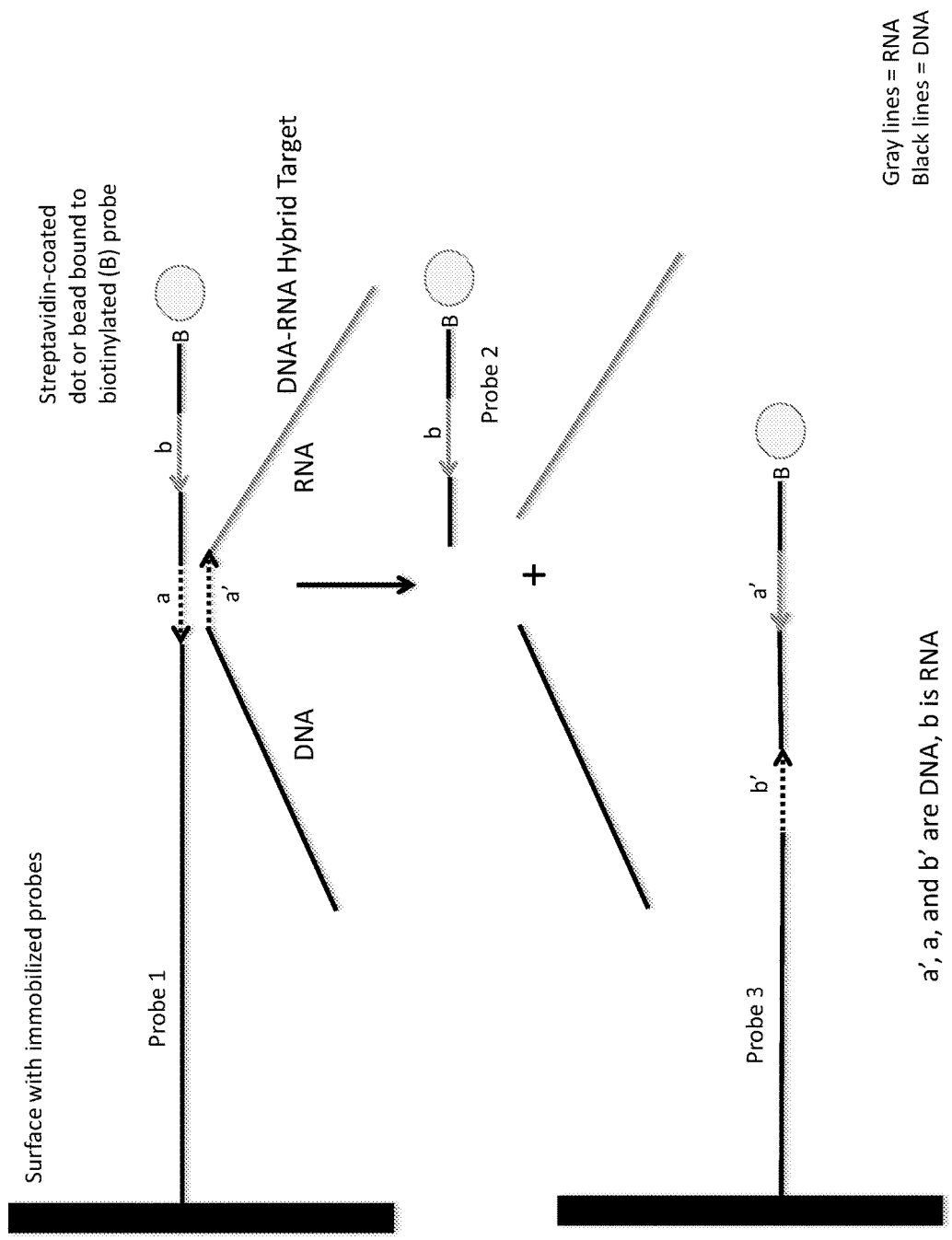
Fig. 51 Exponential DSA of DNA-RNA hybrid nucleic acids

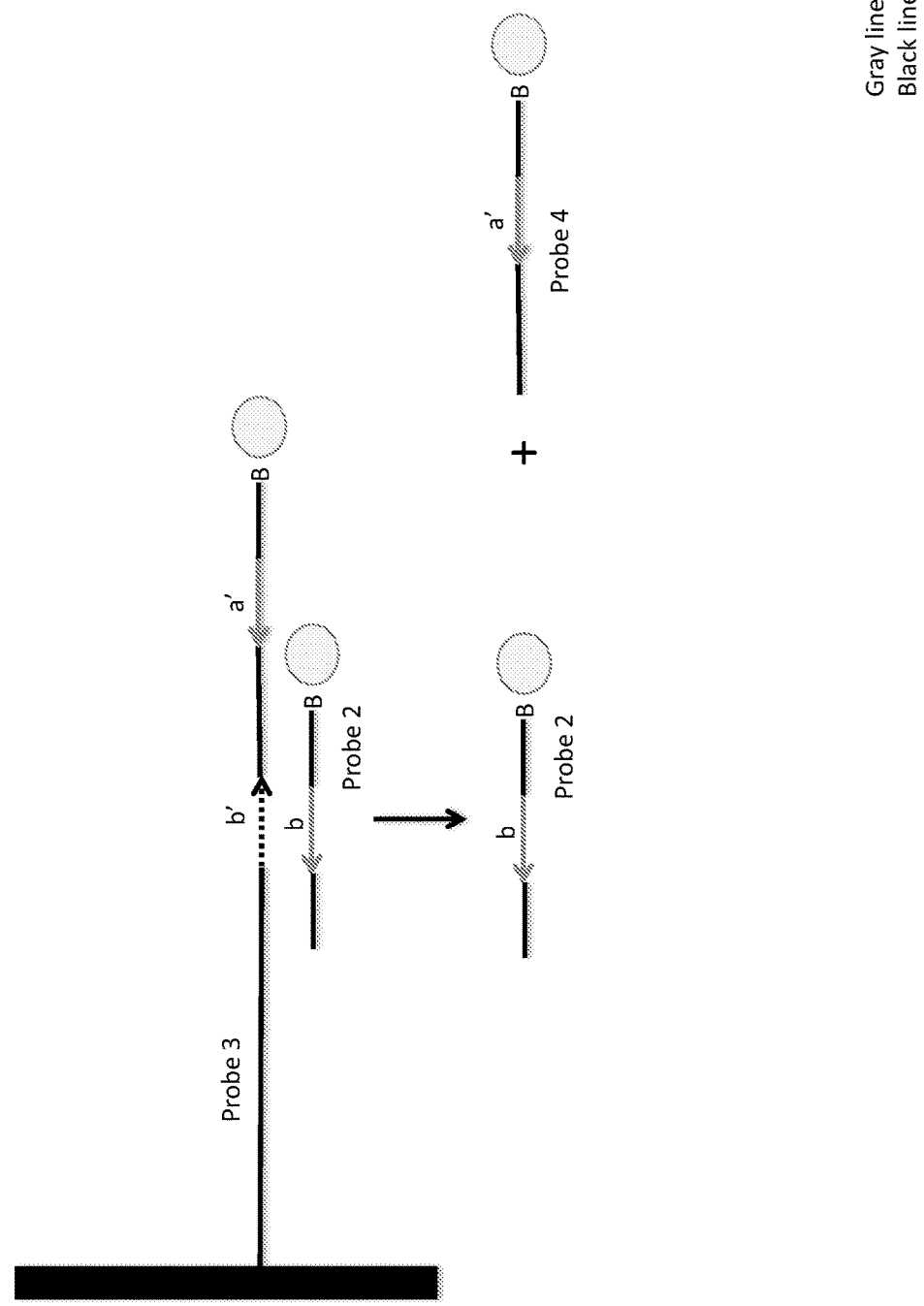
Fig. 52 Exponential DSA of DNA-RNA hybrid nucleic acids

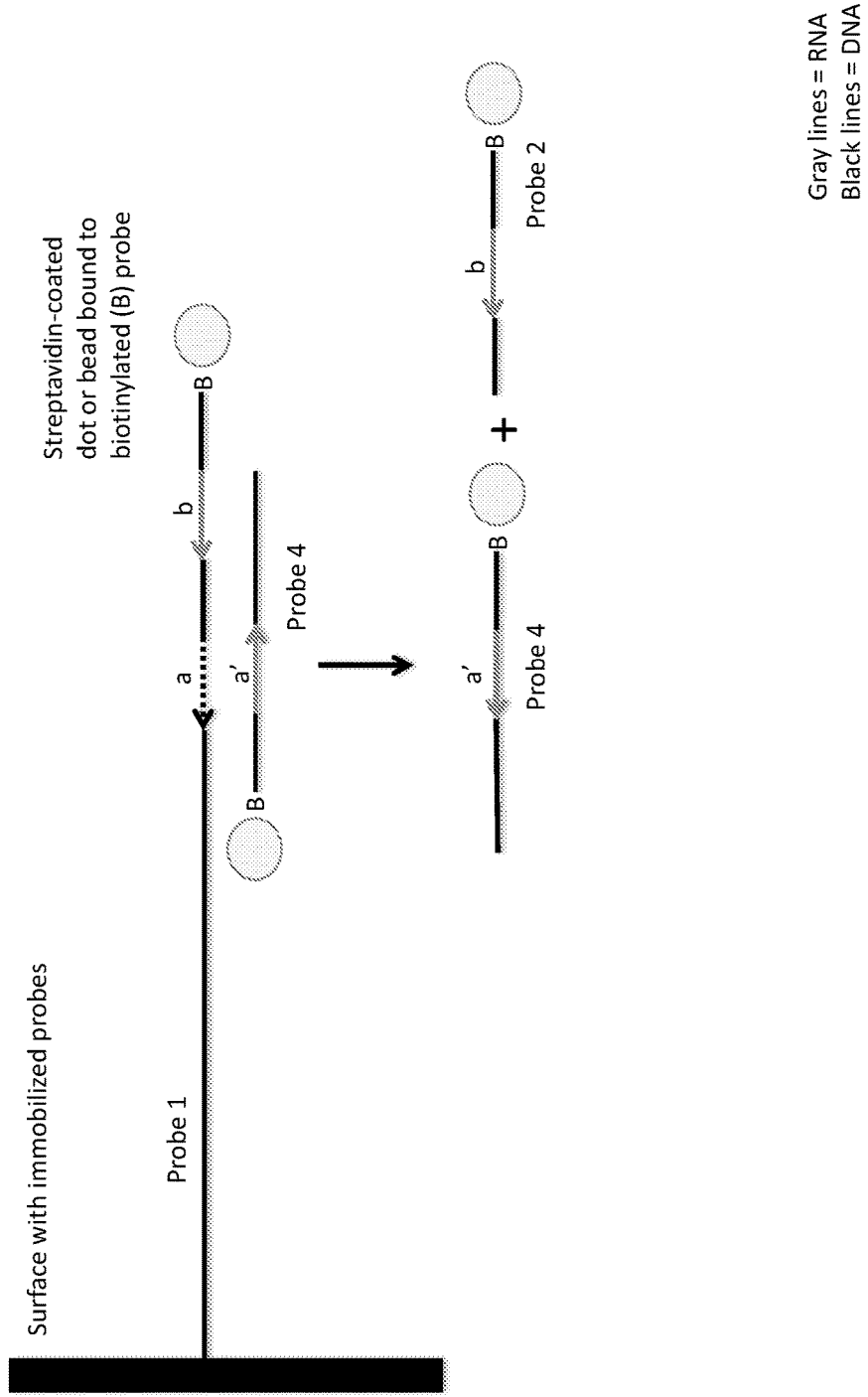
Fig. 53 Exponential DSA of DNA-RNA hybrid nucleic acids

Fig. 54

Exponential DSA of DNA using probes on beads

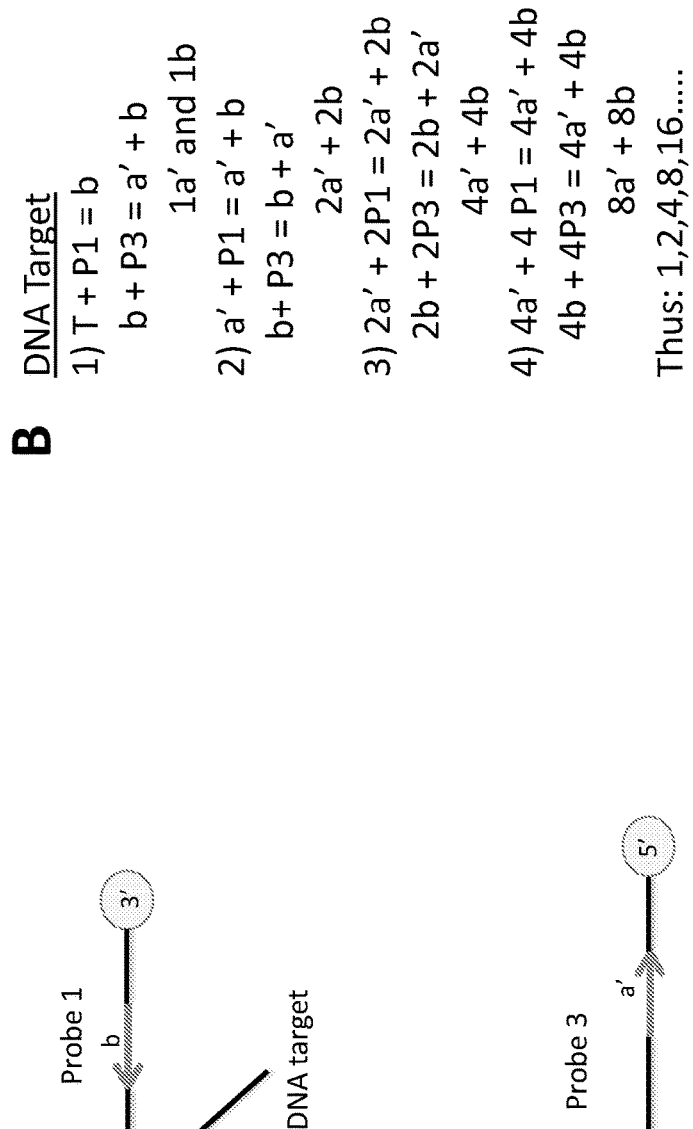

B DNA Target
1) T + P1 = b
   b + P3 = a' + b
   1a' and 1b
2) a' + P1 = a' + b
   b + P3 = b + a'
   2a' + 2b
3) 2a' + 2P1 = 2a' + 2b
   2b + 2P3 = 2b + 2a'
   4a' + 4b
4) 4a' + 4 P1 = 4a' + 4b
   4b + 4P3 = 4a' + 4b
   8a' + 8b
   Thus: 1,2,4,8,16.....

Probes: a and b' are DNA, a' and b are RNA.
Target: a' is DNA
DNA is cleaved, RNA is not cleaved.
Probe 1 and 3 are attached in opposite orientations to prevent them from cleaving each other in absence of target.
Only one probe needs a label.

Gray lines = RNA
Black lines = DNA

Exponential DSA of RNA using probes on beads

B RNA Target

1) T + P1 = b + T
   b + P3 = a' + b
   1a' + 1b + T 2) a' + P1 = a' + b
   b + P3 = a' + b
   T + P1 = b + T
   2a' + 3b + T 3) 2a' + 2P1 = 2a' + 2b
   3b + 3P3 = 3a' + 3b
   T + P1 = b + T
   5a' + 6b 4) 5a' + 5P1 = 5a' + 5b
   6b + 6P3 = 6a' + 6b
   T + P1 = b + T
   11a' + 12 b

Thus: 1,3,6,12,24....

Gray lines = RNA
Black lines = DNA

Probes: a and b' are DNA, a' and b are RNA.
DNA is cleaved, RNA is not cleaved.

Fig. 57 Detection of fluorophore-labeled probe released by DSN digestion

Fig. 58 Linear DSA using a folded template

Fig. 59 Linear DSA using two levels of amplification

Fig. 60  Linear DSA using two levels of amplification

Fig. 61 Exponential DSA using multiple hairpin probes

Fig. 62 Exponential DSA using multiple hairpin probes

Fig. 63 Cleavage and linear DSA for detection on capture strip

Fig. 64  Exponential DSA using multiple hairpin trigger probes

Fig. 66 Target-Independent DSA

Fig. 67 Suppression of Target-Independent DSA

Suppression oligo (thick dashes) can be DNA or RNA, and may contain a mismatch, modified base, or modified backbone that prevents cleavage of hybridized DNA by DSN.

Suppression of Target-Independent DSA

Suppression oligo (thick dashes) can be DNA or RNA, and may contain a mismatch, modified base, or modified backbone that prevents cleavage of hybridized DNA by DSN.

Gray lines = RNA
Dotted black lines = DNA that will be digested by DSN

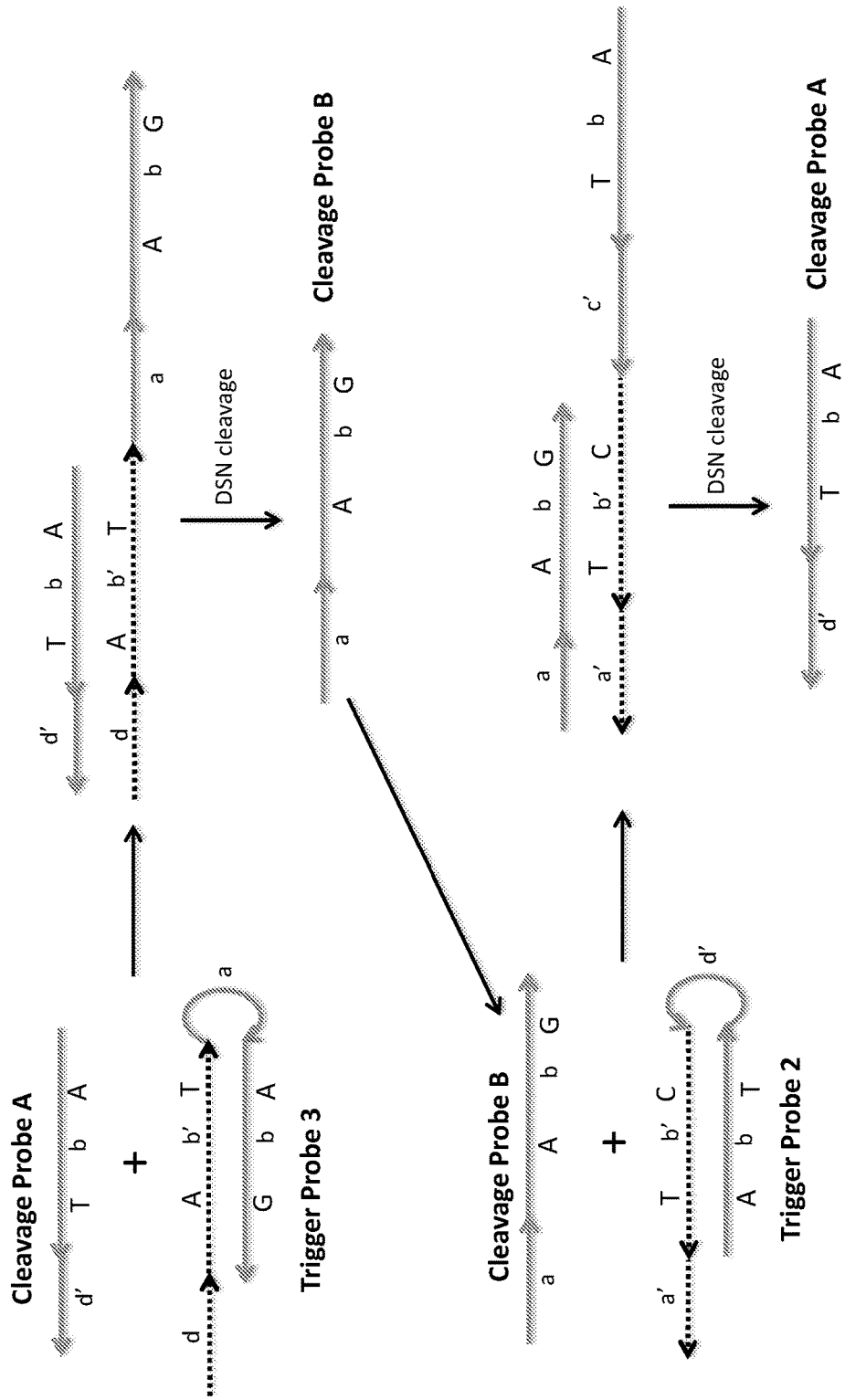
Fig. 71 Exponential DSA of a DNA target

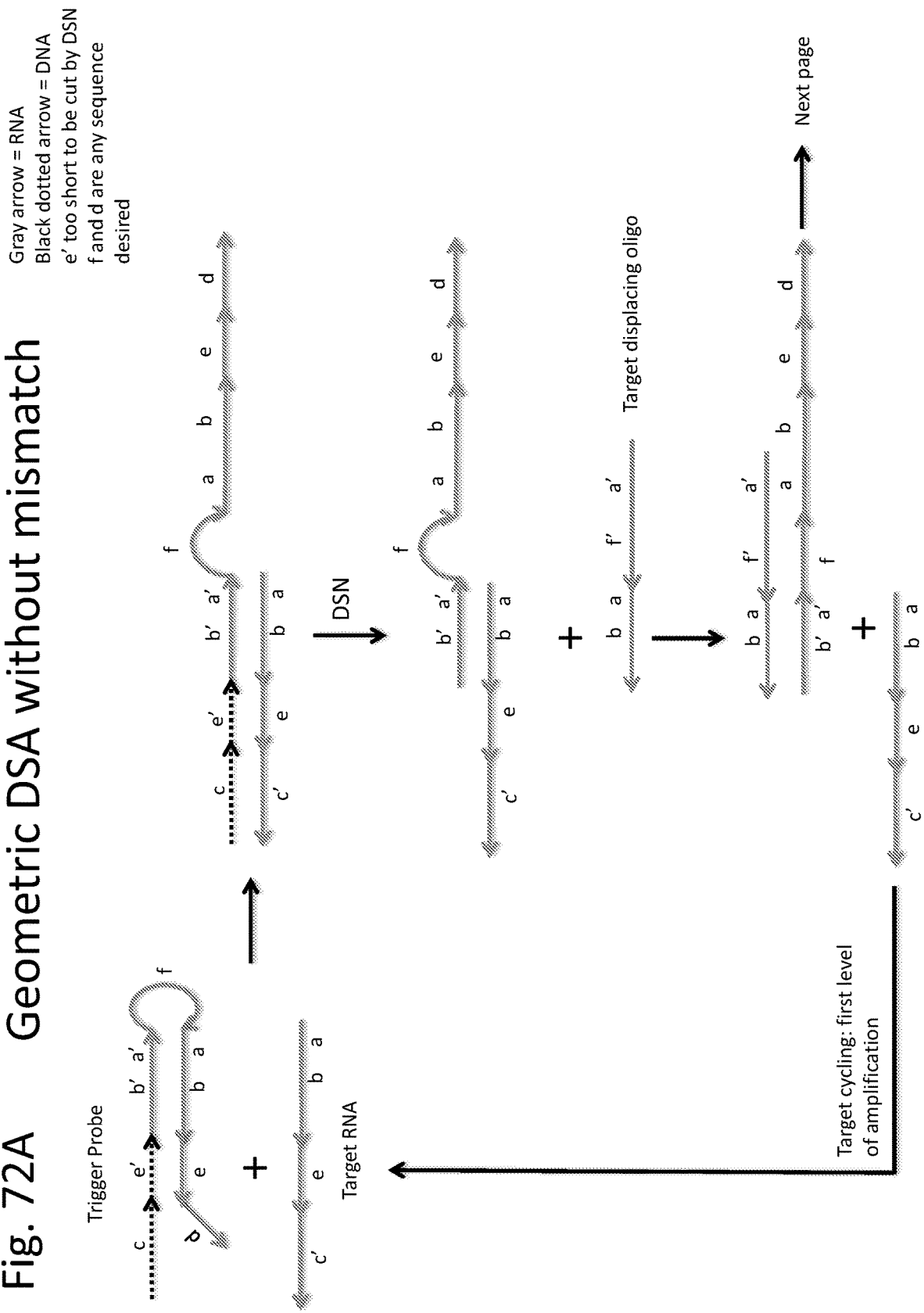
Fig. 72A  Geometric DSA without mismatch

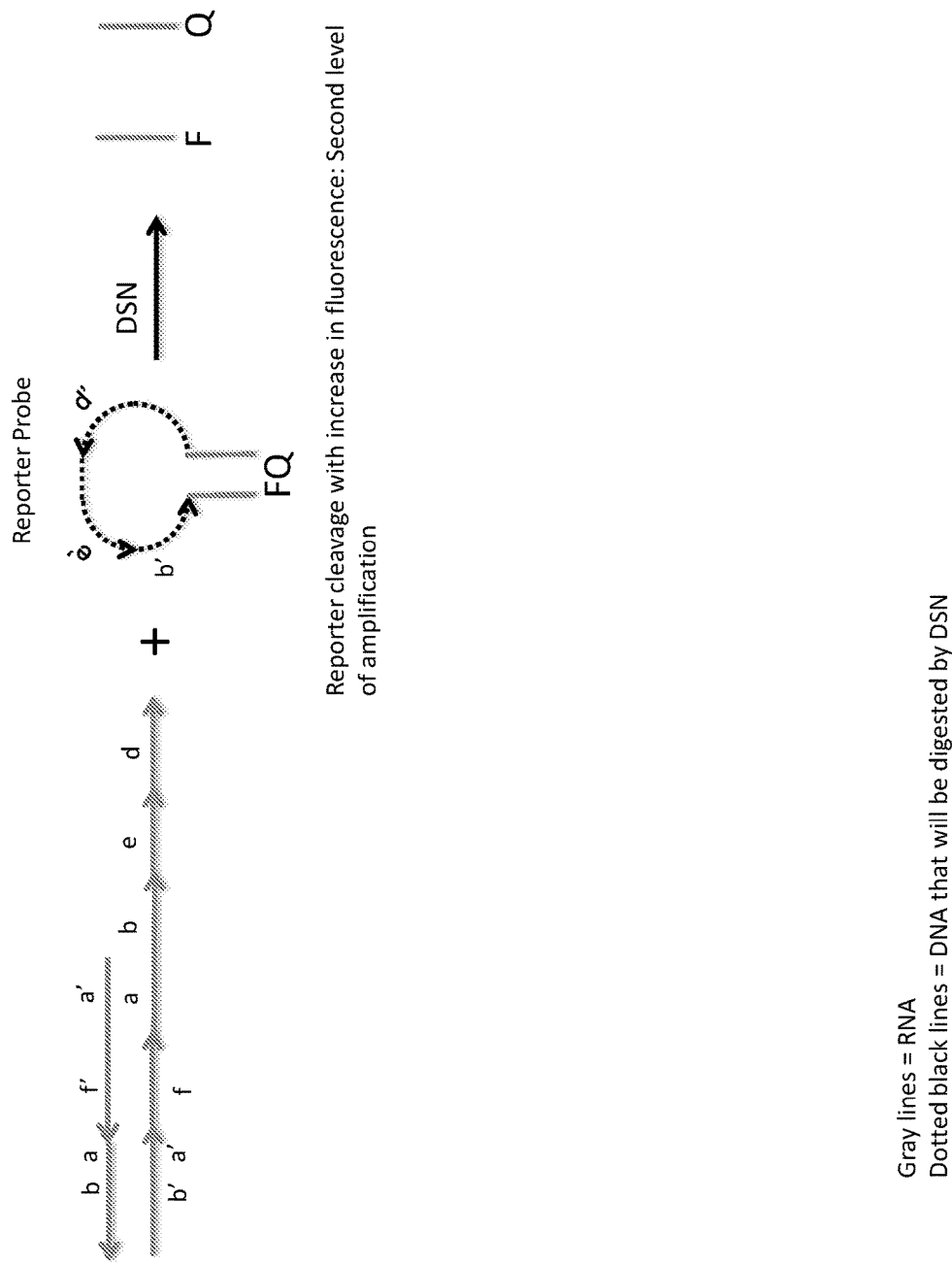
Fig. 72B Geometric DSA without mismatch

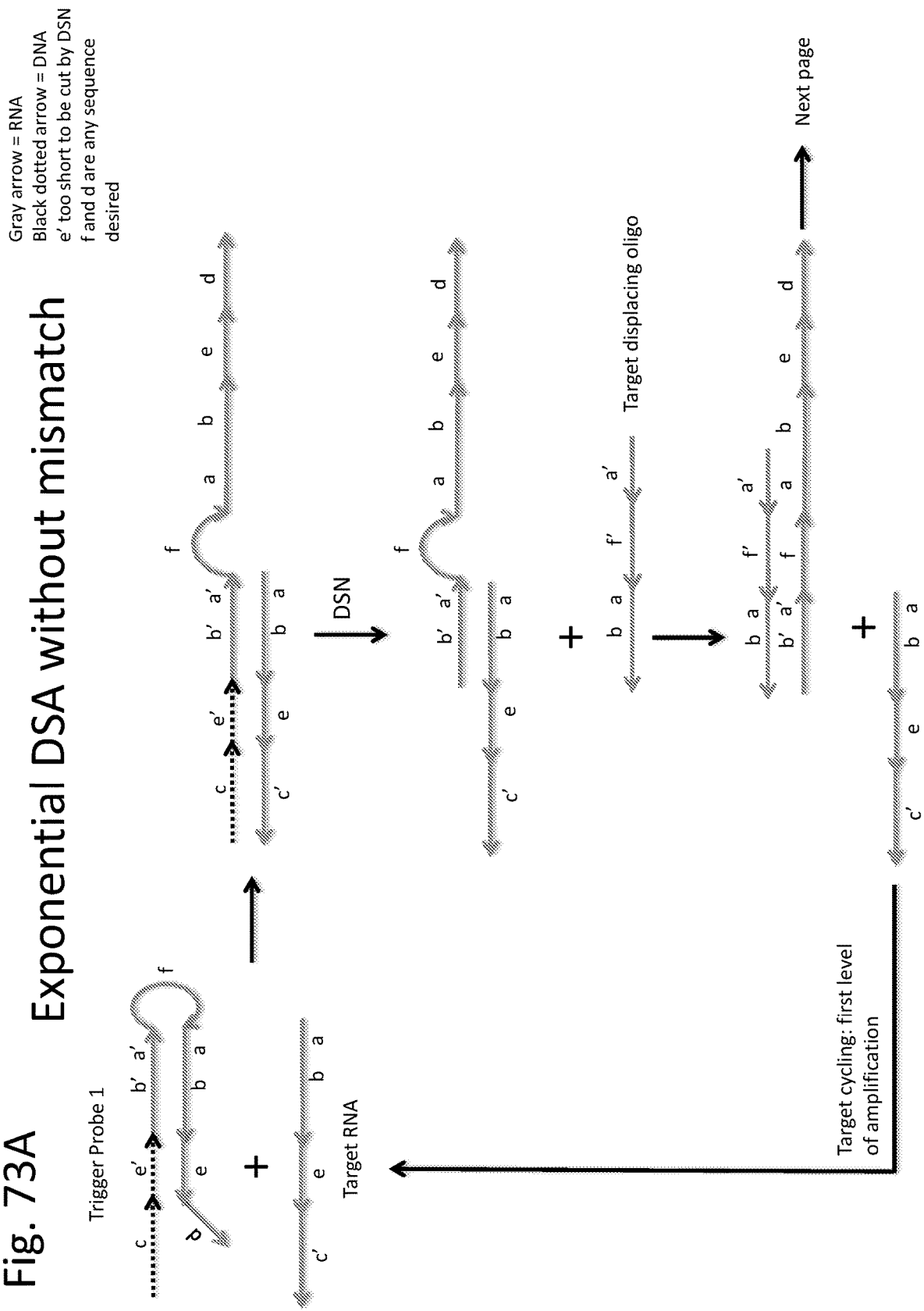

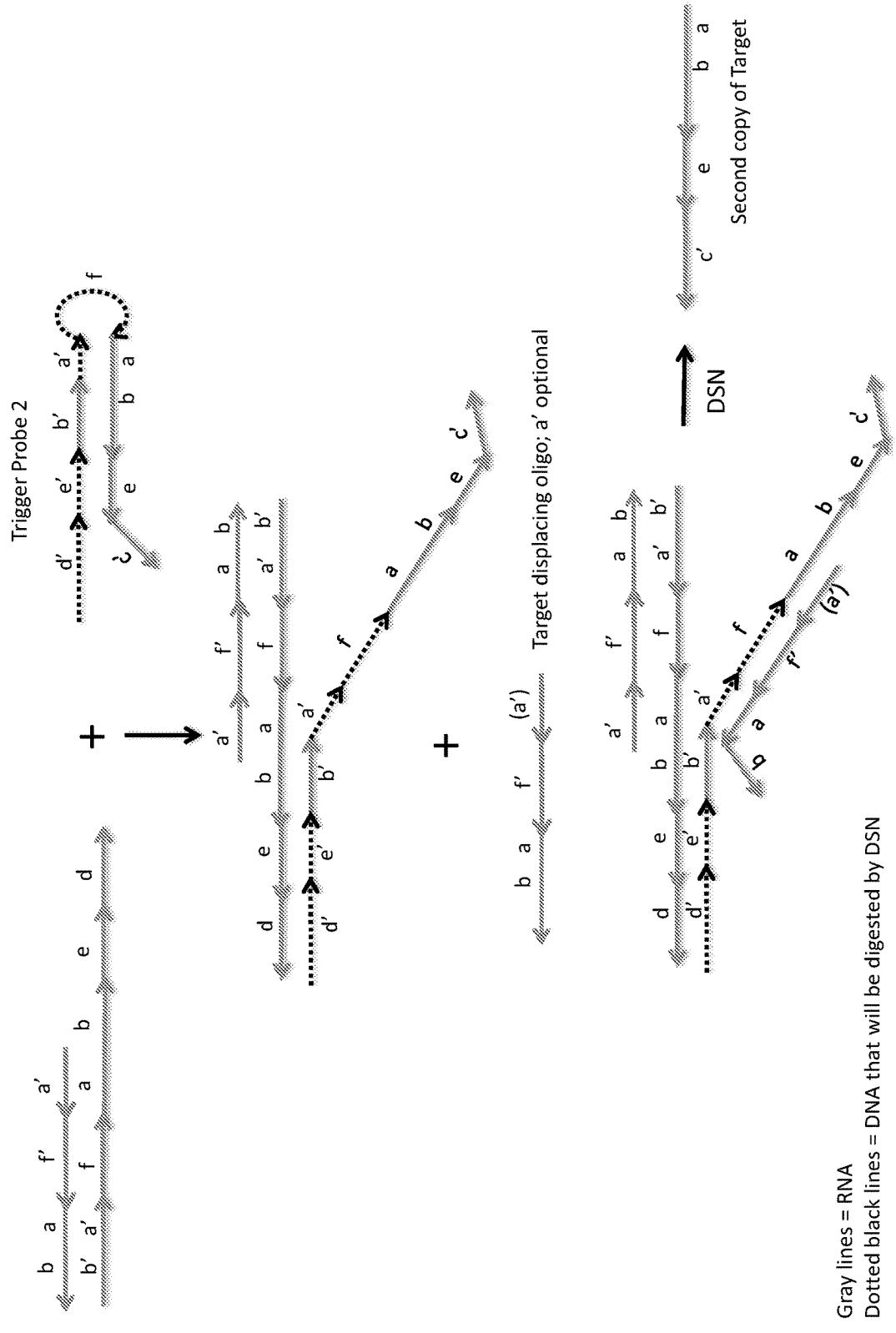
Fig. 73B  Exponential DSA without mismatch

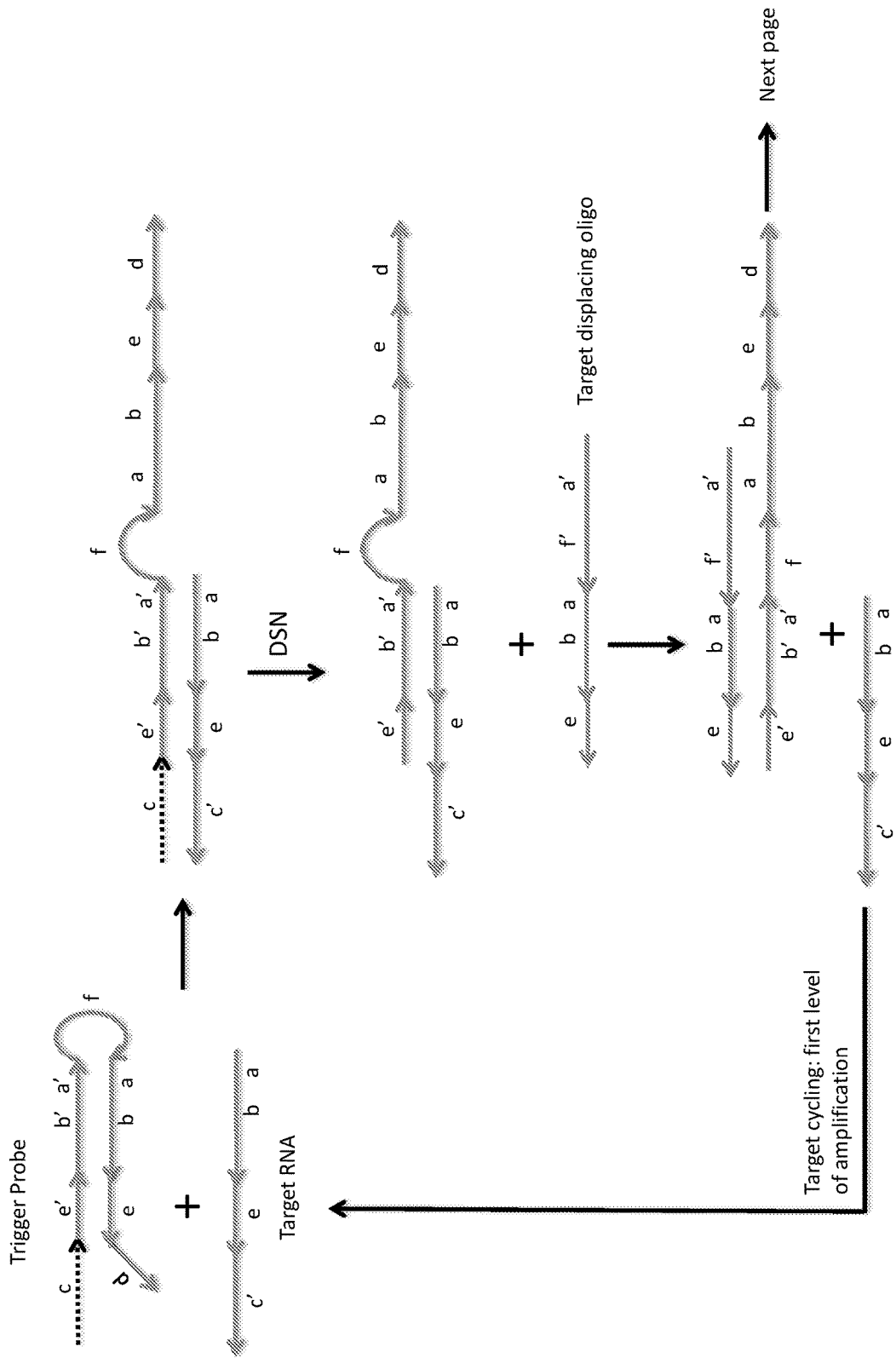

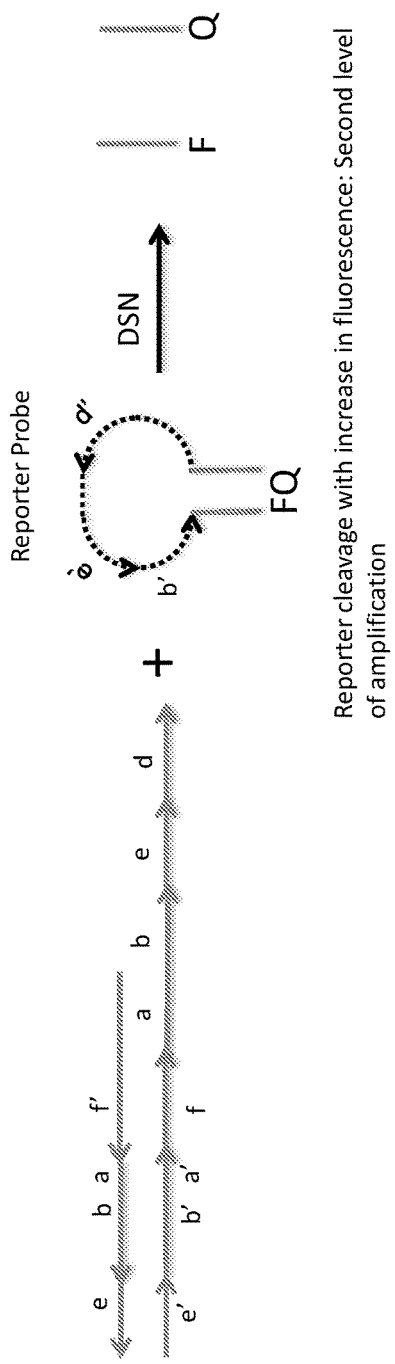
Fig. 74B Geometric DSA without mismatch

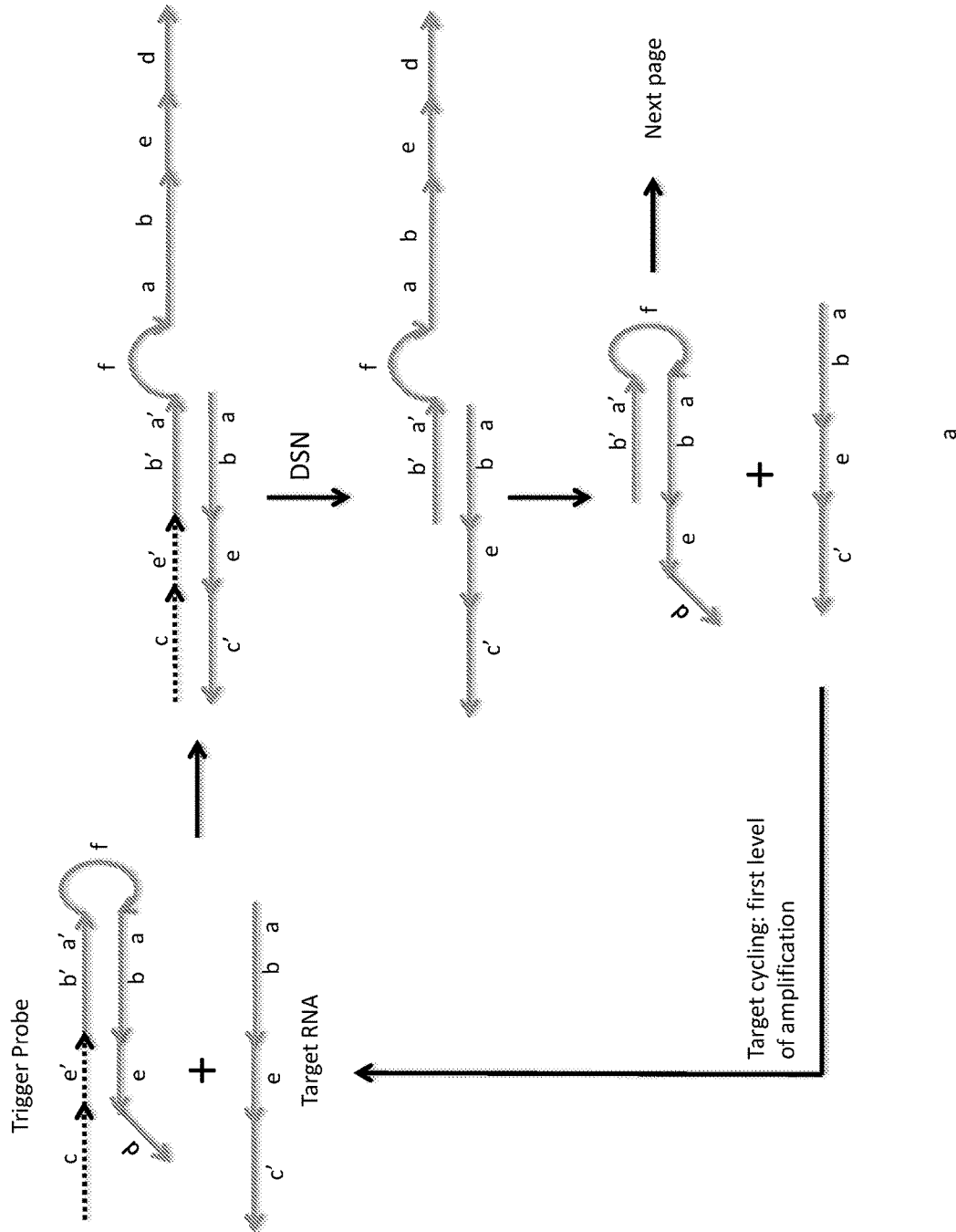
Fig. 75A Geometric DSA without mismatch

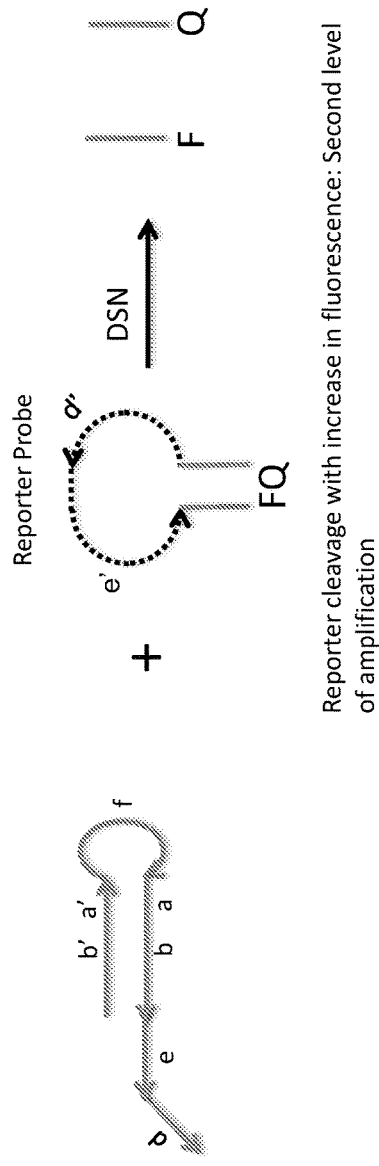
Fig. 75B Geometric DSA without mismatch

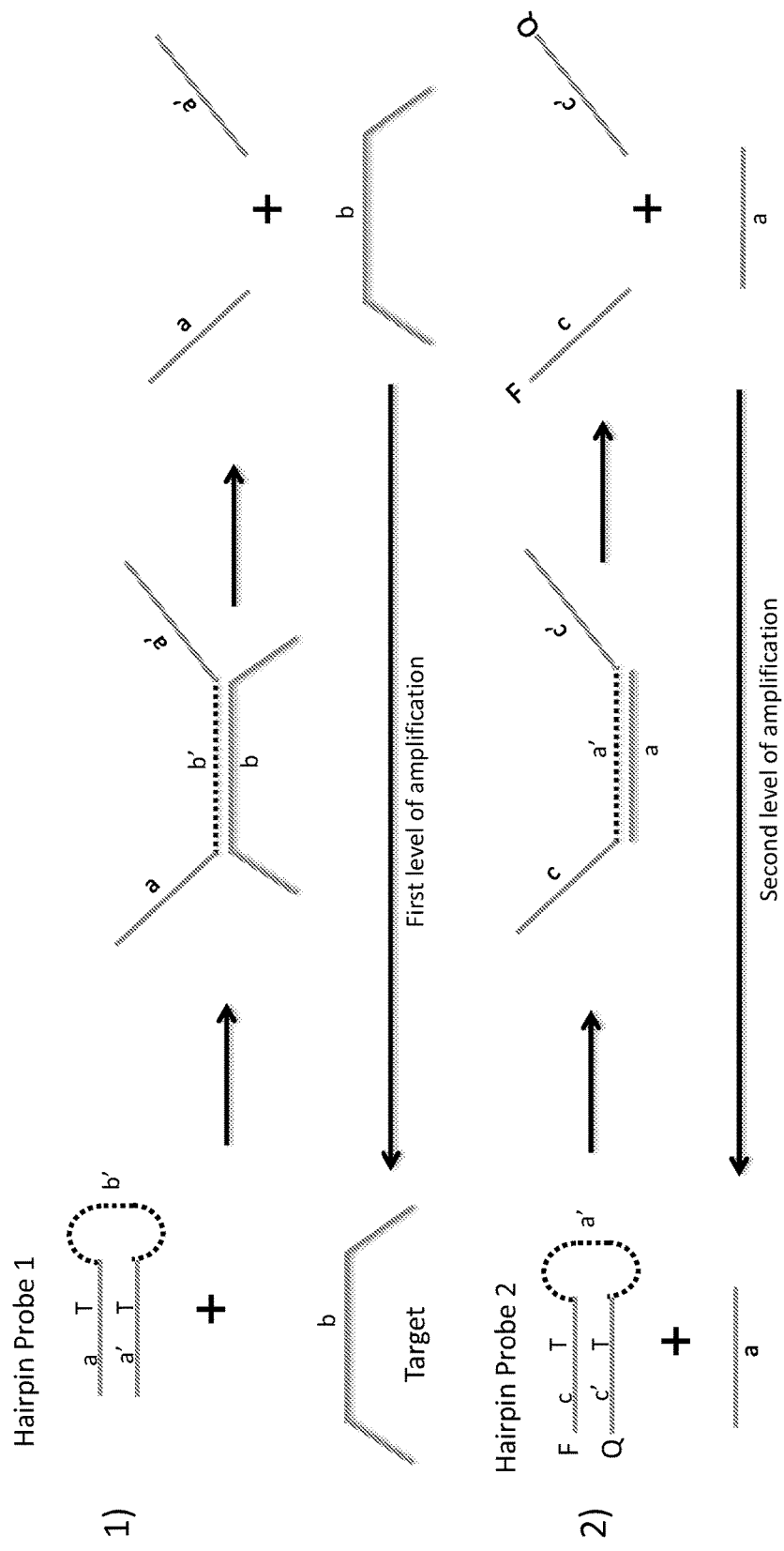
Fig. 76 Geometric DSA with Beacon Detection

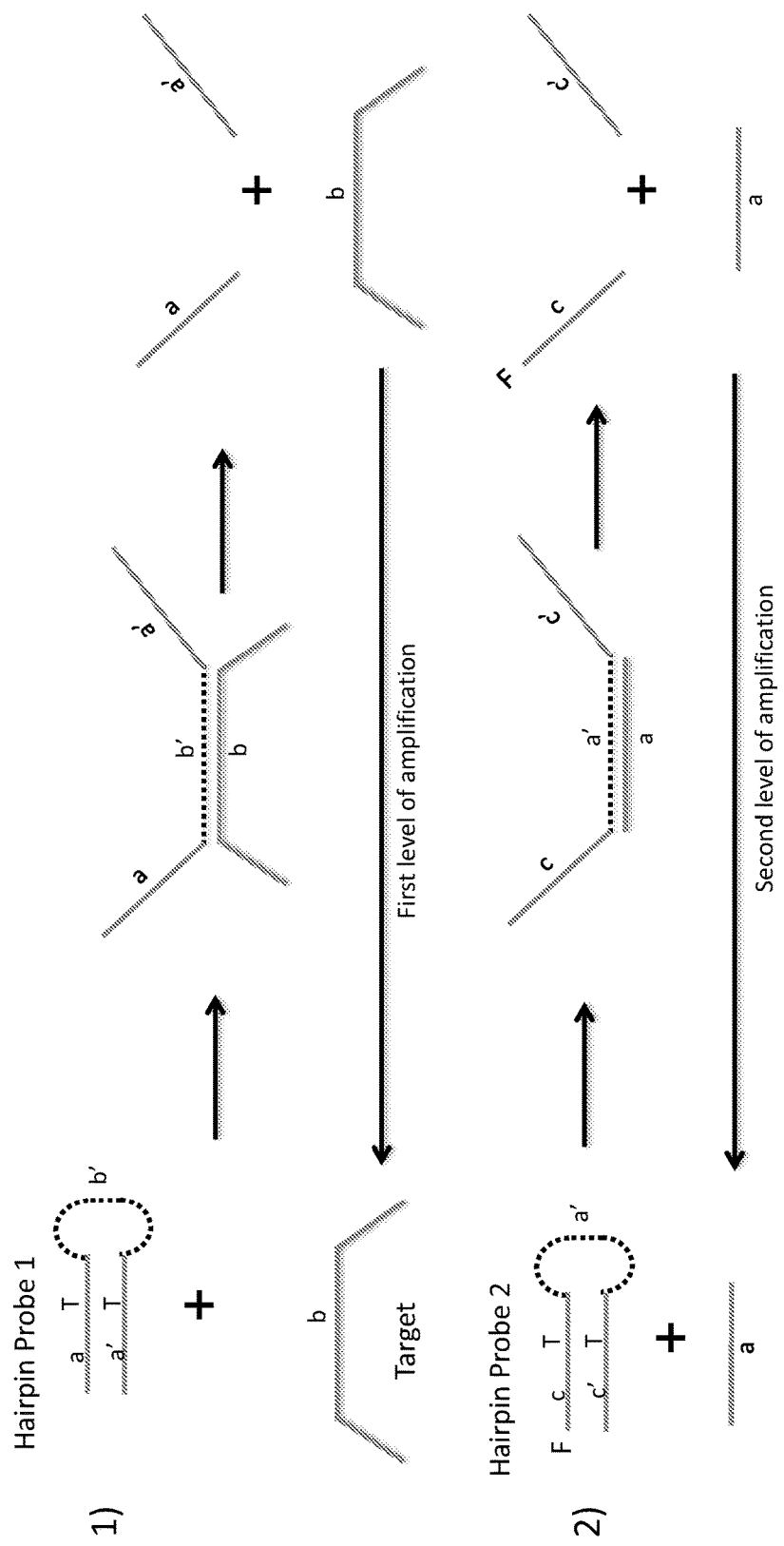
Fig. 77 Geometric DSA with Surface Detection

Fig. 78 Geometric DSA with Surface Detection
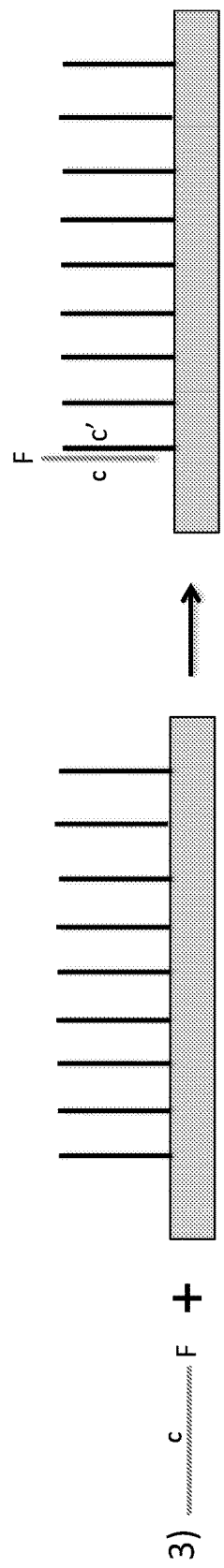
Gray line = RNA
Black line = DNA

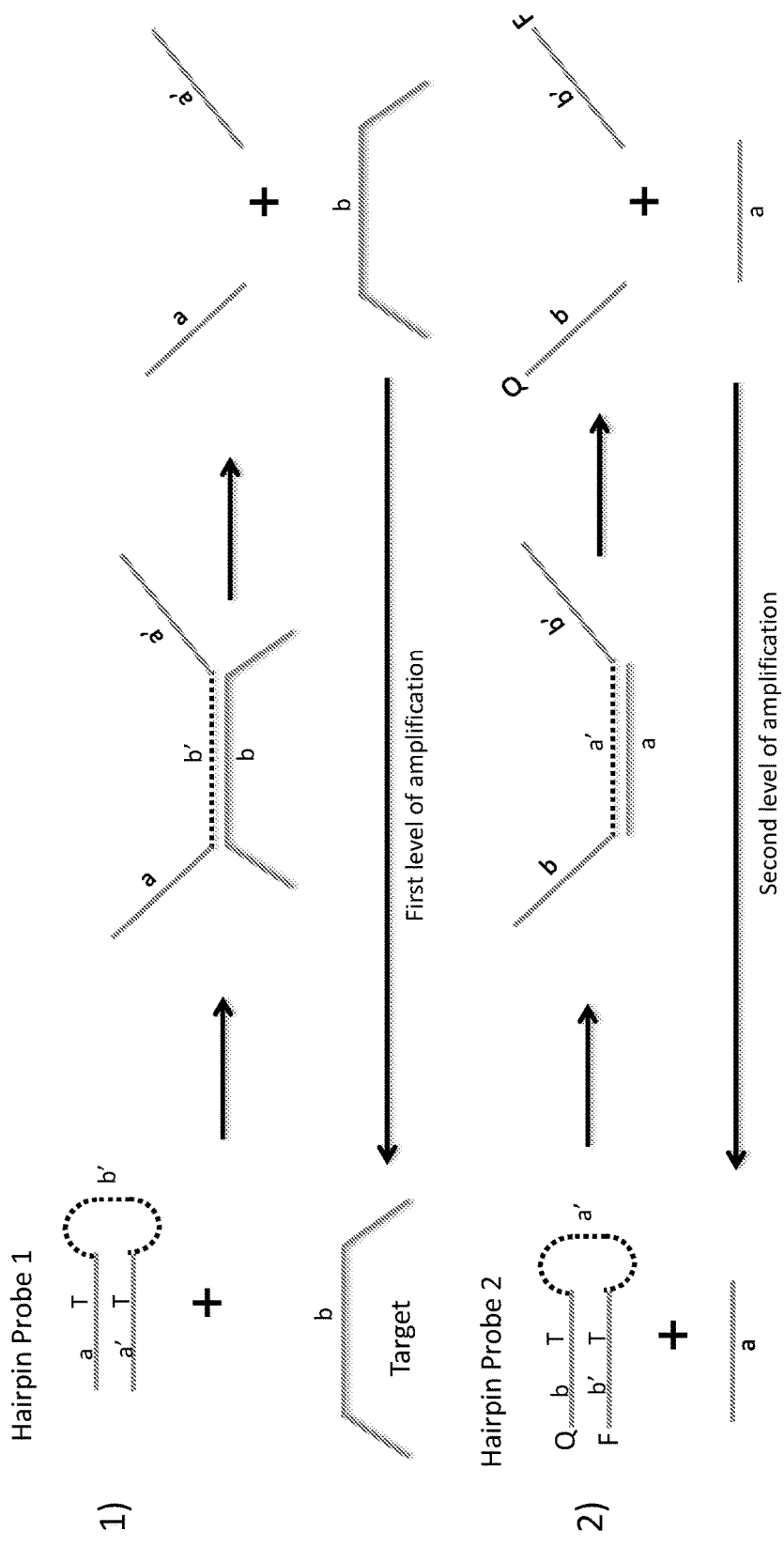
Fig. 79A Exponential DSA with Beacon Detection

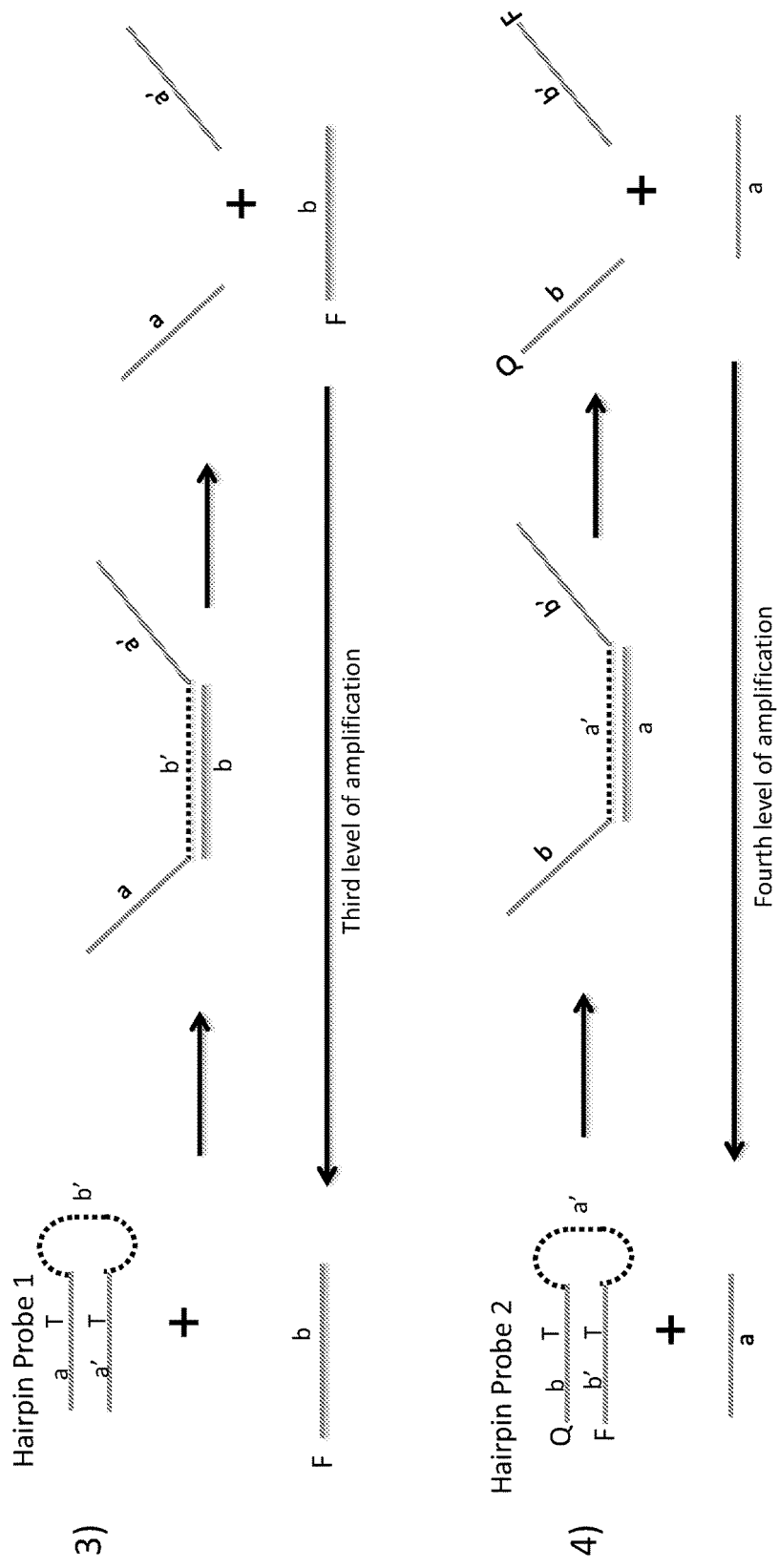

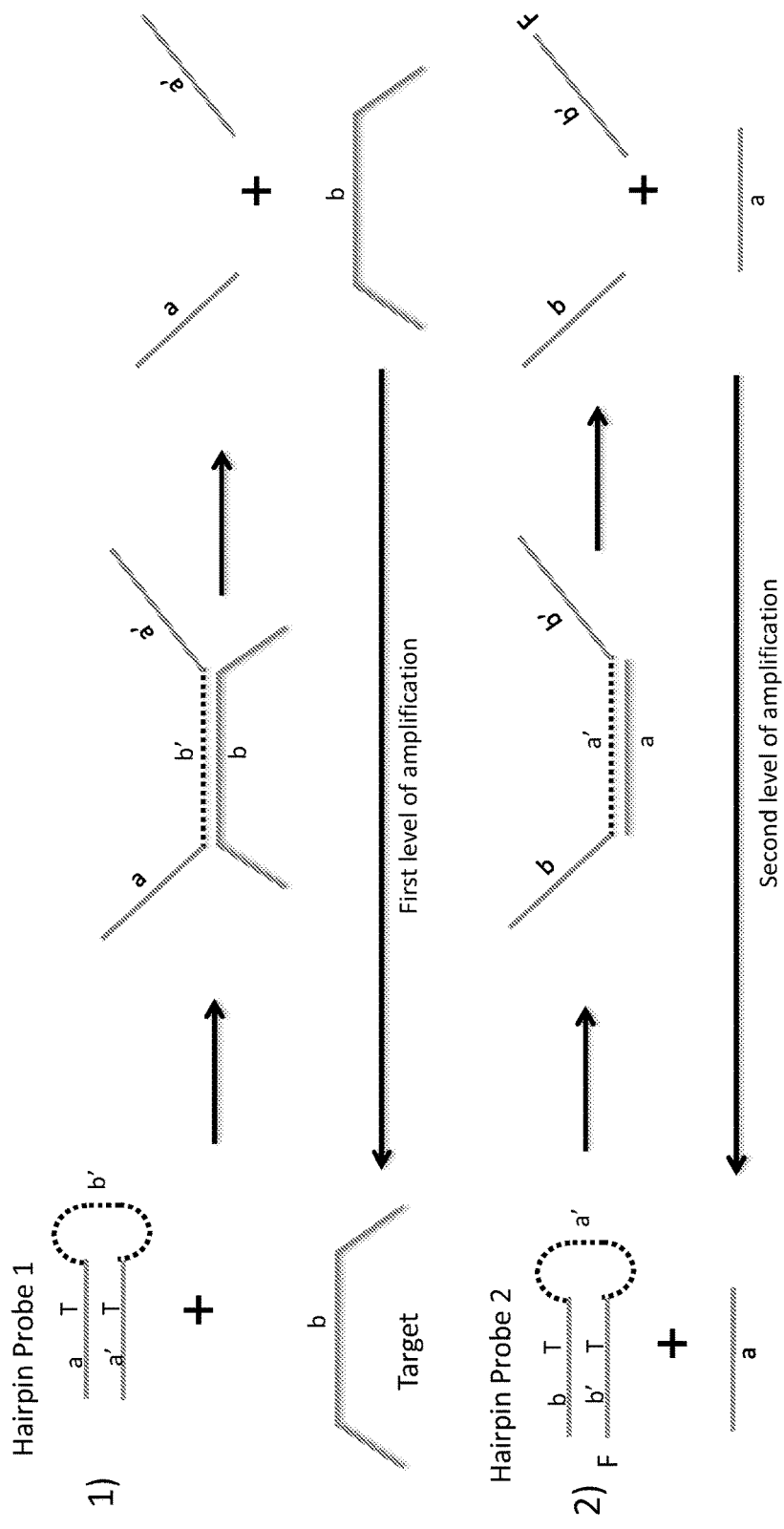
Fig. 80A Exponential DSA with Surface Detection

Exponential DSA with Surface Detection

Gray line = RNA
Black line = DNA

COMPOSITIONS AND METHODS FOR THE DETECTION OF NUCLEIC ACIDS

CROSS-REFERENCE TO RELATED APPLICATIONS

This application claims benefit of U.S. Provisional Application No. 62/067,255, filed Oct. 22, 2014, and U.S. Provisional Application No. 62/081,954, filed Nov. 19, 2014, which are hereby incorporated by reference in their entirety.

FIELD OF THE INVENTION

The present invention relates to methods for detecting nucleic acids in a sample.

BACKGROUND

Assays for detecting specific target nucleic acids are finding increasing use in modern diagnostics as greater numbers of biomarkers are identified and linked to diseases. Hybridization-based methods, such as Southern blotting and Northern blotting, are commonly used to detect nucleic acids such as DNA and RNA, respectively. Polymerase chain reaction-based amplification methods may also be used to detect target nucleic acids in a sample. However, existing nucleic acid detection methods may not provide suitable sensitivity and accuracy, and often require a significant amount of time to perform. Furthermore, existing methods often require purification and amplification steps to be performed prior to detection, in order to produce sufficient starting material. Thus, there exists a need in the art for rapid, sensitive, and accurate methods of detecting target nucleic acids that can be performed in samples obtained directly from a patient.

SUMMARY OF THE INVENTION

The present invention features methods of detecting a target nucleic acid in a sample using a duplex-specific nuclease. For example, the target nucleic acid may be detected by hybridizing the target nucleic acid to a detection probe and digesting the resultant duplex using the duplex-specific nuclease, thus releasing a detectable component of the probe, which can be separated from unbound probe for detection or detected in situ. The methods described herein are therefore useful for rapid, efficient, sensitive, and accurate detection of target nucleic acids in a variety of applications, including, for example, diagnostic tests and laboratory assays.

Compositions

In a first aspect, the invention features a composition including: (a) a clinical specimen including a target nucleic acid, (b) a nucleic acid probe, (c) a lysis buffer, and (d) a duplex-specific nuclease (DSN). In some embodiments of the first aspect, the clinical specimen includes a blood specimen, a buccal specimen, a nasal specimen, a fecal specimen, a tissue specimen, a urine specimen, or a bacterial specimen, or any combination or derivative thereof.

In some embodiments of the first aspect, the composition includes a lysis buffer. In certain embodiments, the lysis buffer includes 0.1-2% sodium dodecyl sulfate (SDS). In one embodiment, the SDS is 1%. In certain embodiments, the lysis buffer includes proteinase K.

In some embodiments of the first aspect, the DSN is a Kamchatka crab DSN.

In some embodiments of the first aspect, the nucleic acid probe is attached to a support (e.g., a surface).

Reaction Mixture—Initial Solution

In a second aspect, the invention features a solution including (a) a nucleic acid probe including a single-stranded region, a double-stranded region, and at least one unhybridized nucleotide located within the double-stranded region, and (b) a target nucleic acid including a nucleic acid sequence complementary to at least a portion of the nucleic acid probe.

In some embodiments of the second aspect, the double-stranded region includes the portion of the nucleic acid probe complementary to the nucleic acid sequence of the target nucleic acid.

In some embodiments of the second aspect, the single-stranded region includes a further portion of the nucleic acid complementary to the nucleic acid sequence of the target nucleic acid.

In some embodiments of the second aspect, the double-stranded region includes a mismatch or bulge.

In some embodiments of the second aspect, the single-stranded region includes a loop or an overhang.

In some embodiments of the second aspect, one strand of the double-stranded region includes DNA and the other strand of the double-stranded region includes RNA.

In some embodiments of the second aspect, the nucleic acid probe includes a hairpin structure including the single-stranded region and the double-straided region.

In some embodiments of the second aspect, the nucleic acid probe includes: (i) a first strand including one strand of the double-stranded region, and (ii) a second strand including the other strand of the double-stranded region and the single-stranded region.

In some embodiments of the second aspect, the solution further includes a DSN. In certain embodiments, the DSN is a Kamchatka crab DSN.

In some embodiments of the second aspect, the solution further includes a lysis buffer.

In a third aspect, the invention features a solution including (a) a target nucleic acid, (b) a nucleic acid probe including a double-stranded region including a nucleic acid sequence complementary to at least a portion of the target nucleic acid, and (c) a DSN.

In some embodiments of the third aspect, the solution further includes a lysis buffer.

In some embodiments of the third aspect, the nucleic acid probe includes a single-stranded region including a nucleic acid sequence complementary to at least a portion of the target nucleic acid.

In some embodiments of the third aspect, the DSN is a Kamchatka crab DSN.

In some embodiments of the second or third aspects, the nucleic acid probe is attached to a detectable label. In certain embodiments, the detectable label is a fluorophore. In particular embodiments, the nucleic acid probe is further attached to a quencher. In one embodiment, the fluorophore is attached to one end of the nucleic acid probe, and the quencher is attached to the opposite end of the nucleic acid probe.

In some embodiments of the second or third aspects, the target nucleic acid includes RNA and/or DNA.

In some embodiments of the second or third aspects, the solution further includes a hairpin probe including a first region, a second region, and a third region capable of hybridizing to the first region, in which the first region is attached to a detectable label and the third region is attached to a quencher.

In some embodiments of the second or third aspects, the solution further includes a second nucleic acid probe including a second single-stranded region and a second double-stranded region, in which the second double-stranded region includes at least one unhybridized nucleotide within the second double-stranded region. In certain embodiments, the second double-stranded region includes a mismatch or bulge.

In some embodiments of the second or third aspects, the nucleic acid probe is attached to a support (e.g., a surface).

Reaction Mixture—Reaction Intermediates

In a fourth aspect, the invention features a solution including a first nucleic acid probe strand, a second nucleic acid probe strand, and a target nucleic acid, in which the first nucleic acid probe strand includes (a) a first region complementary to the target nucleic acid and hybridized to at least a portion of the target nucleic acid, thereby forming a duplex, (b) a second region capable of hybridizing to at least a portion of the second nucleic acid probe strand, the second region not being complementary to the portion of the second nucleic acid probe strand; and the duplex is capable of being digested by a DSN. In certain embodiments, the first nucleic acid probe strand and/or the second nucleic acid probe strand are each attached to a support (e.g., a surface).

In a fifth aspect, the invention features a solution including a nucleic acid probe and a target nucleic acid; in which the nucleic acid probe includes a first region complementary to the target nucleic acid and hybridized to at least a portion of the target nucleic acid, a second region incapable of hybridizing to the target nucleic acid, and a third region incapable of hybridizing to the target nucleic acid; the first region including a portion capable of hybridizing to at least a portion of the third region to form a duplex including at least one unhybridized nucleotide located within the double-stranded region; and the hybridization between the nucleic acid probe and the target nucleic acid forms a duplex capable of being digested by a DSN. In certain embodiments, the nucleic acid probe is attached to a support (e.g., a surface).

In a sixth aspect, the invention features a solution including a DSN, a nucleic acid probe, and a target nucleic acid, in which the nucleic acid probe includes a first region complementary to the target nucleic acid and hybridized to at least a portion of the target nucleic acid, and the hybridized portion of the nucleic acid probe and the target nucleic acid forms a duplex capable of being digested by the DSN. In certain embodiments, the nucleic acid probe is attached to a support (e.g., a surface).

In some embodiments of the fourth through sixth aspects, the DSN is a Kamchatka crab DSN.

In some embodiments of the fourth through sixth aspects, the solution further includes a lysis buffer.

Reaction Mixture—Amplified Product

In a seventh aspect, the invention features a solution including a plurality of copies of a released nucleic acid probe end region, a plurality of copies of a nucleic acid fragment, a target nucleic acid, a DSN, and a lysis buffer, in which the released nucleic acid probe end region, the nucleic acid fragment, and the target nucleic acid are incapable of hybridizing to each other.

In an eighth aspect, the invention features a solution including: (i) a first nucleic acid probe strand, (ii) a second nucleic acid probe strand attached to a detectable label, (iii) a target nucleic acid, (iv) a DSN, and (v) a lysis buffer, in which the first nucleic acid probe strand, the second nucleic acid probe strand, and the target nucleic acid are incapable of hybridizing to each other.

In a ninth aspect, the invention features a solution including: (i) a first nucleic acid probe strand, (ii) a second nucleic acid probe strand attached to a label (e.g., a fluorophore), (iii) a third nucleic acid probe strand attached to a quencher, (iv) a target nucleic acid, (v) a DSN, and (vi) a lysis buffer, in which the first nucleic acid probe strand, the second nucleic acid probe strand, the third nucleic acid probe strand, and the target nucleic acid are incapable of hybridizing to each other.

In some embodiments of any of the seventh through ninth aspects, the DSN is a Kamchatka crab DSN.

Amplification Methods

In a tenth aspect, the invention features a method of linearly amplifying a nucleic acid region. The method involves:
   (a) providing a mixture including:
      a target nucleic acid,
      a plurality of nucleic acid probes, each nucleic acid probe including a first region complementary to at least a portion of the target nucleic acid and a second region capable of hybridizing to the first region, and
      a DSN;
   (b) incubating the mixture under conditions in which:
      the first region of one of the nucleic acid probes hybridizes to the target nucleic acid, thereby forming a first region-target nucleic acid complex including a duplex, and
      the duplex is digested by the DSN, thereby releasing the second region; and
   (c) repeating step (b) with additional the nucleic probes in the mixture, thereby linearly amplifying the second region.

In an eleventh aspect, the invention features a method of exponentially amplifying a nucleic acid region. The method involves:
   (a) providing a mixture including:
      a target nucleic acid,
      a plurality of first nucleic acid probes, each first nucleic acid probe including a first region complementary to at least a portion of the target nucleic acid and a second region,
      a plurality of second nucleic acid probes, each second nucleic acid probe including a third region complementary to the second region and a fourth region complementary to at least a portion of the first region, and
      a DSN;
   (b) incubating the mixture under conditions in which:
      (i) the first region of one of the first nucleic acid probes hybridizes to the target nucleic acid, thereby forming a first region-target nucleic acid complex including a first duplex,
      (ii) the first duplex is digested by the DSN, thereby releasing the second region;
      (iii) the released second region hybridizes to the third region of one of the second nucleic acid probes, thereby forming a released second region-third region complex including a second duplex, and
      (iv) the second duplex is digested by the DSN or a copy thereof, thereby releasing the fourth region;
   (c) optionally, incubating the mixture under conditions in which:
      (i) the released fourth region hybridizes to at least a portion of the first region of an additional copy of the first nucleic acid probe, thereby forming a first region-fourth region complex including a further duplex, and (ii) the further duplex is digested by the DSN, thereby releasing a further copy of the second region; and (d) repeating incubating steps (b) and/or (c) with additional copies of the first nucleic acid probe and the second nucleic acid probe in the mixture, thereby exponentially amplifying the second region and/or the fourth region.

In a twelfth aspect, the invention features a method of amplifying a detectable fluorophore signal. The method involves:

(a) providing a mixture including:
   a target nucleic acid,
   a nucleic acid capture probe including a first region complementary to at least a portion of the target nucleic acid and a second region,
   a plurality of nucleic acid detection probes including a third region attached to a fluorophore, a fourth region complementary to the second region, and a fifth region attached to a quencher of the fluorophore and capable of hybridizing to the third region, and
   a DSN;

(b) incubating the mixture under conditions in which:
   (i) the first region of one of the nucleic acid capture probes hybridizes to the target nucleic acid, thereby forming a first region-target nucleic acid complex including a first duplex,
   (ii) the first duplex is digested by the DSN, thereby releasing the second region;
   (iii) the released second region hybridizes to the fourth region of one of the nucleic acid detection probes, thereby forming a released second region-fourth region complex including a second duplex, and
   (iv) the second duplex is digested by the DSN or a copy thereof, thereby releasing the third region and the fifth region; and (c) repeating steps (i)-(ii) and/or steps (iii)-(iv) with additional copies of the nucleic acid capture probe and the nucleic acid detection probe in the mixture, thereby amplifying the third region.

In a thirteenth aspect, the invention features a method of amplifying a nucleic acid region. The method involves:

(a) providing a mixture including:
   a target nucleic acid,
   a plurality of nucleic acid probes each including a first region, a second region, and a third region capable of hybridizing to the first region, in which the second region includes a nucleic acid sequence complementary to at least a portion of the target nucleic acid, and
   a DSN;

(b) incubating the mixture under conditions to hybridize the second region to the target nucleic acid, thereby forming a nucleic acid probe-target nucleic acid complex including a double-stranded nucleic acid region, and to digest the double-stranded nucleic acid region with the DSN, thereby releasing the first region and the third region, and (c) repeating step (b) with additional copies of the nucleic acid probe, thereby amplifying the first region and/or the third region.

In some embodiments of any of the tenth through thirteenth aspects of the invention, the mixture further includes a lysis buffer. In some embodiments of any of the tenth through thirteenth aspects of the invention, the DSN is a Kamchatka crab DSN. In some embodiments of any of the tenth through thirteenth aspects of the invention, the probes are each attached to a support (e.g., a surface).

One-Step Detection of Immobilized Probes

In a fourteenth aspect, the invention features a method of detecting a target nucleic acid in a sample. The method involves:

(a) providing a mixture including:
   the sample,
   a detection probe including a labeled nucleic acid immobilized to a support, the labeled nucleic acid including a first region complementary to the target nucleic acid, and an end region attached to a label, and
   an enzyme capable of selectively digesting double-stranded nucleic acids;
   the mixture having been incubated under conditions to hybridize the detection probe to the target nucleic acid, thereby forming a detection probe-target nucleic acid complex including a double-stranded nucleic acid region; and to digest the double-stranded nucleic acid region with the enzyme; and (b) detecting the detection probe by detecting the label attached to the end regions, whereby the presence of the label is indicative of the presence of the target nucleic acid.

Duplex-Specific Amplification (DSA) Using a Single Immobilized Probe

In a fifteenth aspect, the invention features a method of detecting a target nucleic acid in a sample. The method involves:

(a) providing a mixture including:
   the sample,
   a detection probe including a labeled nucleic acid immobilized to a support, the labeled nucleic acid including a first region complementary to at least a portion of the target nucleic acid, and a first end region attached to a label, the first end region including a second region capable of hybridizing to a portion of the detection probe, and
   an enzyme capable of selectively digesting double-stranded nucleic acids; the mixture having been incubated under conditions to
   (i) hybridize the detection probe to the target nucleic acid, thereby forming a detection probe-target nucleic acid complex including a first double-stranded nucleic acid region, and to digest the first double-stranded nucleic acid region with the enzyme, thereby releasing the first end region, and
   (ii) hybridize the second region of the released first end region to an additional copy of the detection probe, thereby forming a first end region-detection probe complex including a second double-stranded nucleic acid region, to digest the second double-stranded nucleic acid region with the enzyme or a copy thereof, thereby releasing an additional end region; and (b) detecting the detection probe by detecting the labels attached to the released end regions, whereby the presence of the label is indicative of the presence of the target nucleic acid.

DSA Using Multiple Immobilized Probes

In a sixteenth aspect, the invention features a method of detecting a target nucleic acid in a sample. The method involves:

(a) providing a mixture including:
   the sample,
   a first probe including a first labeled nucleic acid immobilized to a support, the first labeled nucleic acid including a first region complementary to at least a portion of the target nucleic acid, and a first end region attached to a label, the first end region including a second region, a second probe including a second labeled nucleic acid immobilized to a support, the second labeled nucleic acid including a third region complementary to the second region, and a second end region attached to a label, the second end region including a fourth region complementary to the first region, and an enzyme capable of selectively digesting double-stranded nucleic acids;

the mixture having been incubated under conditions to
  (i) hybridize the first probe to the target nucleic acid, thereby forming a first probe-target nucleic acid complex including a first double-stranded nucleic acid region, and to digest the first double-stranded nucleic acid region with the enzyme, thereby releasing the first end region,
  (ii) hybridize the second region of the released first end region to the third region of the second probe, thereby forming a first end region-second probe complex including a second double-stranded nucleic acid region, to digest the second double-stranded nucleic acid region with the enzyme or a copy thereof, thereby releasing the second end region, and
  (iii) hybridize the released second end region to the first region of an additional copy of the first probe, thereby forming a second end region-first probe complex including a third double-stranded nucleic acid region, and to digest the third double-stranded nucleic acid region with the enzyme or a copy thereof, thereby releasing a further copy of the first end region; and (b) detecting the first probe and/or the second probe by detecting the labels attached to the released end regions, whereby the presence of the label is indicative of the presence of the target nucleic acid.

DSA Using a Probe with an RNA Block

In a seventeenth aspect, the invention features a method of detecting a target nucleic acid in a sample. The method involves:

(a) providing a mixture including:
  the sample,
  a detection probe including a labeled nucleic acid immobilized to a support, the labeled nucleic acid including a first region complementary to at least a portion of the target nucleic acid, and a first end region attached to a label, the first end region including a double-stranded block region and a second region capable of hybridizing to a portion of the detection probe, in which the double-stranded block region prevents intramolecular hybridization of the first region to the second region, and
  an enzyme capable of selectively digesting double-stranded nucleic acids;

the mixture having been incubated under conditions to
  (i) hybridize the detection probe to the target nucleic acid, thereby forming a detection probe-target nucleic acid complex including a first double-stranded nucleic acid region, and to digest the first double-stranded nucleic acid region with the enzyme, thereby releasing the first end region, and
  (ii) hybridize the second region of the released first end region to an additional copy of the detection probe, thereby forming a first end region-detection probe complex including a second double-stranded nucleic acid region, to digest the second double-stranded nucleic acid region with the enzyme or a copy thereof, thereby releasing an additional end region; and (b) detecting the detection probe by detecting the labels attached to the released end regions, whereby the presence of the label is indicative of the presence of the target nucleic acid.

DSA Using a Double-Stranded Probe

In an eighteenth aspect, the invention features a method of detecting a target nucleic acid in a sample. The method involves:

(a) providing a mixture including
  the sample,
  a detection probe including (i) a first strand attached to a label, and (ii) a second strand including a region complementary to at least a portion of the target nucleic acid, in which the entire first strand hybridizes to the region complementary to at least a portion of the target nucleic acid, and
  an enzyme capable of selectively digesting double-stranded nucleic acids;

the mixture having been incubated under conditions to:
  (i) separate the first strand from the second strand,
  (ii) hybridize the second strand to the target nucleic acid, thereby forming a second strand-target nucleic acid complex including a double-stranded nucleic acid region, and
  (iii) digest the double-stranded nucleic acid region with the enzyme, thereby preventing rehybridization of the released first strand to the second strand or a copy thereof; and (b) detecting the label attached to the released first strand, whereby the presence of the label is indicative of the presence of the target nucleic acid.

In some embodiments of any of the fourteenth through eighteenth aspects, the label is a fluorescent bead, quantum dot, fluorescent dye, fluorescent protein, biotin, or luciferase enzyme.

Methods of Activating a Probe Using Hairpin Probes

In a nineteenth aspect, the invention features a method of activating a nucleic acid probe. The method involves:

(a) providing a mixture including:
  a target nucleic acid,
  a nucleic acid probe including a first region, a second region, a third region, and a fourth region capable of hybridizing to the second region, in which the first region and the second region form a nucleic acid sequence complementary to at least a portion of the target nucleic acid, and
  an enzyme capable of selectively digesting double-stranded nucleic acids;

(b) incubating the mixture under conditions to hybridize the first region and the second region to the target nucleic acid, thereby forming a nucleic acid probe-target nucleic acid complex including a double-stranded nucleic acid region, and to digest at least a portion of the double-stranded nucleic acid region with the enzyme, thereby releasing an end region including the third region and the fourth region, thereby activating the nucleic acid probe.

In a twentieth aspect, the invention features a method of activating a nucleic acid probe. The method involves:

(a) providing a mixture including:
  a target nucleic acid,
  a first probe including a first region, a second region, a third region, and a fourth region capable of hybridizing to the second region, in which the first region and the second region form a nucleic acid sequence complementary to at least a portion of the target nucleic acid,
- a second probe including a fifth region, a sixth region, a seventh region, and an eighth region capable of hybridizing to the sixth region, in which the fifth region is complementary to at least a portion of the third region, and the sixth region is complementary to at least a portion of the fourth region, and
- an enzyme capable of selectively digesting double-stranded nucleic acids;

(b) incubating the mixture under conditions to:
- (i) hybridize the first region and the second region to the target nucleic acid, thereby forming a first probe-target nucleic acid complex including a first double-stranded nucleic acid region,
- (ii) hybridize the third region and the fourth region to the fifth region and the sixth region, thereby forming a first probe-second probe complex including a second double-stranded nucleic acid region, and
- (iii) digest at least a portion of the second double-stranded nucleic acid region with the enzyme, thereby releasing an end region including the seventh region and the eighth region, thereby activating the second probe.

In a twenty first aspect, the invention features a method of activating a nucleic acid probe. The method involves:

(d) providing a mixture including:
- a target nucleic acid,
- a nucleic acid probe including a first region, a second region, and a third region capable of hybridizing to the first region, in which the second region includes a nucleic acid sequence complementary to at least a portion of the target nucleic acid, and
- an enzyme capable of selectively digesting double-stranded nucleic acids;

(e) incubating the mixture under conditions to hybridize the second region to the target nucleic acid, thereby forming a nucleic acid probe-target nucleic acid complex including a double-stranded nucleic acid region, and to digest the double-stranded nucleic acid region with the enzyme, thereby releasing the first region and the third region, thereby activating the nucleic acid probe.

In some embodiments of the twenty first aspect, the first region includes a portion complementary to at least a portion of the target nucleic acid, and the incubating step further includes hybridizing the portion of the first region to the target nucleic acid. In some embodiments of the twenty first aspect, the third region includes a portion complementary to at least a portion of the target nucleic acid, and the incubating step further includes hybridizing the portion of the third region to the target nucleic acid.

In some embodiments of any of the fourteenth through twenty first aspects, the target nucleic acid includes RNA. In some embodiments of any of the fourteenth through twenty first aspects, the target nucleic acid includes DNA.

In some embodiments of any of the fourteenth through twenty first aspects, the mixture includes a biological sample including the target nucleic acid. In certain embodiments, the biological sample includes a clinical sample. In various embodiments, the biological sample includes blood, peripheral blood, a blood component (e.g., serum, isolated blood cells, or plasma), buccal samples (e.g., buccal swabs), nasal samples (e.g., nasal swabs), urine, fecal material, saliva, amniotic fluid, cerebrospinal fluid (CSF), synovial fluid, tissue (e.g., from a biopsy), pancreatic fluid, chorionic villus sample, cells, extracellular matrix, cultured cells, cellular organelles, cancerous cells, or any combination or derivative thereof. In further embodiments, the biological sample includes a food sample.

In some embodiments of any of the fourteenth through twenty first aspects, the enzyme capable of selectively digesting double-stranded nucleic acids is a DSN. In certain embodiments, the DSN is selected from the group consisting of a Kamchatka crab DSN, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease. In one embodiment, the DSN is a Kamchatka crab DSN.

Additional Methods for Detecting Nucleic Acids by DSA

In a twenty second aspect, the invention features a method of detecting a target nucleic acid in a sample. The method involves:

providing a mixture including
- the sample,
- a nucleic acid detection probe including a support attached to a labeled nucleic acid, the labeled nucleic acid having a first region complementary to the target nucleic acid, and an end region attached to a label, and
- an enzyme capable of selectively digesting double-stranded nucleic acids;

the mixture having been incubated under conditions to hybridize the nucleic acid detection probe to the target nucleic acid, thereby forming a nucleic acid detection probe-target nucleic acid complex including a double-stranded nucleic acid region; and to digest the double-stranded nucleic acid region with the enzyme; and detecting the nucleic acid detection probe by detecting the label attached to the end regions, whereby the presence of the label is indicative of the presence of the target nucleic acid.

In a twenty third aspect, the invention features a method of detecting a target nucleic acid in a sample. The method involves:

providing a mixture including
- the sample,
- a nucleic acid detection probe including a support attached to a first binding moiety,
- a labeled nucleic acid including a second binding moiety specific for the first binding moiety, a first region complementary to the target nucleic acid, and an end region attached to a label, and
- an enzyme capable of selectively digesting double-stranded nucleic acids;

the mixture having been incubated under conditions to hybridize the nucleic acid detection probe to the target nucleic acid, thereby forming a nucleic acid detection probe-target nucleic acid complex including a double-stranded nucleic acid region, and in which the enzyme would have digested the double-stranded nucleic acid region; and detecting the nucleic acid detection probe by detecting the label attached to the end regions, whereby the presence of the label is indicative of the presence of the target nucleic acid.

In some embodiments of the twenty third aspect, the first and second binding moieties are complementary nucleic acids. In certain embodiments, the complementary nucleic acids include modified nucleic acids.

In some embodiments of the twenty second or twenty third aspects, the label includes biotin, a fluorophore, and/or an enzyme. In certain embodiments, the enzyme is luciferase and/or the fluorophore is a quantum dot.

In some embodiments of the twenty second or twenty third aspects, the method further includes immobilizing the digested probes to the surface of a waveguide. In certain embodiments, the detecting measures fluorescence provided by illuminating the digested probes by an evanescent field from light propagating in the waveguide. In particular embodiments, the end region includes biotin and the detecting step includes the biotin binding to a surface of the waveguide.

In some embodiments of the twenty second or twenty third aspects, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca2+-Mg2+$-dependent endonuclease.

DSA Using Immobilized Probes

In some embodiments of the twenty second or twenty third aspects, the labeled nucleic acid further includes a second region located between the first region and the support, and the end region includes a third region complementary to the second region;
   the digestion of the double-stranded nucleic acid region of the nucleic acid detection probe-target nucleic acid complex with the enzyme forms a first released end region; and
   the mixture has been further incubated under conditions to hybridize the third region of the first released end region to the second region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a second released end region; and to hybridize the second released end region to the second region of an additional copy of the nucleic acid detection probe, thereby forming a second released end region-nucleic acid detection probe complex including a double-stranded nucleic acid region, and to digest the double-stranded nucleic acid region of the second released end region-nucleic acid detection probe complex with the enzyme or a copy thereof, thereby forming a further copy of the second released end region.

In certain embodiments, the mixture has been further incubated for a period sufficient to repeat the hybridization of the third region of the first released end region to the second region of an additional copy of the nucleic acid detection probe, and/or the hybridization of the third region of the second released end region to the second region of an additional copy of the nucleic acid detection probe; and the digestion of the formed double-stranded nucleic acid region; thereby exponentially amplifying the second released end region.

In certain embodiments, the second region and the third region are arranged such that looping of the labeled nucleic acid will form a duplex between the second region and the third region that is not anti-parallel.

In certain embodiments, each of the first regions and each of the second regions include DNA and each of the third regions includes RNA.

In certain embodiments, the target nucleic acid includes RNA, DNA, or a DNA-RNA hybrid. In certain embodiments, the target nucleic acid includes RNA and the mixture is further incubated under conditions to hybridize the target nucleic acid or another copy thereof to the first region of the second released end region, thereby forming a double-stranded nucleic acid region, and to digest the double-stranded nucleic acid region with the enzyme or a copy thereof, thereby forming a further copy of the first released end region.

In some embodiments of the twenty second or twenty third aspects, the mixture further includes a nucleic acid amplification probe attached to a support, the nucleic acid amplification probe including an end region attached to a label and a second region, in which the end region of the nucleic acid amplification probe further includes a third region complementary to the first region;
   the end region of the nucleic acid detection probe includes a fourth region complementary to the second region of the nucleic acid amplification probe;
   the digestion of the double-stranded nucleic acid region of the nucleic acid detection probe-target nucleic acid complex with the enzyme forms a first released end region including the fourth region; and
   the mixture has been further incubated under conditions to hybridize the fourth region of the first released end region to the second region of the nucleic acid amplification probe, thereby forming a first released end region-nucleic acid amplification probe complex including a double-stranded nucleic acid region, to digest the double-stranded nucleic acid region with the enzyme or a copy thereof, thereby forming a second released end region including the third region, and to hybridize the third region of the second released end region to the first region of an additional copy of the nucleic acid detection probe, thereby forming a second released end region-nucleic acid detection probe complex including a double-stranded nucleic acid region, and to digest the double-stranded nucleic acid region with the enzyme or a copy thereof, thereby forming a further copy of the first released end region.

In certain embodiments, the mixture has been further incubated for a period sufficient to repeat the hybridization of the fourth region of the first released end region to the second region of an additional copy of the nucleic acid amplification probe, and to repeat:
   the hybridization of the second released end region to the first region of an additional copy of the nucleic acid detection probe and
   the digestion of the formed double-stranded nucleic acid region,
   thereby exponentially amplifying the first released end region and the second released end region.

In certain embodiments, the nucleic acid amplification probe is attached to the support of the nucleic acid detection probe.

In certain embodiments, each of the first regions and each of the second regions include DNA and each of the third regions and each of the fourth regions include RNA.

In certain embodiments, the target nucleic acid includes RNA and/or DNA.

In certain embodiments, the first region is oriented parallel to the fourth region on each of the nucleic acid detection probes In certain embodiments, the second region is oriented parallel to the third region on each of the nucleic acid amplification probes.

In some embodiments of the twenty second or twenty third aspects, the end region includes a second region
complementary to the first region, and
located between the first region and the label;
the digestion of the double-stranded nucleic acid region of the nucleic acid detection probe-target nucleic acid complex with the enzyme forms a first released end region; and
the mixture has been further incubated under conditions to hybridize the second region of the first released end region to the first region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a further first released end region.

In certain embodiments, the mixture has been further incubated for a period sufficient to repeat:
the hybridization of the second region of the first released end region or the second region of the further first released end region to the first region of an additional copy of the nucleic acid detection probe,
and the digestion of the formed double-stranded nucleic acid region;
thereby exponentially amplifying the released end regions.

In certain embodiments, the target nucleic acid includes DNA and/or RNA. In particular embodiments, the target nucleic acid includes RNA and the mixture is incubated under conditions to hybridize the target nucleic acid or another copy thereof to the first region of a further copy of the nucleic acid detection probe, thereby forming a double-stranded nucleic acid region, and to digest the double-stranded nucleic acid region with the enzyme or a copy thereof, thereby forming a further copy of the first released end region.

In certain embodiments, each of the first regions includes DNA and each of the second regions includes RNA.

In certain embodiments, each of the first regions and the second regions includes DNA, and the digestion of the double-stranded nucleic acid region of the first released end region-nucleic acid detection probe complex with the enzyme results in the release of a second released end region including the label from the first released end region. In particular embodiments, the mixture has been further incubated for a period sufficient to repeat the hybridization of the second region of the further first released end region to the first region of an additional copy of the nucleic acid detection probe, and the digestion of the formed double-stranded nucleic acid region; thereby linearly amplifying the released end regions. In various embodiments, the target nucleic acid includes DNA and/or RNA, and the target nucleic acid is cleaved during the digestion of the double-stranded nucleic acid region of the nucleic acid detection probe-target nucleic acid complex.

In particular embodiments, the target nucleic acid includes RNA, and the mixture is incubated under conditions to hybridize the target nucleic acid or another copy thereof to the first region of a further copy of the nucleic acid detection probe, thereby forming a double-stranded nucleic acid region, and to digest the double-stranded nucleic acid region with the enzyme or a copy thereof, thereby forming a further copy of the first released end region; and the mixture has been further incubated for a period sufficient to repeat the hybridization of the second region of the further first released end region to the first region of an additional copy of the nucleic acid detection probe, and the digestion of the formed double-stranded nucleic acid region; thereby geometrically amplifying the released end regions.

In certain embodiments, the second region is oriented anti-parallel to the first region.

DSA Using a Probe with an RNA Block

In some embodiments of the twenty second or twenty third aspects, the nucleic acid detection probe includes a double-stranded block region. In certain embodiments, the double-stranded block region is located within the end region; the end region includes a second region complementary to the first region and located between the double-stranded block region and the label; the digestion of the double-stranded nucleic acid region of the nucleic acid detection probe-target nucleic acid complex with the enzyme forms a first released end region including the label, the second region, and the double-stranded block region; and the mixture has been further incubated under conditions to hybridize the second region of the first released end region to the first region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a further first released end region. In particular embodiments, the mixture has been further incubated for a period sufficient to repeat the hybridization of the second region of the first released end region or the second region of the further first released end region to the first region of an additional copy of the nucleic acid detection probe, and the digestion of the formed double-stranded nucleic acid region; thereby exponentially amplifying the released end regions.

In various embodiments, the target nucleic acid includes RNA and/or DNA. In one embodiment, the target nucleic acid includes RNA and the mixture is incubated under conditions to hybridize the target nucleic acid or another copy thereof to the first region of a further copy of the nucleic acid detection probe, thereby forming a double-stranded nucleic acid region, and to digest the double-stranded nucleic acid region with the enzyme or a copy thereof, thereby forming a further copy of the first released end region. In another embodiment, the target nucleic acid includes DNA, and the target nucleic acid is cleaved during the digestion of the double-stranded nucleic acid region of the nucleic acid detection probe-target nucleic acid complex with the enzyme.

In various embodiments, each of the first regions includes DNA and each of the second regions includes RNA.

In certain embodiments, each of the first regions and the second regions includes DNA, and the digestion of the double-stranded nucleic acid region of the first released end region-nucleic acid detection probe complex with the enzyme results in release of a second released end region from the first released end region. In particular embodiments, the mixture has been further incubated for a period sufficient to repeat the hybridization of the second region of the further first released end region to the first region of an additional copy of the nucleic acid detection probe, and the digestion of the formed double-stranded nucleic acid region; thereby linearly amplifying the released end regions.

In certain embodiments, the first region is oriented parallel to the second region.

In certain embodiments, the double-stranded block region includes RNA.

In some embodiments of the twenty second or twenty third aspects, the nucleic acid detection probe includes a first double-stranded block region and a second double-stranded block region.

In certain embodiments, the labeled nucleic acid further includes a second region and a third region complementary to the second region;
  the first region is located between the first double-stranded block region and the second double-stranded block region;
  the end region includes the second double-stranded block region and the third region;
  the third region is located between the second double-stranded block region and the label;
  the second region is located between the first region and the attachment between the labeled nucleic acid and the support;
  the first double-stranded block region is located between the first region and the second region;
  the digestion of the double-stranded nucleic acid region of the nucleic acid detection probe-target nucleic acid complex with the enzyme forms a first released end region including the label, the third region, and the second double-stranded block region; and
  the mixture has been further incubated under conditions to hybridize the third region of the first released end region to the second region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a second released end region including the first double-stranded block region, the first region, the second double-stranded block region, and the third region of the additional copy of the nucleic acid detection probe, and to
  hybridize the third region of the second released end region to the second region of an additional copy of the nucleic acid detection probe, thereby forming a second released end region-nucleic acid detection probe complex including a double-stranded nucleic acid region, and to digest the double-stranded nucleic acid region of the second released end region-nucleic acid detection probe complex with the enzyme or a copy thereof, thereby forming a further copy of the second released end region.

In particular embodiments, the mixture has been further incubated for a period sufficient to repeat the hybridization of the third region of the first released end region to the second region of an additional copy of the nucleic acid detection probe, and/or the hybridization of the third region of the second released end region to the second region of an additional copy of the nucleic acid detection probe, and the digestion of the formed double-stranded nucleic acid region; thereby exponentially amplifying the second released end region.

In certain embodiments, the first region is oriented antiparallel to the second region and to the third region.

In certain embodiments, the target nucleic acid includes DNA and/or RNA. In particular embodiments, the target nucleic acid includes RNA and the mixture is further incubated under conditions to hybridize the target nucleic acid or another copy thereof to the first region of the second released end region, thereby forming a double-stranded nucleic acid region, and to digest the double-stranded nucleic acid region with the enzyme or a copy thereof, thereby forming a further copy of the first released end region.

In certain embodiments, each of the first regions and each of the second regions includes DNA and each of the third regions includes RNA.

Method of Detecting a Nucleic Acid in a Clinical Sample

In a twenty fourth aspect, the invention features a method of detecting a target nucleic acid in a biological sample. The method involves:
  providing a mixture including:
    (i) the biological sample,
    (ii) an enzyme capable of selectively digesting double-stranded nucleic acids, and
    (iii) a nucleic acid detection probe including a region complementary to the target nucleic acid;
  incubating the mixture under conditions to hybridize the nucleic acid detection probe to the target nucleic acid, thereby forming a nucleic acid detection probe-target nucleic acid complex including a double-stranded nucleic acid region; and to digest the double-stranded nucleic acid region with the enzyme; and
  detecting the nucleic acid detection probe, whereby the presence of the nucleic acid detection probe is indicative of the presence of the target nucleic acid in the biological sample.

In some embodiments of the twenty fourth aspect, the sample is not purified prior to the incubating step. In certain embodiments, the sample is not purified prior to the providing step.

In some embodiments of the twenty fourth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease.

In some embodiments of any of the above aspects, the providing and incubating steps occur within a single container. In certain embodiments, the container is a tube, well, droplet, or emulsion bead.

DSA Using a Double-Stranded Probe

In a twenty fifth aspect, the invention features a method of detecting a target nucleic acid in a sample. The method involves:
  (a) providing a mixture including
    the sample,
    a nucleic acid detection probe including a first strand attached to a label (e.g., a fluorophore), and a second strand including a portion complementary to the target nucleic acid, the portion complementary to the target nucleic acid including at least a secondary portion complementary to the first strand, and
    an enzyme capable of selectively digesting double-stranded nucleic acids;
  the mixture having been incubated under conditions:
    (i) to denature the nucleic acid detection probe, thereby releasing the first strand,
    (ii) to hybridize the second strand to the target nucleic acid, thereby forming a second strand-target nucleic acid complex including a double-stranded nucleic acid region, and
    (iii) to digest the double-stranded nucleic acid region with the enzyme, thereby preventing rehybridization of the released first strand to the second strand or a copy thereof; and (b) detecting the label attached to the released first strand, whereby the presence of the label is indicative of the presence of the target nucleic acid.

In some embodiments of the twenty fifth aspect, the mixture has been further incubated for a period sufficient to repeat the hybridization the target nucleic acid to the second strand of an additional copy of the nucleic acid detection probe, and the digestion of the formed double-stranded nucleic acid region, thereby linearly amplifying the released first strands. In certain embodiments, the further incubation further includes, prior to repeating the hybridization, denaturing the additional copy of the nucleic acid detection prior.

In some embodiments of the twenty fifth aspect, the second strand is attached to a quencher (e.g., a quencher capable of quenching the label). In certain embodiments, the quencher is attached to the same end of the second strand as the end of the first strand attached to the label. In various embodiments, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In some embodiments of the twenty fifth aspect, the label is a fluorescent bead, quantum dot, fluorescent dye, fluorescent protein, biotin, or luciferase enzyme.

In some embodiments of the twenty fifth aspect, the target nucleic acid includes RNA and the first strand and the second strand include DNA. In certain embodiments, the second strand is cleaved during the digestion of the double-stranded nucleic acid region of the second strand-target nucleic acid complex.

In some embodiments of the twenty fifth aspect, the method further involves immobilizing the released first strands to the surface of a waveguide, in which the detecting measures fluorescence provided by illuminating the digested probes by an evanescent field from light propagating in the waveguide. In certain embodiments, the released first strand further includes biotin and the detecting step includes the biotin binding to a surface of the waveguide.

In some embodiments of the twenty fifth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin Ca2+-Mg2+-dependent endonuclease.

In a twenty sixth aspect, the invention features a method of detecting a target nucleic acid in a sample. The method involves:
(a) providing a mixture including:
  the sample,
  a nucleic acid detection probe, the nucleic acid detection probe including a labeled nucleic acid including, in order, a first region attached to a label (e.g., a fluorophore), a second region, a third region capable of hybridizing to the second region, and a fourth region capable of hybridizing to the first region and capable of hybridizing to at least a portion of the target nucleic acid, in which the fourth region is attached to a quencher of the label, and
  an enzyme capable of selectively digesting double-stranded nucleic acids;
the mixture having been incubated under conditions to:
(i) hybridize the third region to the second region, thereby forming a first double-stranded nucleic acid region, to digest the first double-stranded nucleic acid region with the enzyme, and to denature the hybridization between the first region and the fourth region, thereby forming:
  a released label strand including the first region attached to the label, and
  a quencher strand including the fourth region attached to the quencher; and
(ii) hybridize the fourth region of the quencher strand to the target nucleic acid, thereby forming a quencher strand-target nucleic acid complex including a second double-stranded nucleic acid region, and to digest the second double-stranded nucleic acid region with the enzyme or a copy thereof; and
(b) detecting the label of the released label strand, whereby the presence of the label is indicative of the presence of the target nucleic acid.

In some embodiments of the twenty sixth aspect, the mixture has been further incubated for a period sufficient to repeat:
(i) hybridization of the third region of an additional copy of the nucleic acid detection probe to the second region of the additional copy of the nucleic acid detection probe, and digestion of the formed first double-stranded nucleic acid region; and
(ii) hybridization of the target nucleic acid to the fourth region of the additional copy of the quencher strand formed from the digestion of the formed first double-stranded nucleic region, and digestion of the formed second double-stranded nucleic acid region;
thereby linearly amplifying the released label strand.

In some embodiments of the twenty sixth aspect, the 5' end of the labeled nucleic acid is attached to the fluorophore and the 3' end of the labeled nucleic acid is attached to the quencher.

In some embodiments of the twenty sixth aspect, the 3' end of the labeled nucleic acid is attached to the fluorophore and the 5' end of the labeled nucleic acid is attached to the quencher.

In some embodiments of the twenty sixth aspect, the first region, second region, and fourth region include DNA, and the third region includes RNA.

In some embodiments of the twenty sixth aspect, the first region, second region, and third region include DNA, and the fourth region includes RNA.

In some embodiments of the twenty sixth aspect, the target nucleic acid includes RNA and/or DNA.

In some embodiments of the twenty sixth aspect, the target nucleic acid includes a region complementary to the fourth region. In certain embodiments, the target nucleic acid further includes a region capable of hybridizing to the third region.

In some embodiments of the twenty sixth aspect, the first region and the fourth region are complementary except for at least one base pair mismatch.

In some embodiments of the twenty sixth aspect, the first region is directly or indirectly attached to the fluorophore, and/or the fourth region is directly or indirectly attached to the fluorophore.

In some embodiments of the twenty sixth aspect, the label is a fluorescent bead, quantum dot, fluorescent dye, fluorescent protein, biotin, or luciferase enzyme.

In some embodiments of the twenty sixth aspect, the method further involves immobilizing the released label strands to the surface of a waveguide, in which the detecting measures fluorescence provided by illuminating the digested probes by an evanescent field from light propagating in the waveguide. In certain embodiments, the released label strand further includes biotin and the detecting step includes the biotin binding to a surface of the waveguide.

In some embodiments of the twenty sixth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin Ca2+-Mg2+-dependent endonuclease.

In some embodiments of the twenty sixth aspect, the second strand is attached to a quencher. In certain embodiments, the quencher is attached to the same end of the second strand as the end of the first strand attached to the fluorophore. In various embodiments, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

DSA Using Hairpin Probes

In a twenty seventh aspect, the invention features a method of detecting a target nucleic acid in a sample. The method involves:
(a) providing a mixture including:
   the sample,
   a nucleic acid detection probe including, in order, a first region, a second region, a third region, and a fourth region capable of hybridizing to the second region, in which the first region and the second region form a nucleic acid sequence complementary to at least a portion of the target nucleic acid,
   a hairpin probe including, in order, a first terminal region attached to a label, a loop region complementary to at least a portion of the fourth region, and a second terminal region attached to a quencher of the label, in which the first terminal region is capable of hybridizing to the second terminal region, and
   an enzyme capable of selectively digesting double-stranded nucleic acids;
the mixture having been incubated under conditions to:
   (i) hybridize the first region and the second region to the target nucleic acid, thereby forming a nucleic acid detection probe-target nucleic acid complex including a first double-stranded nucleic acid region, and to digest the first double-stranded nucleic acid region with the enzyme, thereby releasing an end region including the third region and the fourth region, and
   (ii) hybridize the end region to the loop region of the hairpin probe, thereby forming an end region-hairpin probe complex including a second double-stranded nucleic region, and to digest the second double-stranded nucleic acid region with the enzyme or a copy thereof, thereby releasing the first terminal region attached to the label and the second terminal region attached to the quencher; and
(b) detecting the label attached to the released first terminal region, whereby the presence of the label is indicative of the presence of the target nucleic acid.

In some embodiments of the twenty seventh aspect, the mixture has been further incubated for a period sufficient to repeat hybridization of the released end region to the loop region of an additional copy of the hairpin probe, and digestion of the formed second double-stranded nucleic acid region; thereby linearly amplifying the released label strand.

In some embodiments of the twenty seventh aspect, the mixture has been further incubated for a period sufficient to repeat:
   (i) hybridization of the first region and the second region of a further copy of the nucleic acid detection probe to the target nucleic acid, and digestion of the formed first double-stranded nucleic acid region, thereby releasing a further end region; and
   (ii) hybridization of the further released end region to the loop region of a further copy of the hairpin probe, and digestion of the formed second double-stranded nucleic acid region;
thereby linearly amplifying the released label strand.

In some embodiments of the twenty seventh aspect, the first region is directly attached to the second region.

In some embodiments of the twenty seventh aspect, the second region and the fourth region are complementary except for at least one base pair mismatch.

In some embodiments of the twenty seventh aspect, the second region has a length of one or more nucleotides greater than the fourth region, or the fourth region has a length of one or more nucleotides greater than the second region. In certain embodiments, the difference in length between the second region and the fourth region results in unhybridized nucleotides between the second region and the fourth region.

In some embodiments of the twenty seventh aspect, hybridization of the released end region to the loop region results in breakage of the hybridization between the first terminal region and the second terminal region.

In some embodiments of the twenty seventh aspect, the method further involves, prior to the detecting step, separating the released first terminal region attached to the label from the released second terminal region attached to the quencher. In certain embodiments, the separating step includes capturing the released first terminal region using a capture moiety. In particular embodiments, the capture moiety is a nucleic acid capture probe capable of hybridizing to at least a portion of the first terminal region. In specific embodiments, the nucleic acid capture probe is attached to a support. In various embodiments, the support includes a bead, hydrogel, strip, slide, or interior wall of a compartment. In particular embodiments, the bead is a magnetic bead and the separating step further includes isolating the magnetic bead from the mixture using a magnet. In one embodiment, the bead is a fluorescent bead and the separating step further includes isolating the fluorescent bead from the mixture (e.g., using fluorescence-activated cell sorting (FACS)).

In some embodiments of the twenty seventh aspect, the first region and the second region include DNA, and the third region and the fourth region include RNA.

In some embodiments of the twenty seventh aspect, the first terminal region and the second terminal region include RNA and the loop region includes DNA.

In some embodiments of the twenty seventh aspect, the first terminal region is located at the 5' end of the hairpin probe and the second terminal region is located at the 3' end of the hairpin probe.

In some embodiments of the twenty seventh aspect, the first terminal region is located at the 3' end of the hairpin probe and the second terminal region is located at the 5' end of the hairpin probe.

In some embodiments of the twenty seventh aspect, the target nucleic acid includes RNA and/or DNA.

In some embodiments of the twenty seventh aspect, the label is a fluorescent bead, quantum dot, fluorescent dye, fluorescent protein, biotin, or luciferase enzyme.

In some embodiments of the twenty seventh aspect, the method further involves immobilizing the released first terminal ends to the surface of a waveguide, in which the detecting measures fluorescence provided by illuminating the digested probes by an evanescent field from light propagating in the waveguide. In certain embodiments, the released first terminal ends further includes biotin and the detecting step includes the biotin binding to a surface of the waveguide.

In some embodiments of the twenty seventh aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca2+$-$Mg2+$-dependent endonuclease.

In some embodiments of the twenty seventh aspect, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In a twenty eighth aspect, the invention features a method of detecting a target nucleic acid in a sample. The method involves:
 (a) providing a mixture including:
  the sample,
  a first probe including, in order, a first region, a second region, a third region, and a fourth region capable of hybridizing to the second region, in which the first region and the second region form a nucleic acid sequence complementary to at least a portion of the target nucleic acid, and the fourth region is attached to a first label,
  a second probe including, in order, a fifth region, a sixth region, a seventh region, and an eighth region capable of hybridizing to the sixth region, in which the fifth region and the sixth region form a nucleic acid sequence complementary to at least the nucleic acid sequence formed by the third region and the fourth region, and the eighth region is attached to a second label, and
  an enzyme capable of selectively digesting double-stranded nucleic acids;
 the mixture having been incubated under conditions to:
  (i) hybridize the first region and the second region to the target nucleic acid, thereby forming a first probe-target nucleic acid complex including a first double-stranded nucleic acid region, and to digest the first double-stranded nucleic acid region with the enzyme, thereby releasing a first end region including the third region and the fourth region, and
  (ii) hybridize the first released end region to the fifth region and the sixth region of the second probe, thereby forming a first released end region-second probe nucleic acid complex including a second double-stranded nucleic acid region, and to digest the second double-stranded nucleic acid region with the enzyme or a copy thereof, thereby releasing a second end region including the seventh region and the eighth region; and
 (b) detecting the first label attached to the released first end region and/or the second label attached to the released second end region, whereby the presence of the first label and/or the second label is indicative of the presence of the target nucleic acid.

In some embodiments of the twenty eighth aspect, the mixture has been further incubated for a period sufficient to repeat hybridization of the released first end region to the loop region of an additional copy of the second probe, and digestion of the formed second double-stranded nucleic acid region; thereby exponentially amplifying the released second end region.

In some embodiments of the twenty eighth aspect, the mixture has been further incubated for a period sufficient to repeat hybridization of the released second end region to the loop region of an additional copy of the first probe, and digestion of the formed first double-stranded nucleic acid region;
thereby exponentially amplifying the released first end region.

In some embodiments of the twenty eighth aspect, the first region is directly attached to the second region, and/or the fifth region is directly attached to the sixth region.

In some embodiments of the twenty eighth aspect, the second region and the fourth region are complementary except for at least one base pair mismatch, and/or the sixth region and the eighth region are complementary except for at least one base pair mismatch.

In some embodiments of the twenty eighth aspect, the second region has a length of one or more nucleotides greater than the fourth region, or the fourth region has a length of one or more nucleotides greater than the second region. In certain embodiments, the difference in length between the second region and the fourth region results in unhybridized nucleotides between the second region and the fourth region. In some embodiments of the twenty eighth aspect, the sixth region has a length of one or more nucleotides greater than the eighth region, or the eighth region has a length of one or more nucleotides greater than the sixth region. In certain embodiments, the difference in length between the sixth region and the eighth region results in unhybridized nucleotides between the sixth region and the eighth region.

In some embodiments of the twenty eighth aspect, hybridization of the target nucleic acid to the second region results in breakage of the hybridization between the second region and the fourth region.

In some embodiments of the twenty eighth aspect, hybridization of the first released end region to theسsixth region results in breakage of the hybridization between the sixth region and the eighth region.

In some embodiments of the twenty eighth aspect, the first region and the second region include DNA, and the third region and the fourth region include RNA.

In some embodiments of the twenty eighth aspect, the fifth region and the sixth region include DNA, and the seventh region and the eighth region include RNA.

In some embodiments of the twenty eighth aspect, the target nucleic acid includes RNA and/or DNA.

In some embodiments of the twenty eighth aspect, the method further involves immobilizing:
 (i) the released first end region, and/or
 (ii) the released second end region
  to the surface of a waveguide, in which the detecting measures fluorescence provided by illuminating the digested probes by an evanescent field from light propagating in the waveguide.

In certain embodiments, the first end region further includes biotin and the detecting step includes the biotin binding to a surface of the waveguide. In various embodiments, the second end region further includes biotin and the detecting step includes the biotin binding to a surface of the waveguide.

In some embodiments of the twenty eighth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin Ca2+-Mg2+-dependent endonuclease.

In some embodiments of the twenty eighth aspect, the first region is attached to a first quencher. In certain embodiments, the first quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In some embodiments of the twenty eighth aspect, the fifth region is attached to a second quencher. In certain embodiments, the second quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In some embodiments of the twenty eighth aspect, the first label is a fluorescent bead, quantum dot, fluorescent dye, fluorescent protein, biotin, or luciferase enzyme; and/or the second label is a fluorescent bead, quantum dot, fluorescent dye, fluorescent protein, biotin, or luciferase enzyme.

In a twenty ninth aspect, the invention features a method of detecting a target nucleic acid in a sample. The method involves:
(a) providing a mixture including:
the sample,
a nucleic acid detection probe, the nucleic acid detection probe including a labeled nucleic acid including, in order, a first region attached to a label, a second region, a third region capable of hybridizing to the first region and attached to a quencher, in which the second region and the third region form a nucleic acid sequence complementary to at least a portion of the target nucleic acid, and
an enzyme capable of selectively digesting double-stranded nucleic acids;
the mixture having been incubated under conditions to hybridize the second region and the third region to the target nucleic acid, thereby forming a nucleic acid detection probe-target nucleic acid complex including a double-stranded nucleic acid region, and to digest the double-stranded nucleic acid region with the enzyme, thereby releasing an end region including the first region attached to the label; and
(b) detecting the label attached to the released end region, whereby the presence of the label is indicative of the presence of the target nucleic acid.

In some embodiments of the twenty ninth aspect, the mixture has been further incubated for a period sufficient to repeat hybridization of the target nucleic acid to the second region and the third region of an additional copy of the nucleic acid detection probe, and digestion of the formed double-stranded nucleic acid region, thereby linearly amplifying the released end region.

In some embodiments of the twenty ninth aspect, the first region is directly attached to the second region and/or the second region is directly attached to the third region.

In some embodiments of the twenty ninth aspect, the first region and the third region are complementary except for at least one base pair mismatch.

In some embodiments of the twenty ninth aspect, the first region includes an insert region not present in the nucleic acid sequence complementary to the nucleic acid sequence of the second region, and/or the second region includes an insert region not present in the nucleic acid sequence complementary to the nucleic acid sequence of the first region.

In some embodiments of the twenty ninth aspect, the insert region does not participate in hybridization between the second region and the fourth region.

In some embodiments of the twenty ninth aspect, hybridization of a portion of the target nucleic acid to the second region occurs prior to hybridization of a further portion of the target nucleic acid to the third region. In certain embodiments, hybridization of a portion of the target nucleic acid to the second region results in strand invasion of the third region by the further portion of the target nucleic acid. In particular embodiments, the strand invasion results in breakage of hybridization between the first region and the third region.

In some embodiments of the twenty ninth aspect, the method further involves, prior to the detecting step, isolating the released end region. In certain embodiments, the isolating includes capturing the released end region using a capture moiety. In particular embodiments, the capture moiety is a nucleic acid capture probe capable of hybridizing to at least a portion of the first region of the released end region. In various embodiments, the capture moiety is attached to a support. In specific embodiments, the support includes a strip, bead, hydrogel, slide, or interior wall of a compartment; preferably a strip.

In some embodiments of the twenty ninth aspect, the method further involves immobilizing the released first terminal ends to the surface of a waveguide, in which the detecting measures fluorescence provided by illuminating the digested probes by an evanescent field from light propagating in the waveguide. In certain embodiments, the released first terminal ends further includes biotin and the detecting step includes the biotin binding to a surface of the waveguide.

In some embodiments of the twenty ninth aspect, the first region is located at the 5' end of the nucleic acid detection probe and the third region is located at the 3' end of the nucleic acid detection probe.

In some embodiments of the twenty ninth aspect, the first region is located at the 3' end of the nucleic acid detection probe and the third region is located at the 5' end of the nucleic acid detection probe.

In some embodiments of the twenty ninth aspect, the first region, the second region, and the third region include DNA.

In some embodiments of the twenty ninth aspect, the target nucleic acid includes RNA and/or DNA.

In some embodiments of the twenty ninth aspect, the label is a fluorescent bead, quantum dot, fluorescent dye, fluorescent protein, biotin, or luciferase enzyme.

In some embodiments of the twenty ninth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin Ca2+-Mg2+-dependent endonuclease.

In some embodiments of the twenty ninth aspect, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In a thirtieth aspect, the invention features a method of detecting a target nucleic acid in a sample. The method involves:

(a) providing a mixture including:
   the sample,
   a first probe including, in order, a first region, a second region, a third region, and a fourth region capable of hybridizing to the second region, in which the second region includes at least one nucleic acid mismatch relative to the fourth region, and in which the first region and the second region form a nucleic acid sequence complementary to at least a portion of the target nucleic acid,
   a second probe including, in order, a fifth region, a sixth region, a seventh region, and an eighth region capable of hybridizing to the sixth region, in which the sixth region includes at least one nucleic acid mismatch relative to the eighth region, and in which the fifth region and the sixth region form a nucleic acid sequence complementary to at least the nucleic acid sequence formed by the third region and the fourth region, and
   an enzyme capable of selectively digesting double-stranded nucleic acids;
the mixture having been incubated under conditions to:
   (i) hybridize the first region and the second region to the target nucleic acid, thereby forming a first probe-target nucleic acid complex including a first double-stranded nucleic acid region, and to digest the first double-stranded nucleic acid region with the enzyme, thereby releasing a first end region including the third region and the fourth region, and
   (ii) hybridize the first released end region to the fifth region and the sixth region of the second probe, thereby forming a first released end region-second probe nucleic acid complex including a second double-stranded nucleic acid region, and to digest the second double-stranded nucleic acid region with the enzyme or a copy thereof, thereby releasing a second end region including the seventh region and the eighth region; and
(b) detecting the released first end region and/or the released second end region, whereby the presence of the released first end region and/or the released second end region is indicative of the presence of the target nucleic acid.

In some embodiments of the thirtieth aspect, the mixture has been further incubated for a period sufficient to repeat: (i) hybridization of the target nucleic acid to the first region and the second region of an additional copy of the first probe, and digestion of the formed double-stranded nucleic acid region, and (ii) hybridization of the first released end region to the fifth region and the sixth region of an additional copy of the second probe, and digestion of the formed double-stranded nucleic acid region, thereby exponentially amplifying the released end regions.

In some embodiments of the thirtieth aspect, hybridization of a portion of the target nucleic acid to the first region occurs prior to hybridization of a further portion of the target nucleic acid to the second region. In certain embodiments, hybridization of a portion of the target nucleic acid to the first region results in strand invasion of the second region by the further portion of the target nucleic acid. In particular embodiments, the strand invasion results in breakage of hybridization between the second region and the fourth region.

In some embodiments of the thirtieth aspect, the method further involves, prior to the detecting step, isolating the released first end region and/or the released second end region. In certain embodiments, the isolating includes capturing the released end regions using a capture moiety. In particular embodiments, the capture moiety is a nucleic acid capture probe capable of hybridizing to at least a portion of the released end region. In various embodiments, the capture moiety is attached to a support. In specific embodiments, the support includes a strip, bead, hydrogel, slide, or interior wall of a compartment; preferably a strip.

In some embodiments of the thirtieth aspect, the first region is located at the 5' end of the first probe and the fourth region is located at the 3' end of the first probe.

In some embodiments of the thirtieth aspect, the first region is located at the 3' end of the first probe and the fourth region is located at the 5' end of the first probe.

In some embodiments of the thirtieth aspect, the first region and the second region include DNA.

In some embodiments of the thirtieth aspect, the third region and the fourth region include RNA.

In some embodiments of the thirtieth aspect, the target nucleic acid includes RNA and/or DNA.

In some embodiments of the thirtieth aspect, the fifth region and the sixth region include DNA.

In some embodiments of the thirtieth aspect, the seventh region and the eighth region include RNA.

In some embodiments of the thirtieth aspect, the first probe and/or the second probe includes a label. In certain embodiments, the label is a fluorescent bead, quantum dot, fluorescent dye, fluorescent protein, biotin, or luciferase enzyme.

In some embodiments of the thirtieth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin Ca2+-Mg2+-dependent endonuclease.

In a thirty first aspect, the invention features a method of detecting a target nucleic acid in a sample. The method involves:

(a) providing a mixture including:
   the sample,
   a first probe including, in order, a first region, a second region, a third region, and a fourth region capable of hybridizing to the second region, in which the second region includes at least one nucleic acid mismatch relative to the fourth region, and in which the first region and the second region form a nucleic acid sequence complementary to at least a portion of the target nucleic acid,
   a second probe including, in order, a fifth region, a sixth region, a seventh region, and an eighth region capable of hybridizing to the sixth region, in which the sixth region includes at least one nucleic acid mismatch relative to the eighth region, and in which the fifth region and the sixth region form a nucleic acid sequence complementary to at least the nucleic acid sequence formed by the third region and the fourth region, a suppression oligo capable of hybridizing to the second region of the first probe, in which if:
   the first probe is fully intact, and
      the second region and the fourth region are not hybridized, then the suppression oligo may hybridize to the second region, thereby preventing hybridization of the second region to the eighth region;
an enzyme capable of selectively digesting double-stranded nucleic acids;
the mixture having been incubated under conditions to:
   (i) hybridize the first region and the second region to the target nucleic acid, thereby forming a first probe-target nucleic acid complex including a first double-stranded nucleic acid region, and to digest the first double-stranded nucleic acid region with the enzyme, thereby releasing a first end region including the third region and the fourth region, and
   (ii) hybridize the first released end region to the fifth region and the sixth region of the second probe, thereby forming a first released end region-second probe nucleic acid complex including a second double-stranded nucleic acid region, and to digest the second double-stranded nucleic acid region with the enzyme or a copy thereof, thereby releasing a second end region including the seventh region and the eighth region; and
(b) detecting the released first end region and/or the released second end region, whereby the presence of the released first end region and/or the released second end region is indicative of the presence of the target nucleic acid.

In some embodiments of the thirty first aspect, the mixture has been further incubated for a period sufficient to repeat:
   (i) hybridization of the target nucleic acid to the first region and the second region of an additional copy of the first probe, and digestion of the formed double-stranded nucleic acid region, and
   (ii) hybridization of the first released end region to the fifth region and the sixth region of an additional copy of the second probe, and digestion of the formed double-stranded nucleic acid region, thereby exponentially amplifying the released end regions.

In some embodiments of the thirty first aspect, the suppression oligo includes DNA and/or RNA.

In some embodiments of the thirty first aspect, hybridization of a portion of the target nucleic acid to the first region occurs prior to hybridization of a further portion of the target nucleic acid to the second region. In certain embodiments, hybridization of a portion of the target nucleic acid to the first region results in strand invasion of the second region by the further portion of the target nucleic acid. In particular embodiments, the strand invasion results in breakage of hybridization between the second region and the fourth region.

In some embodiments of the thirty first aspect, the method further involves, prior to the detecting step, isolating the released first end region and/or the released second end region. In certain embodiments, the isolating includes capturing the released second end regions using a capture moiety. In particular embodiments, the capture moiety is a nucleic acid capture probe capable of hybridizing to at least a portion of the released second end region. In various embodiments, the capture moiety is attached to a support. In specific embodiments, the support includes a strip, bead, hydrogel, slide, or interior wall of a compartment; preferably in which the support includes a strip.

In some embodiments of the thirty first aspect, the first region is located at the 5' end of the first probe and the fourth region is located at the 3' end of the first probe.

In some embodiments of the thirty first aspect, the first region is located at the 3' end of the first probe and the fourth region is located at the 5' end of the first probe.

In some embodiments of the thirty first aspect, the first region and the second region include DNA.

In some embodiments of the thirty first aspect, the third region and the fourth region include RNA.

In some embodiments of the thirty first aspect, the target nucleic acid includes RNA and/or DNA.

In some embodiments of the thirty first aspect, the fifth region and the sixth region include DNA.

In some embodiments of the thirty first aspect, the seventh region and the eighth region include RNA.

In some embodiments of the thirty first aspect, the first probe and/or the second probe includes a label. In certain embodiments, the label is a fluorescent bead, quantum dot, fluorescent dye, fluorescent protein, biotin, or luciferase enzyme.

In some embodiments of the thirty first aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca2+-Mg2+$-dependent endonuclease.

In a thirty second aspect, the invention features a method of detecting a target nucleic acid in a sample. The method involves:
   (a) providing a mixture including:
      the sample,
      a first probe including, in order, a first region, a second region, a third region, and a fourth region capable of hybridizing to the second region, in which the first region is capable of being digested by an enzyme capable of selectively digesting double-stranded nucleic acids, the second region is not capable of being digested by the enzyme and includes at least one nucleic acid mismatch relative to the fourth region, in which the first region is complementary to at least a portion of the target nucleic acid, in which the second region is capable of hybridizing to at least a further portion of the target nucleic acid, and in which the second region includes at least one nucleic acid mismatch relative to the further portion of the target nucleic acid;
      a second probe including, in order, a fifth region, a sixth region, a seventh region, and an eighth region capable of hybridizing to the sixth region, in which the sixth region includes at least one nucleic acid mismatch relative to the eighth region, and in which the fifth region and the sixth region form a nucleic acid sequence complementary to at least the nucleic acid sequence formed by the third region and the fourth region,
      a third probe including, in order, a ninth region, a tenth region, a eleventh region, and a twelfth region capable of hybridizing to the tenth region, in which the tenth region includes at least one nucleic acid mismatch relative to the twelfth region, in which the ninth region and the tenth region form a nucleic acid sequence complementary to at least the nucleic acid sequence formed by the seventh region and the eighth region, and in which the eleventh region and the twelfth region include a nucleic acid sequence identical to the third region and the fourth region, and the enzyme;

the mixture having been incubated under conditions to:
(i) hybridize the first region and the second region to the target nucleic acid, thereby forming a first probe-target nucleic acid complex including a first double-stranded nucleic acid region, and to digest the first double-stranded nucleic acid region with the enzyme, thereby releasing a first end region including the second region, the third region, and the fourth region, in which the second region remains hybridized to the target nucleic acid,
(ii) hybridize the first released end region to the fifth region and the sixth region of the second probe, thereby forming a first released end region-second probe nucleic acid complex including a second double-stranded nucleic acid region, and to digest the second double-stranded nucleic acid region with the enzyme or a copy thereof, thereby releasing a second end region including the seventh region and the eighth region, and
(iii) hybridize the second released end region to the ninth region and the tenth region of the third probe, thereby forming a second released end region-third probe nucleic acid complex including a third double-stranded nucleic acid region, and to digest the third double-stranded nucleic acid region with the enzyme or a copy thereof, thereby releasing a third end region including the eleventh region and the twelfth region; and
(b) detecting the released first end region, the released second end region, and/or the released third end region, whereby the presence of the released first end region, the released second end region, and/or the released third end region is indicative of the presence of the target nucleic acid.

In some embodiments of the thirty second aspect, the mixture has been further incubated for a period sufficient to repeat:
(i) hybridization of the target nucleic acid to the first region and the second region of an additional copy of the first probe, and digestion of the formed double-stranded nucleic acid region,
(ii) hybridization of the first released end region to the fifth region and the sixth region of an additional copy of the second probe, and digestion of the formed double-stranded nucleic acid region, and/or
(iii) hybridization of the second released end region to the ninth region and the tenth region of an additional copy of the third probe, and digestion of the formed double-stranded nucleic acid region, thereby exponentially amplifying the released end regions.

In certain embodiments, the mixture has been incubated under conditions to hybridize the third released end region to a fifth region and a sixth region of a further copy of the second probe, thereby forming a third released end region-second probe nucleic acid complex including a further double-stranded nucleic acid region, and to digest the further double-stranded nucleic acid region with the enzyme or a copy thereof, thereby releasing a further copy of the second end region.

In some embodiments of the thirty second aspect, hybridization of a portion of the target nucleic acid to the first region occurs prior to hybridization of a further portion of the target nucleic acid to the second region. In certain embodiments, hybridization of a portion of the target nucleic acid to the first region results in strand invasion of the second region by the further portion of the target nucleic acid. In particular embodiments, the strand invasion results in breakage of hybridization between the second region and the fourth region.

In some embodiments of the thirty second aspect, the method further involves, prior to the detecting step, isolating the released first end region and/or the released second end region. In certain embodiments, the isolating includes capturing the released second end regions using a capture moiety.

In particular embodiments, the capture moiety is a nucleic acid capture probe capable of hybridizing to at least a portion of the released second end region. In various embodiments, the capture moiety is attached to a support. In specific embodiments, the support includes a strip, bead, hydrogel, slide, or interior wall of a compartment; preferably a strip.

In some embodiments of the thirty second aspect, the first region is located at the 5' end of the first probe and the fourth region is located at the 3' end of the first probe.

In some embodiments of the thirty second aspect, the first region is located at the 3' end of the first probe and the fourth region is located at the 5' end of the first probe.

In some embodiments of the thirty second aspect, the first region and the second region include DNA.

In some embodiments of the thirty second aspect, the third region and the fourth region include RNA.

In some embodiments of the thirty second aspect, the target nucleic acid includes DNA and/or RNA.

In some embodiments of the thirty second aspect, the fifth region and the sixth region include DNA.

In some embodiments of the thirty second aspect, the seventh region and the eighth region include RNA.

In some embodiments of the thirty second aspect, the ninth region and the tenth region include DNA.

In some embodiments of the thirty second aspect, the eleventh region and the twelfth region include RNA.

In some embodiments of the thirty second aspect, the first probe, the second probe, and/or the third probe includes a label. In certain embodiments, the label is a fluorescent bead, quantum dot, fluorescent dye, fluorescent protein, biotin, or luciferase enzyme.

In some embodiments of the thirty second aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease.

In a thirty third aspect, the invention features a method of detecting a target nucleic acid in a sample. The method involves:
(a) providing a mixture including:
the sample,
a nucleic acid detection probe including, in order, a first region, a second region, a third region, a fourth region, a fifth region, a sixth region, and a seventh region, in which the second region and the third region are capable of hybridizing to the sixth region and the fifth region, respectively, in which the first region, the second region, and the third region form a nucleic acid sequence complementary to at least a portion of the target nucleic acid, and in which the first region and the second region are capable of being digested by an enzyme capable of selectively digesting double-stranded nucleic acids, and the third region is not capable of being digested by the enzyme, a hairpin probe including, in order, a first terminal region attached to a label, a loop region complementary to at least a portion of the fifth region, the sixth region, and/or the seventh region, and a second terminal region attached to a quencher of the label, in which the first terminal region is capable of hybridizing to the second terminal region, a target displacing oligonucleotide capable of hybridizing to the fourth region and the third region and, optionally, at least a portion of the fifth region, and the enzyme;

the mixture having been incubated under conditions to:
(i) hybridize the first region, the second region, and the third region to the target nucleic acid, thereby forming a nucleic acid detection probe-target nucleic acid complex including a first double-stranded nucleic acid region, and to digest the first double-stranded nucleic acid region with the enzyme, thereby releasing an end region including the third region, the fourth region, the fifth region, the sixth region, and the seventh region, in which the third region remains hybridized to the target nucleic acid;
(ii) hybridize the target displacing oligonucleotide to the end region, thereby displacing the target nucleic acid from the end region; and
(iii) hybridize the end region to the loop region of the hairpin probe, thereby forming an end region-hairpin probe complex including a second double-stranded nucleic region, and to digest the second double-stranded nucleic acid region with the enzyme or a copy thereof, thereby releasing the first terminal region attached to the label and the second terminal region attached to the quencher; and (b) detecting the label attached to the released first terminal region, whereby the presence of the label is indicative of the presence of the target nucleic acid.

In some embodiments of the thirty third aspect, the mixture has been further incubated for a period sufficient to repeat:
(i) hybridization of the first region, the second region, and the third region of an additional copy of the nucleic acid detection probe to the target nucleic acid, and digestion of the formed double-stranded nucleic acid region, and
(ii) hybridization of the end region of the additional copy of the nucleic acid detection probe to the loop region of an additional copy of the hairpin probe, and digestion of the formed double-stranded nucleic acid region,
thereby geometrically amplifying the released end regions.

In some embodiments of the thirty third aspect, the target displacing oligonucleotide includes DNA and/or RNA.

In some embodiments of the thirty third aspect, hybridization of a portion of the target nucleic acid to the first region occurs prior to hybridization of a further portion of the target nucleic acid to the second region. In certain embodiments, hybridization of a portion of the target nucleic acid to the first region results in strand invasion of the second region and the third region by the further portion of the target nucleic acid. In particular embodiments, the strand invasion results in breakage of hybridization between the second region and the fifth region, and between the third region and the sixth region.

In some embodiments of the thirty third aspect, the method further involves, prior to the detecting step, isolating the released first terminal region. In certain embodiments, the isolating includes capturing the first terminal region using a capture moiety. In particular embodiments, the capture moiety is a nucleic acid capture probe capable of hybridizing to at least a portion of the first region of the first terminal region. In various embodiments, the capture moiety is attached to a support. In specific embodiments, the support includes a strip, bead, hydrogel, slide, or interior wall of a compartment; preferably a strip.

In some embodiments of the thirty third aspect, the first region and the second region include DNA.

In some embodiments of the thirty third aspect, the third region, the fourth region, the fifth region, the sixth region, and the seventh region include RNA.

In some embodiments of the thirty third aspect, the target nucleic acid includes RNA and/or DNA.

In some embodiments of the thirty third aspect, the label is a fluorescent bead, quantum dot, fluorescent dye, fluorescent protein, biotin, or luciferase enzyme.

In some embodiments of the thirty third aspect, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In some embodiments of the thirty third aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease.

In a thirty fourth aspect, the invention features a method of detecting a target nucleic acid in a sample. The method involves:
(a) providing a mixture including:
the sample,
a first probe including, in order, a first region, a second region, a third region, a fourth region, a fifth region, a sixth region, and a seventh region, in which the second region and the third region are capable of hybridizing to the sixth region and the fifth region, respectively, in which the first region, the second region, and the third region form a nucleic acid sequence complementary to at least a portion of the target nucleic acid, and in which the first region and the second region are capable of being digested by an enzyme capable of selectively digesting double-stranded nucleic acids, the third region is not capable of being digested by the enzyme,
a second probe including, in order, an eighth region, a ninth region, a tenth region, an eleventh region, a twelfth region, a thirteenth region, a fourteenth region, and a fifteenth region, in which the eighth region, the ninth region, the eleventh region, and the twelfth region are capable of being digested by the enzyme, in which the tenth region is not capable of being digested by the enzyme, and in which the fourteenth region, the fifteenth region, and at least a portion of the thirteenth region include a nucleic acid sequence are identical to the nucleic acid sequence of the target nucleic acid;

at least two copies of a target displacing oligonucleotide capable of hybridizing to the third region and the fourth region and, optionally, at least a portion of the fifth region, in which the target displacing oligonucleotide is further capable of hybridizing to the eleventh region, the twelfth region, and/or at least a portion of the thirteenth region, and the enzyme;

the mixture having been incubated under conditions to:
  (i) hybridize the first region, the second region, and the third region to the target nucleic acid, thereby forming a first probe-target nucleic acid complex including a first double-stranded nucleic acid region, and to digest the first double-stranded nucleic acid region with the enzyme, thereby releasing a first end region including the third region, the fourth region, the fifth region, the sixth region, and the seventh region, in which the third region remains hybridized to the target nucleic acid;
  (ii) hybridize one copy of the target displacing oligonucleotide to the first end region, thereby displacing the target nucleic acid from the first end region;
  (iii) hybridize the first end region to the second probe, thereby forming a first end region-second probe nucleic acid complex including a second double-stranded nucleic acid region and maintaining the second probe in an open conformation,
  (iv) hybridize one copy of the target displacing oligonucleotide to the second probe, thereby forming a target displacing oilgonucleotide-second probe nucleic acid complex including a third double-stranded nucleic acid region, and
  (v) digest the third double-stranded nucleic acid region with the enzyme, or a copy thereof, thereby releasing a second end region including the fourteenth region, the fifteenth region, and at least a portion of the thirteenth region; and (b) detecting the first end region and/or the second end region, whereby the presence of the first end region and/or the second end region is indicative of the presence of the target nucleic acid.

In some embodiments of the thirty fourth aspect, the mixture has been further incubated for a period sufficient to repeat:
  (i) hybridization of the target nucleic acid to an additional copy of the first probe, and digestion of the formed double-stranded nucleic acid region, and
  (ii) hybridization of the first end region to an additional copy of the second probe, and digestion of the formed double-stranded nucleic acid region,
thereby exponentially amplifying the released end regions.

In some embodiments of the thirty fourth aspect, each of the target displacing oligonucleotides includes DNA and/or RNA.

In some embodiments of the thirty fourth aspect, hybridization of a portion of the target nucleic acid to the first region occurs prior to hybridization of a further portion of the target nucleic acid to the second region. In certain embodiments, hybridization of a portion of the target nucleic acid to the first region results in strand invasion of the second region and third region by the further portion of the target nucleic acid. In particular embodiments, the strand invasion results in breakage of hybridization between the second region and the sixth region, and between the third region and the fifth region.

In some embodiments of the thirty fourth aspect, the method further involves, prior to the detecting step, isolating the released end regions. In certain embodiments, the isolating includes capturing the released end regions using a capture moiety. In particular embodiments, the capture moiety includes a nucleic acid capture probe capable of hybridizing to at least a portion of the released end regions. In various embodiments, the capture moiety is attached to a support. In specific embodiments, the support includes a strip, bead, hydrogel, slide, or interior wall of a compartment; preferably a strip.

In some embodiments of the thirty fourth aspect, the first region and the second region include DNA.

In some embodiments of the thirty fourth aspect, the third region, the fourth region, the fifth region, the sixth region, and the seventh region include RNA.

In some embodiments of the thirty fourth aspect, the target nucleic acid includes RNA and/or DNA.

In some embodiments of the thirty fourth aspect, the first probe and/or the second probe includes a label.

In some embodiments of the thirty fourth aspect, the label is a fluorescent bead, quantum dot, fluorescent dye, fluorescent protein, biotin, or luciferase enzyme.

In some embodiments of the thirty fourth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease.

In a thirty fifth aspect, the invention features a method of detecting a target nucleic acid in a sample. The method involves:

(a) providing a mixture including:
  the sample,
  a nucleic acid detection probe including, in order, a first region, a second region, a third region, a fourth region, a fifth region, a sixth region, and a seventh region, in which the second region and the third region are capable of hybridizing to the sixth region and the fifth region, respectively, in which the first region, the second region, and the third region form a nucleic acid sequence complementary to at least a portion of the target nucleic acid, and in which the first region is capable of being digested by an enzyme capable of selectively digesting double-stranded nucleic acids, and the second region and the third region are not capable of being digested by the enzyme,
  a hairpin probe including, in order, a first terminal region attached to a label, a loop region complementary to at least a portion of the fifth region, the sixth region, and/or the seventh region, and a second terminal region attached to a quencher of the label, in which the first terminal region is capable of hybridizing to the second terminal region,
  a target displacing oligonucleotide capable of hybridizing to the second region, the third region, the fourth region, and, optionally, at least a portion of the fifth region, and
  the enzyme;
the mixture having been incubated under conditions to:
  (i) hybridize the first region, the second region, and the third region to the target nucleic acid, thereby forming a nucleic acid detection probe-target nucleic acid complex including a first double-stranded nucleic acid region, and to digest the first double-stranded nucleic acid region with the enzyme, thereby releasing an end region including the second region, the third region, the fourth region, the fifth region, the sixth region, and the seventh region, in which the second region and the third region remain hybridized to the target nucleic acid;

(ii) hybridize the target displacing oligonucleotide to the end region, thereby displacing the target nucleic acid from the end region; and (iii) hybridize the end region to the loop region of the hairpin probe, thereby forming an end region-hairpin probe complex including a second double-stranded nucleic region, and to digest the second double-stranded nucleic acid region with the enzyme or a copy thereof, thereby releasing the first terminal region attached to the label and the second terminal region attached to the quencher; and (b) detecting the label attached to the released first terminal region, whereby the presence of the label is indicative of the presence of the target nucleic acid.

In some embodiments of the thirty fifth aspect, the mixture has been further incubated for a period sufficient to repeat:

(i) hybridization of an additional copy of the nucleic acid detection probe to the target nucleic acid, and digestion of the formed double-stranded nucleic acid region, and (ii) hybridization of the end region of the additional copy of the nucleic acid detection probe to the loop region of an additional copy of the hairpin probe, and digestion of the formed double-stranded nucleic acid region, thereby geometrically amplifying the released end regions.

In some embodiments of the thirty fifth aspect, the target displacing oligonucleotide includes DNA and/or RNA.

In some embodiments of the thirty fifth aspect, hybridization of a portion of the target nucleic acid to the first region occurs prior to hybridization of a further portion of the target nucleic acid to the second region. In certain embodiments, hybridization of a portion of the target nucleic acid to the first region results in strand invasion of the second region and the third region by the further portion of the target nucleic acid. In particular embodiments, the strand invasion results in breakage of hybridization between the second region and the sixth region, and between the third region and the fifth region.

In some embodiments of the thirty fifth aspect, the method further involves, prior to the detecting step, isolating the released first terminal region. In certain embodiments, the isolating includes capturing the first terminal region using a capture moiety. In particular embodiments, the capture moiety is a nucleic acid capture probe capable of hybridizing to at least a portion of the first region of the first terminal region. In various embodiments, the capture moiety is attached to a support. In specific embodiments, the support includes a strip, bead, hydrogel, slide, or interior wall of a compartment; preferably a strip.

In some embodiments of the thirty fifth aspect, the first region includes DNA.

In some embodiments of the thirty fifth aspect, the second region, the third region, the fourth region, the fifth region, the sixth region, and the seventh region include RNA.

In some embodiments of the thirty fifth aspect, the target nucleic acid includes RNA and/or DNA.

In some embodiments of the thirty fifth aspect, the label is a fluorescent bead, quantum dot, fluorescent dye, fluorescent protein, biotin, or luciferase enzyme.

In some embodiments of the thirty fifth aspect, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In some embodiments of the thirty fifth aspect, the enzyme capable of selectively digesting double-stranded nucleic acids is a duplex-specific nuclease. In certain embodiments, the nuclease is selected from the group consisting of Kamchatka Crab double stranded nuclease, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease.

In a thirty sixth aspect, the invention features a method of detecting a target nucleic acid in a sample. The method involves:

(a) providing a mixture including:
the sample,
a nucleic acid detection probe including, in order, a first region, a second region, a third region, a fourth region, a fifth region, a sixth region, and a seventh region, in which the second region and the third region are capable of hybridizing to the sixth region and the fifth region, respectively, in which the first region, the second region, and the third region form a nucleic acid sequence complementary to at least a portion of the target nucleic acid, and in which the first region and the second region are capable of being digested by an enzyme capable of selectively digesting double-stranded nucleic acids, and the third region is not capable of being digested by the enzyme,
a hairpin probe including, in order, a first terminal region attached to a label, a loop region complementary to at least a portion of the sixth region and, optionally, the seventh region, and a second terminal region attached to a quencher of the label, in which the first terminal region is capable of hybridizing to the second terminal region, and
the enzyme;
the mixture having been incubated under conditions to:
(i) hybridize the first region, the second region, and the third region to the target nucleic acid, thereby forming a nucleic acid detection probe-target nucleic acid complex including a first double-stranded nucleic acid region, and to digest the first double-stranded nucleic acid region with the enzyme, thereby releasing an end region including the third region, the fourth region, the fifth region, the sixth region, and the seventh region, in which the third region remains hybridized to the target nucleic acid;

(ii) hybridize the fifth region of the end region to the third region of the end region, thereby displacing the target nucleic acid from the end region and forming a hairpin end region; and (iii) hybridize the hairpin end region to the loop region of the hairpin probe, thereby forming an hairpin end region-hairpin probe complex including a second double-stranded nucleic region, and to digest the second double-stranded nucleic acid region with the enzyme or a copy thereof, thereby releasing the first terminal region attached to the label and the second terminal region attached to the quencher; and (b) detecting the label attached to the released first terminal region, whereby the presence of the label is indicative of the presence of the target nucleic acid.

In some embodiments of the thirty sixth aspect, the mixture has been further incubated for a period sufficient to repeat:
(i) hybridization of an additional copy of the nucleic acid detection probe to the target nucleic acid, and digestion of the formed double-stranded nucleic acid region, and
(ii) hybridization of the hairpin end region of the additional copy of the nucleic acid detection probe to the loop region of an additional copy of the hairpin probe, and digestion of the formed double-stranded nucleic acid region,
thereby geometrically amplifying the released end regions.

In some embodiments of the thirty sixth aspect, hybridization of a portion of the target nucleic acid to the first region occurs prior to hybridization of a further portion of the target nucleic acid to the second region. In certain embodiments, hybridization of a portion of the target nucleic acid to the first region results in strand invasion of the second region and the third region by the further portion of the target nucleic acid. In particular embodiments, the strand invasion results in breakage of hybridization between the second region and the sixth region, and between the third region and the fifth region.

In some embodiments of the thirty sixth aspect, the method further involves, prior to the detecting step, isolating the released first terminal region. In certain embodiments, the isolating includes capturing the first terminal region using a capture moiety. In particular embodiments, the capture moiety is a nucleic acid capture probe capable of hybridizing to at least a portion of the first terminal region. In various embodiments, the capture moiety is attached to a support. In specific embodiments, the support includes a strip, bead, hydrogel, slide, or interior wall of a compartment; preferably a strip.

In some embodiments of the thirty sixth aspect, the first region and the second region include DNA.

In some embodiments of the thirty sixth aspect, the third region, the fourth region, the fifth region, the sixth region, and the seventh region include RNA.

In some embodiments of the thirty sixth aspect, the target nucleic acid includes RNA and/or DNA.

In some embodiments of the thirty sixth aspect, the label is a fluorescent bead, quantum dot, fluorescent dye, fluorescent protein, biotin, or luciferase enzyme.

In some embodiments of the thirty sixth aspect, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3.

In some embodiments of the thirty sixth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca^{2+}-Mg^{2+}$-dependent endonuclease.

DSA with Beacon or Surface Detection

In a thirty seventh aspect, the invention features a method of detecting a target nucleic acid in a sample. The method involves:

(a) providing a mixture including:
the sample,
a first probe including, in order, a first region, a second region complementary to at least a portion of the target nucleic acid, and a third region capable of hybridizing to the first region,
a second probe including, in order, a fourth region attached to a label, a fifth region complementary to at least a portion of the first region, and a sixth region capable of hybridizing to the fourth region, and
an enzyme capable of selectively digesting double-stranded nucleic acids;
the mixture having been incubated under conditions to:
(i) hybridize the second region to the target nucleic acid, thereby forming a first probe-target nucleic acid complex including a first double-stranded nucleic acid region, and to digest the first double-stranded nucleic acid region with the enzyme, thereby releasing a first end region including the first region and a second end region including the third region,
(ii) hybridize the released first end region to the fifth region, thereby forming a first end region-second probe nucleic acid complex including a second double-stranded nucleic acid region, and to digest the second double-stranded nucleic acid region with the enzyme, or a copy thereof, thereby releasing a third end region including the fourth region and a fourth end region including the sixth region; and
(b) detecting the label, whereby the presence of the label is indicative of the presence of the target nucleic acid.

In some embodiments of the thirty seventh aspect, the mixture has been further incubated for a period sufficient to repeat hybridization of the released first end region to an additional copy of the second probe, and digestion of the formed second double-stranded nucleic acid region; thereby geometrically amplifying the released third end region.

In some embodiments of the thirty seventh aspect, the detecting step includes: (i) isolating the released third end region, and (ii) detecting the label attached to the isolated third end region. In certain embodiments, the isolating step includes hybridizing the released third end region to a capture probe attached to a surface, thereby immobilizing the released third end region, and separating the immobilized third end region, capture probe, and surface from the remainder of the solution. In particular embodiments, the surface includes a strip, bead, hydrogel, slide, or interior wall of a compartment; preferably a strip.

In some embodiments of the thirty seventh aspect, the sixth region is attached to a quencher capable of quenching the label when the fourth region is hybridized to the sixth region. In certain embodiments, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3. In particular embodiments, the digesting of the second double-stranded nucleic acid region separates the label and the quencher, thereby activating the label. In specific embodiments, the detecting step includes detecting the activated label.

In some embodiments of the thirty seventh aspect, the label is a fluorescent bead, quantum dot, fluorescent dye, fluorescent protein, biotin, or luciferase enzyme.

In some embodiments of the thirty seventh aspect, the first region and the third region include RNA. In certain embodiments, the second region includes DNA.

In some embodiments of the thirty seventh aspect, the fourth region and the sixth region include RNA.

In some embodiments of the thirty seventh aspect, the fifth region includes DNA.

In some embodiments of the thirty seventh aspect, the target nucleic acid includes RNA and/or DNA.

In some embodiments of the thirty seventh aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin Ca2+-Mg2+-dependent endonuclease.

In a thirty eighth aspect, the invention features a method of detecting a target nucleic acid in a sample. The method involves:
(a) providing a mixture including:
the sample,
a first probe including, in order, a first region, a second region complementary to at least a portion of the target nucleic acid, and a third region capable of hybridizing to the first region,
a second probe including, in order, a fourth region attached to a label, a fifth region complementary to at least a portion of the first region, and a sixth region, in which the fourth region includes a portion complementary to at least a portion of the second region of the first probe, and the sixth region is capable of hybridizing to the fourth region, and
an enzyme capable of selectively digesting double-stranded nucleic acids;
the mixture having been incubated under conditions to:
(i) hybridize the second region to the target nucleic acid, thereby forming a first probe-target nucleic acid complex including a first double-stranded nucleic acid region, and to digest the first double-stranded nucleic acid region with the enzyme, thereby releasing a first end region including the first region and a second end region including the third region,
(ii) hybridize the released first end region to the fifth region, thereby forming a first end region-second probe nucleic acid complex including a second double-stranded nucleic acid region, and to digest the second double-stranded nucleic acid region with the enzyme, or a copy thereof, thereby releasing a third end region including the fourth region and a fourth end region including the sixth region; and
(b) detecting the label, whereby the presence of the label is indicative of the presence of the target nucleic acid.

In some embodiments of the thirty eighth aspect, the mixture has been further incubated for a period sufficient to:
(i) repeat hybridization of the released first end region to an additional copy of the second probe, and digestion of the formed second double-stranded nucleic acid region, and/or
(ii) hybridize the released third end region to an additional copy of the first probe, thereby forming a third end region-first probe nucleic acid complex including a further double-stranded nucleic acid region, and to digest the further double-stranded nucleic acid region with the enzyme, or a copy thereof, thereby releasing additional copies of the first end region and the second end region;
thereby exponentially amplifying the released third end region.

In some embodiments of the thirty eighth aspect, the detecting step includes: (i) isolating the released third end region, and (ii) detecting the label attached to the isolated third end region. In certain embodiments, the isolating step includes hybridizing the released third end region to a capture probe attached to a surface, thereby immobilizing the released third end region, and separating the immobilized third end region, capture probe, and surface from the remainder of the solution. In particular embodiments, the surface includes a strip, bead, hydrogel, slide, or interior wall of a compartment; preferably a strip.

In some embodiments of the thirty eighth aspect, the sixth region is attached to a quencher capable of quenching the label when the fourth region is hybridized to the sixth region. In certain embodiments, the quencher is selected from the group consisting of: DDQ-I, DDQ-II, Dabcyl, Eclipse, Iowa Black FQ, Iowa Black RQ, QSY-7, QSY-21, BHQ-1, BHQ-2, and BHQ-3. In particular embodiments, the digesting of the second double-stranded nucleic acid region separates the label and the quencher, thereby activating the label. In one embodiment, the detecting step includes detecting the activated label.

In some embodiments of the thirty eighth aspect, the label is a fluorescent bead, quantum dot, fluorescent dye, fluorescent protein, biotin, or luciferase enzyme.

In some embodiments of the thirty eighth aspect, the first region and the third region include RNA. In certain embodiments, the second region includes DNA.

In some embodiments of the thirty eighth aspect, the fourth region and the sixth region include RNA. In certain embodiments, the fifth region includes DNA.

In some embodiments of the thirty eighth aspect, the target nucleic acid includes RNA and/or DNA.

In some embodiments of the thirty eighth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin Ca2+-Mg2+-dependent endonuclease.

In a thirty ninth aspect, the invention features a method of detecting a target nucleic acid in a sample. The method involves:
(a) providing a mixture including:
the sample,
a detection probe including, in order, a first region, a second region complementary to at least a portion of the target nucleic acid, and a third region capable of hybridizing to the first region, and
an enzyme capable of selectively digesting double-stranded nucleic acids;
the mixture having been incubated under conditions to hybridize the second region to the target nucleic acid, thereby forming a detection probe-target nucleic acid complex including a double-stranded nucleic acid region, and to digest the double-stranded nucleic acid region with the enzyme, thereby releasing a first end region including the first region and a second end region including the third region; and
(b) detecting the released first end region and/or the released second end region, whereby the presence of the released first end region and/or the released second end region is indicative of the presence of the target nucleic acid.

In some embodiments of the thirty ninth aspect, the mixture has been further incubated for a period sufficient to repeat hybridization of the target nucleic acid to an additional copy of the detection probe, and digestion of the formed double-stranded nucleic acid region; thereby linearly amplifying the released first end region and/or the released second end region.

In some embodiments of the thirty ninth aspect, the first region is attached to a label and the detecting step includes: (i) isolating the released first end region, and (ii) detecting the label attached to the isolated first end region. In certain embodiments, the isolating step includes hybridizing the released first end region to a capture probe attached to a surface, thereby immobilizing the released first end region, and separating the immobilized first end region, capture probe, and surface from the remainder of the solution. In particular embodiments, the surface includes a strip, bead, hydrogel, slide, or interior wall of a compartment; preferably a strip.

In some embodiments of the thirty ninth aspect, the label is a fluorescent bead, quantum dot, fluorescent dye, fluorescent protein, biotin, or luciferase enzyme.

In some embodiments of the thirty ninth aspect, the first region and the third region include RNA. In certain embodiments, the second region includes DNA.

In some embodiments of the thirty ninth aspect, the target nucleic acid includes RNA and/or DNA.

In some embodiments of the thirty ninth aspect, the enzyme capable of selectively digesting double-stranded nucleic acids is a duplex-specific nuclease. In certain embodiments, the duplex-specific nuclease is selected from the group consisting of a Kamchatka Crab DSN, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease.

Samples and Reaction Conditions

In some embodiments of any of the aspects of the invention, the sample is obtained directly from a subject or specimen. In certain embodiments, the sample is not purified prior to the incubating step. In particular embodiments, the sample is not purified prior to the providing step.

In some embodiments of any of the aspects of the invention, the enzyme is capable of digesting double-stranded nucleic acids in a buffer that inhibits other nucleases. In certain embodiments, the mixture includes the buffer. In particular embodiments, the buffer is an SDS lysis buffer. In specific embodiments, the buffer includes at least about 1% SDS and/or 5 mM $Mg^{2+}$. In various embodiments, the buffer includes proteinase K and/or an anionic detergent.

In some embodiments of any of the aspects of the invention, the enzyme is capable of digesting double-stranded nucleic acids at temperatures of about 37° C.-60° C. (e.g., about 37° C., 40° C., 45° C., 50° C., 55° C., or 60° C.). In certain embodiments, the incubation occurs at a temperature between about 37° C.-60° C. (e.g., about 37° C., 40° C., 45° C., 50° C., 55° C., or 60° C.).

In some embodiments of any of the aspects of the invention, the enzyme has high mismatch specificity. In certain embodiments, a single nucleotide difference between two strands in a double-stranded nucleic acid prevents digestion by the enzyme.

In some embodiments of any of the aspects of the invention, the enzyme can be stopped from digesting double stranded nucleic acids by EDTA.

In some embodiments of any of the methods of the invention, the method further involves, prior to the detecting step, separating the undigested nucleic acid detection probes from the digested nucleic acid probes by isolating the end region attached to a label from the undigested nucleic acid detection probes bound to the support, in which the detecting step includes detecting the label attached to the isolated end regions.

In some embodiments of any of the methods of the invention, the method further involves, prior to the detecting step, separating the undigested nucleic acid detection probes from the digested nucleic acid probes by immobilizing the undigested nucleic acid detection probes on the support through binding of the first and second binding moieties, and isolating the end region attached to a label from the immobilized undigested nucleic acid detection probes, in which the detecting step includes detecting the label attached to the isolated end regions.

In some embodiments of any of the methods of the invention, the support includes a magnetic bead and the isolating the end region includes exposing the magnetic bead to a magnetic field. In other embodiments, the support includes an array and the isolating the end region includes removing the sample from the array.

Further Methods for Detecting Nucleic Acids

In a fortieth aspect, the invention features a method of detecting a target nucleic acid in a sample involving:
providing a mixture including
the sample,
a nucleic acid detection probe including a support attached to a labeled nucleic acid, the labeled nucleic acid having a first region complementary to the target nucleic acid, and an end region attached to a label, and
an enzyme capable of selectively digesting double-stranded nucleic acids;
the mixture having been incubated under conditions to hybridize the nucleic acid detection probe to the target nucleic acid, thereby forming a nucleic acid detection probe-target nucleic acid complex including a double-stranded nucleic acid region; and to digest the double-stranded nucleic acid region with the enzyme; and
detecting the nucleic acid detection probe by detecting the label attached to the end regions, whereby the presence of the label is indicative of the presence of the target nucleic acid.

In a forty first aspect, the invention features a method of detecting a target nucleic acid in a sample involving:
providing a mixture including
the sample,
a nucleic acid detection probe including a support attached to a first binding moiety,
a labeled nucleic acid including a second binding moiety specific for the first binding moiety, a first region complementary to the target nucleic acid, and an end region attached to a label, and
and an enzyme capable of selectively digesting double-stranded nucleic acids;
the mixture having been incubated under conditions to hybridize the nucleic acid detection probe to the target nucleic acid, thereby forming a nucleic acid detection probe-target nucleic acid complex including a double-stranded nucleic acid region, and in which the enzyme would have digested the double-stranded nucleic acid region; and
detecting the nucleic acid detection probe by detecting the label attached to the end regions, whereby the presence of the label is indicative of the presence of the target nucleic acid.

In some embodiments, the first and second binding moieties are complementary nucleic acids.

In certain embodiments, the complementary nucleic acids include modified nucleic acids.

In some embodiments, the label is biotin, a fluorophore, or an enzyme. In certain embodiments, the enzyme is luciferase or the fluorophore is a quantum dot.

In some embodiments, the method further includes immobilizing the digested probes to the surface of a waveguide, in which the detecting measures fluorescence provided by illuminating the digested probes by an evanescent field from light propagating in the waveguide.

In some embodiments, the end region includes biotin and the detecting step includes the biotin binding to a surface of the waveguide.

In some embodiments, the enzyme capable of selectively digesting double-stranded nucleic acids is a duplex-specific nuclease.

In certain embodiments, the nuclease is selected from the group consisting of Kamchatka Crab double stranded nuclease, Gammarus putative nuclease, Glass shrimp putative nuclease, Mangrove fiddler crab putative nuclease, Kamchatka crab DNase K, a DNase I nuclease, and sea urchin $Ca2+$-$Mg2+$-dependent endonuclease.

In some embodiments of the fortieth and forty first aspects, the labeled nucleic acid further includes a second region located between the first region and the support, and the end region includes a third region complementary to the second region;
   the digestion of the double-stranded nucleic acid region of the nucleic acid detection probe-target nucleic acid complex with the enzyme forms a first released end region; and
   the mixture has been further incubated under conditions to hybridize the third region of the first released end region to the second region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a second released end region; and to
   hybridize the second released end region to the second region of an additional copy of the nucleic acid detection probe, thereby forming a second released end region-nucleic acid detection probe complex including a double-stranded nucleic acid region, and to digest the double-stranded nucleic acid region of the second released end region-nucleic acid detection probe complex with the enzyme or a copy thereof, thereby forming a further copy of the second released end region.

In certain embodiments, the mixture has been further incubated for a period sufficient to repeat:
   the hybridization of the third region of the first released end region to the second region of an additional copy of the nucleic acid detection probe, and/or the hybridization of the third region of the second released end region to the second region of an additional copy of the nucleic acid detection probe; and
   the digestion of the formed double-stranded nucleic acid region;
   thereby exponentially amplifying the second released end region.

In particular embodiments, the second region and the third region are arranged such that looping of the labeled nucleic acid will form a duplex between the second region and the third region that is not anti-parallel.

In certain embodiments, each of the first regions and each of the second regions include DNA and each of the third regions includes RNA.

In various embodiments, the target nucleic acid includes RNA, DNA, or a DNA-RNA hybrid.

In specific embodiments, the target nucleic acid includes RNA and the mixture is further incubated under conditions to hybridize the target nucleic acid or another copy thereof to the first region of the second released end region, thereby forming a double-stranded nucleic acid region, and to digest the double-stranded nucleic acid region with the enzyme or a copy thereof, thereby forming a further copy of the first released end region.

In some embodiments of the fortieth and forty first aspects, the mixture further includes a nucleic acid amplification probe attached to a support, the nucleic acid amplification probe including an end region attached to a label and a second region, in which the end region of the nucleic acid amplification probe further includes a third region complementary to the first region;
   the end region of the nucleic acid detection probe includes a fourth region complementary to the second region of the nucleic acid amplification probe;
   the digestion of the double-stranded nucleic acid region of the nucleic acid detection probe-target nucleic acid complex with the enzyme forms a first released end region including the fourth region; and
   the mixture has been further incubated under conditions to hybridize the fourth region of the first released end region to the second region of the nucleic acid amplification probe, thereby forming a first released end region-nucleic acid amplification probe complex including a double-stranded nucleic acid region, to digest the double-stranded nucleic acid region with the enzyme or a copy thereof, thereby forming a second released end region including the third region, and to
   hybridize the third region of the second released end region to the first region of an additional copy of the nucleic acid detection probe, thereby forming a second released end region-nucleic acid detection probe complex including a double-stranded nucleic acid region, and to digest the double-stranded nucleic acid region with the enzyme or a copy thereof, thereby forming a further copy of the first released end region.

In certain embodiments, the mixture has been further incubated for a period sufficient to repeat the hybridization of the fourth region of the first released end region to the second region of an additional copy of the nucleic acid amplification probe, and to repeat
   the hybridization of the second released end region to the first region of an additional copy of the nucleic acid detection probe and
   the digestion of the formed double-stranded nucleic acid region,
   thereby exponentially amplifying the first released end region and the second released end region.

In particular embodiments, the nucleic acid amplification probe is attached to the support of the nucleic acid detection probe.

In specific embodiments, each of the first regions and each of the second regions include DNA and each of the third regions and each of the fourth regions include RNA.

In certain embodiments, the target nucleic acid includes RNA or DNA.

In various embodiments, the first region is oriented parallel to the fourth region on each of the nucleic acid detection probes. In certain embodiments, the second region is oriented parallel to the third region on each of the nucleic acid amplification probes.

In some embodiments of the fortieth and forty first aspects, the end region includes a second region
complementary to the first region, and
located between the first region and the label;
the digestion of the double-stranded nucleic acid region of the nucleic acid detection probe-target nucleic acid complex with the enzyme forms a first released end region; and
the mixture has been further incubated under conditions to hybridize the second region of the first released end region to the first region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a further first released end region.

In certain embodiments, the mixture has been further incubated for a period sufficient to repeat:
the hybridization of the second region of the first released end region or the second region of the further first released end region to the first region of an additional copy of the nucleic acid detection probe,
and the digestion of the formed double-stranded nucleic acid region;
thereby exponentially amplifying the released end regions.

In particular embodiments, the target nucleic acid includes DNA or RNA.

In an embodiment, the target nucleic acid includes RNA and the mixture is incubated under conditions to hybridize the target nucleic acid or another copy thereof to the first region of a further copy of the nucleic acid detection probe, thereby forming a double-stranded nucleic acid region, and to digest the double-stranded nucleic acid region with the enzyme or a copy thereof, thereby forming a further copy of the first released end region.

In certain embodiments, each of the first regions includes DNA and each of the second regions includes RNA.

In particular embodiments, each of the first regions and the second regions includes DNA, and the digestion of the double-stranded nucleic acid region of the first released end region-nucleic acid detection probe complex with the enzyme results in the release of a second released end region including the label from the first released end region.

In specific embodiments, the mixture has been further incubated for a period sufficient to repeat
the hybridization of the second region of the further first released end region to the first region of an additional copy of the nucleic acid detection probe,
and the digestion of the formed double-stranded nucleic acid region;
thereby linearly amplifying the released end regions.

In certain embodiments, the target nucleic acid includes DNA, and the target nucleic acid is cleaved during the digestion of the double-stranded nucleic acid region of the nucleic acid detection probe-target nucleic acid complex.

In an embodiment, the target nucleic acid includes RNA, and the mixture is incubated under conditions to hybridize the target nucleic acid or another copy thereof to the first region of a further copy of the nucleic acid detection probe, thereby forming a double-stranded nucleic acid region, and to digest the double-stranded nucleic acid region with the enzyme or a copy thereof, thereby forming a further copy of the first released end region; and
the mixture has been further incubated for a period sufficient to repeat
the hybridization of the second region of the further first released end region to the first region of an additional copy of the nucleic acid detection probe,
and the digestion of the formed double-stranded nucleic acid region;
thereby non-linearly amplifying the released end regions.

In certain embodiments, the second region is oriented anti-parallel to the first region.

In some embodiments of the fortieth and forty first aspects, the nucleic acid detection probe includes a double-stranded block region. In certain embodiments, the double-stranded block region is located within the end region;
the end region includes a second region complementary to the first region and located between the double-stranded block region and the label;
the digestion of the double-stranded nucleic acid region of the nucleic acid detection probe-target nucleic acid complex with the enzyme forms a first released end region including the label, the second region, and the double-stranded block region; and
the mixture has been further incubated under conditions to hybridize the second region of the first released end region to the first region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a further first released end region.

In particular embodiments, the mixture has been further incubated for a period sufficient to repeat
the hybridization of the second region of the first released end region or the second region of the further first released end region to the first region of an additional copy of the nucleic acid detection probe,
and the digestion of the formed double-stranded nucleic acid region;
thereby exponentially amplifying the released end regions.

In specific embodiments, the target nucleic acid includes RNA or DNA.

In an embodiment, the target nucleic acid includes RNA and the mixture is incubated under conditions to hybridize the target nucleic acid or another copy thereof to the first region of a further copy of the nucleic acid detection probe, thereby forming a double-stranded nucleic acid region, and to digest the double-stranded nucleic acid region with the enzyme or a copy thereof, thereby forming a further copy of the first released end region.

In another embodiment, the target nucleic acid includes DNA, and the target nucleic acid is cleaved during the digestion of the double-stranded nucleic acid region of the nucleic acid detection probe-target nucleic acid complex with the enzyme.

In certain embodiments, each of the first regions includes DNA and each of the second regions includes RNA.

In particular embodiments, each of the first regions and the second regions includes DNA, and the digestion of the double-stranded nucleic acid region of the first released end region-nucleic acid detection probe complex with the enzyme results in release of a second released end region from the first released end region.

In an embodiment, the mixture has been further incubated for a period sufficient to repeat the hybridization of the second region of the further first released end region to the first region of an additional copy of the nucleic acid detection probe,
and the digestion of the formed double-stranded nucleic acid region;
thereby linearly amplifying the released end regions.

In certain embodiments, the first region is oriented parallel to the second region.

In particular embodiments, the double-stranded block region includes RNA.

In some embodiments of the fortieth and forty first aspects, the nucleic acid detection probe includes a first double-stranded block region and a second double-stranded block region. In certain embodiments, the labeled nucleic acid further includes a second region and a third region complementary to the second region;
the first region is located between the first double-stranded block region and the second double-stranded block region;
the end region includes the second double-stranded block region and the third region;
the third region is located between the second double-stranded block region and the label;
the second region is located between the first region and the attachment between the labeled nucleic acid and the support;
the first double-stranded block region is located between the first region and the second region;
the digestion of the double-stranded nucleic acid region of the nucleic acid detection probe-target nucleic acid complex with the enzyme forms a first released end region including the label, the third region, and the second double-stranded block region; and
the mixture has been further incubated under conditions to hybridize the third region of the first released end region to the second region of an additional copy of the nucleic acid detection probe, thereby forming a first released end region-nucleic acid detection probe complex including a double-stranded nucleic acid region, to digest the double-stranded nucleic acid region of the first released end region-nucleic acid detection probe complex with the enzyme or a copy thereof, thereby forming a second released end region including the first double-stranded block region, the first region, the second double-stranded block region, and the third region of the additional copy of the nucleic acid detection probe, and to
hybridize the third region of the second released end region to the second region of an additional copy of the nucleic acid detection probe, thereby forming a second released end region-nucleic acid detection probe complex including a double-stranded nucleic acid region, and to digest the double-stranded nucleic acid region of the second released end region-nucleic acid detection probe complex with the enzyme or a copy thereof, thereby forming a further copy of the second released end region.

In particular embodiments, the mixture has been further incubated for a period sufficient to repeat:
the hybridization of the third region of the first released end region to the second region of an additional copy of the nucleic acid detection probe, and/or the hybridization of the third region of the second released end region to the second region of an additional copy of the nucleic acid detection probe, and the digestion of the formed double-stranded nucleic acid region;
thereby exponentially amplifying the second released end region.

In specific embodiments, the first region is oriented anti-parallel to the second region and to the third region.

In certain embodiments, the target nucleic acid includes DNA or RNA.

In an embodiment, the target nucleic acid includes RNA and the mixture is further incubated under conditions to hybridize the target nucleic acid or another copy thereof to the first region of the second released end region, thereby forming a double-stranded nucleic acid region, and to digest the double-stranded nucleic acid region with the enzyme or a copy thereof, thereby forming a further copy of the first released end region.

In certain embodiments, each of the first regions and each of the second regions includes DNA and each of the third regions includes RNA.

In some embodiments of any of the aspects of the invention, the sample is obtained directly from a subject or specimen. In certain embodiments, the sample is not purified prior to the incubating step. In particular embodiments, the sample is not purified prior to the providing step.

In some embodiments of any of the aspects of the invention, the enzyme is capable of digesting double-stranded nucleic acids in a buffer that inhibits other nucleases. In certain embodiments, the mixture includes the buffer. In particular embodiments, the buffer is an SDS lysis buffer. In a specific embodiment, the buffer includes at least about 1% SDS and/or 5 mM $Mg^{2+}$.

In certain embodiments, the buffer includes proteinase K and/or an anionic detergent.

In some embodiments of any of the aspects of the invention, the enzyme is capable of digesting double-stranded nucleic acids at temperatures of 37-60° C. In certain embodiments, the incubation occurs at a temperature between 37-60° C.

In some embodiments of any of the aspects of the invention, the enzyme has high mismatch specificity. In certain embodiments, a single nucleotide difference between two strands in a double-stranded nucleic acid prevents digestion by the enzyme.

In some embodiments of any of the aspects of the invention, the enzyme can be stopped from digesting double stranded nucleic acids by EDTA.

In some embodiments of the fortieth and forty first aspects of the invention, the method further includes, prior to the detecting step, separating the undigested nucleic acid detection probes from the digested nucleic acid probes by isolating the end region attached to a label from the undigested nucleic acid detection probes bound to the support, in which the detecting step includes detecting the label attached to the isolated end regions.

In some embodiments of the forty first aspect of the invention, the method further includes, prior to the detecting step, separating the undigested nucleic acid detection probes from the digested nucleic acid probes by immobilizing the undigested nucleic acid detection probes on the support through binding of the first and second binding moieties, and isolating the end region attached to a label from the immobilized undigested nucleic acid detection probes, in which the detecting step includes detecting the label attached to the isolated end regions.

In embodiments of any of the aspects of the invention, the support includes a magnetic bead and the isolating the end region includes exposing the magnetic bead to a magnetic field. In alternate embodiments, the support includes an array and the isolating the end region includes removing the sample from the array.

In a forty second aspect, the invention features a method of detecting a target nucleic acid in a biological sample involving:

providing a mixture including:
(i) the biological sample,
(ii) an enzyme capable of selectively digesting double-stranded nucleic acids, and
(iii) a nucleic acid detection probe including a region complementary to the target nucleic acid;

incubating the mixture under conditions to hybridize the nucleic acid detection probe to the target nucleic acid, thereby forming a nucleic acid detection probe-target nucleic acid complex including a double-stranded nucleic acid region; and to digest the double-stranded nucleic acid region with the enzyme; and detecting the nucleic acid detection probe, whereby the presence of the nucleic acid detection probe is indicative of the presence of the target nucleic acid in the biological sample.

In some embodiments of the forty second aspect, the sample is not purified prior to the incubating step. In certain embodiments, the sample is not purified prior to the providing step.

In some embodiments of the forty second aspect, the enzyme capable of selectively digesting double-stranded nucleic acids is a duplex-specific nuclease. In particular embodiments, the nuclease is selected from the group consisting of Kamchatka Crab double stranded nuclease, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease.

In some embodiments of the forty second aspect, the providing and incubating steps occur within a single container. In particular embodiments, the container is a tube, well, droplet, or emulsion bead.

Definitions

By "support" is meant a substrate to which a molecule (e.g., a nucleic acid, such as a nucleic acid detection probe or a nucleic acid construct) can be attached and/or immobilized. The attachment can be a removable attachment (e.g., non-covalent binding of two moieties. Such moieties may include complementary nucleic acids or antibody-antigen pairs). Non-limiting examples of a support useful in the methods of the invention include a hydrogel, bead (e.g., a magnetic bead), or surface (e.g., the surface of a bead, such as a magnetic bead, a surface of a hydrogel, an interior surface of a container or chamber, or a surface of a flat substrate). A molecule removably attached to a support may be detached from the support by, e.g., enzymatic cleavage of a cleavage site on the molecule.

A "complement" of a nucleic acid sequence or a "complementary" nucleic acid sequence, as used herein, refers to a nucleic acid sequence or a region thereof that is in "antiparallel association" when it is aligned with a second nucleic acid sequence, such that the 5' end of one sequence is paired with the 3' end of the other. A pair of nucleic acids are referred to as being "complementary" if they contain nucleotides or nucleotide homologues that can form hydrogen bonds according to Watson-Crick base-pairing rules (e.g., G with C, A with T, or A with U) or other hydrogen bonding motifs such as, for example, diaminopurine with T, 5-methyl C with G, 2-thiothymidine with A, inosine with C, pseudoisocytosine with G, etc. Two nucleic acids of different types (e.g., a DNA and an RNA) can be complementary. A complementary nucleic acid sequence may include non-naturally-occurring bases, e.g., inosine and 7-deazaguanine. "Complementarity," which refers to the degree to which sequences of the two complementary strands match, e.g., according to Watson-Crick base pairing rules, may or may not be perfect (i.e., the duplexed portion of two strands have exactly complementary sequences). For example, stable duplexes of complementary nucleic acids may contain mismatched base pairs or unmatched bases. A given duplexed region may contain, e.g., at least about 20%, 30%, 40%, 50%, 60%, 70%, 80%, 90%, 95%, 99%, or 100% complementarity. Those skilled in the art of nucleic acid technology can determine duplex stability empirically considering a number of variables including, for example, the length of the nucleic acid, percent concentration of cytosine and guanine bases in the nucleic acid, ionic strength, and incidence of mismatched base pairs.

By "double-stranded nucleic acid," "double-stranded region," "duplex" or "duplexed" nucleic acid(s) is meant a pair of complementary single-stranded nucleic acids that have formed hydrogen bonds with each other, e.g., according to Watson-Crick base-pairing rules, to form a "double-stranded" nucleic acid. A duplex may include the entirety of one or both of the nucleic acids, or may include a portion of one or both of the nucleic acids. A duplex may include two nucleic acids of the same type (e.g., two DNAs or two RNAs), or may include two nucleic acids of different types (e.g., a DNA and an RNA). When complementary nucleic acid sequences form a stable duplex, they are said to "hybridize" or to be "hybridized." A nucleic acid strand that is not hybridized to another nucleic acid strand is referred to as "single-stranded." A nucleic acid strand including, in order, a first region, a single-stranded second region, and a third region hybridized to the first region, thereby forming a stem-loop structure, may be referred to as a "hairpin."

As used herein, "immobilize" refers to a state in which a molecule (e.g., a nucleic acid detection probe) is held at an approximately constant position relative to a substrate (e.g., a support). The molecule may be attached to the substrate directly or indirectly (e.g., by magnetic attraction or through an intermediary molecule). Immobilization of a molecule can be reversible or irreversible.

A "digested" nucleic acid, as used herein, means a nucleic acid that has been cleaved by a nuclease, such as, for example, a duplex-specific nuclease (e.g., Kamchatka Crab double stranded nuclease, Gammarus putative nuclease, Glass shrimp putative nuclease, Mangrove fiddler crab putative nuclease, Kamchatka crab DNase K, a DNase I nuclease, and sea urchin $Ca^{2+}$-$Mg^{2+}$-dependent endonuclease). An "undigested" nucleic acid is an intact nucleic acid, e.g., a nucleic acid that has not been cleaved by a nuclease. A nucleic acid including at least one duplexed portion can be cleaved by a duplex-specific nuclease at the duplexed portion, thereby producing a digested nucleic acid. The product of digestion by a duplex-specific nuclease can be, for example, a pair of single-stranded nucleic acids. Alternatively, digestion by a duplex-specific nuclease can yield one or more nucleic acids having a duplexed portion and/or a single-stranded portion.

By "quantum dot" is meant a semiconductor nanoparticle that can be excited by an external light source and then re-emit the absorbed light. Typically, a quantum dot of the invention is between 10 to 100 (e.g., about 10, 20, 30, 40, 50, 60, 70, 80, 90, or 100) atoms in diameter, and/or two to ten (e.g., about 2, 3, 4, 5, 6, 7, 8, 9, or 10) nm in diameter. A quantum dot can include a cadmium selenide (CdSe) core, a zinc sulfide (ZnS) shell, and/or a TOPO coating. A quantum dot may re-emit energy from absorbed light at a wavelength distinct from that of the absorbed light. The wavelength of photons re-emitted from a quantum dot can vary according to the size of the quantum dot.

A "label," as used herein, refers to a detectable moiety that may be attached to a molecule (e.g., a nucleic acid). Exemplary labels include, without limitation, a fluorophore, an affinity tag, an epitope tag, an enzyme, or any other label known in the art.

As used herein, "fluorophore" refers to a molecule or complex that can re-emit light upon excitation by an external light source. A fluorophore may absorb light energy and re-emit the energy at a longer wavelength than the absorbed light. Exemplary fluorophores include, but are not limited to, quantum dots, fluorescent proteins (e.g., GFP, YFP, EGFP, dsRed, mCherry, and CFP), fluorescent compounds (e.g., fluorescein, FITC, rhodamine, TRITC, DAPI, coumarin, cyanine, xanthene, naphthalene, oxadiazole, anthracene, pyrene, oxazine, acridine, arylmethine, tetrapyrroles, Alexa Fluor compounds, BODIPY, and/or derivatives thereof). A fluorescent protein may be fused to another protein to form a fusion protein, or may be attached to a compound such as biotin or streptavidin. A fluorophore may be prevented from fluorescing (or "quenched") by a "quencher." In some instances, a quencher may only prevent the fluorophore from fluorescing if the quencher is in close physical proximity to the fluorophore, as is well understood in the art.

By "probe," "nucleic acid probe," or "detection probe" is meant a molecule or complex useful for detection of a desired target molecule (e.g., a nucleic acid). A probe may include a nucleic acid sequence capable of hybridizing with a target nucleic acid or a portion thereof. A probe of the invention may include a support and/or a label. For example, a probe may include a nucleic acid labeled with a fluorophore (e.g., a quantum dot). The fluorophore may be attached to the nucleic acid it labels via biotin and streptavidin moieties. A probe may further include a nucleic acid construct capable of hybridizing to at least a portion of a labeled nucleic acid. The nucleic acid construct may be attached to the support, thereby bridging the support to the labeled nucleic acid.

By "sample" is meant any mixture containing one or more target nucleic acids. A sample can be, for example, a biological sample obtained from a subject (e.g., a mammal, preferably a human). Exemplary biological samples that may be used in the methods of the invention include, without limitation, blood, peripheral blood, a blood component (e.g., serum, isolated blood cells, or plasma), buccal samples (e.g., buccal swabs), nasal samples (e.g., nasal swabs), urine, fecal material, saliva, amniotic fluid, cerebrospinal fluid (CSF), synovial fluid, tissue (e.g., from a biopsy), pancreatic fluid, chorionic villus sample, cells, extracellular matrix, cultured cells, cellular organelles, cancerous cells, or any combination or derivative thereof. In certain embodiments, the biological sample is or includes blood. In certain embodiments, the biological sample includes a clinical sample (i.e., a sample obtained from a subject) or a food sample (i.e., a sample suitable for consumption by a subject). Furthermore, the tested sample can be processed (e.g., washed) prior to testing in the methods of the invention. Alternatively, the sample can be an unprocessed sample.

"Lysis buffer," as used herein, means any solution capable of inducing the lysis of one or more cells, as are well known in the art. Cell lysis may result in the release of nucleic acids detectable by the methods described herein. Lysis buffers may include, for example, sodium dodecyl sulfate (SDS) and/or proteinase K. A lysis buffer may be added to a sample (e.g., a clinical sample) to induce the lysis of cells present in the sample.

As used herein, the term "binding moiety" refers to a molecule or a portion of a molecule capable of binding to another molecule, e.g., a desired target molecule. In particular, a binding moiety can be a nucleic acid sequence capable of hybridizing to a desired target nucleic acid or a portion thereof. For example, a detection probe may contain a binding moiety complementary to at least a portion of a target nucleic acid and/or a binding moiety complementary to a portion of a labeled nucleic acid that, in turn, includes a region capable of hybridizing with a target nucleic acid. Other binding moieties are known in the art, and include antibodies, biotin, etc.

BRIEF DESCRIPTION OF THE DRAWINGS

FIG. 1 shows a duplex-specific nuclease (DSN)-based scheme for detecting a target RNA molecule. A biotinylated detection probe, which is attached to a streptavidin coated fluorophore (e.g., a quantum dot or fluorescent bead) and is immobilized on a surface, hybridizes to an RNA target. The portions of the detection probe and the target that hybridize form a duplex that is cleaved by a duplex-specific nuclease, releasing an end portion of the detection probe, depicted as the probe particle. Probe particles, which include the fluorophores, are captured on a strip, in which biotinylated capture probes are immobilized on a detection surface of the strip. The biotinylated capture probes bind to the streptavidin coating the fluorophores, thereby capturing the probe particles.

FIG. 2 shows a DSN-based scheme for detecting a target RNA molecule. This strategy utilizes a detection probe that includes a magnetic particle attached to a nucleic acid with a poly-T region, which, in turn, is hybridized to a poly-A region on a biotinylated nucleic acid. The biotinylated nucleic acid is bound to a streptavidin-coated fluorophore (e.g., a quantum dot or fluorescent bead). Upon binding of an RNA target to the biotinylated nucleic acid, a duplex-specific nuclease cleaves the resultant duplex, releasing an end portion of the biotinylated nucleic acid with the attached fluorophore, depicted as the probe particle. The resulting mixture is then applied to a strip containing magnetic strips along a surface, which capture the magnetic particles. Uncleaved detection probes, in which the fluorophores are attached to the magnetic bead, are also captured by the magnetic strips. The probe particles can then be isolated using a detection surface on which biotinylated capture probes are attached.

FIG. 3 shows a scheme for exponential duplex-specific amplification (DSA) using a single probe. Probe 1 is attached to a surface and includes DNA regions a and b', as well as RNA region b. Region a is complementary to region a' on an RNA target. The probe is biotinylated and attached to a streptavidin-coated fluorophore. Cleavage of region a of Probe 1 by a duplex-specific nuclease after hybridization with the target RNA results in the production of Probe 2, leaving a small amount of the Probe 1 segment including region b' attached to the surface.

FIG. 4 shows further stages in a scheme for exponential DSA, in which Probe 2 hybridizes to Probe 1, resulting in cleavage and production of Probe 3. Each of Probes 2 and 3 then proceed to different pathways, as shown in FIGS. 5A and 5B.

FIGS. 5A and 5B show further stages in a scheme for exponential DSA: the Probe 3 pathway and the Probe 2 pathway, respectively. In the Probe 3 pathway (FIG. 5A), region b of Probe 3 hybridizes with region b' of another copy of Probe 1, which is cleaved to yield an additional copy of Probe 3. Note that the original Probe 3 is not cleaved. In the Probe 2 pathway (FIG. 5B), region b of Probe 2 hybridizes with region b' of another copy of Probe 1, which is cleaved to yield an additional copy of Probe 3. Note that the original Probe 2 is not cleaved.

FIG. 6 shows the results of multiple rounds of exponential duplex-specific nuclease-based amplification strategy as depicted in FIGS. 3, 4, and 5. T=target RNA; P1=Probe 1; P2=Probe 2; P3=Probe 3.

FIG. 8 shows a scheme for exponential DSA using multiple probes. Probe 1 includes regions a and b, of which region a is DNA and region b is RNA. Region a is complementary to region a' on an RNA target. Probe 3 includes regions b' and a', of which region b' is DNA and region a' is RNA. Both probes are biotinylated and attached to streptavidin-coated labels (e.g., fluorophores, such as a quantum dot or bead). Hybridization of the RNA target to region a of Probe 1 leads to duplex-specific nuclease degradation of region a of Probe 1, producing Probe 2.

FIGS. 9A and 9B show further stages of a scheme for exponential DSA. FIG. 9A shows how region b of Probe 2 hybridizes to region b' of Probe 3, resulting in cleavage of region b' and the production of Probe 4. Probe 2 is not cleaved, as region b is composed of RNA. FIG. 9B shows how region a' of Probe 4 hybridizes to region a of Probe 1, resulting in cleavage of region a and the production of a new copy of Probe 2. Probe 4 is not cleaved, as region a' is composed of RNA.

FIGS. 10A and 10B show the results of multiple rounds of an exponential DSA scheme as depicted in FIGS. 8, 9A, and 9B. T=target RNA; P1=Probe 1; P2=Probe 2; P3=Probe 3; P4=Probe 4.

FIG. 11 shows a probe design and scheme for exponential DSA of a DNA target utilizing two distinct probes.

FIG. 12 shows a second probe design and further stages of a scheme for exponential DSA of a DNA target.

FIG. 13 shows further stages of a scheme for exponential DSA of a DNA target utilizing two distinct probes.

FIG. 14 shows the results of multiple rounds of a scheme for exponential DSA of a DNA target as depicted in FIGS. 11, 12, and 13. T=target DNA; P1=Probe 1; P2=Probe 2; P3=Probe 3; P4=Probe 4.

FIG. 17 shows the results of multiple rounds of a scheme for exponential DSA of a DNA target using a single probe as depicted in FIGS. 15 and 16. T=target DNA; P1=Probe 1; P2=Probe 2.

FIG. 20 shows the results of multiple rounds of a scheme for exponential DSA of an RNA target using a single probe as depicted in FIGS. 18 and 19. T=target RNA; P1=Probe 1; P2=Probe 2.

FIG. 23 shows the results of multiple rounds of a scheme for linear DSA of a DNA target using a single probe as depicted in FIGS. 21 and 22. T=target DNA; P1=Probe 1; P2=Probe 2; P3=Probe 3.

FIG. 26 shows the results of multiple rounds of a scheme for geometric DSA of an RNA target as depicted in FIGS. 24 and 25. T=target RNA; P1=Probe 1; P2=Probe 2; P3=Probe 3.

FIG. 27 shows the results of further rounds of a scheme for geometric DSA of an RNA target as depicted in FIGS. 24 and 25. T=target RNA; P1=Probe 1; P2=Probe 2; P3=Probe 3.

FIG. 28 shows the results of multiple rounds of a scheme for exponential DSA of an RNA target as depicted in FIGS. 18 and 19. T=target RNA; P1=Probe 1; P2=Probe 2.

FIG. 29 shows the results of additional rounds of a scheme for exponential DSA of an RNA target, and a comparison of rate of amplification between this scheme and polymerase chain reaction (PCR) as depicted in FIGS. 18 and 19. T=target RNA; P1=Probe 1; P2=Probe 2.

FIG. 32 shows the results of multiple rounds of a scheme for exponential DSA of an RNA target utilizing a probe containing a double-stranded RNA block as depicted in FIGS. 30 and 31. T=target RNA; P1=Probe 1; P2=Probe 2.

FIG. 35 shows the results of multiple rounds of a scheme for linear DSA of a DNA target utilizing a probe containing a double-stranded RNA block as depicted in FIGS. 33 and 34. T=target DNA; P1=Probe 1; P2=Probe 2; P3=Probe 3.

FIG. 38 shows the results of multiple rounds of a scheme for exponential DSA of a DNA target utilizing a probe containing a double-stranded RNA block as depicted in FIGS. 36 and 37. T=target DNA; P1=Probe 1; P2=Probe 2.

FIG. 43 shows a probe design and the initial stages of a scheme for exponential DSA of a DNA target using a probe containing two double-stranded RNA blocks.

FIG. 44 shows how an RNA target can participate in further cleavage of a cleaved probe (Probe 3) in the scheme for exponential DSA of an RNA target described in FIGS. 39-42.

FIG. 45A shows the results of multiple rounds of a scheme for exponential DSA of an RNA target using a probe containing two double-stranded RNA blocks as depicted in FIGS. 39, 40, 41, 42, and 44. T=target RNA; P1=Probe 1; P2=Probe 2; P3=Probe 3.

FIG. 45B shows the results of multiple rounds of a scheme for exponential DSA of a DNA target using a probe containing two double-stranded RNA blocks as depicted in FIG. 43. T=target RNA; P1=Probe 1; P2=Probe 2; P3=Probe 3.

FIG. 47 shows further stages of a scheme for exponential DSA of a DNA target using a probe with two cleavage sites, which bifurcates along two pathways: the Probe 2 pathway and the Probe 3 pathway.

FIG. 48 illustrates the Probe 3 pathway for a scheme for exponential DSA of a DNA target using a probe with two cleavage sites.

FIG. 49 illustrates the Probe 2 pathway for a scheme for exponential DSA of a DNA target using a probe with two cleavage sites.

FIG. 50 shows the results of multiple rounds of a scheme for exponential DSA of a DNA target using a probe with two cleavage sites as depicted in FIGS. 46, 47, 48, and 49. T=target RNA; P1=Probe 1; P2=Probe 2; P3=Probe 3.

FIG. 51 shows probe designs and a scheme for exponential DSA of a DNA-RNA hybrid target nucleic acid.

FIG. 52 shows further stages of a scheme for exponential DSA of a DNA-RNA hybrid target nucleic acid.

FIG. 53 shows additional stages of a scheme for exponential DSA of a DNA-RNA hybrid target nucleic acid.

FIG. 54A show probe designs and a scheme for exponential DSA of a DNA target nucleic acid.

FIG. 54B shows the results of multiple rounds of a scheme for exponential DSA of a DNA target nucleic acid as depicted in FIG. 54A. T=target RNA; P1=Probe 1; P3=Probe 3.

FIG. 71 shows additional probe designs and steps in a scheme for exponential DSA of a DNA target using multiple hairpin trigger probes.

FIGS. 72A-72B show probe designs and a scheme for geometric DSA of an RNA target using a hairpin trigger probe lacking mismatches, a target displacing oligo, and a hairpin reporter probe.

FIGS. 73A-73B show probe designs and a scheme for exponential DSA of an RNA target using two hairpin trigger probes lacking mismatches and a target displacing oligo.

FIGS. 74A-74B show probe designs and an alternate scheme for geometric DSA of an RNA target using a hairpin trigger probe lacking mismatches, a target displacing oligo, and a hairpin reporter probe.

FIGS. 75A-75B show probe designs and an alternate scheme for geometric DSA of an RNA target using a hairpin trigger probe lacking mismatches and a hairpin reporter probe.

FIG. 76 shows probe designs and a scheme for geometric DSA with beacon detection using two hairpin probes.

FIG. 77 shows probe designs and a scheme for geometric DSA with surface detection using two hairpin probes.

FIG. 78 shows a scheme for detection of a fluorescent probe generated according to the schemes shown in FIGS. 76 and 77.

FIGS. 79A-79B show probe designs and a scheme for exponential DSA with beacon detection using two hairpin probes.

FIGS. 80A-80B show probe designs and a scheme for exponential DSA with surface detection using two hairpin probes.

DETAILED DESCRIPTION OF THE INVENTION

Figure 5B:
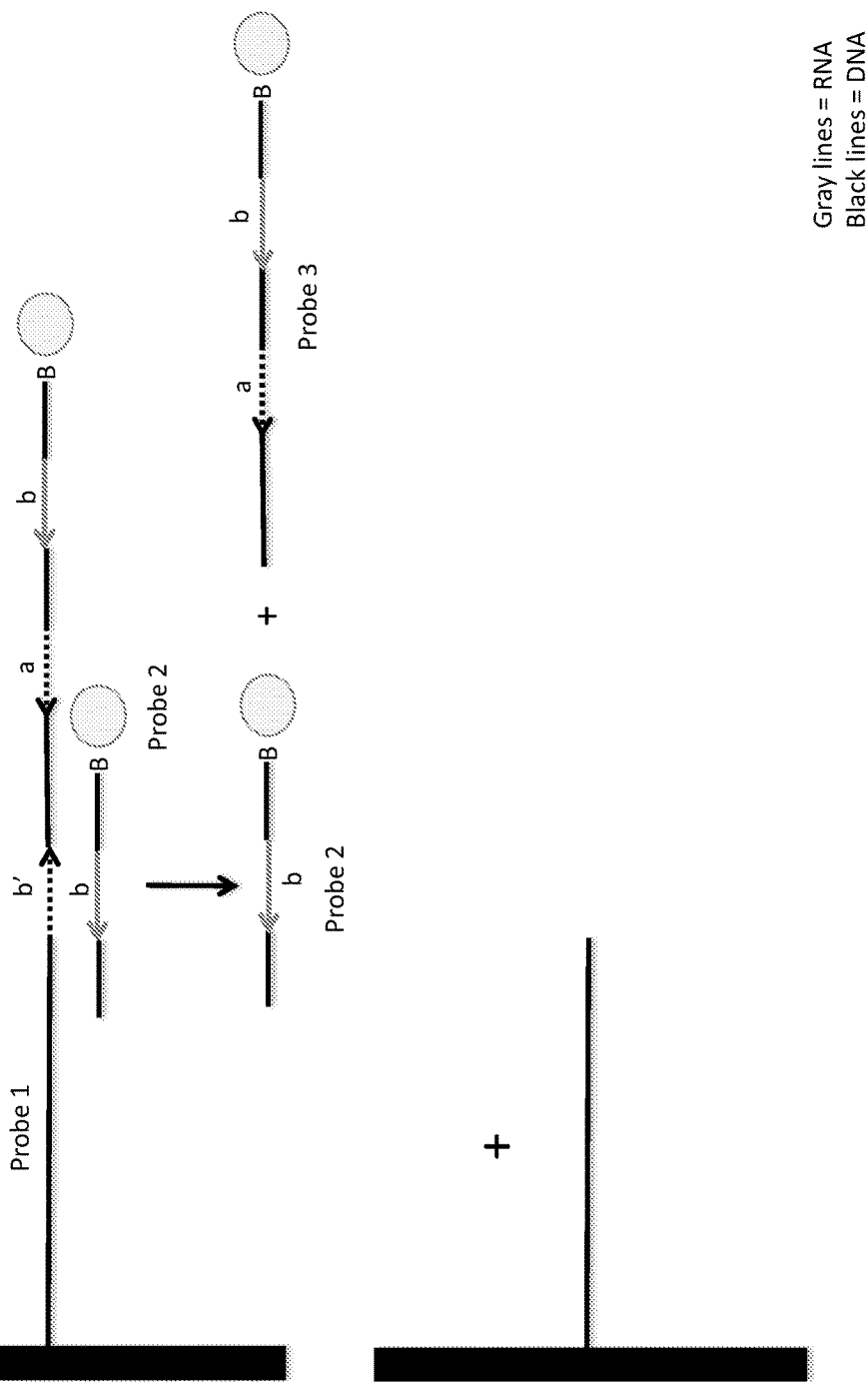

The present invention provides methods for detecting a target nucleic acid in a sample. The presence of a target nucleic acid is determined, by incubating, for example, the target nucleic acid with a detection probe (e.g., a detection probe containing a nucleic acid sequence complementary to at least a portion of the target nucleic acid) and a nuclease enzyme (e.g., a duplex-specific nuclease) that specifically cleaves double-stranded nucleic acids. The detection probe may be attached to a support. Hybridization between the detection probe and the target nucleic acid leads to cleavage of the detection probe by the nuclease, releasing a portion of the probe attached to a fluorophore (e.g., a quantum dot), enzyme, binding moiety, or other detectable agent. The portions of the digested probes attached to the fluorophore can be separated from unbound and/or undigested probe and detected in order to determine the presence of the target nucleic acid in the sample. The target nucleic acid may be present in a sample (e.g., a biological sample), such as a sample that has not been purified. Detection of digested probe may involve directly detecting a signal generated as a result of DSN cleavage, or alternatively, may involving separation of cleaved probes, followed by detection. Thus, the invention enables rapid and accurate analysis of a sample for the presence of desired nucleic acid biomarkers.

Targets

The invention provides methods for detecting target nucleic acids of interest in a sample, e.g., by using detection probes that contain a detectable moiety (e.g., a fluorophore) and that are capable of hybridizing with the target nucleic acids. For example, the detection probe may contain a nucleic acid sequence complementary to at least a portion of the target nucleic acid. A detection probe/target nucleic acid duplex can be cleaved by a duplex-specific nuclease to free a portion of the detection probe (e.g., the detectable moiety), which can then be separated from unbound probe and detected. Target nucleic acids may include, for example, RNA (e.g., mRNA, rRNA, tRNA, non-coding RNA, and fragments thereof), DNA (e.g., cDNA, genomic DNA, plasmids, cosmids, fosmids, and fragments thereof), modified nucleic acids (e.g., epigenetically modified nucleic acids, for example, methylated nucleic acids), and artificial nucleic acids (e.g., PNA, morpholinos, LNA, GNA, ZNA, and TNA). In certain embodiments, a target nucleic acid includes mRNA. For example, mRNA molecules can be isolated from other nucleic acids using a detection probe containing a poly-T sequence. Alternatively, a particular mRNA of interest (e.g., an mRNA encoding a polypeptide of interest) may be detected using a detection probe containing a sequence capable of hybridizing with at least a portion of the mRNA of interest (e.g., a sequence complementary to a portion of the mRNA of interest). The mRNA may, for example, encode a biomarker of interest. In other embodiments, the target nucleic acid includes ribosomal RNA (rRNA).

Nucleases

The present invention utilizes nucleases (e.g., duplex-specific nucleases) to digest detection probes that have annealed to a target nucleic acid in a sample. Nucleases are a class of enzymes capable of cleaving the phosphodiester bonds connecting nucleotides in nucleic acids (e.g., RNA or DNA). Duplex-specific nucleases (DSNs) are a subcategory of nucleases that selectively cleave double-stranded nucleic acids, for example, a detection probe-target nucleic acid complex. Enzymatic cleavage of a detection probe-target nucleic acid duplex can result in the release of a portion of the detection probe, e.g., containing one or more detectable moieties (e.g., fluorophores), which can, in turn, subsequently be detected to determine the presence of the target nucleic acid in the sample. A duplex-specific nuclease may preferentially cleave a particular nucleic acid type in a duplex of two different nucleic acid types. For example, a duplex-specific nuclease may preferentially cleave the DNA strand in a DNA-RNA duplex. A duplex-specific nuclease may also cleave nucleic acids of the same type in a duplex (e.g., a DNA/DNA duplex). Furthermore, a duplex-specific nuclease may preferentially cleave duplexes in which the two strands have greater complementarity in the duplexed region. For example, a duplex having perfect complementarity can be preferentially cleaved over a duplex having one or more mismatched base pairs (e.g., about 1, 2, 3, 4, 5, 6, 7, 8, 9, 10, 15, 20, 25, 30, 35, 40, 50, 60, 70, 80, 90, or 100 mismatched base pairs).

Duplex-specific nucleases, such as those described herein, may be robust. For example, the duplex-specific nucleases may be capable of digesting duplexed nucleic acids in, e.g., a buffer that inhibits other nucleases (e.g., SDS lysis buffer). In certain embodiments, duplex-specific nucleases are active in a solution having one or more of the following properties: containing at least about 1% SDS and/or 5 mM $Mg^{2+}$. Furthermore, the duplex-specific nucleases may be resistant to proteases (e.g., proteinase K). Duplex-specific nucleases can also be thermophilic, for example, such that nuclease activity occurs at temperatures of 37-60° C. Moreover, duplex-specific nucleases can have high mismatch specificity, such that single nucleotide differences between two strands in a duplex may be able to prevent duplex-specific nuclease cleavage. Duplex-specific nuclease reactions may be stopped, for example, by EDTA. As such, duplex-specific nucleases can, in some embodiments, carry out cleavage of duplexed nucleic acids directly in a biological sample obtained from a subject or specimen (e.g., without requiring an intermediate purification step).

In preferred embodiments, lysis buffers that release nucleic acid for detection may also inhibit nucleases. Thus, such embodiments support cell lysis and inactivate nucleases. Two general approaches useful in the disclosed methods involve the use of anionic detergents to inactivate the nucleases and/or the use of proteinase K to digest away the nucleases. In the presence of detergent (e.g., SDS), both lysis and nuclease inactivation can be achieved, for example, at 1% SDS.

In preferred embodiments, a duplex-specific nuclease (DSN) is a nuclease that typically exhibits a preference, if not a strong specificity, for duplex versus single-stranded nucleic acids. DSNs are typically characterized by cleavage of double-stranded DNA or double-stranded DNA of an RNA/DNA duplex or both, and little or no cleavage of single-stranded nucleic acids. Exemplary proteins of the DSN family include, without limitation, Kamchatka crab DSN (also referred to as Kamchatka crab nuclease), southern house mosquito DSN, mitochondrial nuclease from *Drosophila melanogaster*, and a nuclease from arctic shrimp, as well as other arthropods identified by BLAST searches (see, for example, Gene 418, 41-48 (2008), the sequences of which are incorporated herein by reference). The Kamchatka crab DSN mRNA sequence can be found at GenBank accession number AF520591. Additional members include kurma prawn and Fiddler crab (PloS One 5, e10295 (2010), the sequences of which incorporated herein by reference). DSNs may be characterized by highly conserved amino acids including, for example, conserved amino acids in a conserved NUC domain (Gene 418, 41-48 (2008) and PloS One 5, e10295 (2010)).

Other DSNs include Gammarus putative nuclease, Glass shrimp (Palaemonidae) putative nuclease, and Mangrove fiddler crab (*Uca crassipes*) putative nuclease. And still other DSNs include Kamchatka crab DNase K, DNase I family members, non-specific shrimp nuclease, Sea urchin $Ca^{2+}$—$Mg^{2+}$-dependent endonuclease, RNase H, and ExoIII. Such duplex-specific nucleases and conditions suitable for their use are described, e.g., in U.S. Pat. Nos. 7,435,794 and 5,011,769, each of which is incorporated herein by reference for the purpose of their sequences. The Enzyme Commission (EC) number for DNase I is 3.1.2.1.1. The EC number for RNase H is EC 3.1.26.4. The EC number for Exo III is 3.1.11.2.

The Kamchatka crab DSN, like the other described nucleases, is especially useful because it is active in the presence of proteinase K, 1% SDS, or both.

Detection Probes

The methods of the present invention involve detection of a target nucleic acid in a sample using, e.g., detection probes capable of binding to the target nucleic acid. Detection probes of the invention may include one or more of each of the following: a support, a labeled nucleic acid, and/or a binding moiety. For example, a detection probe may include a support attached to a labeled nucleic acid (e.g., a labeled nucleic acid containing a region capable of hybridizing to at least a portion of the target nucleic acid). Alternatively, a detection probe may include a support attached to an attachment moiety (e.g., a nucleic acid, such as a nucleic acid having a region complementary to a labeled nucleic acid), in which the attachment moiety is capable of binding to a labeled nucleic acid (e.g., by hybridization), which in turn contains a region capable of hybridizing to the target nucleic acid (e.g., a sequence complementary to at least a portion of the target nucleic acid). A labeled nucleic acid and the target nucleic acid may include the same type of nucleotide (e.g., labeled RNA and target RNA, or labeled DNA and target DNA) or different types of nucleotides (e.g., labeled DNA and target RNA, or labeled RNA and target DNA).

A labeled nucleic acid can further include an end region attached to a label or an end region that is a label. Exemplary labels include fluorophores, including, but not limited to, quantum dots, fluorescent proteins (e.g., GFP, YFP, EGFP, dsRed, mCherry, and CFP), fluorescent compounds (e.g., fluorescein, FITC, rhodamine, TRITC, DAPI, coumarin, cyanine (e.g., Cy2, Cy3, and Cy5), xanthene, naphthalene, oxadiazole, anthracene, pyrene, oxazine, acridine, arylmethine, tetrapyrroles, Alexa Fluor compounds, BODIPY, and/ or derivatives or conjugates thereof). Further examples of labels that may be used to label nucleic acids (e.g., a labeled nucleic acid in a detection probe) include a binding moiety (e.g., biotin or streptavidin) or an enzyme (e.g., horseradish peroxidase, glucose oxidase, β-galactosidase, luciferase, or alkaline phosphatase).

In preferred embodiments, the label includes a quantum dot. The quantum dot may be, for example, conjugated to at least one binding moiety (e.g., streptavidin, avidin, or neutravidin) that recognizes a counterpart binding moiety (e.g., biotin) attached to a capture probe that recognizes the target nucleic acid. The target nucleic acid may also bind a reporter probe containing a further label, thus forming a sandwiched hybrid containing the target nucleic acid, the reporter probe, and the capture probe. The sandwiched hybrid can then bind to the streptavidin-conjugated quantum dot to form a nanosensor assembly. In certain embodiments, the pair of labels can be used for fluorescence resonance energy transfer (FRET). For example, the quantum dot can be exposed to light having a first wavelength, which then transfers some of the energy from the absorbed light to the label on the reporter probe (the remainder is re-emitted as light having a second wavelength). The reporter probe then re-emits the energy as light having a third wavelength. In a particular embodiment, the photon exciting the quantum dot has a first wavelength of 488 nm, the photon emitted by the quantum dot has a second wavelength of 605 nm, and the photon emitted by the capture probe label has a third wavelength of 670 nm.

In any of the embodiments of the invention, a labeled nucleic acid can include a region capable of hybridizing with a target nucleic acid (e.g., a region complementary to at least a portion of the target nucleic acid) to form a duplex (e.g., a duplex that can be cleaved by a duplex-specific nuclease). Cleavage of a duplex formed between the labeled nucleic acid and a target nucleic acid by, for example, a duplex-specific nuclease may result in the release of an end portion of the labeled nucleic acid (e.g., release of the end portion into the surrounding solution). In certain embodiments, the label is attached to the end portion of the labeled nucleic acid, such that the released end portion remains attached to the label.

Particular target nucleic acids can be preferentially targeted using certain detection probes. For example, mRNA targets can be selected using detection probes that contain, as the binding moiety, a poly-T region capable of hybridizing to a poly-A tail. Alternatively, denatured cDNAs can be selected using detection probes that contain, as the binding moiety, a poly-T region and/or a poly-A region. A specific nucleic acid sequence of interest can be targeted using detection probes that contain sequences capable of hybridizing to the specific nucleic acid sequence (e.g., a sequence complementary to the specific nucleic acid sequence to be targeted). Increased specificity can be obtained, for example, by increasing the length of the complementary sequence in the detection probe.

Supports

Detection probes are typically attached to a support, which can be used to immobilize the detection probes and/or be used to separate excess probes from probes that have bound to target nucleic acids. Exemplary supports useful in the disclosed methods include, without limitation, hydrogels, beads (e.g., magnetic beads), or surfaces (e.g., an interior surface of a container or a surface of a flat substrate). For example, one or more detection probes can be attached to a magnetic bead prior to incubation with a sample containing target nucleic acids, thus permitting separation of detection probes (and portions thereof) attached to the magnetic beads from the surrounding supernatant by exposing the sample solution to a magnetic field (e.g., a magnetic field generated by magnetic strips attached to a surface).

Alternatively, the support can include immobilized capture probes (e.g., capture probes attached to a surface, bead, or hydrogel) that can recognize (e.g., by hybridization to) a portion of a target nucleic acid and/or a portion of a detection probe, such that the capture probe target (e.g., the target nucleic acid and/or the detection probe) is immobilized upon binding to the capture probe. The capture probes may include a binding moiety such as a nucleic acid capable of hybridization to the capture probe's target. The binding moiety may be directly attached to the support. In certain embodiments, the capture probe is directly attached to the support and includes a binding moiety that recognizes the label on a released portion of a detection probe. For example, the capture probe may include a biotin moiety, which binds to a streptavidin moiety on the label of the capture probe. Because each streptavidin can bind to multiple biotins, the capture probe itself can be made up of, e.g., a biotinylated nucleic acid bound to the streptavidin. Alternatively, the capture probe may include a further binding moiety that can bind to a substrate attached to the support. For example, the capture probe may include a biotinylated binding moiety (e.g., a nucleic acid capable of hybridizing to the capture probe's target), and the support can include immobilized streptavidin, which strongly binds to biotin.

Samples

The present invention features methods of detecting a target nucleic acid in a sample. Samples useful in the methods described herein may include any mixture containing at least one target nucleic acid. Typically, the sample will be a biological sample, such as a biological sample obtained from a subject (e.g., a human) or a specimen, or an in vitro biological sample (e.g., one or more cells in culture, a tissue culture, a cell extract, or a cell-free system). The sample may also be, in some instances, a food sample, environmental sample, or industrial sample. Biological samples that may be used in the methods of the invention include, for example, blood, whole blood, peripheral blood, a blood component (e.g., serum, isolated blood cells, or plasma), buccal samples (e.g., buccal swabs), nasal samples (e.g., nasal swabs), urine, fecal material, saliva, amniotic fluid, cerebrospinal fluid (CSF), synovial fluid, tissue (e.g., from a biopsy), pancreatic fluid, chorionic villus sample, cells, extracellular matrix, cultured cells, cellular organelles, cancerous cells, pathogens (e.g., bacterial cells, such as *E. coli*), or any combination or derivative thereof. In some instances, the biological sample includes a clinical sample. A biological sample may include, e.g., live cells and/or cells that have been lysed. In some embodiments of the invention, detection probes and/or duplex-specific nucleases can be added directly to a sample (e.g., a biological sample obtained from a subject or a specimen), such that, for example, the detection probes hybridize to the at least one target nucleic acids in the sample in the context of the biological sample. In certain instances, a sample may be incubated with a DSN at a temperature of approximately 60° C. (e.g., between about 55° C.-65° C.). In various instances, a reaction mixture including a sample, a DSN, and a probe capable of detecting the sample may have a volume of about 100 µl.

Owing to the robustness of the duplex-specific nucleases described herein, cleavage of detection probe-target nucleic acid duplexes can also occur directly in the biological sample, without need for a purification and/or amplification step. In particular, the nucleic acid detection methods described herein may be used in complex samples, such as unprocessed biological samples (e.g., biological samples that have not undergone purification and/or amplification). For example, the methods may be useful for detection of target nucleic acids in clinical samples or food samples. In some instances, the biological samples may include cells that have been lysed to release nucleic acids into the solution. Lysis of cells in a sample may be performed according to methods well understood in the art. In certain instances, cells are lysed using a lysis buffer including one or more of the following: SDS (0-1.0%), DTT, $MgCl_2$, $CaCl_2$, and/or Tris buffer. In other instances, the biological samples may include cells that have not been lysed.

Clinical Samples

Biological samples that may be tested using the methods described herein include clinical samples. For example, the methods of the invention may be used to detect one or more target nucleic acids in a clinical sample obtained, e.g., directly from a subject (e.g., a human subject). Preferably, the clinical sample has not undergone purification or amplification. In some instances, a lysis buffer may be added to a clinical sample, e.g., to lyse cells from the subject. Exemplary clinical samples that may be tested using the methods of the invention include, without limitation, blood, whole blood, peripheral blood, a blood component (e.g., serum, isolated blood cells, or plasma), buccal samples (e.g., buccal swabs), nasal samples (e.g., nasal swabs), urine, fecal material, saliva, amniotic fluid, cerebrospinal fluid (CSF), synovial fluid, tissue (e.g., from a biopsy), pancreatic fluid, chorionic villus sample, cells, extracellular matrix, cultured cells, cellular organelles, cancerous cells, pathogens (e.g., bacterial cells, such as *E. coli*), a tissue fluid specimen, a viral specimen, a cerebrospinal specimen, a lymphoid specimen, a lung specimen (e.g., bronchial alveolar lavage), a bone marrow specimen, a nasopharyngeal specimen, a pericardial specimen, a peritoneal specimen, a pleural specimen, a synovial specimen, or any combination or derivative thereof.

In some instances, the target nucleic acid to be detected originates from the clinical sample (e.g., a nucleic acid indicative of a disease or disorder, such as cancer, an immune disorder, a neurological disorder, or any other disorder known in the art). In other instances, the target nucleic acid to be detected originates from a pathogen infecting the subject from which the clinical sample is obtained. For example, the pathogen may contain or release a nucleic acid (e.g., DNA or RNA) that can be detected according to the methods of the invention. Non-limiting examples of pathogens from which target nucleic acids can be detected according to the methods of the invention include bacteria, viruses, and/or fungi (e.g., any infectious pathogen known in the art).

Food Samples

The methods of the invention may be used to detect a target nucleic acid in a food sample (i.e., a sample suitable for consumption by a subject). Preferably, a food sample is suitable for consumption by a human subject, but a food sample may also be suitable for consumption by subjects such as, for example, non-human animals (e.g., fish, birds, reptiles, insects, crustaceans, or mammals, such as domesticated mammals) and crops. Exemplary food samples include, without limitation, meat (e.g., beef, pork, chicken, turkey, duck, goose, fish, lamb, venison, goat, rabbit, or combinations, portions, and derivatives thereof) and plants (e.g., leaves, stems, grains, roots, tubers, flowers, fruits, or combinations, portions, or derivatives thereof). Meat samples can include, for example, any body tissues or fluids (e.g., muscle, dermal tissue, connective tissue, blood, urine, cerebrospinal fluid (CSF), synovial fluid, bone, marrow, or brain). Food samples can include fresh samples and/or samples that have been prepared, e.g., by cooking, brining, chopping, mincing, slicing, and/or mixing with substances such as, for example, preservatives. In some instances, the target nucleic acid to be detected originates from the food sample. In other instances, the target nucleic acid to be detected originates from a contaminant of the food sample, such as a pathogen. For example, the pathogen may contain or release a nucleic acid (e.g., DNA or RNA) that can be detected according to the methods of the invention. Non-limiting examples of pathogens from which target nucleic acids can be detected according to the methods of the invention include bacteria, viruses, and/or fungi (e.g., any pathogen known to contaminate food samples). For example, the methods described herein may be used to detect nucleic acids originating from, e.g., *Salmonella* (e.g., *Salmonella enterica*, such as *Salmonella* of a serovar selected from the group consisting of *Enteritidis, Typhimurium*, Newport, and Javiana), *E. coli* (e.g., *E. coli* O157:H7), *Clostridium* (e.g., *Clostridium perfringens* or *Clostridium botuilinum*), *Campylobacter* (e.g., *Campylobacter jejuni*), *Staphylococcus aureus, Listeria monocytogenes, Norovirus, Toxoplasma gondii, Shigella, Vibrio* (e.g., *Vibrio cholera, Vibrio parahaemolyticus*, or *Vibrio vulnificus*), and *Yersinia enterocolitica*.

Buffers

The methods of the invention involve nucleic acid cleavage reactions that occur, e.g., in a solution. In some instances, the solution is a biological sample (e.g., a clinical sample or food sample). The solution may include buffers or other reagents that, for example, enable or improve the efficacy of reactions, such as DSN-mediated cleavage reactions. In some instances, the solution may include a lysis buffer capable of inducing the lysis of cells in the sample. For example, the buffer may be an SDS lysis buffer (e.g., a buffer including at least about 1% SDS and/or 5 mM $Mg^{2+}$). In one example, a lysis buffer may include one or more of the following: SDS (0-1.0%), DTT, $MgCl_2$, $CaCl_2$, and/or Tris buffer. Lysis buffers that release nucleic acid for detection may also inhibit nucleases (e.g., non-DSN nucleases). Such buffers may thus support cell lysis and inactivate unwanted nucleases. Two general, non-limiting approaches useful in the disclosed methods involve the use of anionic detergents to inactivate the nucleases or proteinase K to digest away the nucleases. When employing SDS, both lysis and nuclease inactivation can be achieved, for example, at 1% SDS.

Separation

In some embodiments, one or more detection probes can be attached to a magnetic bead prior to incubation with a sample containing target nucleic acids. Upon incubation with the sample, the target nucleic acids can bind to the detection probes to form target nucleic acid-detection probe duplexes, which are subsequently digested by a duplex-specific nuclease, releasing a labeled portion of the bound detection probes into the surrounding solution. Detection probes that do not bind to a target nucleic acid will not form a duplex and will therefore not be digested. The released labeled portions can thus be isolated by exposing the sample to a magnet, such that the magnetic beads, the attached unbound detection probes, and the attached portions of the bound detection probes that were not released by duplex-specific nuclease digestion, are pulled towards the magnet to form an immobilized pellet. Thus, the only labeled molecules in the supernatant will be the released portions of detection probes that had bound target molecules. The supernatant can therefore be separated from the pellet, e.g., using a pipette.

Detection

In the methods of the present invention, a detection probe is incubated with a sample containing a target nucleic acid of interest, such that the target nucleic acid are bound to the detection probe, which is in turn cleaved by a duplex-specific nuclease. The released portion of the detection probe includes a detectable moiety (e.g., a label, such as a fluorophore, binding moiety, or enzyme), and can be separated from the remainder of the detection probe as well as any unbound detection probes as described herein. The separated detectable moieties can then be detected according to methods known in the art. For example, fluorescent detectable moieties can be detected by their light emissions. Exemplary means for detecting detectable moieties include, without limitation, by use of a planar waveguide, microscopy (e.g., epifluorescence microscopy, confocal microscopy, and two-photon microscopy), FRET, immunostaining, flow cytometry, and other methods as well known in the art. In certain embodiments, fluorophores are detected using a planar waveguide, as described in U.S. Pat. No. 8,300,993, incorporated herein in its entirety. Briefly, a light beam can be directed through a coupling lens into a planar waveguide. The light beam thus propagates parallel to the waveguide surface, such that one or more fluorophores (e.g., a fluorophore attached to the released portion of a detection probe) in an adjacently-positioned sample solution (e.g., a sample solution including labeled nucleic acids produced according to the methods of the invention) are excited by an evanescent field penetrating into the adjacent solution. The excitation of the fluorophores results in re-emission of light at a particular wavelength, which can be detected using a standard imaging device (e.g., a plate reader, microplate reader, or microscope). In certain embodiments, the planar waveguide is part of a strip.

Below are described a series of exemplary methods for detecting a target nucleic acid utilizing DSNs, which may utilize any of the components or processes described herein.

One-Step Detection of Immobilized Probes

The invention provides methods for detection of nucleic acid targets using DSNs capable of selectively degrading double-stranded nucleic acids. For example, detection of a target nucleic acid (e.g., a target RNA or target DNA) may be achieved using a nucleic acid detection probe that is attached on one end to a surface (e.g., a bead, chip, inner wall of a tube, or any other surface known in the art) and attached on the other end to a label (e.g., a fluorophore). In certain instances, the end attached to a surface may be attached via a nucleic acid sequence capable of hybridizing to an anchor nucleic acid directly attached to the surface. At least a portion of the detection probe includes a sequence complementary to at least a portion of the target nucleic acid. In the presence of a DSN, the duplex formed between the target and the detection probe will be degraded, resulting in release of the end region of the probe attached to the label. The released end region may be separated from the portion of the probe still attached the surface (e.g., according to methods known in the art) and then the label may be detected, for example, according to methods known in the art. For example, released end regions from such detection probes may be flowed along a waveguide or a detection surface to which capture probes capable of capturing the released end regions are immobilized, resulting in capture of released end regions. In one example, the label is a streptavidin-coated quantum dot or bead attached to a biotin moiety at the end of the probe. As such, the released end region may be captured using capture probes with biotin moieties.

Other such methods are illustrated in Examples 1 and 2 as is described herein.

DSA Using a Single Immobilized Probe

The invention provides methods of performing DSA using a single nucleic acid probe immobilized to a surface. In one example, the probe is attached on one end to a surface (e.g., a bead, chip, inner wall of a tube, or any other surface known in the art) and attached on the other end to a label (e.g., a fluorophore). In some instances, the probe may include a targeting region complementary to at least a portion of a target nucleic acid (e.g., an RNA or DNA) positioned between two cognate regions that are complementary to each other. As such, DSN cleavage of the duplex formed between the target and the targeting region of the probe results in release of a first end region including one of the two cognate regions complementary to each other. The end region may then hybridize to its cognate region in an additional copy of the probe, thereby leading to DSN cleavage of the additional copy of the probe and release of a second end region. In other instances, the probe may include a targeting region complementary to at least a portion of a target nucleic acid (e.g., an RNA or DNA) and a cognate region complementary to the targeting region that is positioned between the targeting region and the label. In such instances, DSN cleavage of a target/probe duplex results in release of an end region including the cognate region and the attached label, which can hybridize to the targeting regions of further copies of the probe and induce DSN cleavage, thereby resulting in the release of further copies of the end region.

Released end regions may be subsequently detected by their attached labels, for example, as described herein (see, e.g., FIG. 2). In some instances, the second end region includes one of the two cognate regions of the probe, which may be in turn cleaved after hybridizing to a released end region that includes the other cognate region. Thus, the end regions produced by DSN cleavage of the duplex formed between the probe and its target may be, in turn, capable of inducing cleavage of further copies of the probe based on the presence of the cognate regions, thereby resulting in amplification of the detectable signal from released end regions attached to labels.

Other such methods employing a single immobilized probe are illustrated in Examples 3, 6-9, and 14 as is described herein.

DSA Using Multiple Immobilized Probes

The invention also provides methods of performing DSA using multiple nucleic acid probe immobilized to a surface. In one example, the method features two probes. Both probes (the first probe and the second probe) are attached on one end to a surface (e.g., a bead, chip, inner wall of a tube, or any other surface known in the art) and attached on the other end to a label (e.g., a fluorophore). The first probe may include a targeting region complementary to at least a portion of a target nucleic acid (e.g., an RNA or DNA) positioned between the end attached to the surface and a region complementary to a cognate region located on the second probe. The cognate region on the second probe may be positioned between the end attached to the surface and a region complementary to the targeting region of the first probe. As such, DSN cleavage of the duplex formed between the target and the targeting region of the first probe results in release of a first end region including the label and the region capable of hybridizing to the cognate region on the second probe. This first end region may then hybridize to its cognate region on the second probe, thereby leading to DSN cleavage of the second probe and release of a second end region, which includes a label and the region complementary to the targeting region. Thus, the second end region can induce DSN cleavage of a further copy of the first probe, thereby yielding a further copy of the first end region, which can induce DSN cleavage of a further copy of the second probe. This process may be repeated, thereby resulting in amplification of the label signal associated with the end regions. The labeled end regions may be subsequently detected by their attached labels, for example, as described herein.

Such methods employing multiple immobilized probes in DSA are illustrated in Examples 4, 5, and 15 as is described herein.

DSA Using a Probe with an RNA Block

The invention further provides methods of performing DSA using a nucleic acid probe including an RNA block region (e.g., a region including an RNA-RNA duplex). An RNA block region positioned between two regions of a nucleic acid probe capable of hybridizing to each other may prevent intramolecular association between the two regions, thereby preventing the probe from inducing DSN self-cleavage. In one example, the probe is attached on one end to a surface (e.g., a bead, chip, inner wall of a tube, or any other surface known in the art) and attached on the other end to a label (e.g., a fluorophore). In some instances, the probe may include a targeting region complementary to at least a portion of a target nucleic acid (e.g., an RNA or DNA) and a cognate region complementary to the targeting region that is positioned between the targeting region and the label. In certain instances, the RNA block may be positioned between the targeting region and the cognate region, thereby preventing the cognate region from hybridizing to the targeting region and thus preventing intramolecular DSN cleavage. DSN cleavage of the target/probe duplex results in release of an end region including the cognate region, the attached label, and, optionally, the RNA block region. The released end region can hybridize to the targeting regions of further copies of the probe and induce DSN cleavage, thereby resulting in the release of further copies of the end region. The released end regions may be subsequently detected by their attached labels, for example, as described herein. The net result is that the end region products of DSN cleavage between the probe and its target may be, in turn, capable of inducing cleavage of further copies of the probe, thereby resulting in amplification of the detectable signal from released end regions attached to labels.

Methods employing a probe with an RNA block are illustrated in Examples 10-13 as is described herein.

DSA Using a Double-Stranded Probe

The invention also provides methods of detecting nucleic acids using double-stranded probes. Such probes may, for example, only produce a detectable signal after binding to a target nucleic acid and undergoing DSN-mediated cleavage. Methods using double-stranded probes may involve, for example, incubating a mixture including the double-stranded probe, a target nucleic acid, and a DSN, whereby one strand of the double-stranded probe hybridizes to the target nucleic acid, and the resultant duplex undergoes DSN cleavage. The DSN cleavage may result in the generation of a detectable signal.

In some instances, the double-stranded probe includes two separate strands that are capable of hybridizing to each other. The two probe strands may form a duplex resistant to DSN cleavage, for example, as described herein. One strand may include a region complementary to at least a portion of a target nucleic acid (e.g., a target DNA or a target RNA). In certain instances, one of the strands may be attached to a label (e.g., a fluorophore) and the other strand may be attached to a quencher, such that when the two strands are hybridized, the quencher quenches the label. For example, the strand including the region complementary to at least a portion of the target nucleic acid may be bound to the quencher.

In alternate instances, the methods of the invention may utilize a probe that includes a single contiguous nucleic acid strand that folds back upon itself and self-hybridizes, e.g., to form a hairpin structure. The self-hybridized probe duplex may be resistant to DSN cleavage, for example, as described herein. In some instances, the portion of the probe complementary to at least a portion of the target nucleic acid is located in a double-stranded portion of the probe (e.g., in a stem region of a stem-loop structure or in an overhang region). In other instances, the portion of the probe complementary to at least a portion of the target nucleic acid is located in a single-stranded portion of the probe (e.g., in the loop region of a stem-loop structure). In further instances, the portion of the probe complementary to at least a portion of the target nucleic acid is located in both a double-stranded portion and a single-stranded portion of the probe.

In certain instances, the strand including the region complementary to at least a portion of the target nucleic acid may further include a single-stranded region, which may include a further portion capable of hybridizing to at least a portion of the target nucleic acid. In other instances, the probe may include a duplex region capable of being degraded by a DSN, which results in the generation of a single-stranded portion to which a portion of the target nucleic acid may be able to hybridize. In either instance, the target nucleic acid may hybridize to the single-stranded region of the probe and then undergo strand invasion into the duplex formed by hybridization between the two probe strands, thereby dislodging the strand attached to the label from the strand attached to the quencher. This results in separation of the label and the quencher, thus permitting the label to produce detectable signal. Further, DSN cleavage of the duplex formed between the probe strand attached to the quencher and the target nucleic acid may result in the degradation of the portion of the probe strand attached to the quencher capable of hybridizing to the probe strand attached to the label. As such, the probe strand attached to the label would not be able to re-hybridize to the other probe strand, thereby maintaining separation between the label and the quencher. The resultant single-stranded labeled strands may then be detected, for example, as described herein.

Other such methods using a double-stranded probe are illustrated in Examples 18 and 19 as is described herein.

Targeting Regions in the Stalk

A double-stranded probe useful in the methods described herein may include a hairpin structure, as described above. In some instances, the portion of the double-stranded probe complementary to at least a portion of a target nucleic acid is located in the stalk region of the hairpin, and may further include a portion exterior to the stalk region (e.g., an overhang region or a loop region). Thus, the target nucleic acid may be able to initially bind to an exposed single-stranded region of the probe (e.g., the overhang region or loop region), and then undergo strand invasion into the double-stranded portion of the probe (e.g., the stalk region). This results in the formation of a duplex between a portion of the probe stalk region and the target nucleic acid, which, in certain instances, may undergo DSN cleavage. DSN cleavage may in turn result in the generation of a detectable signal. In certain instances, DSN cleavage of at least a portion of the stalk may result in release of an end region (e.g., an end region attached to a label and/or an end region including a region capable of hybridizing to and inducing DSN cleavage of another probe and/or another copy of the same double-stranded probe).

Such methods using a double-stranded probe with a targeting region in the stalk are illustrated in Examples 20-29 as is described herein.

Targeting Regions in the Loop

A double-stranded probe useful in the methods described herein may include a hairpin structure, in which the portion of the hairpin that binds to a target nucleic acid is in the loop region. For example, two hybridized strands of the stalk region may be capable, when separated, of generating a detectable signal and/or acting to promote DSN cleavage of further probes and/or copies of the same probe. However, the stalk strands may be maintained in a hybridized state when the hairpin is intact due to their close physical proximity. Hybridization of at least a portion of the loop to a complementary portion of a target nucleic acid may result in DSN cleavage of that portion of the loop. Thus, there is no longer a covalent bond linking the stalk strands, which, if denatured, may not as readily rehybridized, thus resulting in separation of the stalk strands.

Such methods using a double-stranded probe with a targeting region in the loop are illustrated in Examples 30-34 as is described herein.

The following examples are intended to illustrate, rather than limit, the invention.

EXAMPLES

Example 1. Detection of RNA Targets Using a DSN and a Detection Probe Immobilized on a Surface Referring to FIG. 1, a scheme is shown for detecting an RNA target using a DSN. DSNs may be used to detect duplexing between a nucleic acid probe and a target nucleic acid.

In an example, a nucleic acid (e.g., DNA) detection probe includes a region complementary to the RNA target and an attached detectable moiety (e.g., a biotin moiety that binds to a streptavidin-coated fluorophore (e.g., a quantum dot, a fluorescent bead, or any other fluorophore described herein)). In this example, the detection probe is immobilized by attachment to a surface (e.g., a bead, slide, plate, or well) at the opposite end from the detectable moiety. A plurality of such detection probes may be attached the same surface.

The initiation of this scheme involves hybridization of an RNA target to a detection probe, thereby forming an RNA-DNA duplex between the target and the probe. A duplex-specific nuclease may then cleave this duplex. The DSN may be present in the solution prior to formation of the duplex or may be added after the duplex has formed. Cleavage of the duplex by the DSN results in the release of an end portion of the detection probe, depicted in FIG. 1 as a probe particle, which includes at least the fluorophore, and may further include a portion of the detection probe attached to the fluorophore. The released probe particle is thereby untethered from the surface and may be separated from the remainder of the bound, cleaved detection probe and/or unbound detection probes, both of which remain immobilized on the surface. For example, the supernatant, which only contains free-floating substituents such as the probe particle, may be removed using a liquid handling device (e.g., a micropipette, pipetteman, transfer pipette, pipettor, dropper, Pasteur pipette, air displacement pipette, mouth pipette, microfluidic pipette, or an automated liquid handling device).

Once the released probe particle has been separated from unbound detection probe, it may be captured and analyzed by the fluorescence of the attached fluorophore. For example, one or more released probe particles may be flowed along a strip towards a detection surface labeled with immobilized capture probes capable of recognizing the probe particles (e.g., biotinylated nucleic acid capture probes). In this example, as a given streptavidin moiety may bind to multiple biotins, the streptavidin components of the probe particles will bind to the biotin molecules of the capture probes, thus immobilizing and capturing the probe particles. The captured probe particles may be analyzed while immobilized on the detection surface using, for example, any standard imaging device. Alternatively, the captured probe particles may be subsequently detached from the capture probes, or the capture probe-probe particle complexes may be detached from the detection surface, and the solution containing the probe particles may be analyzed at a later time point.

Example 2. Detection of RNA Targets Using a DSN and a Detection Probe with a Magnetic Bead Referring to FIG. 2, a scheme for detection of an RNA target involving a detection probe that includes a labeled nucleic acid bound to a magnetic particle (e.g., a magnetic bead, such as a universal bead) is shown. In this example, the labeled nucleic acid is bound to the magnetic particle, e.g., via hybridization to a nucleic acid attached to the magnetic particle. For example, the labeled nucleic acid may include a poly-A region that hybridizes to a poly-T region on the nucleic acid attached to the magnetic bead. The labeled nucleic acid may be labeled, e.g., with a fluorophore (e.g., a quantum dot or a fluorescent bead, or any other fluorophore described herein). For example, the labeled nucleic acid may be biotinylated, such that the biotinylated labeled nucleic acid binds to streptavidin attached to the fluorophore. The labeled nucleic acid may include a region capable of hybridizing to the RNA target (e.g., a region complementary to at least a portion of the RNA target).

The initiation of this scheme involves hybridization of the labeled nucleic acid to the RNA target, thereby forming a duplex, which may be subsequently cleaved by a DSN. Cleavage of the duplex by the DSN results in the release of an end portion of the labeled nucleic acid, depicted in FIG. 2 as a probe particle, which includes at least the fluorophore, and may further include a portion of the labeled nucleic acid attached to the fluorophore. The released probe particle is thereby untethered from the magnetic particle, and may be separated from the remainder of the bound, cleaved detection probe and/or unbound detection probes, both of which remain immobilized on the magnetic particle. For example, the sample solution may be exposed to a magnetic field by applying the sample to a strip containing one or more magnetic strips. The magnetic particles, along with the attached unbound detection probe and/or the uncleaved portions of bound detection probes, will be pulled down by the magnetic strips, while the released probe particles will flow through.

The released probe particles may then be captured and subsequently analyzed by the fluorescence of the attached fluorophore. For example, one or more released probe particles may be flowed along the strip to a detection surface labeled with immobilized capture probes capable of recognizing the probe particles (e.g., biotinylated nucleic acid capture probes). As a given streptavidin moiety may bind to multiple biotins, the streptavidin components of the probe particles will bind to the biotin molecules of the capture probes, thus immobilizing and capturing the probe particles. The captured probe particles may be analyzed while immobilized on the detection surface using, for example, any standard imaging device. Alternatively, the captured probe particles may be subsequently detached from the capture probes, or the capture probe-probe particle complexes may be detached from the detection surface, and the solution containing the probe particles may be analyzed at a later time point.

Example 3. DSA Using a Single Probe

Referring to FIGS. 3-7, a DSA scheme is shown for detecting the presence of a target nucleic acid, such as an RNA target, and exponentially amplifying a resultant detectable signal.

FIG. 3 shows a probe design (Probe 1) immobilized on a surface and including, in order, DNA regions b' and a, and RNA region b. Regions b and b' are capable of hybridizing to each other. In some instances, regions b and b' are complementary. Region a is complementary to at least a portion of an RNA target. Regions a and b are oriented parallel to each other and antiparallel to region b'.

The initiation of this DSA scheme involves hybridization of the RNA target with region a of Probe 1 (FIG. 3). This forms an RNA-DNA duplex that may be cleaved by a DSN, which results in the release of the end region of the probe (Probe 2). Probe 2 includes region b and a fluorophore attached to the probe by biotin-streptavidin binding. The remainder of the probe, containing the b' region, remains attached to the surface. Within a single copy of Probe 1, regions b and b' are not cleaved even if they hybridize with each other, because when regions b and b' loop to form a duplex, the resultant duplex is not anti-parallel. Moreover, regions a and b' are DNA, and are thus preferentially digested by the DSN over the RNA that make up regions a' and b.

Turning to FIG. 4, additional copies of Probe 1 immobilized on the surface may interact with Probe 2, as the b' region of Probe 1 hybridizes to the b region of Probe 2. The resultant duplex may then be cleaved by a DSN. Again, region b of Probe 2 is made up of RNA and is not cleaved. Thus, digestion results in the release of Probe 2 and a new Probe 3, which includes a region a and a region b. Probes 2 and 3 then proceed to interact with further copies of Probe 1 according to the Probe 2 or Probe 3 pathways, respectively.

FIG. 5A shows the Probe 3 pathway, in which region b of Probe 3 hybridizes with region b' of another Probe 1, resulting in duplex-specific cleavage and the release of the original Probe 3 as well as the production of a new copy of Probe 3. FIG. 5B shows the Probe 2 pathway, in which region b of Probe 2 hybridizes with region b' of another Probe 1, resulting in duplex-specific cleavage and the release of the original Probe 2 and the production of a new copy of Probe 3. In both the Probe 2 and Probe 3 pathways, only the b' region of Probe 1 is composed of DNA and is thus cleaved. The b region is always RNA and is not cleaved by the DSN.

Figure 7:
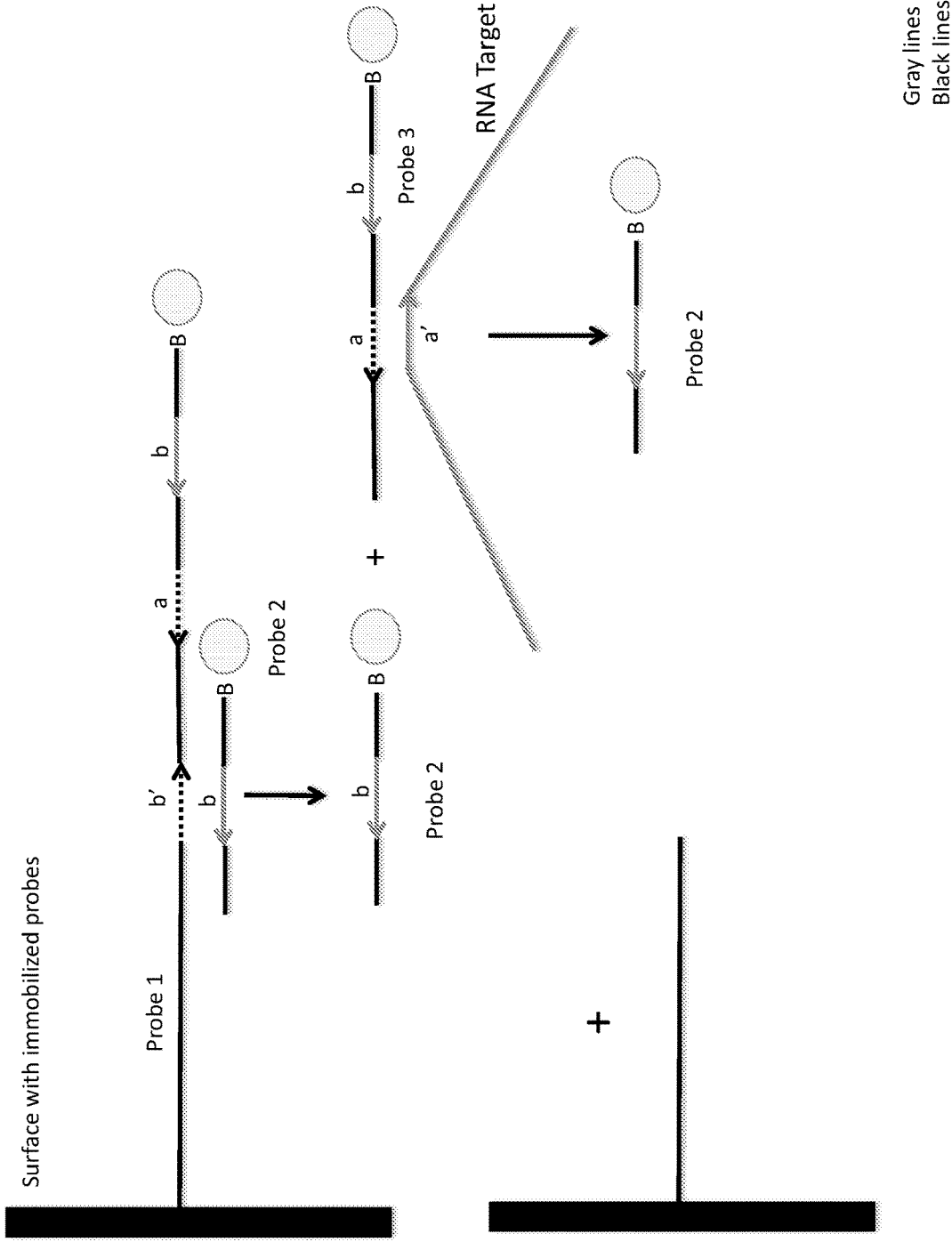
FIG. 7 shows a scheme for exponential DSA with a single probe. Probe 3 is produced as a result of hybridization between Probe 2 and Probe 1 and subsequent cleavage by a duplex-specific nuclease. Region a' of the RNA target, which is still present because RNA is not cleaved by duplex-specific nucleases, hybridizes to region a of Probe 3. This leads to degradation of region a by a duplex-specific nuclease and the production of another copy of Probe 2.

The above DSA scheme may be repeated multiple times. As shown in FIG. 6, repeated rounds of amplification produces additional cleaved copies of Probe 3 at exponential rates. In the DSA scheme presented above, the target RNA (T) is never cleaved. In alternate embodiments, the target is a DNA molecule. A DNA target would be digested in the initial step, but all subsequent reactions would continue as described. Thus, exponential amplification may be achieved regardless of whether the target is RNA or DNA. If the target is RNA, however, the copies of Probe 3 may continue to interact with copies of the RNA target, which will not have been degraded by the nucleases. Region a of Probe 3 (composed of DNA) hybridizes to region a' of the RNA target (FIG. 7). Duplex-specific cleavage of region a of Probe 3 thus produces another copy of Probe 2. This cleavage pathway may be minor when target levels are less than P1.

Example 4. Exponential DSA of RNA with Multiple Probes

Referring to FIGS. 8-10, a scheme is shown for exponential DSA using multiple probes. This scheme involves two probe designs immobilized on a surface, as shown in FIG. 8: (i) Probe 1, which includes, in order, regions a and b, of which region a is DNA and region b is RNA; and (ii) Probe 3, which includes, in order, regions b' and a', of which region a' is RNA and region b' is DNA. Both Probe 1 and Probe 3 include an end region containing a streptavidin-coated fluorophore (e.g., a quantum dot, fluorescent bead, or any other fluorophore described herein) bound to a biotin moiety attached to the probe. Only DNA is digested by the duplex-specific nuclease.

The initiation of this DSA scheme involves hybridization of region a of Probe 1 to a target RNA containing the sequence of region a' (FIG. 8). This results in cleavage of region a by a DSN, producing Probe 2, which only contains region b. Probe 2 may subsequently hybridize with region b' of Probe 3, resulting in DSN cleavage of region b' on Probe 3. This leads to the release of the original Probe 2 and the production of Probe 4, which includes region a' (FIG. 9A). Region a' of Probe 4 may, in turn, hybridize with region a of another copy of Probe 1, resulting in degradation of region a and the release of the original Probe 4 and the production of a new copy of Probe 2 (FIG. 9B). Each copy of Probe 2 and Probe 4 may proceed to hybridize with additional copies of Probe 3 and Probe 1, respectively, to drive further cleavage events and amplification of Probes 2 and 4 at approximately equal ratios. This process may be repeated multiple times, with each round increasing the number of copies of Probes 2 and 4 present at an exponential rate (FIGS. 10A and 10B). Note that if the target nucleic acid is RNA, as depicted here, it will not be digested by the DSN. If the target nucleic acid is DNA, it will be digested away in the first step, but all subsequent reactions will continue as described. Therefore, this scheme may trigger exponential signal amplification whether the target nucleic acid is DNA or RNA.

Example 5. Exponential DSA of DNA by Multiple Probes

Referring to FIGS. 11-14, a DSA scheme is provided that utilizes a detectable probe for a DNA target, in which the target binding region of the probe is oriented parallel relative to the released region.

The scheme features the probe designs shown in FIG. 11 as Probe 1 and Probe 3. Probe 1 features a DNA region a and an RNA region b located between one end immobilized to a surface and another end attached to a biotin moiety bound to a streptavidin-coated fluorophore (e.g., a quantum dot, fluorescent bead, or any other fluorophore described herein). Probe 3 features a DNA region b' complementary to region b, an RNA region a' complementary to region a, and an end attached to a biotin moiety bound to a streptavidin-coated fluorophore (e.g., a quantum dot, fluorescent bead, or any other fluorophore described herein).

The initiation of this DSA scheme involves hybridization of a DNA target containing a region a' complementary to region a with region a of Probe 1, leading to DSN-mediated degradation of region a (on Probe 1) and region a' (on the DNA target). This results in release of an end region (Probe 2), which contains region b and the fluorophore (FIG. 11). Probe 2 may proceed to hybridize to Probe 3. Region b' is cleaved by a DSN, thus releasing Probe 4, which contains region a'. Region a' of Probe 4 may, in turn, hybridize to region a on a further copy of Probe 1, thus resulting in DSN cleavage of region a and release of a further copy of Probe 2 (FIG. 13). The net result is exponential amplification of detectable Probes 2 and 4, such that the total number of copies of Probe 1 and Probe 2 yielded doubles for each successive reaction round (FIG. 14).

Example 6. Exponential DSA of DNA with a Single Probe

Figure 15:
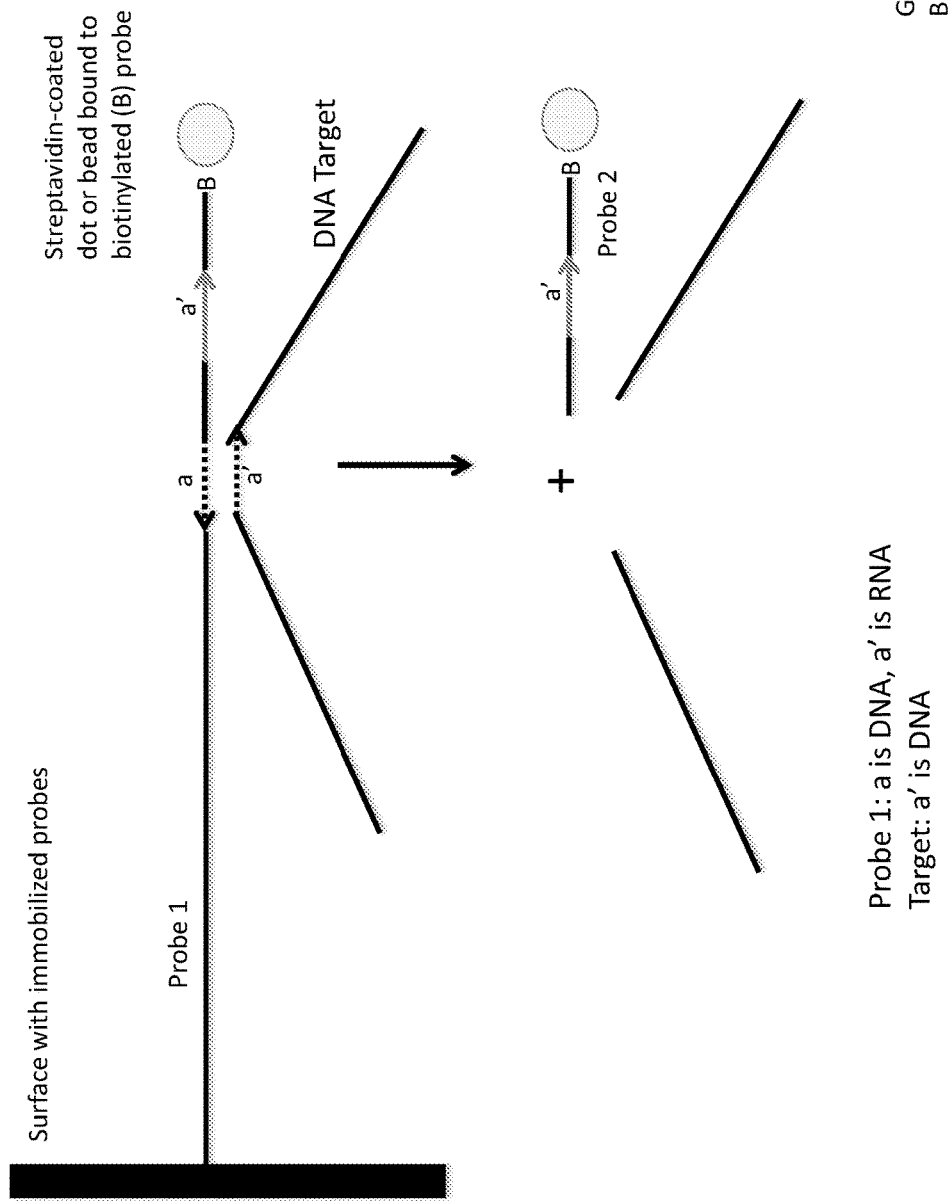
FIG. 15 shows a probe design and scheme for exponential DSA of a DNA target using a single probe.
Figure 16:
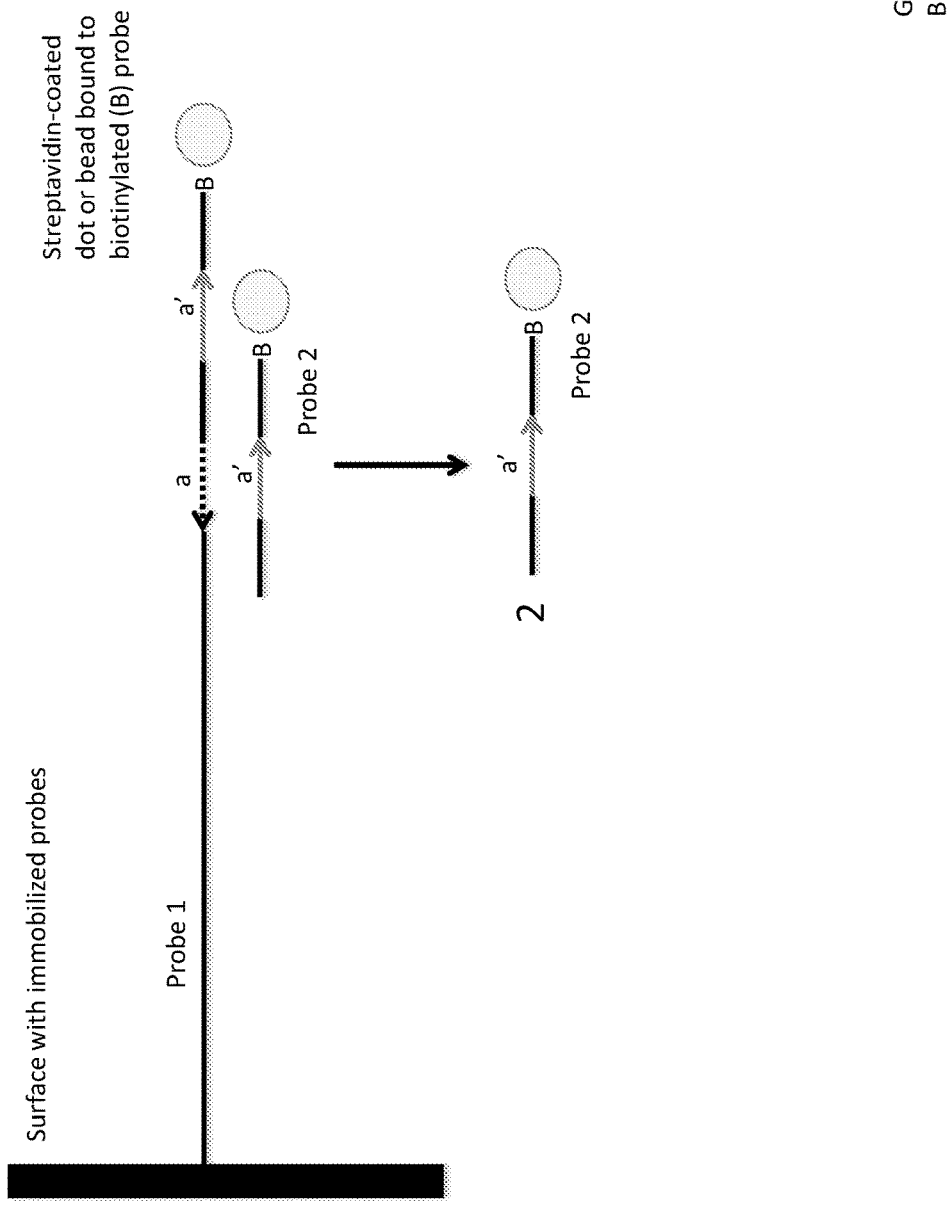
FIG. 16 shows further stages of a scheme for exponential DSA of a DNA target using a single probe.

Referring to FIGS. 15-17, a scheme is provided for exponential DSA of a DNA target using a single probe, shown in FIG. 15 as Probe 1.

Probe 1 includes a nucleic acid immobilized at one end to a surface; the nucleic acid includes regions a and a', of which region a is DNA and region a' is RNA. In this scheme, the target binding region of the probe is oriented anti-parallel relative to the released end region. Region a is complementary to a region a' present on a DNA target molecule. Region a' is located in an end region containing the terminal end of the nucleic acid and a biotin moiety. The biotin is bound to a streptavidin-coated fluorophore (e.g., a quantum dot, fluorescent bead, or any other fluorophore described herein).

The initiation of this DSA scheme involves hybridization of region a of Probe 1 with region a' of the DNA target, which results in DSN cleavage of both region a and region a', thus releasing the end region (shown in FIG. 15 as Probe 2). The released Probe 2 contains region a', which matches the region a present on the original DNA target and is complementary to region a of the original Probe 1.

Turning to FIG. 16, Probe 2 may therefore proceed to hybridize with region a on another copy of Probe 1. The resultant duplex between region a' of Probe 2 and region a of the further copy of Probe 1 may be cleaved by a DSN, with only the DNA of region a being cleaved. The first copy of Probe 2 is thus released, and the cleavage of the further copy of Probe 1 produces a new copy of Probe 2. As a result, additional copies of Probe 2 are produced at an exponential rate, such that each successive round yields twice the number of copies of Probe 2 of the previous round (FIG. 17).

Example 7. Exponential DSA of RNA Using a Single Probe

Figure 18:
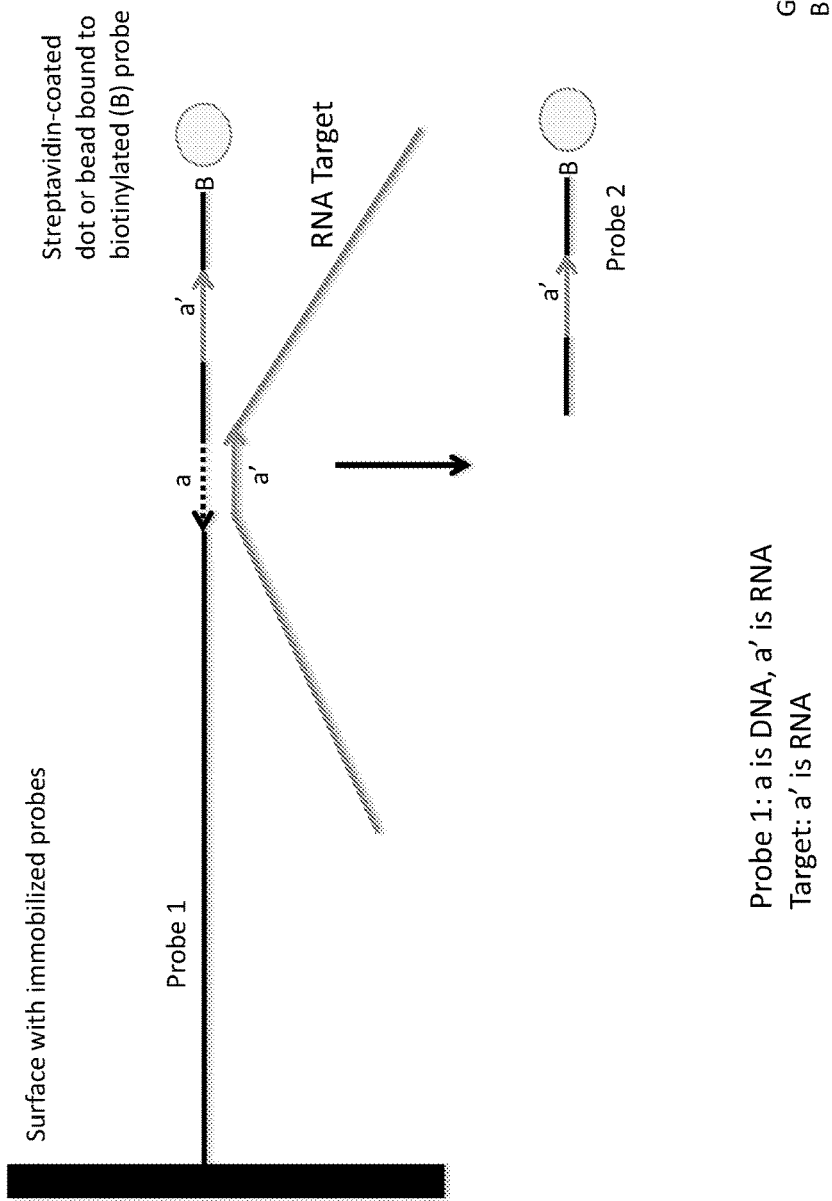
FIG. 18 shows a probe design and scheme for exponential DSA of an RNA target using a single probe.
Figure 19:
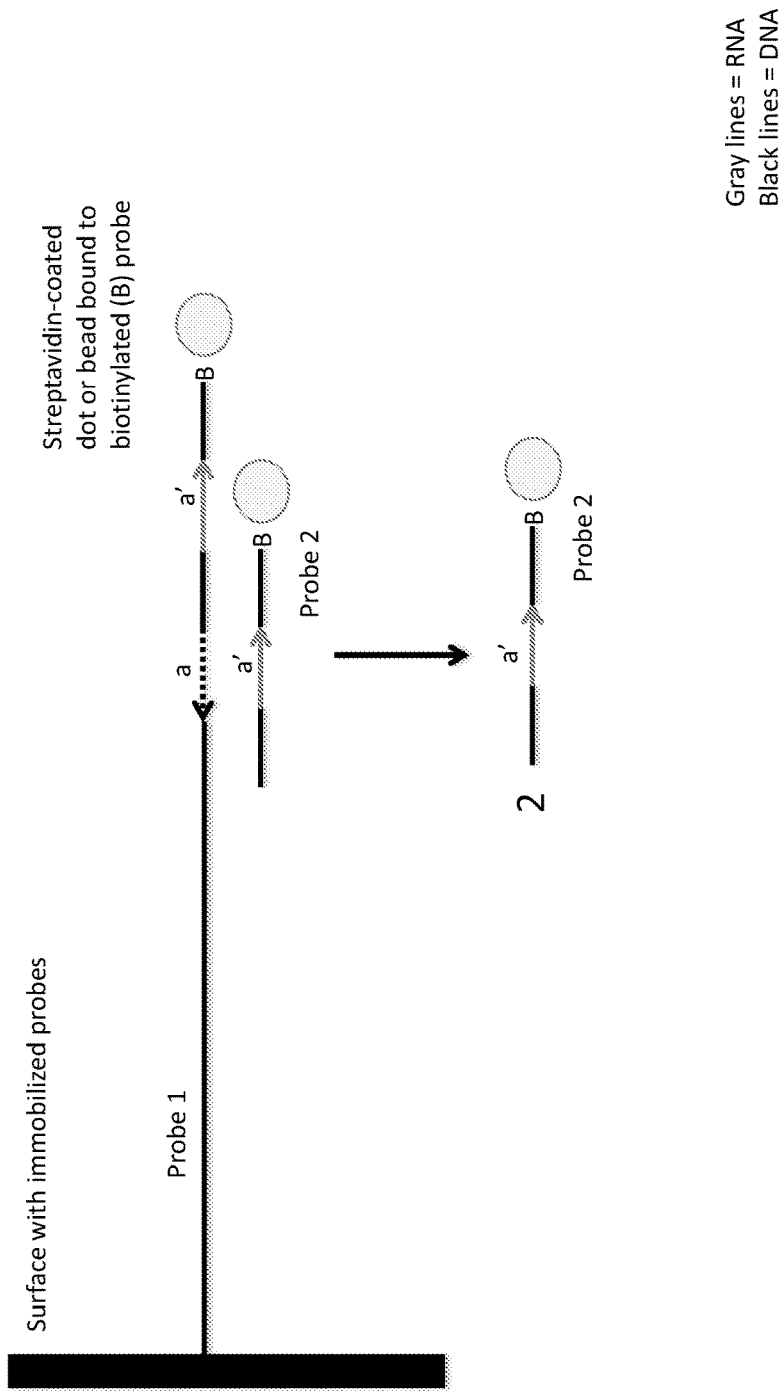
FIG. 19 shows further stages of a scheme for exponential DSA of an RNA target using a single probe.

Referring to FIGS. 18-20, a scheme is provided for exponential DSA of an RNA target using a single probe. As shown in FIG. 18, the scheme involves a probe design (Probe 1) featuring a DNA region (region a) located between an RNA region (region a') complementary to region a, and a surface to which the probe is immobilized. In this scheme, the target binding region of the probe is oriented anti-parallel relative to the released end region. The opposite end of Probe 1 is attached to a biotin moiety bound to a streptavidin-coated fluorophore (e.g., a quantum dot, fluorescent bead, or any other fluorophore described herein).

The initiation of the scheme involves hybridization of an RNA target containing a region a' to region a, forming a duplex that may be cleaved by a DSN. The nuclease cleaves the DNA of region a, thereby releasing an end region (Probe 2), which contains RNA region a'. Thus, region a' of Probe 2 may subsequently hybridize to region a of a further copy of Probe 1, thus inducing DSN cleavage of the DNA region a on the further copy of Probe 1 and releasing a further copy of Probe 2 (FIG. 19). Thus, this scheme permits exponential amplification without the need for target cycling (FIG. 20).

Example 8. Linear DSA of DNA with a Single Probe

Figure 21:
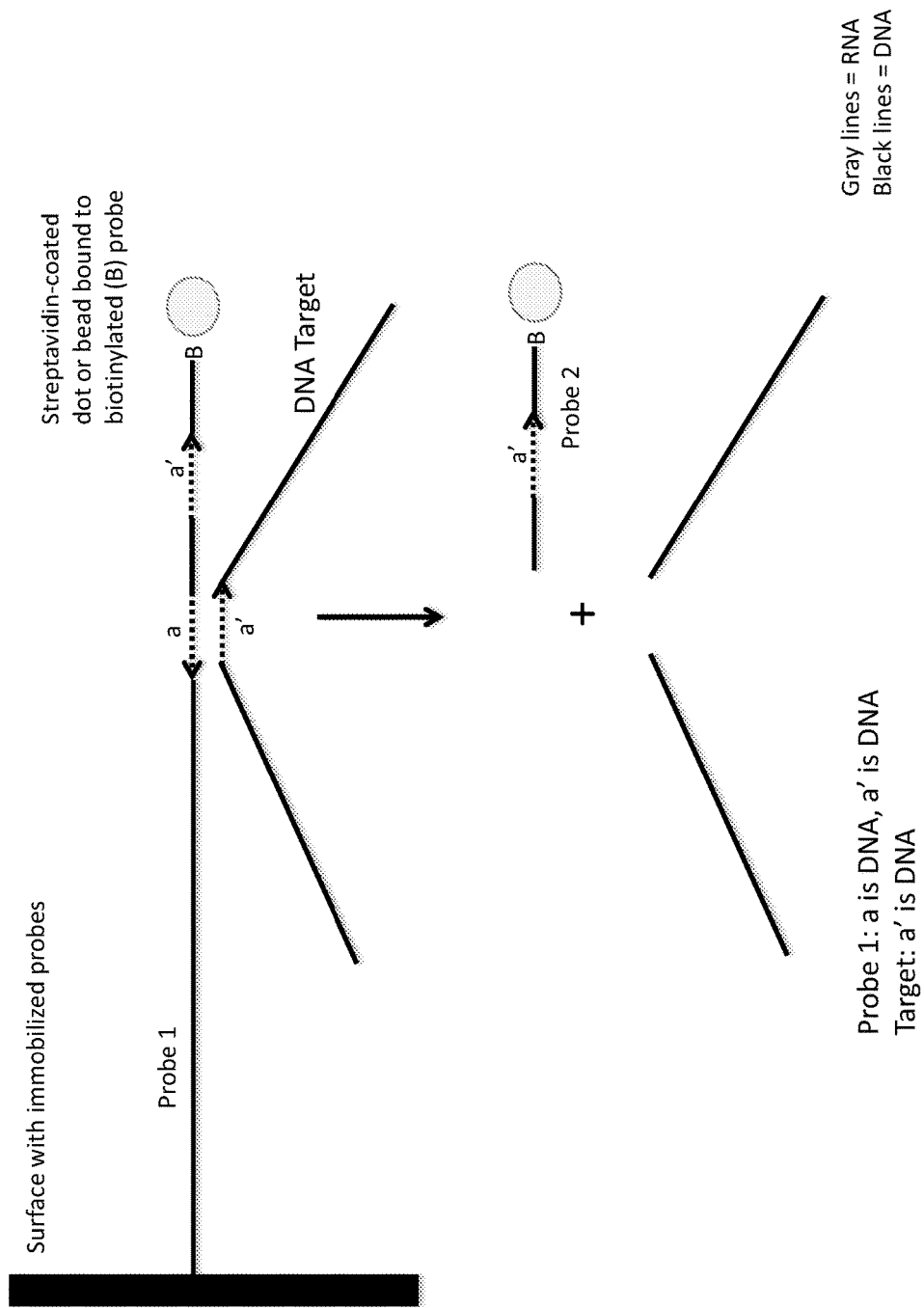
FIG. 21 shows a probe design and scheme for linear DSA of a DNA target using a single probe.
Figure 22:
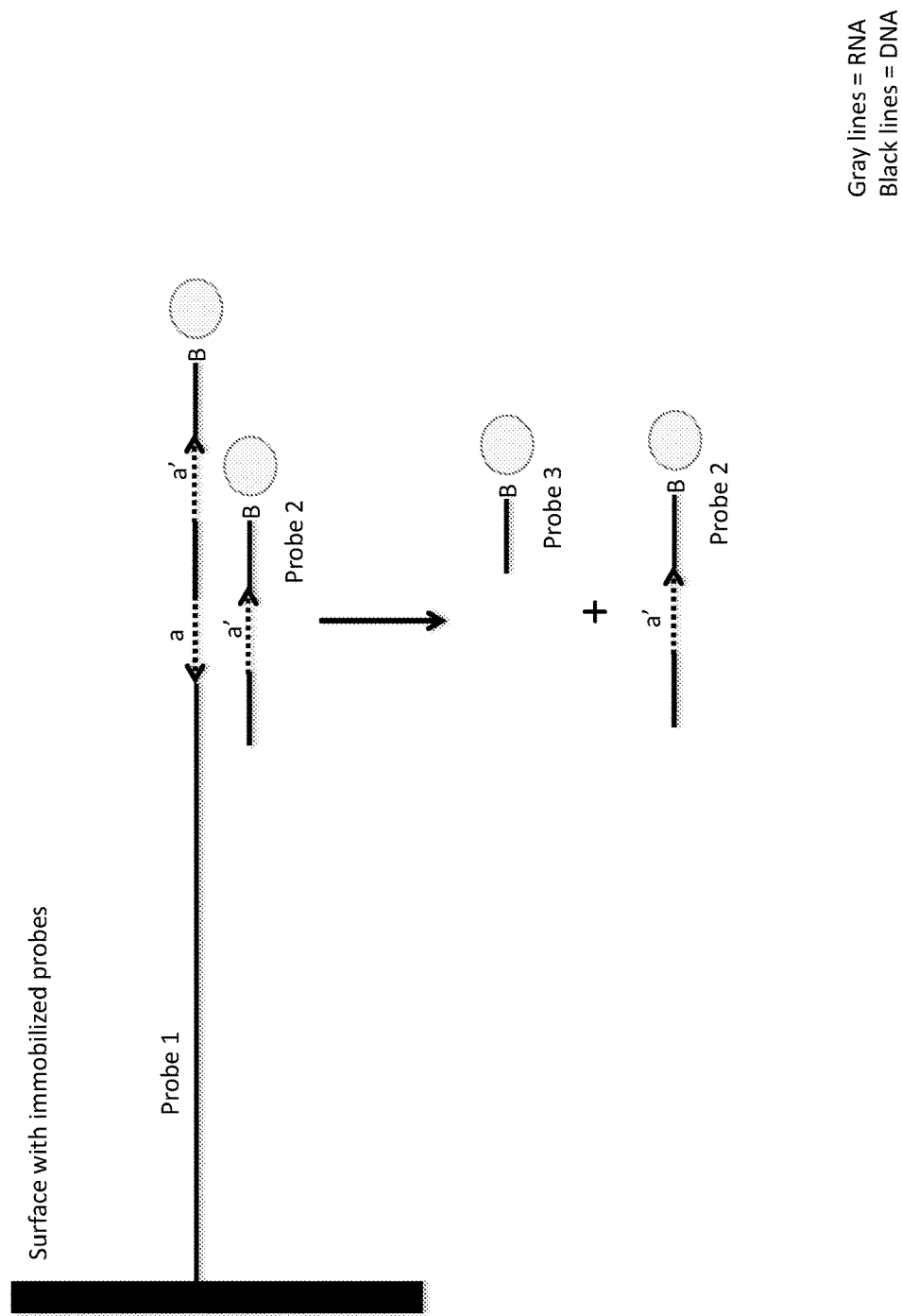
FIG. 22 shows further stages of a scheme for linear DSA of a DNA target using a single probe.

Referring to FIGS. 21-23, a scheme is provided for linear DSA of a DNA target using a single probe, shown in FIG. 21 as Probe 1. Probe 1 contains DNA region a and an end region containing DNA region a', which is complementary to region a, and a terminal biotin moiety bound to a streptavidin-coated fluorophore (e.g., a quantum dot, fluorescent bead, or any other fluorophore described herein). Probe 1 is immobilized to a surface on the other end.

The initiation of the scheme involves hybridization of a DNA target containing region a', which is complementary to region a, to Probe 1. Both strands of the resultant duplex between region a of Probe 1 and region a' of the DNA target may thus undergo DSN cleavage (FIG. 21). As a result, the target DNA is cleaved and the end region containing DNA region a' (Probe 2) is released. As shown in FIG. 22, region a' of Probe 2 may subsequently hybridize to region a of a further copy of Probe 1, resulting in DSN cleavage of the resultant duplex and release of a further copy of Probe 2. Because DNA region a' of the initial copy of Probe 2 is cleaved, this also results in the production of a copy of Probe 3. The net result is that additional copies of Probe 3 are produced in linear fashion, with each successive round of amplification yielding one additional copy of Probe 3 (FIG. 23).

Example 9. Geometric DSA of RNA

Figure 24:
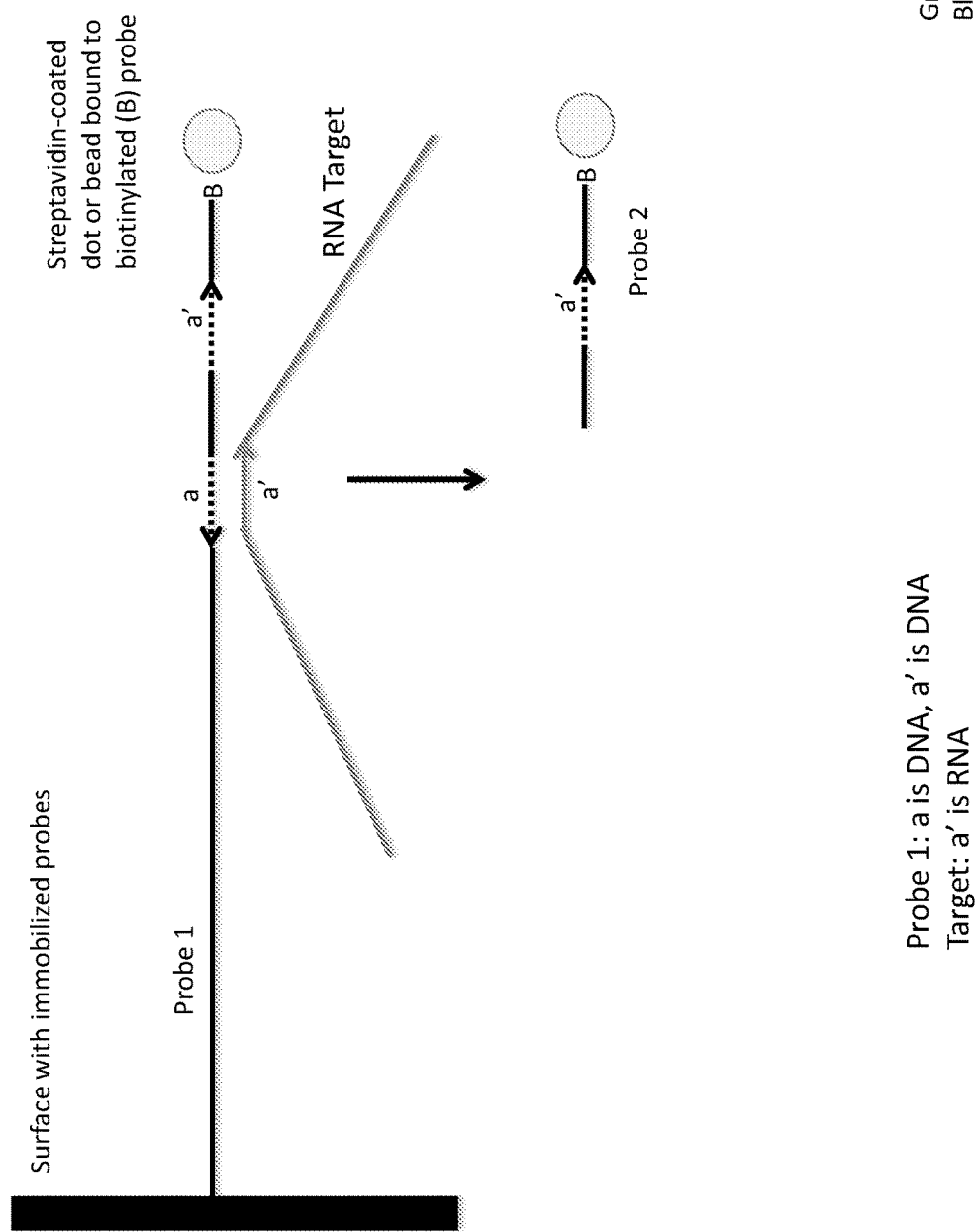
FIG. 24 shows a probe design and scheme for geometric DSA of an RNA target.

Referring to FIGS. 24-29, a scheme for geometric DSA of an RNA target is provided, which utilizes the probe design depicted in FIG. 24 as Probe 1. In this scheme, Probe 1 is immobilized to a surface and contains a DNA region a and an end region containing a complementary DNA region a' and a terminal biotin moiety bound to a streptavidin-coated fluorophore (e.g., a quantum dot, fluorescent bead, or any other fluorophore described herein).

Figure 25:
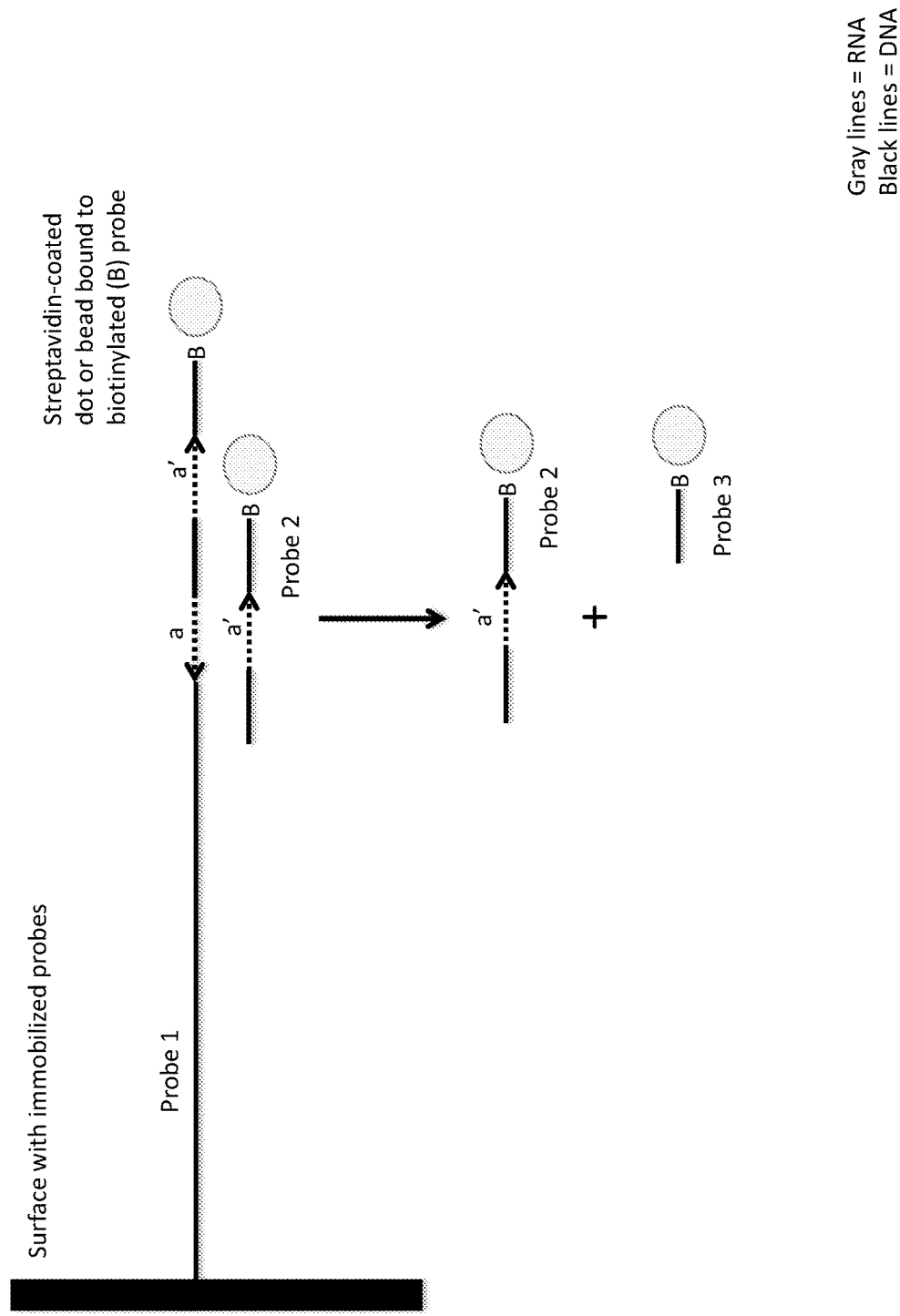
FIG. 25 shows further stages of a scheme for geometric DSA of an RNA target.

The initiation of this scheme, shown in FIG. 24, involves hybridization of an RNA target containing a region a' to Probe 1, thereby resulting in DSN cleavage of region a and release of an end region including region a' and the fluorophore (shown in FIG. 24 as Probe 2). As shown in FIG. 25, Probe 2 may subsequently hybridize to region a of a further copy of Probe 1, resulting in degradation of region a of the further copy of Probe 1 and of region a' of Probe 2, thus yielding a new copy of Probe 2 and the production of Probe 3. However, because the RNA target is not degraded in the first hybridization step, it is free to hybridize to further copies of Probe 1 as well. Thus, one additional copy of Probe 2 is produced per round due to reactions involving the target RNA, resulting in linear production of Probe 2. As each copy of Probe 2 may generate a copy of Probe 3 in every successive round, copies of Probe 3 are produced at a rate of one additional copy of Probe 3 per copy of Probe 2 present. As a result, the amplification of cleaved probe signal is geometric, although not exponential (FIGS. 26 and 27). By comparison, in the exponential cleavage scheme described in Example 7 (see, e.g., FIGS. 18-20), each additional copy of released probe may repeatedly trigger cleavage of additional immobilized probes to form further copies of the released probe, thus driving exponential amplification, such that the first round yields a single copy of Probe 2, while the second round yields three copies, the third round yields seven copies, and the fourth round yields fifteen copies (FIGS. 28 and 29).

Example 10. Exponential DSA of RNA Using an RNA Block

Figure 30:
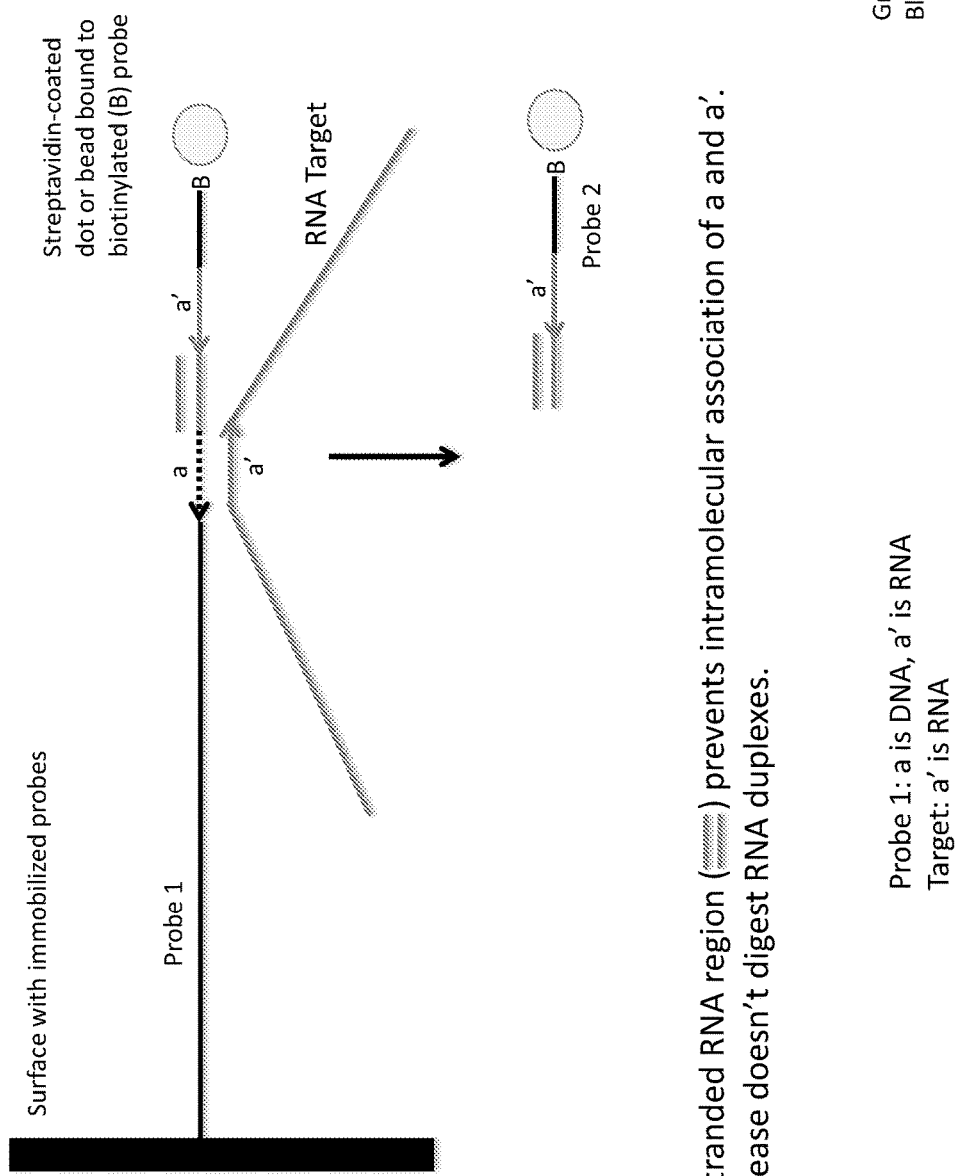
FIG. 30 shows a probe design and scheme for exponential DSA of an RNA target utilizing a probe containing a double-stranded RNA block.
Figure 31:
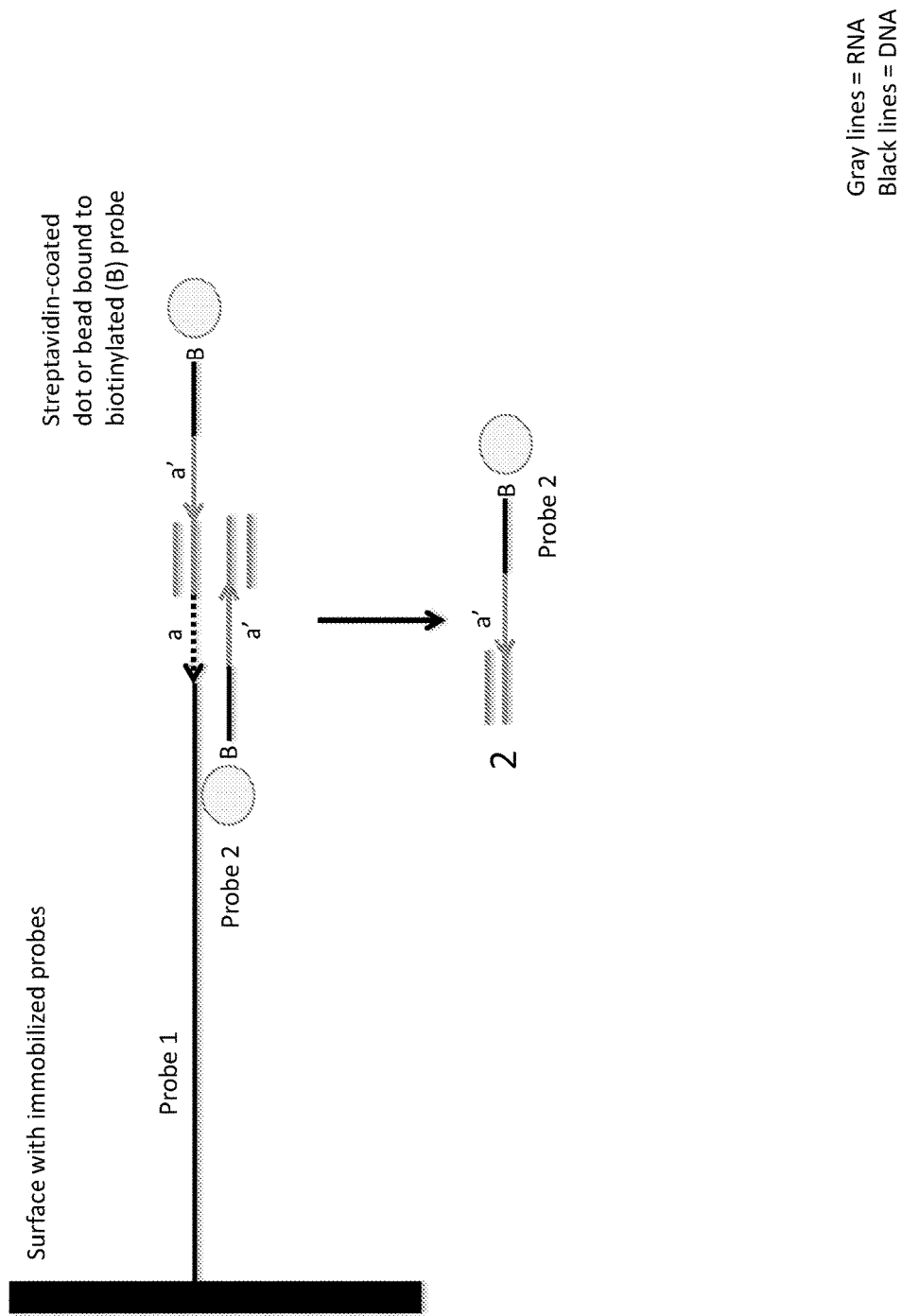
FIG. 31 shows further stages of a scheme for exponential DSA of an RNA target utilizing a probe containing a double-stranded RNA block.

Referring to FIGS. 30-32, a scheme is provided for exponential DSA of an RNA target using a probe including an RNA block. A double-stranded RNA region, referred to herein as a block, may be used, in some instances, in a probe to prevent intramolecular association of two complementary regions on the same probe, thus preventing self-cleaving of the probe in the presence of a duplex-specific nuclease. FIG. 30 illustrates a probe design (Probe 1) including such a double-stranded RNA block, in which the target binding region of the probe is oriented parallel to the end region to be released. Probe 1 is immobilized on a surface and includes a DNA region a and an end region including, in order, the double-stranded RNA region, an RNA region a' complementary to region a, and a terminal biotin moiety bound to a streptavidin-coated fluorophore (e.g., a quantum dot, fluorescent bead, or any other fluorophore described herein).

The initiation of this scheme involves hybridization of an RNA target containing a region a' to region a of Probe 1 (FIG. 30), resulting in duplex-specific degradation of region a by a DNA-degrading DSN and release of the end region (Probe 2). Region a' of Probe 2 may subsequently hybridize to region a of a further copy of Probe 1, resulting in DSN cleavage of region a of the further copy of Probe 1 and the release of an additional copy of Probe 2 (FIG. 31). Because Probe 2 is not cleaved, each copy of Probe 2 may induce the cleavage of multiple copies of Probe 1, thus leading to exponential amplification (FIG. 32).

Example 11. Linear DSA of DNA Using an RNA Block

Figure 33:
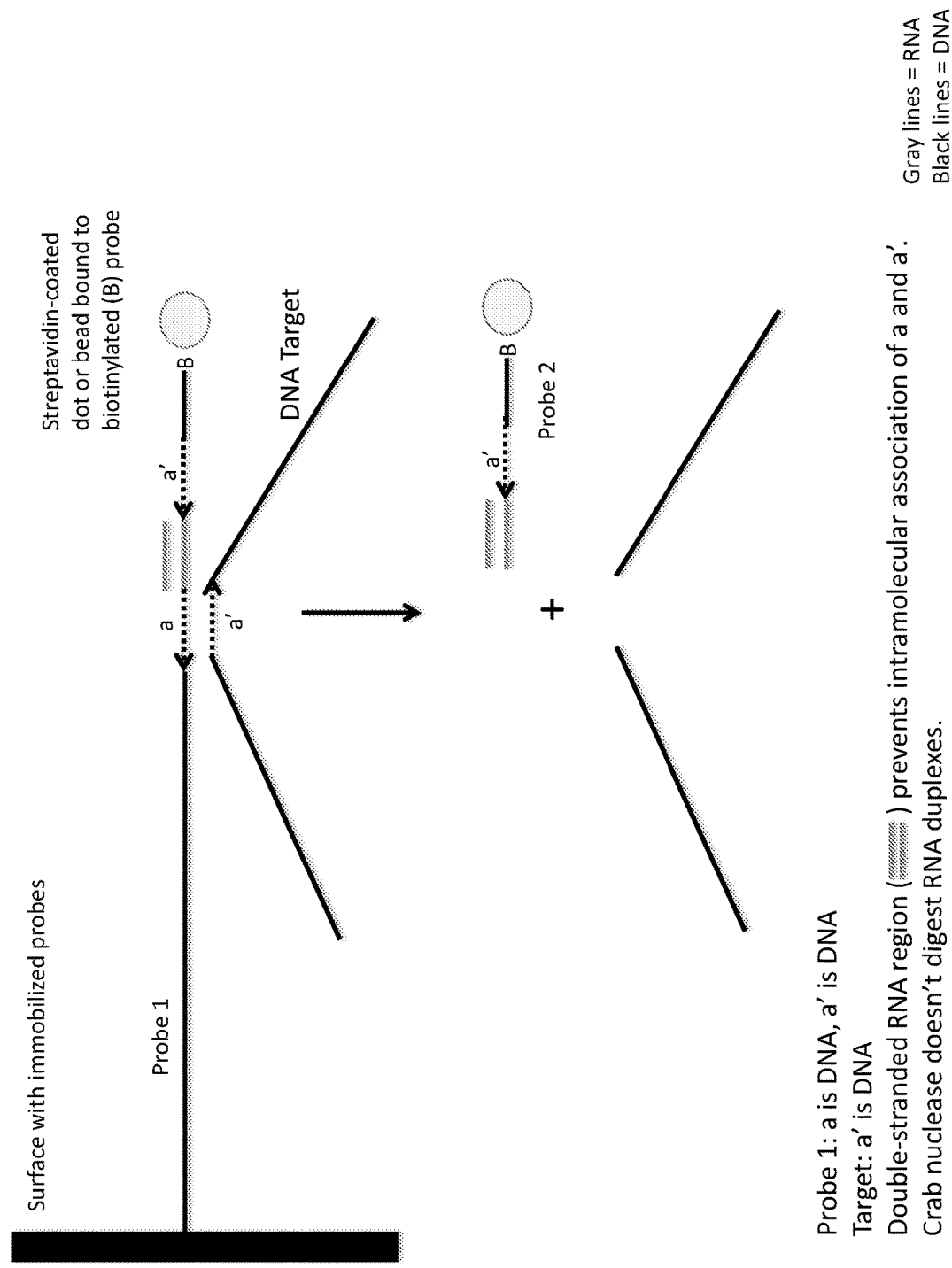
FIG. 33 shows a probe design and scheme for linear DSA of a DNA target utilizing a probe containing a double-stranded RNA block.
Figure 34:
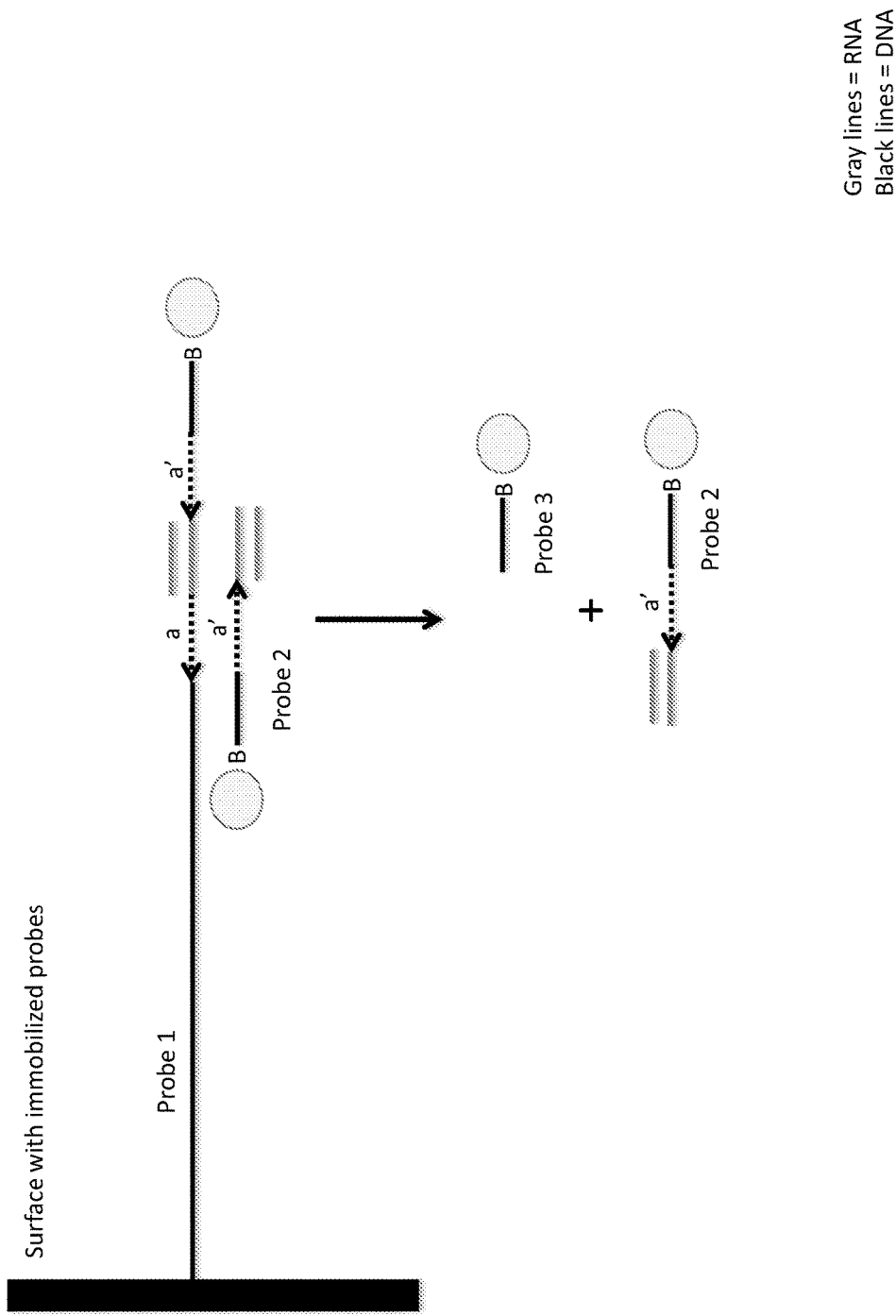
FIG. 34 shows further stages of a scheme for linear DSA of a DNA target utilizing a probe containing a double-stranded RNA block.

Referring to FIGS. 33-35, a scheme is provided for linear DSA of a DNA target using a probe including an RNA block. A double-stranded RNA block may also be used in a DNA-targeting probe to prevent intramolecular association of two complementary regions on the same probe, thus preventing self-cleaving of the probe in the presence of a duplex-specific nuclease. FIG. 33 shows a probe design (Probe 1) including such a double-stranded RNA region positioned between two complementary DNA regions, region a and region a', oriented parallel to each other. The double-stranded RNA region and region a' are also part of an end region that further includes a terminal biotin moiety bound to a streptavidin-coated fluorophore (e.g., a quantum dot, fluorescent bead, or any other fluorophore described herein).

The initiation of the scheme involves hybridization of a DNA target containing a region a' to region a of Probe 1 (FIG. 33), resulting in DSN cleavage of region a of Probe 1 and region a' of the DNA target, and releasing the end region (shown in FIG. 33 as Probe 2). As shown in FIG. 34, region a' of Probe 2 may subsequently hybridize with region a of a further copy of Probe 1, leading to duplex-specific nuclease degradation of region a' of Probe 2 and region a of the further copy of Probe 1, thus producing a further copy of Probe 2. This reaction also results in cleavage of the double-stranded RNA region from the first copy of Probe 2, producing Probe 3. Because the target DNA and each copy of Probe 2 are cleaved during hybridization to Probe 1, thus removing their respective copies of region a', this amplification reaction proceeds at a linear rate. Each reaction yields one copy of Probe 2, and n−1 copies of Probe 3, in which n=the number of rounds of reactions. For example, the first round yields one copy of Probe 2, the second round yields one copy of Probe 2 and one copy of Probe 3, the third round yields one copy of Probe 2 and two copies of Probe 3, and the fourth round yields 1 copy of Probe 2 and three copies of Probe 3 (FIG. 35).

Example 12. Exponential DSA of DNA Using an RNA Block

Figure 36:
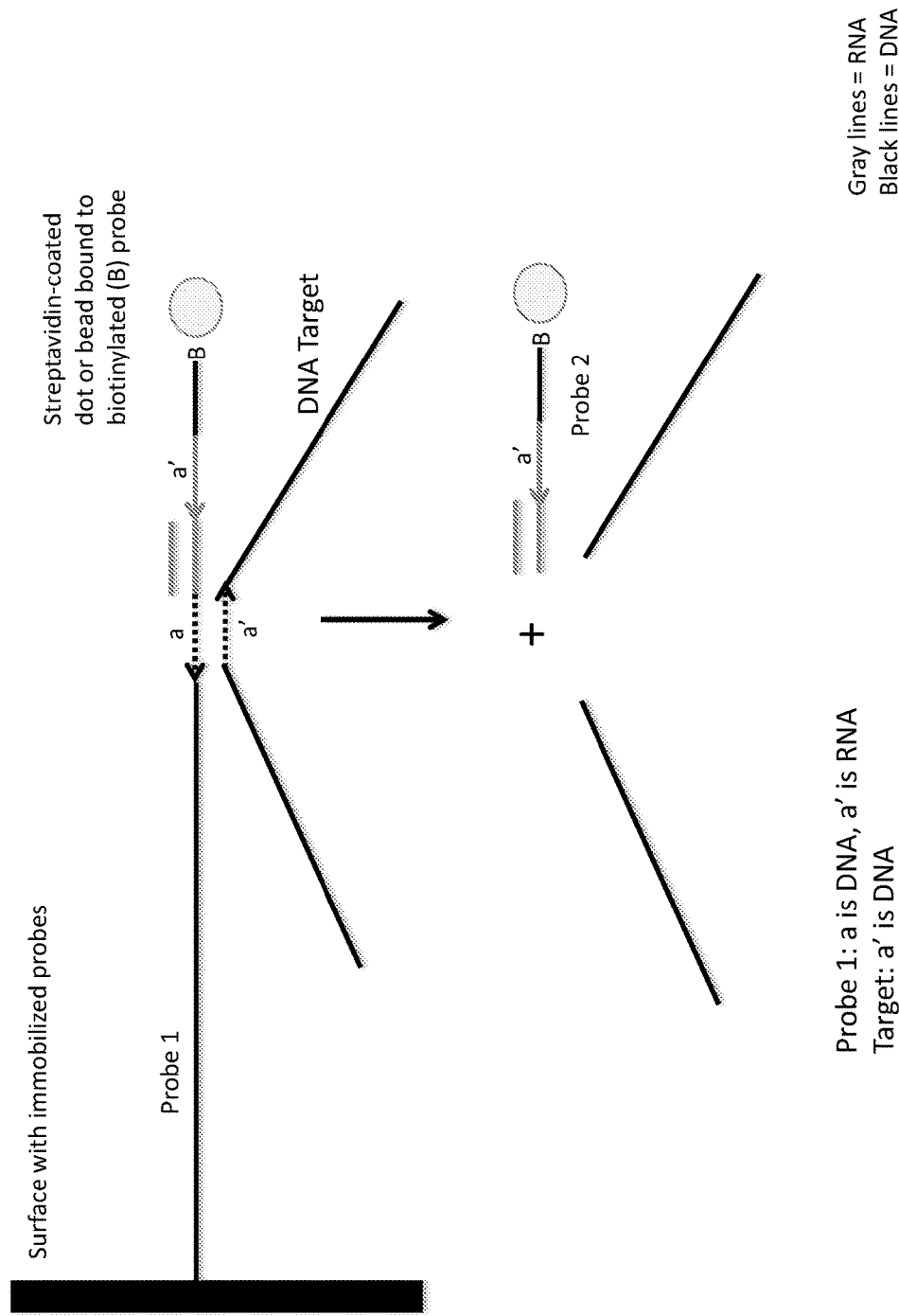
FIG. 36 shows a probe design and scheme for exponential DSA of a DNA target utilizing a probe containing a double-stranded RNA block.
Figure 37:
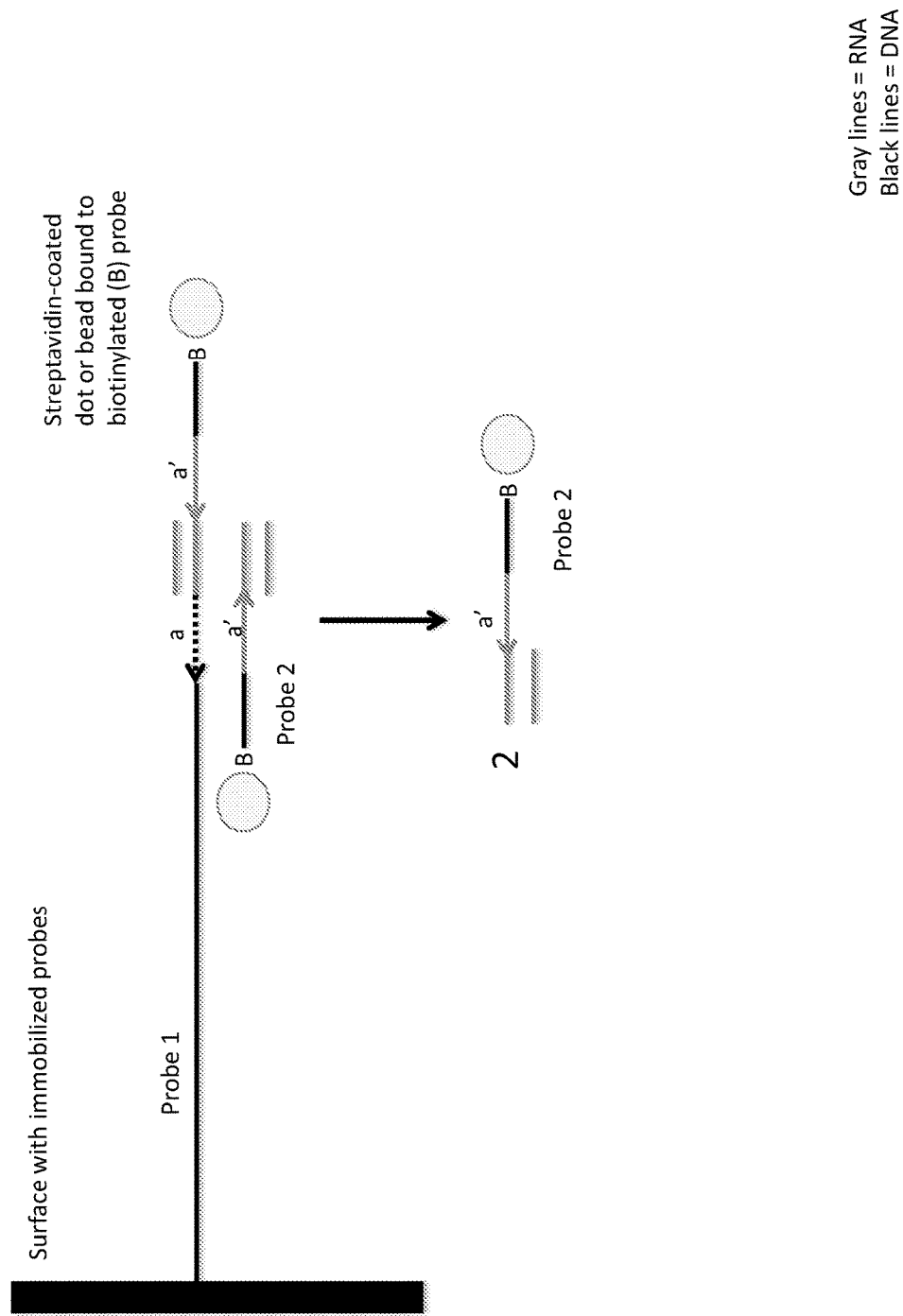
FIG. 37 shows further stages of a scheme for exponential DSA of a DNA target utilizing a probe containing a double-stranded RNA block.
Figure 39:
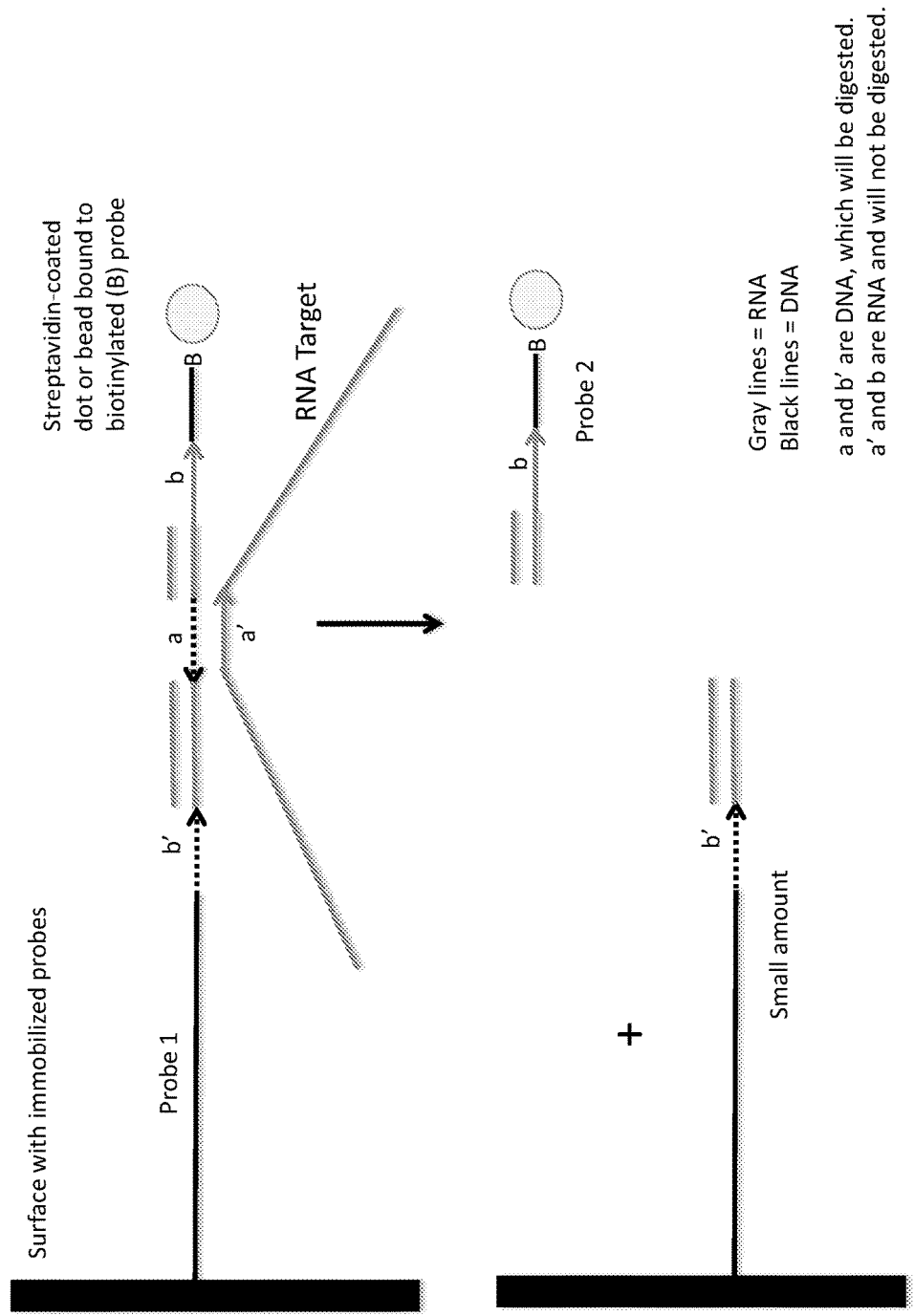
FIG. 39 shows a probe design and scheme for exponential DSA of an RNA target using a probe containing two double-stranded RNA blocks.

Referring to FIGS. 36-38, a scheme is provided for exponential DSA of a DNA target using a probe including an RNA block. A double-stranded RNA block may be used, in some instances, to prevent intramolecular association of two complementary regions on the same probe, thus preventing self-cleaving of the probe in the presence of a DSN. FIG. 36 shows a probe design (Probe 1) including such a double-stranded RNA block, in which the target binding region of the probe is oriented parallel to the end region to be released. Probe 1 is immobilized on a surface and includes a DNA region a and an end region including, in order, a double-stranded RNA region (the block), an RNA region a' complementary to region a, and a terminal biotin moiety bound to a streptavidin-coated fluorophore (e.g., a quantum dot, fluorescent bead, or any other fluorophore described herein).

The initiation of the scheme involves hybridization of a DNA target containing a region a' to region a of Probe 1 (FIG. 36), resulting in DSN cleavage of region a of Probe 1 and of region a' of the DNA target and release of the end region (Probe 2). Region a' of Probe 2 may subsequently hybridize to region a of a further copy of Probe 1, resulting in DSN cleavage of region a of the further copy of Probe 1 and the release of an additional copy of Probe 2 (FIG. 37). Because Probe 2 is not cleaved, each copy of Probe 2 may induce the cleavage of multiple copies of Probe 1, thereby leading to exponential amplification (FIG. 38).

Example 13. Exponential DSA of RNA Using a Probe with Two RNA Blocks

Referring to FIGS. 39-45, a scheme is provided for exponential DSA of an RNA target using a probe that includes two RNA block regions. One or more double-stranded RNA regions may be used, in some instances, in a probe to prevent intramolecular association of two complementary regions on the same probe, thus preventing self-cleaving of the probe in the presence of a DSN. This scheme, which is based on that described in Example 3, instead utilizes a probe design (shown in FIG. 39 as Probe 1) featuring two RNA block regions consisting of double-stranded RNA. Probe 1 is immobilized on a surface and includes three regions: in order, region b', region a, and region b, of which regions a and b' are DNA, and region b is RNA. Regions b and b' are complementary sequences. Region a is complementary to at least a portion of an RNA target (region a'). Regions b and b' are oriented parallel to each other and antiparallel to region a. The end of Probe 1 opposite of the surface includes a fluorophore attached to the probe by biotin-streptavidin binding.

The initiation of the scheme involves hybridization of region a' of the RNA target with region a of Probe 1 in the presence of a DSN, thereby resulting in cleavage of region a of Probe 1. This in turn results in the release of the end region of the probe (Probe 2), which includes one of the double-stranded RNA regions (region b) and the fluorophore. The remainder of the probe, containing the b' region and the other double-stranded RNA region, remains attached to the surface. Note that regions b and b' within a single copy of Probe 1 cannot hybridize due to the presence of the double-stranded RNA blocks.

Figure 40:
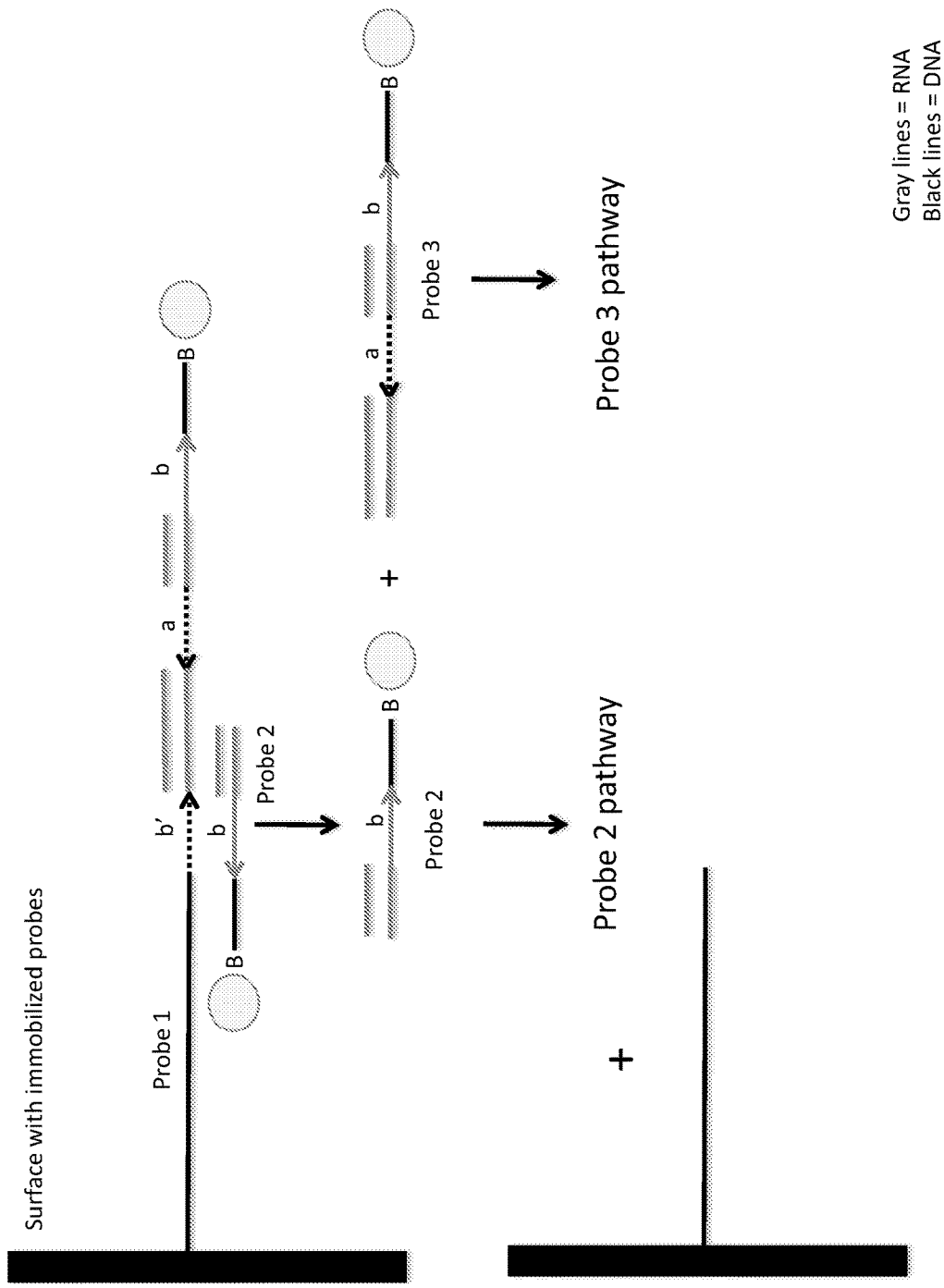
FIG. 40 shows further stages of a scheme for exponential DSA of an RNA target using a probe containing two double-stranded RNA blocks, which bifurcates along two pathways: the Probe 2 pathway and the Probe 3 pathway.
Figure 41:
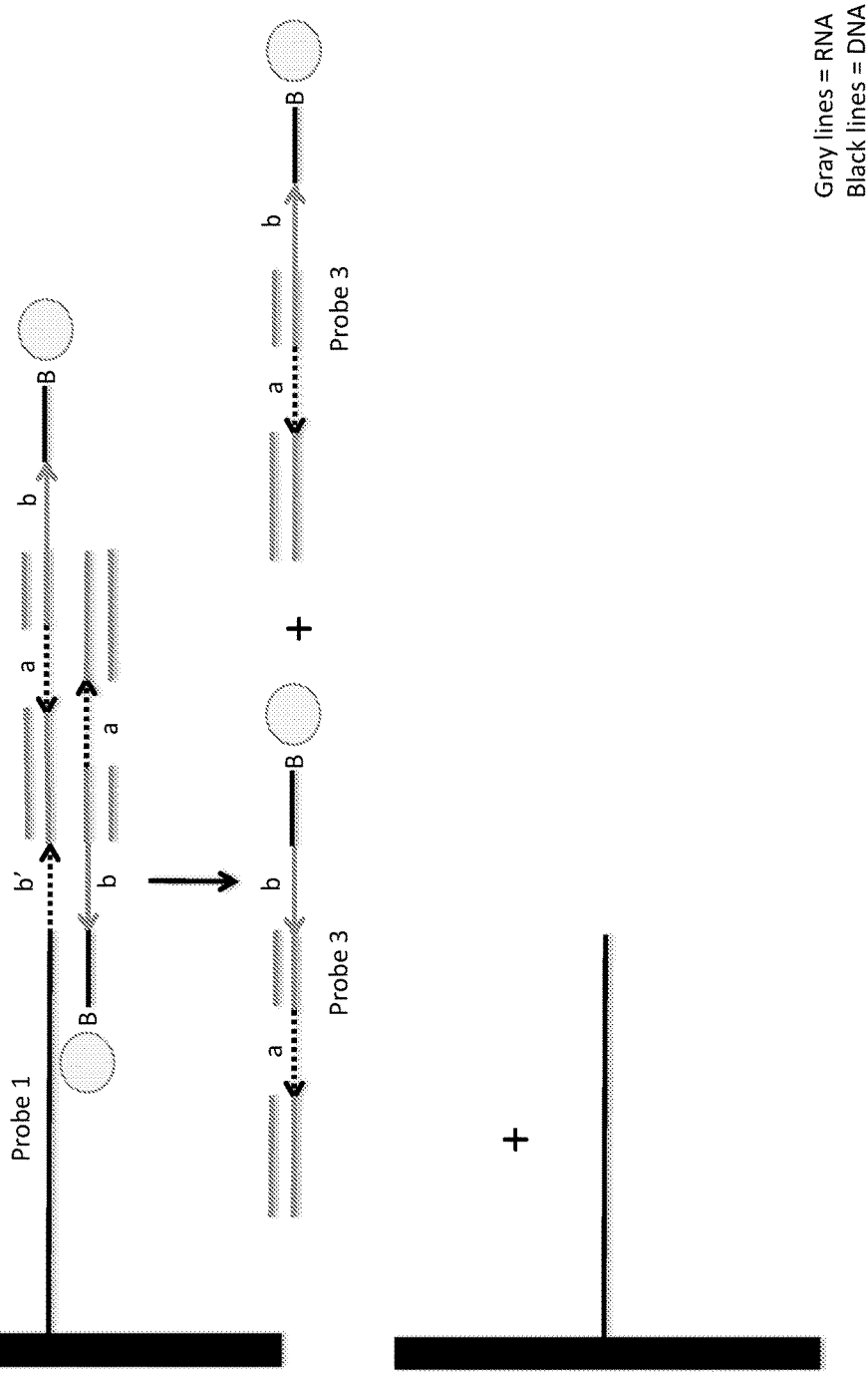
FIG. 41 illustrates the Probe 3 pathway for a scheme for exponential DSA of an RNA target using a probe containing two double-stranded RNA blocks.
Figure 42:
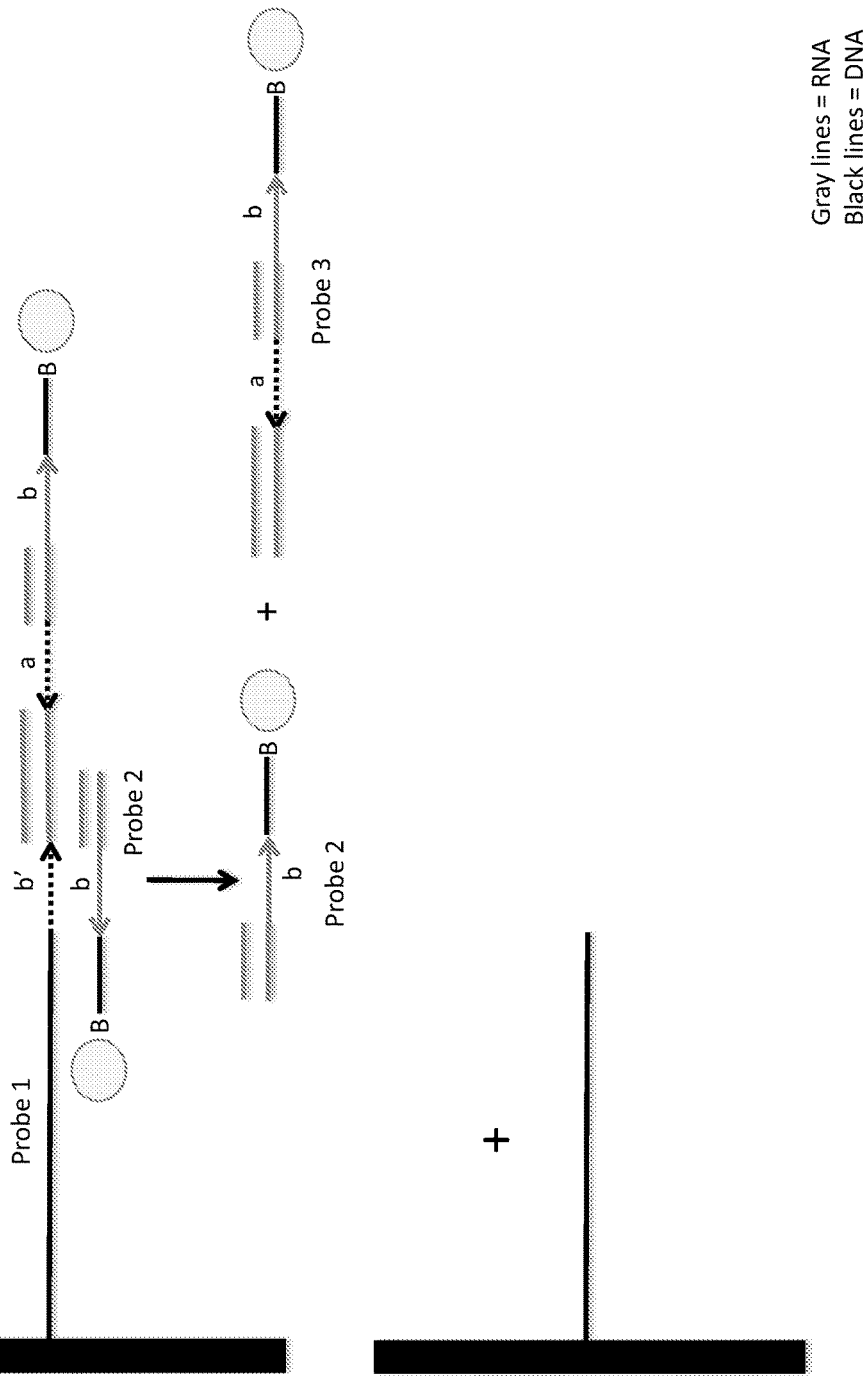
FIG. 42 illustrates the Probe 2 pathway for a scheme for exponential DSA of an RNA target using a probe containing two double-stranded RNA blocks.

Turning to FIG. 40, additional copies of Probe 1 immobilized on the surface may interact with Probe 2, as the b' region of Probe 1 hybridizes to the b region of Probe 2. The resultant duplex is then cleaved by a DSN. Again, region b of Probe 2 is made up of RNA and is not cleaved. Thus, DSN cleavage results in the release of Probe 2 and production of Probe 3, which includes a region a, a region b, and two double-stranded RNA block regions. Probes 2 and 3 then proceed to hybridize with further copies of Probe 1 according to the Probe 2 or Probe 3 pathways, respectively. FIG. 41 shows the Probe 3 pathway, in which region b of Probe 3 hybridizes with region b' of another Probe 1, resulting in DSN cleavage and the release of the original Probe 3 as well as the production of a new copy of Probe 3. FIG. 42 shows the Probe 2 pathway, in which region b of Probe 2 hybridizes with region b' of another Probe 1, resulting in DSN cleavage, the release of the original Probe 2, and the production of a new copy of Probe 3. In both the Probe 2 and Probe 3 pathways, only the b' region of Probe 1 is composed of DNA and is thus cleaved. The b region is always RNA and is not cleaved by the DSN.

Turning to FIGS. 43 and 44, repeated rounds of amplification produces additional cleaved copies of Probe 3 at exponential rates. In this scheme, the target RNA (T) is never digested. In alternate embodiments, the target may be a DNA molecule (FIG. 43). A DNA target would be digested in the initial step, but all subsequent reactions would continue as described. Thus, exponential amplification may be achieved regardless of whether the target is RNA or DNA. If the target is RNA, however, the copies of Probe 3 may continue to interact with copies of the RNA target, which will not have been degraded by the nucleases. Region a of Probe 3 (composed of DNA) hybridizes to region a' of the RNA target (FIG. 44). DSN cleavage of region a of Probe 3 thus produces another copy of Probe 2. The end result of the RNA DSA scheme is to produce copies of Probe 2 at exponential rates, such that additional Probe 2 copies are produced linearly and additional Probe 3 copies are produced exponentially (FIG. 45A). For the DNA DSA scheme, only a single copy of Probe 2 is produced, but the numbers of copies of Probe 3 increase exponentially after each round of reactions (FIG. 45B).

Example 14. Exponential DSA of DNA Using Probe with Two Cleavage Sites

Figure 46:
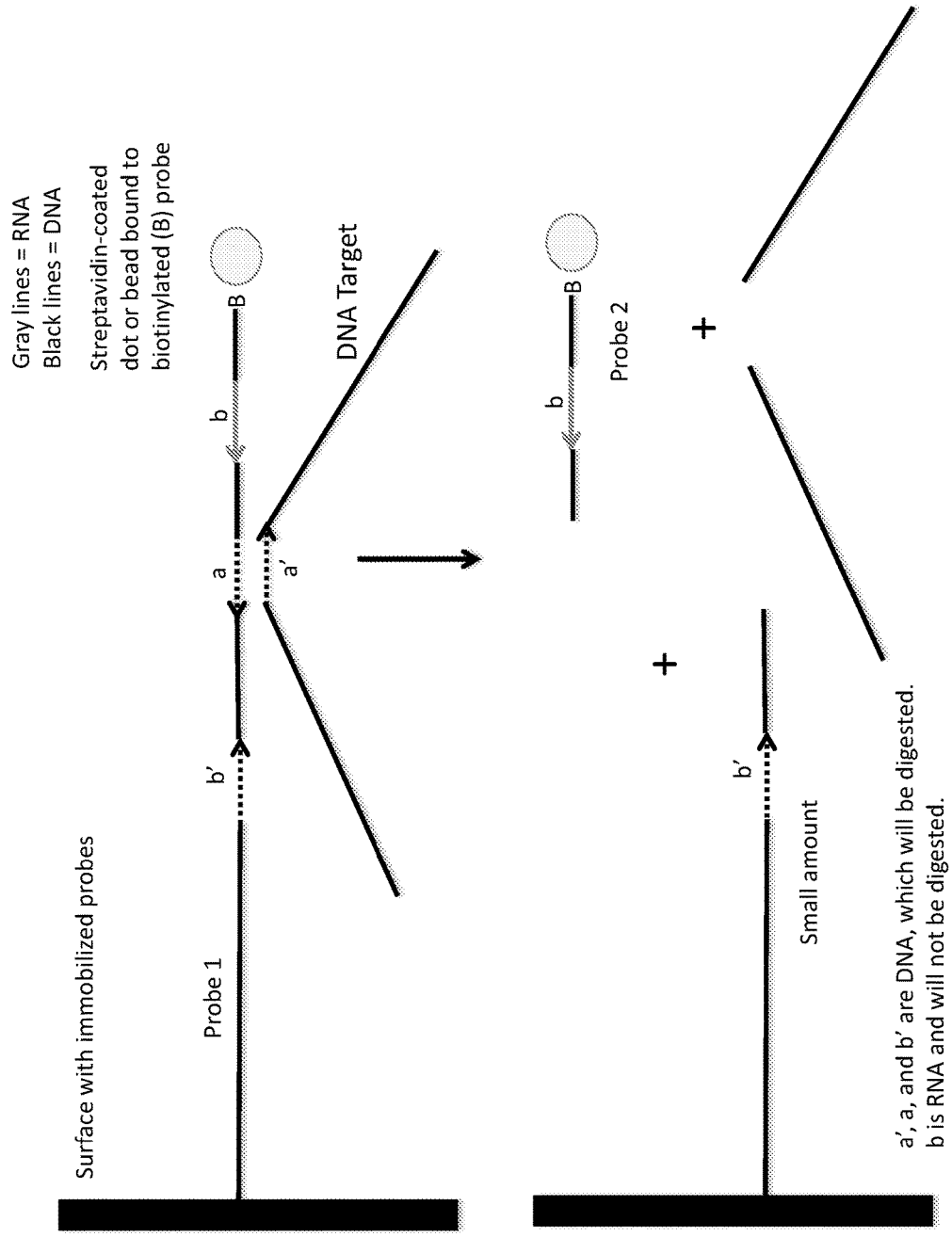
FIG. 46 shows a probe design and scheme for exponential DSA of a DNA target using a probe with two cleavage sites.

Referring to FIGS. 46-50, a scheme is provided for exponential DSA of a DNA target using a probe including two cleavage sites. This scheme may be used, for example, to detect the presence of a target DNA and exponentially amplify the resultant detectable signal. FIG. 46 shows a probe design (Probe 1) immobilized on a surface and including three regions: a, b, and b', of which a and b' are DNA, and b is RNA. Regions b and b' are complementary sequences. Region a is complementary to at least a portion of the DNA target (region a'). Regions a and b are oriented parallel to each other and antiparallel to region b'.

The initiation of the scheme involves hybridization of region a' of the DNA target with region a in the presence of a DSN. This results in cleavage of region a of Probe 1 and region a' of the DNA target, leading to release of the end region of the probe, which includes region b and a fluorophore attached to the probe by biotin-streptavidin binding. The released end region is shown in FIG. 46 as Probe 2. The remainder of the probe, containing the b' region, remains attached to the surface. Note that regions b and b' within a single copy of Probe 1 are not cleaved as a result of hybridization with each other, because when they loop to form a duplex, the duplex is not anti-parallel.

Turning to FIG. 47, additional copies of Probe 1 immobilized on the surface may hybridize with Probe 2, as the b' region of an additional copy of Probe 1 hybridizes to the b region of Probe 2. The DNA portion of the resultant duplex (region b') is then cleaved by a DSN. Region b of Probe 2 is made up of RNA and is not cleaved. DSN cleavage of region b' results in the release of Probe 2 and release of Probe 3, which includes a region a and a region b. Probes 2 and 3 may then proceed to interact with further copies of Probe 1 according to the Probe 2 or Probe 3 pathways, shown in FIGS. 48 and 49, respectively. As shown in FIG. 48, in the Probe 3 pathway, region b of Probe 3 hybridizes with region b' of another Probe 1, resulting in DSN cleavage and the release of the original Probe 3 as well as the production of a new copy of Probe 3. As shown in FIG. 49, in the Probe 2 pathway, region b of Probe 2 hybridizes with region b' of another Probe 1, resulting in DSN cleavage and the release of the original Probe 2 and the production of a new copy of Probe 3. In both the Probe 2 and Probe 3 pathways, only the b' region of Probe 1 is composed of DNA and is thus cleaved. The b region is always RNA and is not cleaved by the DSN.

Although the DNA target is digested in the initial step, the subsequent reactions produce probes (Probes 2 and 3) that may induce cleavage of further copies of Probe 1, and which themselves are not cleaved during the reaction. Thus, exponential amplification may be achieved (FIG. 50).

Example 15. Exponential DSA of DNA-RNA Hybrid Nucleic Acids

Referring to FIGS. 51-53, a scheme is provided for exponential DSA of DNA-RNA hybrid nucleic acids. This scheme may be used for detection of a target consisting of an DNA-RNA hybrid. For example, FIG. 51 shows a probe design (Probe 1) that may hybridize to a target nucleic acid including a DNA containing a target sequence a' and attached to an RNA. The target binding region of Probe 1 is oriented parallel relative to an RNA region (region b) located within an end region. Specifically, Probe 1 features a DNA region a, complementary to region a' of the target nucleic acid, and an RNA region b located between one end immobilized to a surface and an opposite end attached to a biotin moiety bound to a streptavidin-coated fluorophore (e.g., a quantum dot, fluorescent bead, or any other fluorophore described herein). Also shown in FIG. 51 is Probe 3, which includes, in order, an end attached to a surface (e.g., the same surface as Probe 1 or a different surface from Probe 1), a DNA region b' (complementary to region b of Probe 1), an RNA region a', and an end attached to a biotin moiety bound to a streptavidin-coated fluorophore (e.g., a quantum dot, fluorescent bead, or any other fluorophore described herein). Region b' and region a' of Probe 3 are oriented antiparallel to each other.

The initiation of the scheme involves hybridization of region a' of the target nucleic acid with region a of Probe 1, leading to DSN cleavage of both region a of Probe 1 and region a' of the target nucleic acid (FIG. 51). This results in release of an end region (Probe 2), which contains region b and the fluorophore. Region b of Probe 2 may proceed to hybridize to region b' of Probe 3 (FIG. 52). Region b' is cleaved by a DSN, thus releasing Probe 4, which contains region a' and the fluorophore. As shown in FIG. 53, region a' of Probe 4 may, in turn, hybridize to region a on a further copy of Probe 1, thus resulting in DSN cleavage of region a of the further copy of Probe 1 and release of a further copy of Probe 2. The net result is exponential amplification of detectable Probes 2 and 4.

Example 16. Exponential DSA of DNA Using Probes on Beads

Referring to FIG. 54, a scheme is provided for exponential DSA of a DNA target using probes attached to surfaces (e.g., one or more beads). As shown in FIG. 54A, the scheme involves two probe designs (Probe 1 and Probe 3). In this example, Probes 1 and 3 are immobilized to bead supports. Probes 1 and 3 are attached to the beads in opposite orientations to prevent them from cleaving each other in the absence of target. Probe 1 features a DNA region a complementary to a portion of the target DNA and an RNA region b. Regions a and b are oriented parallel to each other, and are located between the end of Probe 1 immobilized to the bead and the opposite end, which may be, optionally, attached to a fluorophore, for example, by a biotin moiety bound to a streptavidin-coated fluorophore, (e.g., a quantum dot, fluorescent bead, or any other fluorophore described herein). Probe 3 features, in order, an end attached to the bead, a DNA region b' complementary to region b of Probe 1, an RNA region a' complementary to region a of Probe 1, and, optionally, an end attached to a fluorophore, for example, by a biotin moiety bound to a streptavidin-coated fluorophore, (e.g., a quantum dot, fluorescent bead, or any other fluorophore described herein). Regions b' and a' of Probe 3 are oriented parallel to each other. Region a of Probe 1 and region b' of Probe 3 may be directly attached to the surface of the corresponding bead.

The initiation of the scheme involves hybridization of a DNA target, containing a region a' complementary to region a of Probe 1, with Probe 1, leading to cleavage of both region a (on Probe 1) and region a' (on the DNA target) by a DSN. In this example, only DNA is cleaved by the DSN. This results in release of a first end region from Probe 1, which contains region b and the fluorophore. Region b of the released first end region may proceed to hybridize to region b' of Probe 3. Region b' may then be cleaved by a DSN, thus releasing a second end region, which contains region a' and the fluorophore of Probe 3. Region a' of the released second end region may, in turn, hybridize to region a on a further copy of Probe 1, thus resulting in DSN cleavage of region a and release of a further copy of the first end region. The net result is exponential amplification of the released end regions, such that the total number of copies of each released end region yielded doubles for each successive reaction round (FIG. 54B).

Example 17. Exponential DSA of RNA Using Probes on Beads

Figure 55:
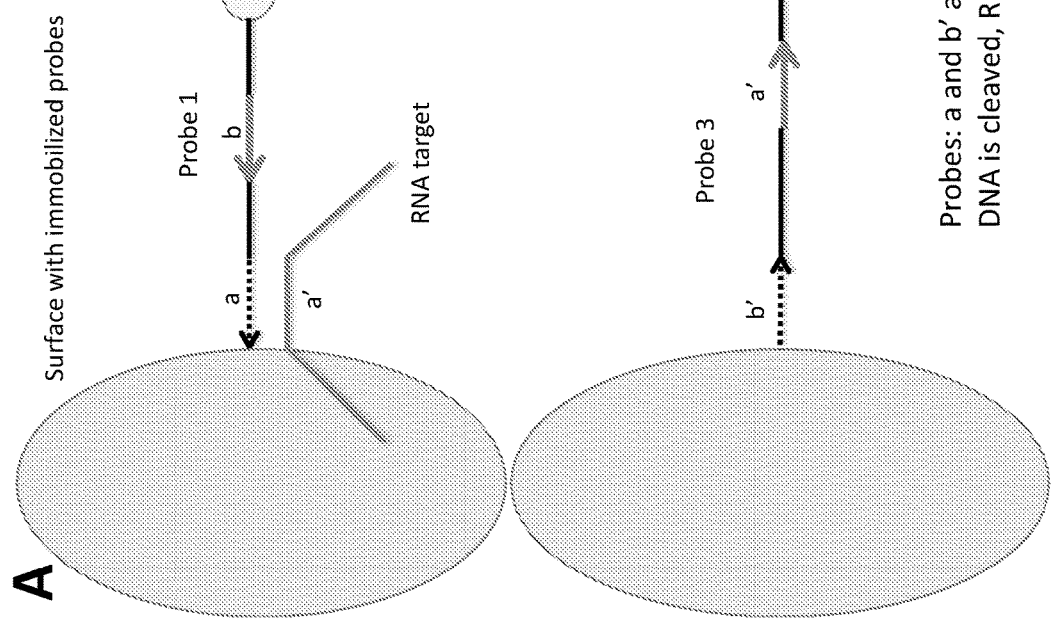
FIG. 55A show probe designs and a scheme for exponential DSA of an RNA target nucleic acid.
FIG. 55B shows the results of multiple rounds of a scheme for exponential DSA of an RNA target nucleic acid as depicted in FIG. 55A. T=target RNA; P1=Probe 1; P3=Probe 3.

Referring to FIG. 55, a scheme is provided for exponential DSA of an RNA target using probes attached to surfaces (e.g., one or more beads). As shown in FIG. 55A, this scheme features two probe designs (Probe 1 and Probe 3), each immobilized on a bead support (e.g., the same bead or different beads). Probe 1 includes parallel regions a and b, of which region a is DNA and region b is RNA. Probe 3 includes parallel regions b' and a', of which region a' is RNA and region b' is DNA. Probes 1 and 3 are attached to their respective beads in opposite orientations to prevent them from cleaving each other in the absence of target. Each of Probe 1 and Probe 3 may include an end region, optionally containing a fluorophore, for example, by a biotin moiety bound to a streptavidin-coated fluorophore, (e.g., a quantum dot, fluorescent bead, or any other fluorophore described herein). Only DNA is digested by the duplex-specific nuclease.

The initiation of the scheme involves hybridization of region a of Probe 1 to a target RNA containing the sequence of region a' (FIG. 55A). This results in cleavage of region a by a DSN, producing a released first end region, which contains region b. Because the target nucleic acid is DNA, it will be cleaved in this first step. The released first end region may subsequently hybridize with region b' of Probe 3, resulting in DSN cleavage of region b'. This leads to the release of the original first end region and the production of a released second end region, which includes region a'. Region a' of the released second end region may, in turn, hybridize with region a of another copy of Probe 1, resulting in DSN cleavage of region a and the release of the original second end region and of a new copy of the first end region. Each copy of the first and second released end regions may proceed to hybridize with additional copies of Probe 3 and Probe 1, respectively, to drive further cleavage events and amplification of the released end regions at similar ratios. This process may be repeated multiple times, with each round increasing the number of copies of the released end regions present at an exponential rate (FIG. 55B).

Example 18. Linear DSA Using a Free-Floating Double-Stranded Probe

Figure 56:
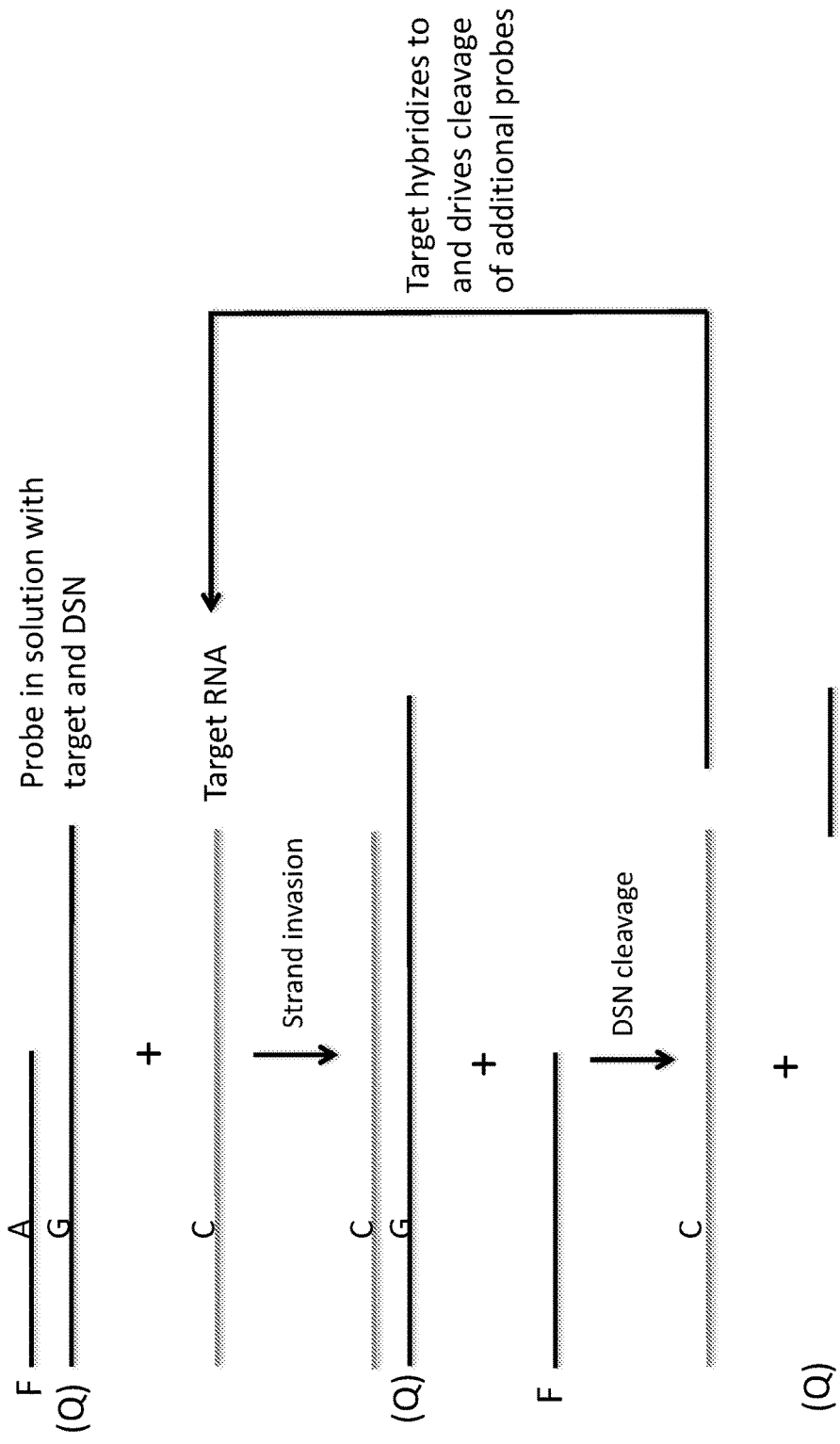
FIG. 56 shows probe designs and a scheme for linear DSA using a free-floating double-stranded probe.

Referring to FIG. 56, a scheme for linear DSA is shown that involves the use of a free-floating double-stranded probe not attached to a support. A solution is provided that includes the probe, a target nucleic acid (e.g., a target RNA), and a DSN.

In one example, the probe includes two hybridized DNA strands: a short strand attached to a fluorophore (e.g., a quantum dot, fluorescent bead, or any other fluorophore described herein) and a long strand. The long strand is optionally attached to a quencher, e.g., at the same end as the fluorophore is attached to the short strand, such that hybridization of the long strand and the short strand places the fluorophore in close enough proximity to the quencher to quench the fluorophore. Exemplary quenchers useful for incorporating into hybridization probes are described in, e.g., Table 4 on page 13 of Marras (*Methods Mol. Biol.* 335: 3-16, 2006). Such quenchers, without limitation, include DDQ-I, DDQ-II, Dabcyl, Eclipse, Iowa Black FQ, Iowa Black RQ, QSY-7, QSY-21, BHQ-1, BHQ-2, or BHQ-3. Further, the long strand typically includes a region complementary to at least a portion of the target nucleic acid (in this case, the target RNA molecule). In some instances, the entire long strand is complementary to at least a portion of the target RNA molecule (e.g., the entire RNA molecule).

The DSN may, for example, only be capable of cleaving duplex regions of perfect complementarity. Cleavage by a DSN may thus be blocked by designing the probe, for example, to include an intentional mismatched base pair in the double-stranded region of the probe according to standard methods. Alternatively, an intentional unpaired base that creates an undigestable bulge (e.g., a bulge region) may be incorporated into the double-stranded region of the probe. Alternatively, the strand attached to the fluorophore may include one or more RNA or 2'-O-methylated bases to prevent cleavage of the double-stranded region of the probe.

Hybridization of the RNA target to the long strand of the probe, e.g., by a strand invasion process, forms a RNA-DNA duplex which, in turn, enables DSN cleavage and release of the fluorophore-bound short strand of the probe. Strand invasion typically involves the insertion of a single-strand nucleic acid into a duplex, such that the single-strand nucleic acid hybridizes with one strand of the duplex while simultaneously displacing the other strand of the duplex, effectively unzipping the duplex. In this example, the target RNA hybridizes to the exposed portion of the long strand of the probe (e.g., the portion on the opposite end from the optional quencher), followed by strand invasion of the target RNA into the short strand-long strand duplex. This leads to displacement of the short strand from the duplex and the formation of a target RNA-long strand duplex.

In this example, a double-stranded probe which includes a single-strand overhang, such as shown in the probe of FIG. 56, is hybridized with a nucleic acid complementary to the overhang, such as the target RNA. Because the target RNA contains a region complementary to the overhang of the probe, the target RNA subsequently invades the double-stranded probe formed by the hybridization between the short strand and the long strand of the probe. Thus, the short strand-long strand duplex is unzipped as the target RNA hybridizes with the long strand of the probe, yielding the target RNA-probe complex shown in FIG. 56 as the product of strand invasion. A DSN then cleaves the portion of the long strand (e.g., the entire long strand) hybridized to the RNA target, thus releasing the RNA target, which subsequently hybridizes with and induces DSN cleavage of the long strands of additional copies of the probe. As a result, released copies of the fluorophore-bound short strands are produced at a linear rate.

Figure 57:
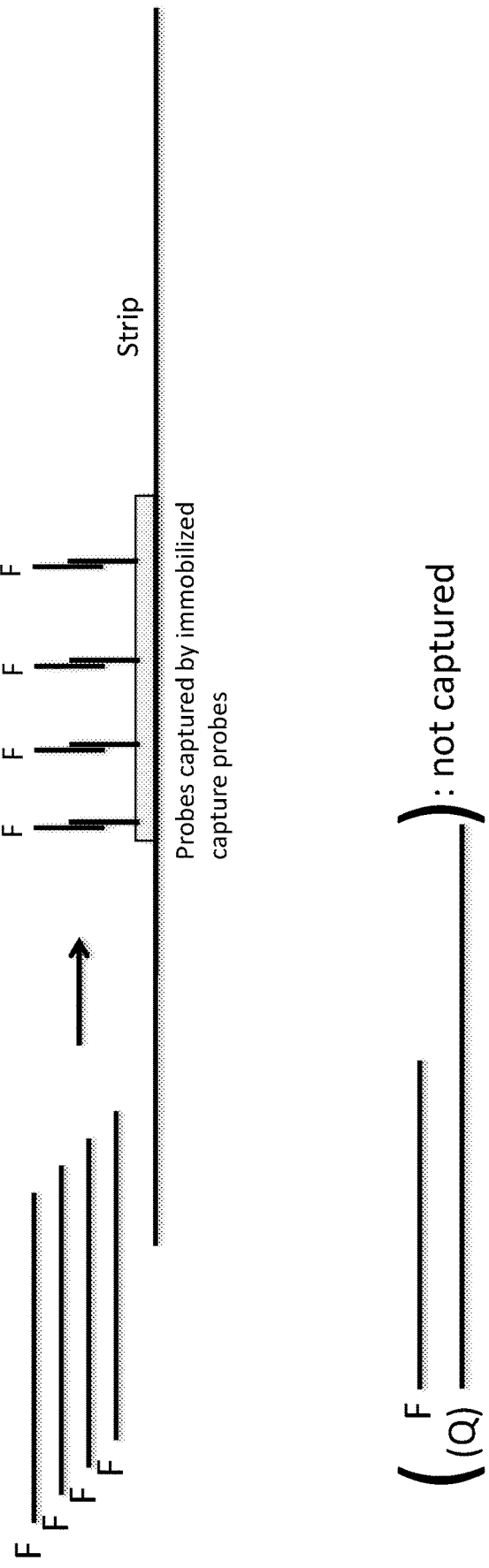
FIG. 57 shows further stages of a scheme for linear DSA using a free-floating double-stranded probe, involving capture of digested probe fragments on a strip.

Turning to FIG. 57, released fluorophore-bound short strands may then be detected using capture probes capable of hybridizing to (e.g., complementary to) at least a portion of the fluorophore-bound short strand (e.g, the portion of the short strand opposite the fluorophore-bound end); for example. The capture probes may be immobilized to a support (e.g., a strip, bead, chip, or well; preferably a strip). Captured short strands may subsequently be quantified, e.g., by the fluorescence of the bound fluorophores. Short strands that remain hybridized to long strands will not be captured. Thus, the number of short strands detected using the capture probes may directly reflects the amount of target RNA present in the sample solution, with the signal amplified in a linear fashion. Alternatively, if the probe has a quencher molecule, target binding may be detected without capture, for example, by measuring an increase in the fluorescence of the solution.

Example 19. Linear DSA Using a Folded Template

Figure 58:
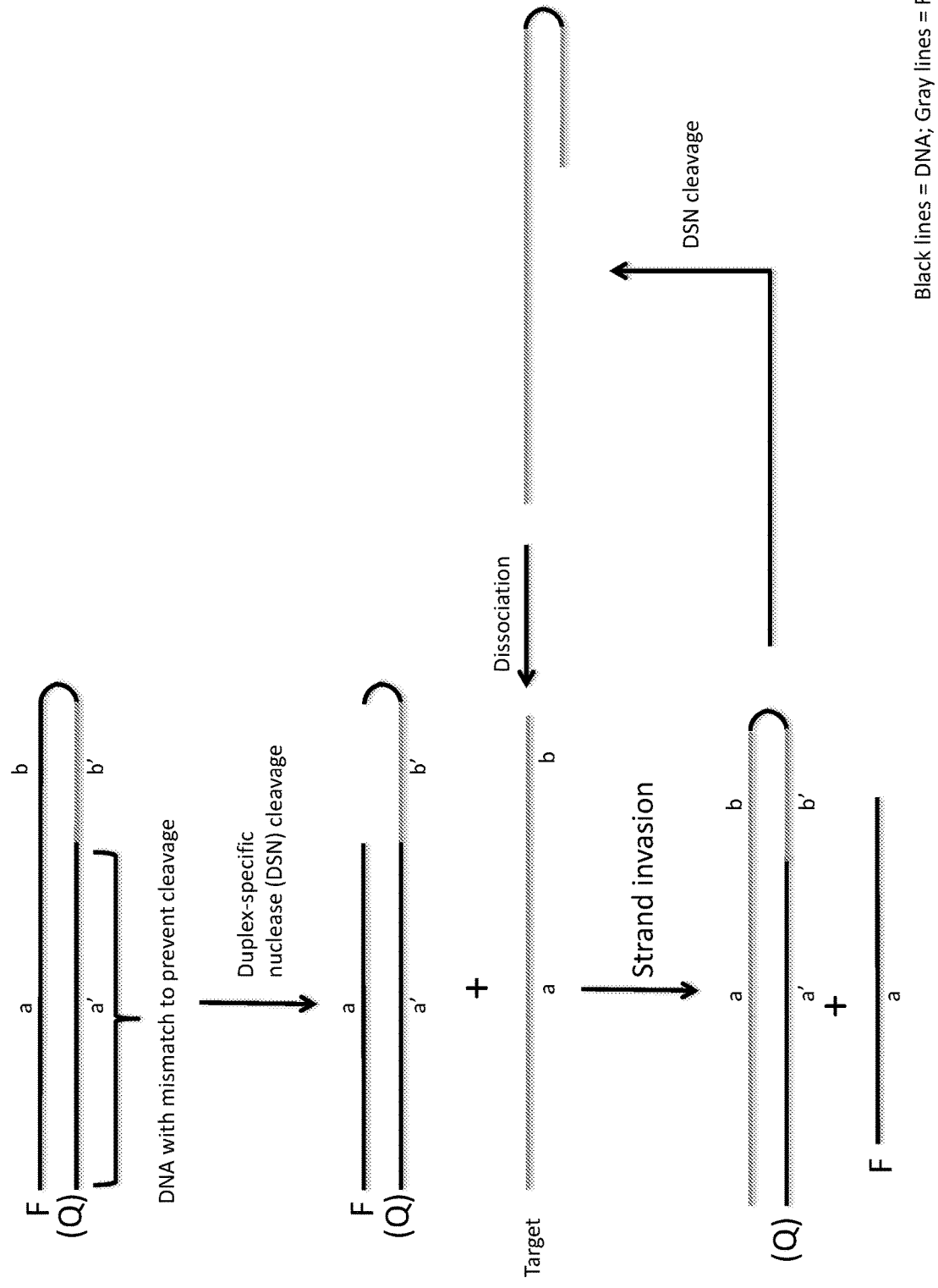
FIG. 58 shows probe designs and a scheme for linear DSA of an RNA target using a folded template.

Referring to FIG. 58, a linear DSA scheme is shown that utilizes a self-hybridizing nucleic acid detection probe.

Attached to one end of the detection probe is a fluorophore (e.g., a quantum dot, fluorescent bead, or any other fluorophore described herein). A quencher (e.g., a quencher as described herein) may be, optionally, attached to the opposite end of the detection probe.

In an example, as shown in FIG. 58, the detection probe includes, in order, DNA regions a and b, RNA region b', and DNA region a'. DNA regions a and a' are capable of hybridizing to each other. Hybridization of regions a and a' may bring the fluorophore and quencher into close enough proximity so as to quench the fluorophore.

In some instances, region a is attached to the fluorophore and region a' is attached to the quencher. Because both region a and region a' are DNA, the region a-region a' duplex may be cleaved by a DSN such as those described herein. To prevent such DSN cleavage, region a' may further contain at least one mismatch or bulge region (not shown) relative to region a, such that the region a and region a' sequences are not perfectly complementary. Alternatively, the strand attached to the fluorophore may include one or more RNA or 2'-O-methylated bases to prevent cleavage of the double-stranded region of the probe. The detection probe further contains a DNA region b and an RNA region b', for example, located between regions a and a'. For example, region b may be located between region a and region b', as shown in FIG. 58. In certain embodiments, region b is capable of hybridizing to region b', thereby forming an RNA-DNA duplex. In particular embodiments, region b and region b' are complementary, such that the region b of the RNA-DNA duplex may be cleaved by a DSN. The detection probe may also include, for example, an additional internal portion incapable of hybridizing with any portion of the detection probe, such that the detection probe may form a hairpin structure.

The initiation of the scheme, as shown in FIG. 58, involves DSN cleavage of DNA region b of the region b-region b' DNA-RNA duplex, leaving the hairpin intact and resulting in the production of two probe strands, one containing region a and the fluorophore, and one containing region a', region b', and the quencher. The two probe strands, in this example, are still hybridized to each other at region a and region a'. A target RNA containing a region a and a region b complementary to regions a' and b' of the cleaved probe may hybridize to regions a' and b' of the cleaved probe, e.g., by a strand invasion process (e.g., as described herein), thereby forming a DNA-RNA duplex. For example, region b of the target RNA may hybridize to region b' of the cleaved probe, followed by strand invasion (e.g., as described herein) of the target RNA into region a' of the cleaved probe. Formation of the duplex between the RNA target and the probe strand containing region a' releases the single strand containing region a, which is attached to the fluorophore. Thus, in instances in which the probe includes a quencher, the fluorophore and quencher are separated, allowing fluorescence to occur. A DSN may then cleave the DNA portion of the DNA-RNA duplex formed by region a of the target RNA and region a' of the cleaved probe. Because the target RNA is not degraded, it may also be also released, and may hybridize to and induce the degradation of region a' on further copies of the cleaved probe, resulting in linear amplification over time.

In sum, this process results in the linear accumulation of released fluorophore strands. If the probe has a quencher molecule, target binding may be detected directly by measuring an increase in the fluorescence of the solution. Alternatively, fluorophore strands may separated or captured, and the fluorophores detected, according to methods known in the art, such as those described herein.

Example 20. Linear DSA Using Two Levels of Amplification

Figure 59:
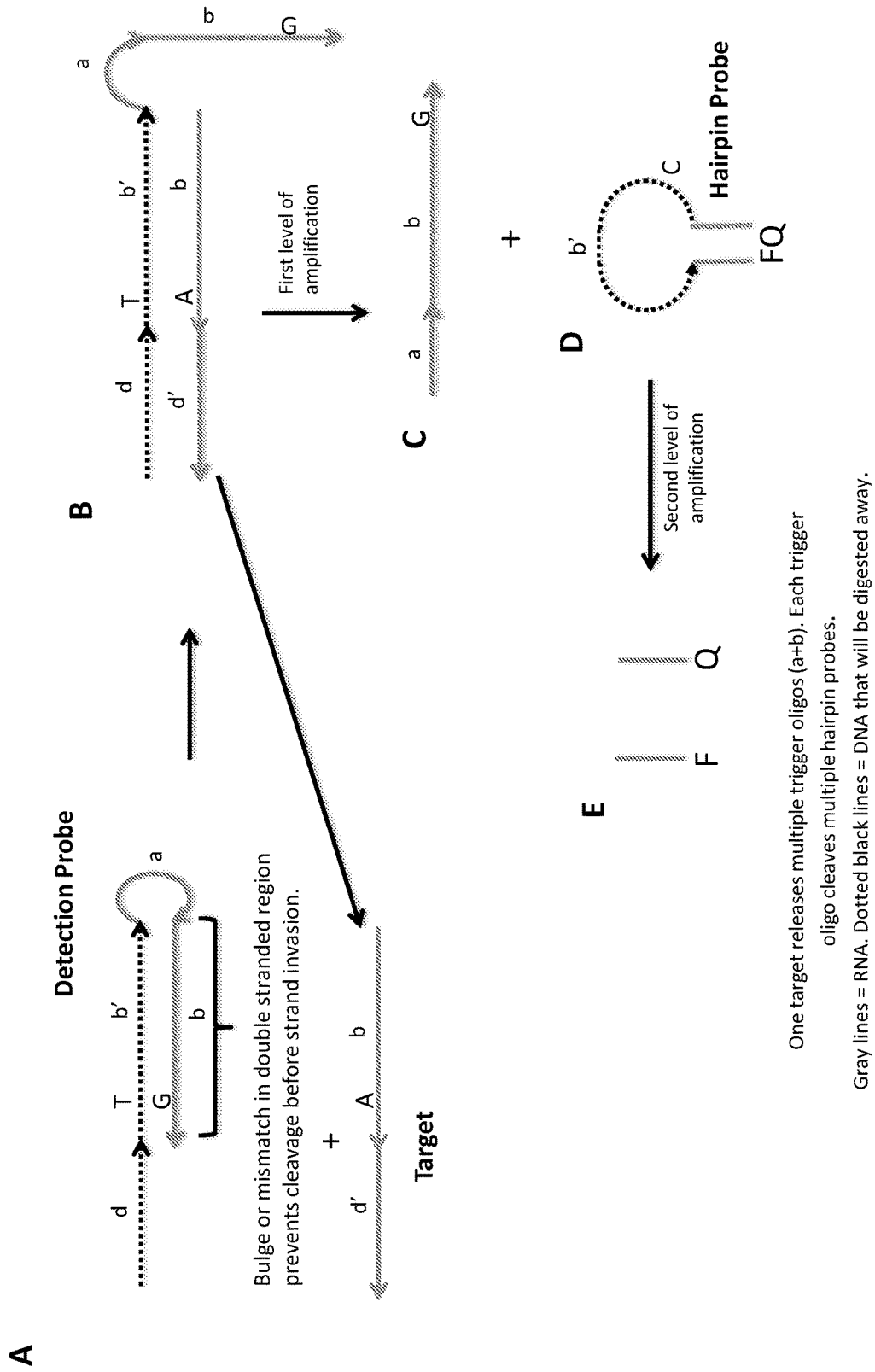
FIGS. 59A-59E show probe designs and a scheme for linear DSA of an RNA target using two folded probes and two levels of amplification.

Referring to FIG. 59, a linear DSA scheme is shown that utilizes two distinct nucleic acid probe constructs for target detection.

In an example, the first probe construct, shown in FIG. 59A as a detection probe, includes two regions, DNA region b' and RNA region b, which are hybridized to form an intraprobe duplex. Regions b and b' are designed such that the intraprobe duplex includes at least one bulge region or mismatch (e.g., a T-G mismatch) in order to prevent cleavage of the intraprobe duplex by a DSN. The detection probe further includes an RNA region a located between regions b and b', and a DNA region d attached to the end of region b'. DNA regions d and b' are complementary to at least a portion of an RNA target, shown as regions d' and b. As such, the RNA target hybridizes to the detection probe only if region b and region b' are separated, for example, by strand invasion (e.g., as described herein) of the RNA target strand into the region b-region b' duplex.

The second probe construct, shown in FIG. 59D as a hairpin probe, includes two terminal RNA regions capable of internally hybridizing to each other to form a stem, and a DNA region b' complementary to region b of the detection probe. Because certain DSNs described herein do not cleave RNA duplexes, the hairpin probe will not be degraded by such DSNs until DNA region b' of the hairpin probe is bound by RNA containing region b, thereby forming a DNA-RNA duplex that may be cleaved by such DSNs. As shown in FIG. 59D, the hairpin probe may include a cytosine (C) nucleotide capable of pairing with a guanine (G) nucleotide on region b of the detection probe, as shown in FIG. 59B. A fluorophore (e.g., a quantum dot, fluorescent bead, or any other fluorophore described herein) may be attached to one end of the hairpin probe, and a quencher (e.g., a quencher as described herein) may be attached to the opposite end, such that hybridization of the terminal regions results in placement of the fluorophore and quencher in close proximity, thereby quenching the fluorophore. As such, the hairpin probe may form a hairpin secondary structure in which the fluorophore is maintained in a quenched state while region b' is available to hybridize to, for example, single-stranded copies of region b.

This example involves two levels of amplification. In the first level of amplification, a DNA-RNA duplex is formed between regions d and b' of the detection probe (FIG. 59A) and complementary regions d' and b of the RNA target. This permits DSN cleavage of regions d and b' of the detection probe (FIG. 59B), thereby releasing RNA regions a and b as a single-stranded nucleic acid (FIG. 59C). The RNA target is not cleaved, and is therefore freed to hybridize with regions d and b' of an additional copy of the detection probe, triggering another round of the first level of amplification and thereby leading to linear amplification. In the second level of amplification, released region b of the detection probe hybridizes to region b' of the hairpin probe, forming a duplex and leading to DSN cleavage of region b' of the hairpin probe (FIGS. 59D and 59E). Upon cleavage of region b', the terminal RNA regions of the stem of the hairpin probe dissociate, releasing the fluorophore and the quencher, thereby resulting in an increase in the fluorescence of the solution. Dissociation of the two terminal RNA regions may be accelerated, for example, by any method known in the art for inducing denaturation of nucleic acid duplexes (e.g., by application of heat). Since the released region b of the detection probe is RNA, it is not degraded, but is instead freed to hybridize with region b' on an additional copy of the hairpin probe, triggering a second round of amplification. In addition to a hairpin probe, the released RNA containing regions a and b may bind to the probes described in, for example, FIGS. 56, 58 and 63.

Figure 60:
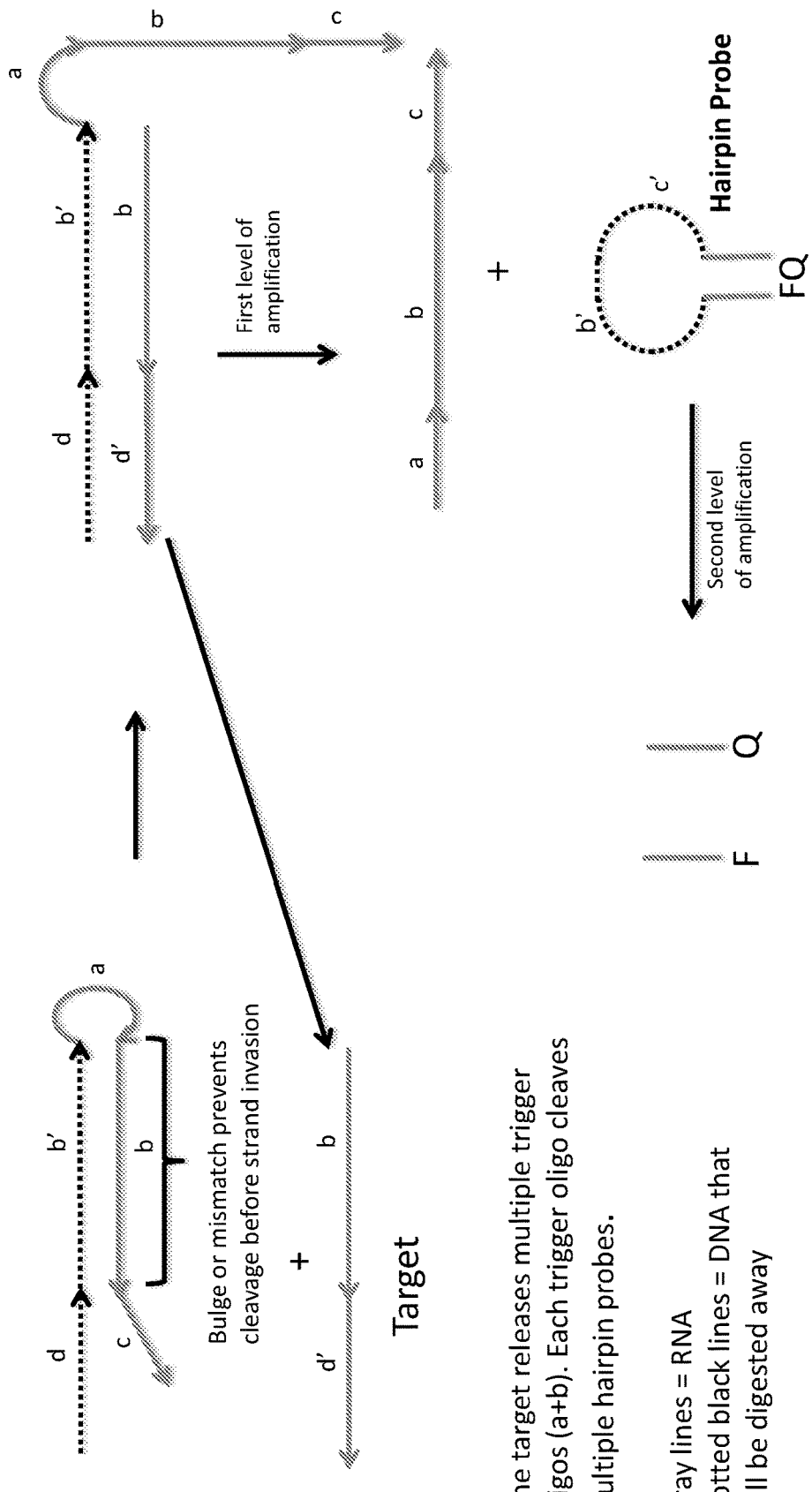
FIG. 60 shows alternate probe designs and an alternate scheme for linear DSA of an RNA target using two folded probes and two levels of amplification.

FIG. 60 illustrates an alternate version of this DSA scheme, in which the detection probe further includes an additional terminal RNA region c, on the opposite end from region d. In this version of the scheme, the hairpin probe further includes a DNA region c', which is complementary to region c of the detection probe. After hybridization of the target to the detection probe and subsequent DSN cleavage of the detection probe, the released RNA regions therefore include regions a, b, and c. Released regions b and c may hybridize to regions b' and c' of the hairpin, leading to the degradation of regions b' and c', and release of the terminal ends bound to the fluorophore and the quencher.

Example 21. Exponential DSA Using Multiple Hairpin Probes

Figure 61:
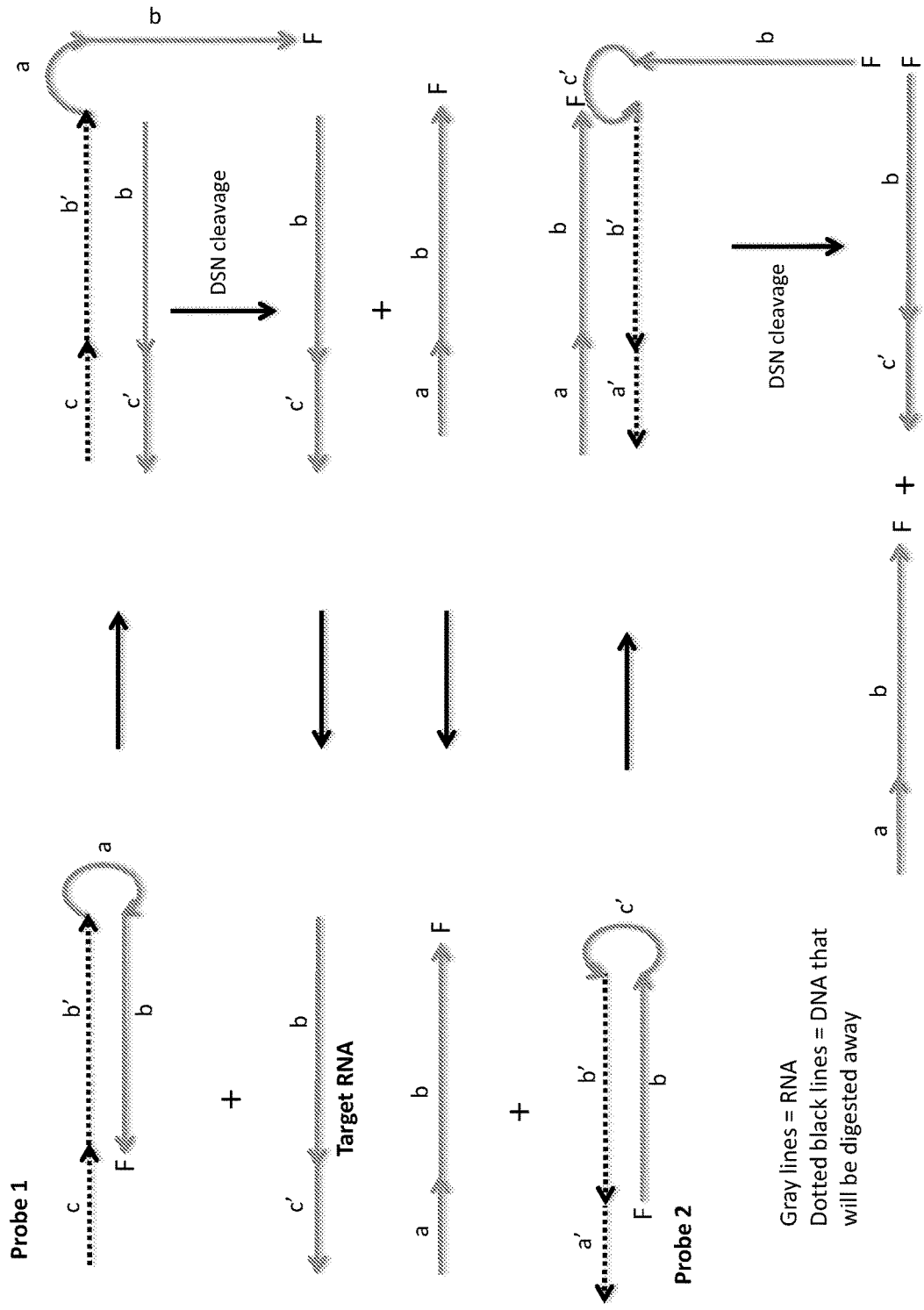
FIG. 61 shows probe designs and a scheme for exponential DSA of an RNA target using multiple hairpin probes, in which each hairpin probe includes a fluorophore.

Referring to FIG. 61, an exponential DSA scheme is shown in which at least two distinct probes (Probe 1 and Probe 2) are used, with each probe being capable of self-hybridizing to form a hairpin structure.

In an example, Probe 1 includes, in order, DNA regions c and b' and RNA regions a and b. Region b may be attached to a fluorophore (e.g., a quantum dot, fluorescent bead, or any other fluorophore described herein). Regions b' and b are capable of hybridizing to each other, but are not perfectly complementary, including at least one mismatch and/or a region of one or more extra nucleotides on one strand that results in formation of a bulge region in the duplex. Region c does not hybridize to another part of Probe 1 and thus forms an overhang. Region a also does not hybridize to another portion of Probe 1 and thus forms a loop of the hairpin structure.

In this example, Probe 2 includes, in order, DNA regions a' and b', RNA region c', and RNA region b. Region b may be attached to a fluorophore (e.g., a quantum dot, fluorescent bead, or any other fluorophore described herein). DNA region b' and RNA region b of Probe 2 are capable of hybridizing to each other, but are not perfectly complementary, including at least one mismatch and/or a region of one or more extra nucleotides on one strand that results in formation of a bulge region in the duplex. DNA region a' does not hybridize to another part of Probe 2 and thus forms an overhang. RNA region c' also does not hybridize to any other portion of Probe 2 and thus forms a loop of the hairpin structure.

Probe 1 is capable of hybridizing to a target RNA molecule, which includes regions c' and b, complementary to regions c and b' of Probe 1, respectively. As such, the initiation of this scheme involves separation of the self-hybridized strands of Probe 1 and hybridization of the RNA target to regions c and b'. This may occur, for example, by denaturation of Probe 1, followed by target hybridization. Alternatively, region c' of the target may anneal to region c of Probe 1, followed by strand invasion (e.g., as described herein) of the target RNA into region b' of Probe 1. This results in unzipping of the b'-b duplex of Probe 1 and hybridization of regions c' and b of the target RNA to regions c and b' of Probe 1, thereby forming a target RNA-Probe 1 duplex. A DSN may then cleave the target RNA-Probe 1 duplex, thereby releasing the portion of Probe 1 containing regions a and b, as well as the fluorophore attached to region b, into the surrounding solution. The RNA target is also released and may hybridize to, and induce DSN cleavage of, additional copies of Probe 1.

The released portion of Probe 1 may then propagate the reaction by hybridizing to complementary regions a' and b' of a copy of Probe 2. This may occur, for example, by denaturation of Probe 2, followed by hybridization of the released portion of Probe 1 with the complementary portion of Probe 2. Alternatively, region a of the released portion of Probe 1 may anneal to region a' of Probe 2, followed by strand invasion (e.g., as described herein) of the released portion of Probe 1 into region b' of Probe 2. This results in unzipping of Probe 2 and hybridization of regions a and b of the released portion of the first region to regions a' and b' of Probe 2, thus forming a duplex. The resultant cleavage of this duplex by the DSN (or a copy thereof) releases the portion of Probe 2 including region c' and region b, as well as the fluorophore attached to region b, into the solution. The released portion of Probe 2 is thus freed to hybridize to and induce DSN cleavage of additional copies of Probe 1. The released portion of Probe 1, being RNA, is not cleaved during this process and is also freed into solution, thus permitting hybridization to and cleavage of additional copies of Probe 2 and thereby leading to exponential amplification. The amplified released regions, and the fluorophores attached thereto, may be isolated and/or detected according to any of the methods described herein.

Figure 62:
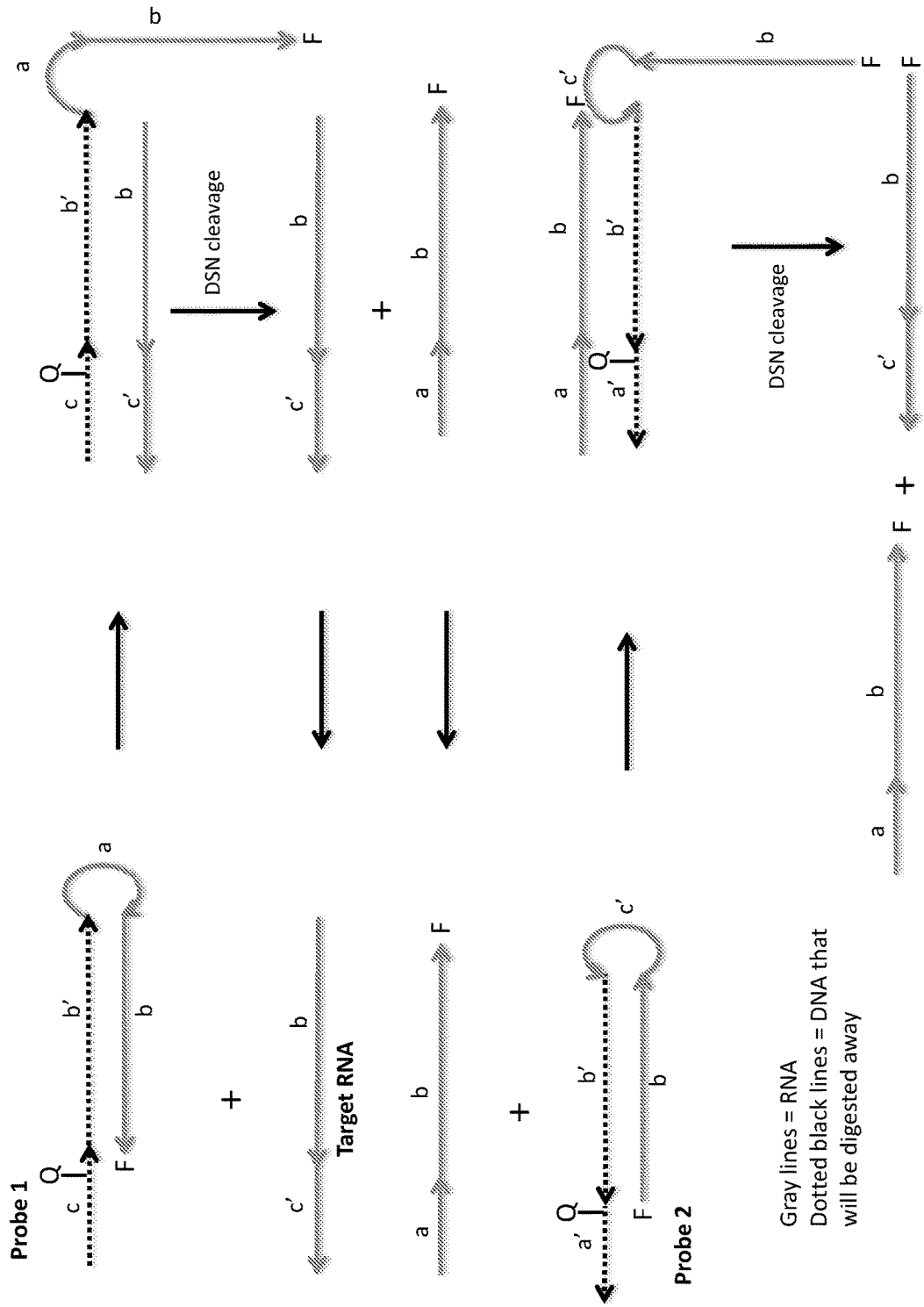
FIG. 62 shows alternate probe designs and an alternate scheme for exponential DSA of an RNA target using multiple hairpin probes, in which each hairpin probe includes a fluorophore and a quencher.

Turning to FIG. 62, DSA schemes utilizing probes including a hairpin structure, as described herein (e.g., the above exponential DSA scheme), may, in some instances, be carried out using probes attached to quenchers (e.g., a quencher as described herein). In this example, Probe 1 and/or Probe 2 may further include quenchers attached at DNA regions c and a', respectively, as shown in FIG. 62. In these probes, the intraprobe hybridization between regions b and b' brings the fluorophore and quencher into close proximity, thereby quenching the fluorescent signal. Hybridization of a target RNA to Probe 1, e.g., by strand invasion, thus separates the fluorophore and quencher of Probe 1, thereby permitting the fluorophore to fluoresce. The subsequent degradation of DNA regions c and b' as a result of target RNA hybridization prevents re-association of the quencher and fluorophore of Probe 1. The released end region of Probe 1 thus includes a freed fluorophore. This released end region may hybridize to DNA regions a' and b' of Probe 2, e.g., by strand invasion (e.g., as described herein), thereby separating the quencher and fluorophore of Probe 2. The resultant degradation of DNA regions a' and b' prevents re-association between the quencher and fluorophore of Probe 2 and releases an end region including regions c' and b (and the attached fluorophore) of Probe 2. This released end region may proceed to hybridize and induce DSN cleavage of additional copies of Probe 1, as described above. As such, target RNA binding to Probe 1 initiates an exponential amplification of fluorescent signal as additional copies of Probes 1 and 2 are cleaved.

Example 22. Cleavage and Linear DSA for Detection on Capture Strip

Figure 63:
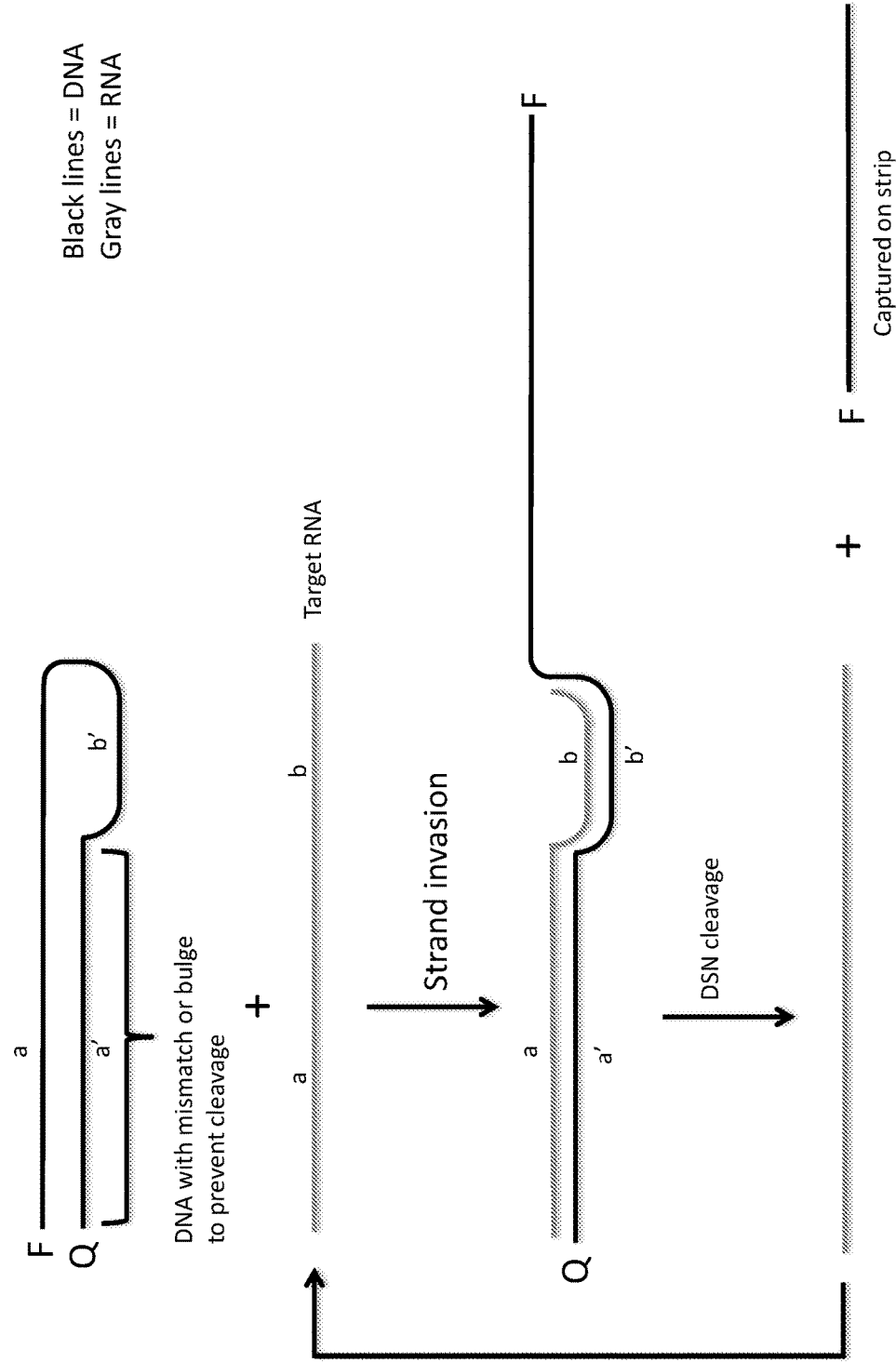
FIG. 63 shows a probe design and scheme for DSN cleavage of an RNA target and linear DSA of a signal that may be captured on a capture strip.

Referring to FIG. 63, a scheme is shown that utilizes a probe attached at opposite ends to a fluorophore (e.g., a quantum dot, fluorescent bead, or any other fluorophore described herein) and, optionally, a quencher (e.g., a quencher as described herein).

In an example, the probe includes the following DNA regions in order: regions a, b', and a', of which region a is attached to the fluorophore and region a' is attached to the quencher. Regions a and a' are capable of hybridizing to each other, but include at least one internal mismatch or bulge, thereby preventing DSN cleavage. Alternatively, the strand attached to the fluorophore may include one or more RNA or 2'-O-methylated bases to prevent cleavage of the double-stranded region of the probe. Region b does not hybridize to any other portion of the probe, and may thus form a loop, or a portion thereof, in a hairpin structure. Regions a' and b' of the probe are complementary to regions a and b of a target RNA. As such, the target RNA may hybridize to regions a' and b' of the probe. For example, region b of the target RNA may hybridize first, followed by strand invasion (e.g., as described herein) of region a of the RNA target into region a' of the probe, thereby unzipping the duplex formed between regions a and a' of the probe.

Because the hybridization of the target RNA and regions a' and b' of the probe results in a RNA-DNA duplex and is formed between complementary sequences, a DSN, such as those described herein, may recognize and cleave the DNA strand of the duplex. As a result, the portion of the probe containing region a and the fluorophore is released from the quencher and is freed for capture and/or direct detection in solution. In some instances, this released portion may be captured on, e.g., a strip for subsequent detection of the fluorophore. The RNA target is also freed and may proceed to hybridize with regions a' and b' of an additional copy of the probe, thereby leading to linear DSA of the released fluorophore-containing probe fragment over time.

Example 23. Exponential DSA Using Multiple Hairpin Trigger Probes

Figure 64:
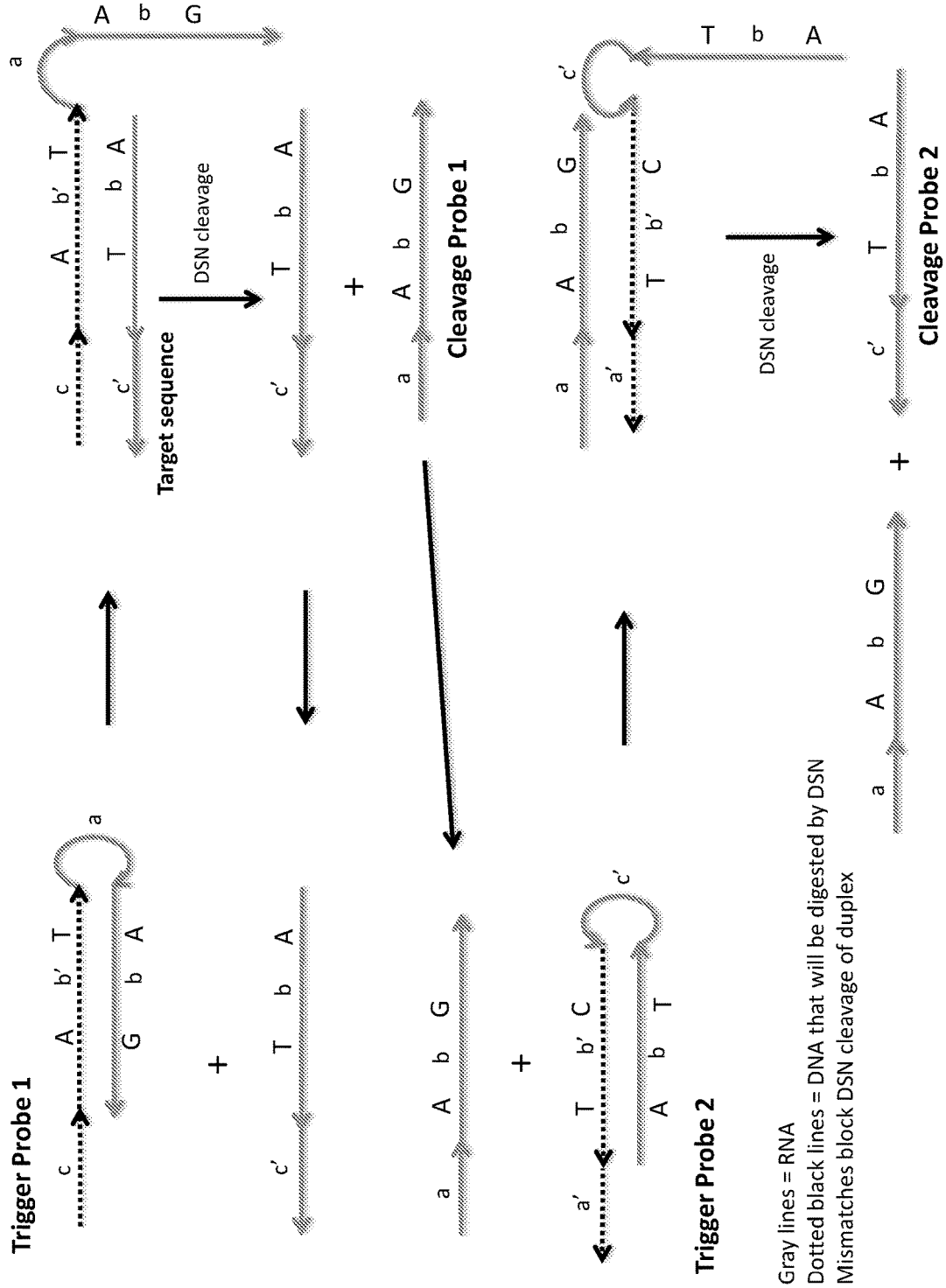
FIG. 64 shows probe designs and schemes for exponential DSA of an RNA target using multiple hairpin trigger probes.

Referring to FIG. 64, a DSA scheme is provided that utilizes at least two distinct trigger probes, shown as Trigger Probe 1 and Trigger Probe 2. Each of the trigger probes is capable of self-hybridizing to form a hairpin structure. Each trigger probe includes a cleavage probe (respectively referred to herein as Cleavage Probe 1 and Cleavage Probe 2) that is released upon DSN cleavage. And as is described below, Cleavage Probe 2 is exponentially produced in this DSA scheme.

In this example, Trigger Probe 1 includes, in order, DNA regions c and b' and RNA regions a and b, of which Cleavage Probe 1 includes RNA regions a and b (FIG. 64). Region b may be, in some instances, attached to a fluorophore (e.g., a quantum dot, fluorescent bead, or any other fluorophore described herein). Regions b' and b are capable of hybridizing to each other, but include at least one mismatch or bulge region, such that the two regions are not perfectly complementary. For example, region b' includes an adenine (A) nucleobase, while the corresponding position in region b includes a guanine (G) nucleobase, which cannot form a base-pair. In this example, region b' also includes a thymine (T) nucleobase and the corresponding position in region b includes an adenine (A) nucleobase, such that this position forms a base-pair. Thus, the duplex formed by hybridization between regions b' and b is resistant to degradation by a DSN. Region c does not hybridize to another part of Trigger Probe 1 and thus forms an overhang. Region a also does not hybridize to any other part of Trigger Probe 1 and thus forms a loop of the hairpin structure. Regions c and b' of Trigger Probe 1 are capable of hybridizing to a target RNA molecule that includes regions c' and b. In some instances, region b' of Trigger Probe 1 is perfectly complementary to region b of the target RNA molecule. In certain instances, regions c and b' of Trigger Probe 1 are perfectly complementary to regions c' and b, respectively, of the target RNA molecule.

In this example, Trigger Probe 2 includes, in order, DNA regions a' and b' and RNA regions c' and b, of which Cleavage Probe 2 includes RNA regions c' and b (FIG. 64). Region b may be, in some instances, attached to a fluorophore (e.g., a quantum dot, fluorescent bead, or any other fluorophore described herein). Regions b' and b of Trigger Probe 2 may hybridize to each other, but include at least one mismatch or bulge region that prevents degradation of the resultant duplex by a DSN. For example, region b' may include a cytosine (C) nucleobase, while the corresponding position in region b has a thymine (T) nucleobase, which cannot form a base-pair. In certain instances, region b' includes a thymine (T) nucleobase and the corresponding position in region b includes an adenine (A) nucleobase, such that this position forms a base-pair. These T and C nucleobases of region b' of Trigger Probe 2, for example, hybridize to the corresponding A and G of region b of Trigger Probe 1. Region a' of Trigger Probe 2 does not hybridize to any other portion of Trigger Probe 2 and thus forms an overhang. Region c' of Trigger Probe 2 also does not hybridize to any other part of Trigger Probe 2 and thus forms a loop of the hairpin structure. Region b' of Trigger Probe 2 is perfectly complementary to region b of Trigger Probe 1. In some instances, region a' is perfectly complementary to region a of Trigger Probe 1.

The initiation of this DSA scheme involves separation of the self-hybridized strands of Trigger Probe 1 and hybridization of the target RNA molecule to regions c and/or b' of Trigger Probe 1. This may occur, for example, by denaturation of Trigger Probe 1, followed by hybridization to the target RNA molecule. Alternatively, region c' of the target RNA molecule may hybridize to region c of Trigger Probe 1, followed by strand invasion (e.g., as described herein) of the target RNA molecule into region b' of Trigger Probe 1. This results in unzipping of the b'-b duplex of Trigger Probe 1 and hybridization of, for example, regions c' and b of the target RNA molecule to regions c and b' of Trigger Probe 1, thereby forming a duplex that may be cleaved by a DSN. Cleavage by the DSN releases Cleavage Probe 1. The RNA target, being resistant to DSN cleavage, is also released, and may subsequently hybridize to and induce cleavage of additional copies of Trigger Probe 1.

Cleavage Probe 1, which includes RNA regions a and b of Trigger Probe 1, may hybridize to DNA regions a' and b' of Trigger Probe 2. This may occur, for example, by denaturation of Trigger Probe 2, followed by hybridization to Cleavage Probe 1. Alternatively, region a of Cleavage Probe 1 may hybridize to region a' of Trigger Probe 2, followed by strand invasion (e.g., as described herein) of Cleavage Probe 1 into region b' of Trigger Probe 2. This results in unzipping of the b'-b duplex of Trigger Probe 2 and hybridization of, for example, regions a and b of Cleavage Probe 1 to regions a' and b' of Trigger Probe 2, thereby forming a duplex that may be cleaved by a DSN (e.g., the same DSN as that which cleaved Trigger Probe 1, or a copy thereof). Cleavage of this duplex by the DSN results in the release of Cleavage Probe 2 from Trigger Probe 2, as well as release of Cleavage Probe 1. Cleavage Probe 1 may subsequently hybridize to and induce cleavage of additional copies of Trigger Probe 2. As a result, copies of Cleavage Probe 2 are produced at an exponential rate.

Figure 65:
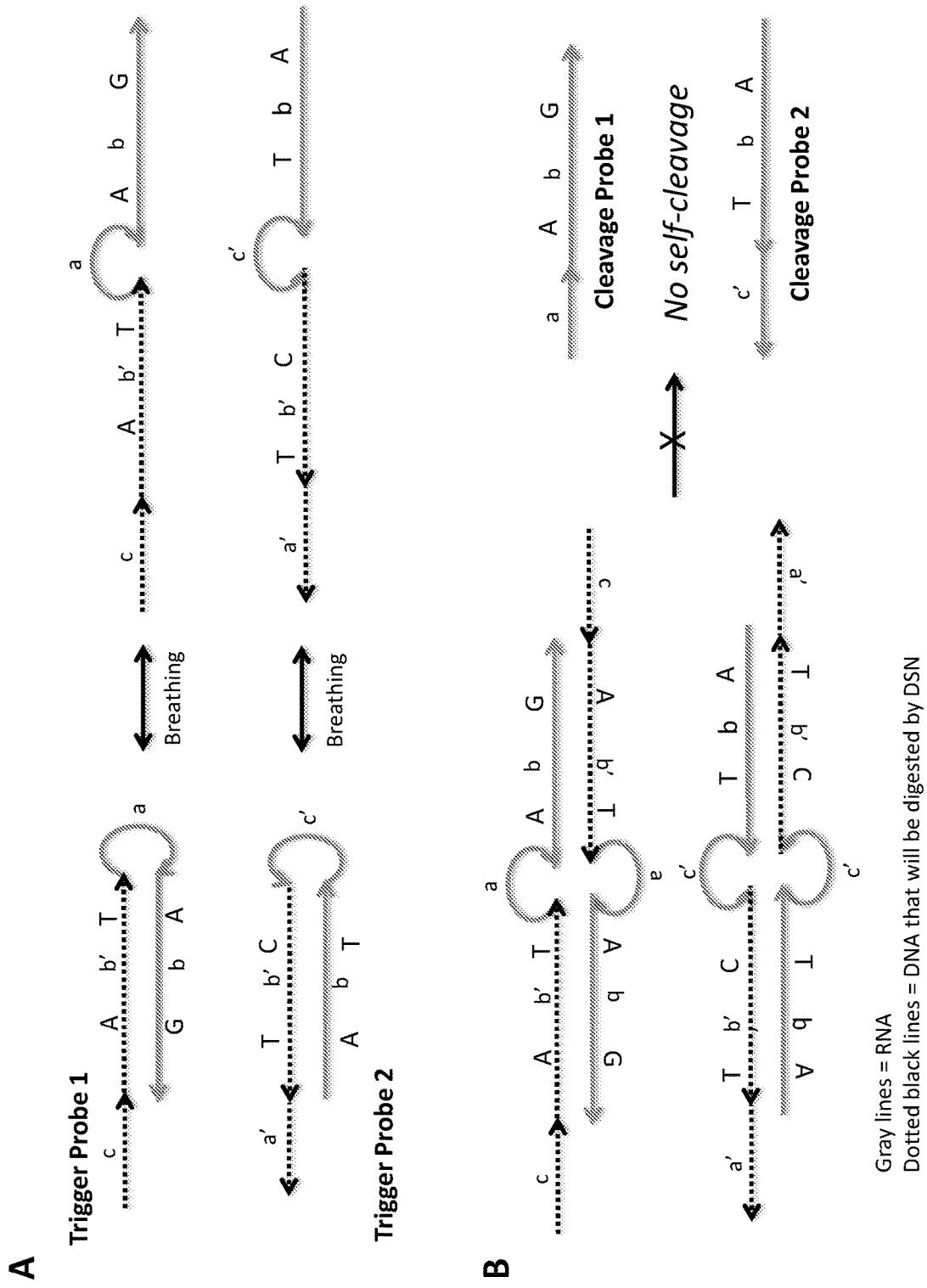
FIGS. 65A-65B show how the above hairpin trigger probes are designed to prevent target-independent DSA by hybridization of identical two copies of the probes.

Turning to FIG. 65, the two trigger probes are designed to minimize target-independent DSA, in which a probe undergoes DSN cleavage without hybridizing to a target nucleic acid (e.g., the target RNA molecule). As shown in FIG. 65A, each of the trigger probes spontaneously self-hybridizes and separates in solution, in a process referred to as "breathing." For example, the b'-b duplex of Trigger Probe 1 or Trigger Probe 2, in its hairpin state, may denature to form an open, linear nucleic acid strand. Conversely, regions b' and b of the linear nuclear acid strand may hybridize, thereby forming the hairpin state of Trigger Probe 1 or Trigger Probe 2, respectively. A given trigger probe may breathe between the two states repeatedly. In some instances, the trigger probe may preferentially take the form of one state or the other. For example, the trigger probe may primarily take the form of the hybridized hairpin state. In its open state, a given trigger probe may hybridize to another copy of itself, as shown in FIG. 65B. Specifically, regions b' and b of a single copy of Trigger Probe 1 may hybridize to regions b and b', respectively, of another copy of Trigger Probe 1, or regions b' and b of a single copy of Trigger Probe 2 may hybridize to regions b and b', respectively, of another copy of Trigger Probe 2. However, because each of the resultant duplexes includes at least one mismatch or bulge region, the duplexes cannot be cleaved by a DSN. As a result, no self-cleavage occurs.

Figure 66:
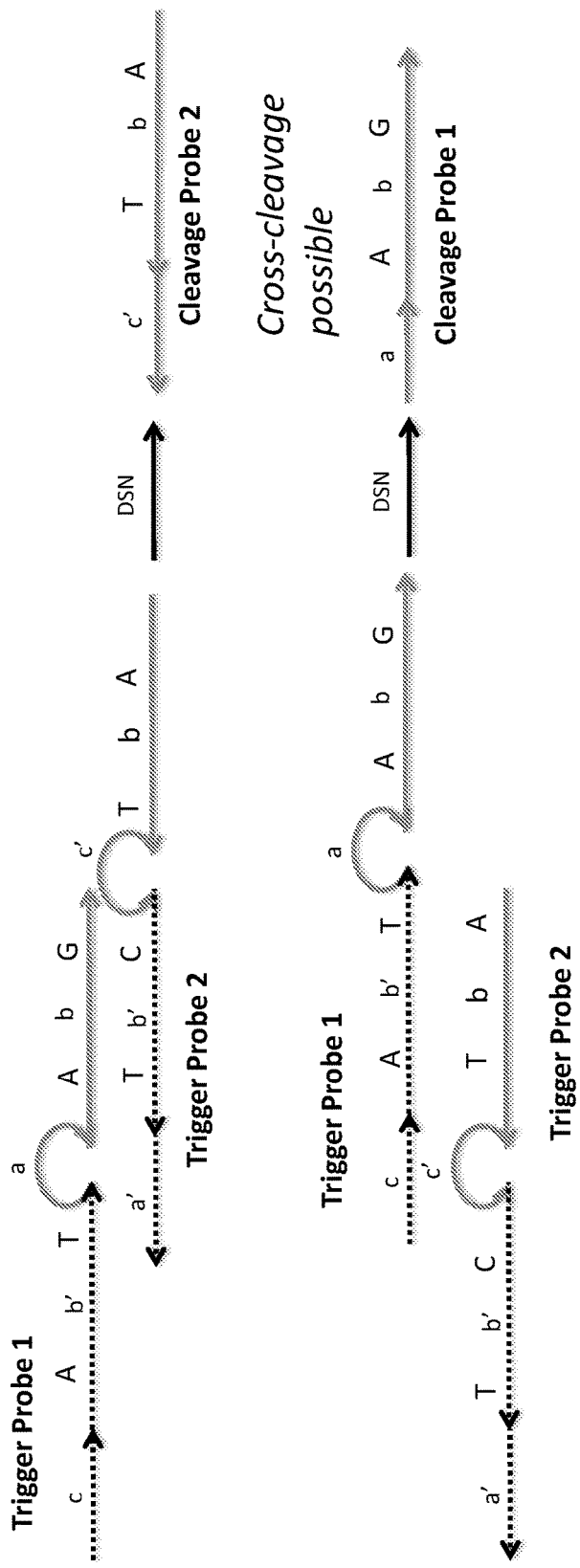
FIG. 66 shows that the two hairpin trigger probes are capable of cross-cleavage and target-independent DSA when one of the hairpin trigger probes hybridizes to the other.

Turning to FIG. 66, the designs of Trigger Probes 1 and 2 permit some cross-cleavage between the two trigger probes in solution, and may thus result in target-independent DSA. First, RNA region b of Trigger Probe 1 and DNA region b' of Trigger Probe 2 are complementary, and may thus hybridize to form a duplex that is cleaved by a DSN. Cleavage of this duplex releases RNA regions c' and b of Trigger Probe 2 as Cleavage Probe 2. Second, DNA region b' of Trigger Probe 1 and RNA region b of Trigger Probe 2 are complementary, and therefore hybridize to form a duplex cleavable by a DSN. Cleavage of this duplex releases RNA regions a and b of Trigger Probe 1, thus forming a copy of Cleavage Probe 1.

Example 24. Suppression of Target-Independent DSA

Figure 67:
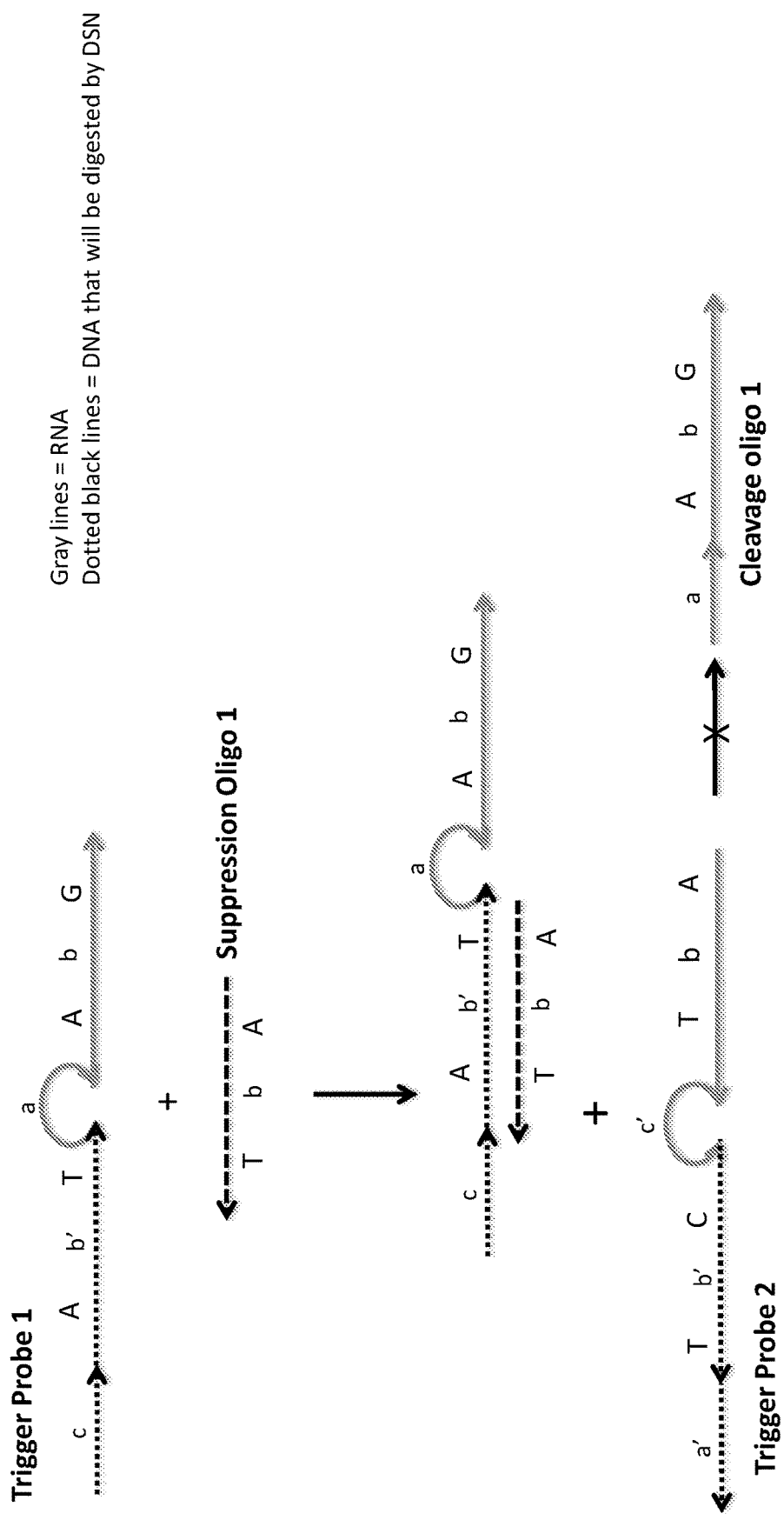
FIG. 67 shows a scheme for suppression of target-independent DSA using a suppression oligo to block hybridization between two trigger probes.

Referring to FIG. 67, a scheme is provided in which the target-independent DSA shown in FIG. 66 is suppressed by adding a suppression oligo (shown as Suppression Oligo 1) that blocks hybridization between two trigger probes (shown as Trigger Probe 1 and Trigger Probe 2). This scheme may be applicable to any DSA scheme utilizing multiple probes, such as that described above in Example 23. The suppression oligo may be, for example, a DNA or an RNA, or hybrid thereof. As such, this scheme for suppression of target-independent DSA is useful for minimizing or preventing false positive signals in any of the DSA schemes provided herein.

For example, Suppression Oligo 1 may include a targeting region b capable of hybridizing to region b' of a probe, such as Trigger Probe 1. Targeting region b includes at least one mismatch, modified based, modified backbone, or bulge region, relative to region b' of Trigger Probe 1, thereby preventing cleavage of the duplex formed by hybridization of targeting region b to region b' of Trigger Probe 1 by a DSN. As Trigger Probe 1 breathes into its open state, in which regions b' and b are not hybridized, Suppression Oligo 1 hybridizes to region b' of Trigger Probe 1, thereby blocking hybridization to complementary RNA region b of Trigger Probe 2. Thus, duplex formation between region b' of Trigger Probe 1 and region b of Trigger Probe 2 is impeded, thereby preventing DSN cleavage of region b' of Trigger Probe 1 and release of Cleavage Oligo 1.

Figure 68:
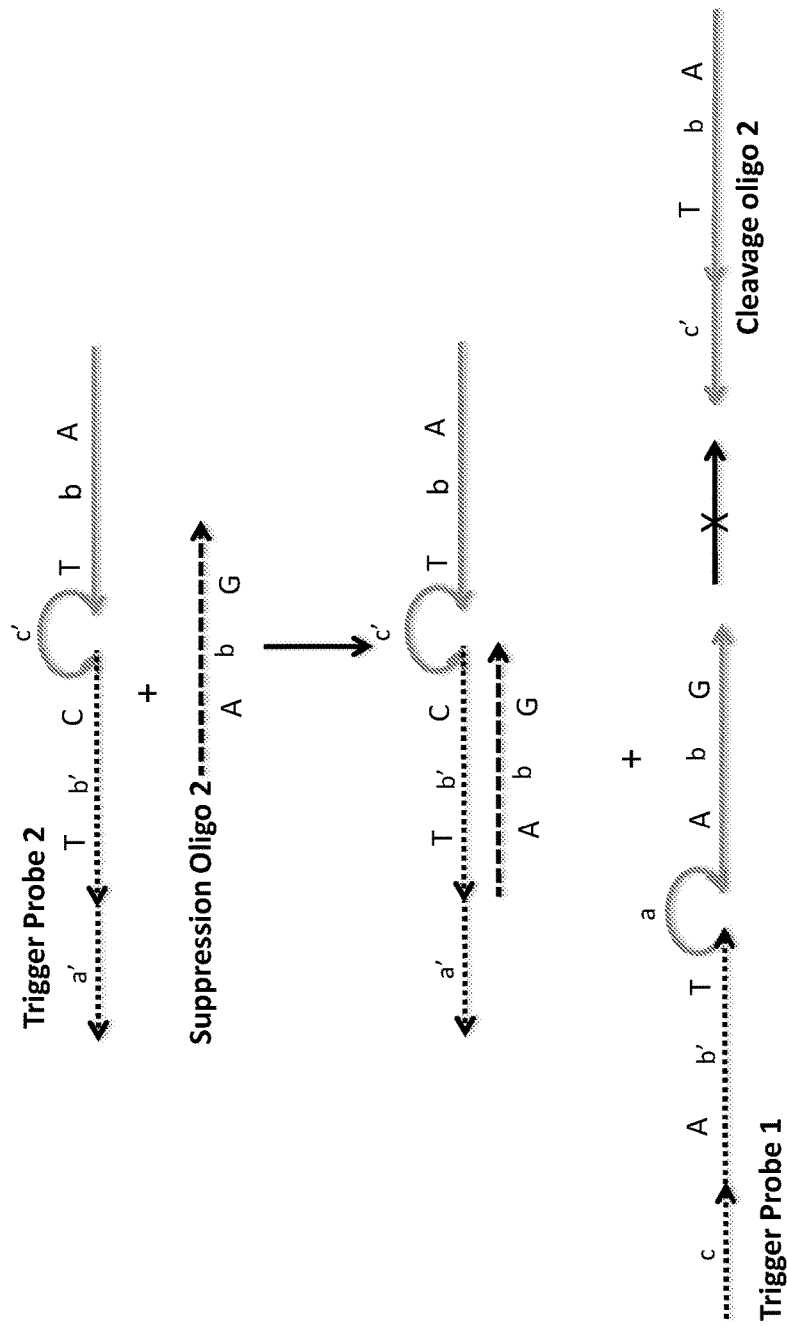
FIG. 68 shows a second scheme for suppression of target-independent DSA using a suppression oligo to block hybridization between two trigger probes.

Turning to FIG. 68, target-independent DSA may also be suppressed for Trigger Probe 2 using Suppression Oligo 2. For example, Suppression Oligo 2 may include a targeting region b capable of hybridizing to region b' of Trigger Probe 2. Targeting region b includes at least one mismatch, modified based, modified backbone, or bulge region, relative to region b' of Trigger Probe 2, thereby preventing cleavage of the duplex formed by hybridization of targeting region b to region b' of Trigger Probe 2 by a DSN. As Trigger Probe 2 breathes into its open state, in which regions b' and b are not hybridized, Suppression Oligo 2 hybridizes to region b' of Trigger Probe 2, thereby blocking it from hybridizing to complementary RNA region b of Trigger Probe 1. Thus, duplex formation between region b' of Trigger Probe 2 and region b of Trigger Probe 1 is impeded, thereby preventing DSN cleavage of region b' of Trigger Probe 2 and release of Cleavage Oligo 2.

In some instances, Suppression Oligo 1 and Suppression Oligo 2 may be used simultaneously to suppress target-independent DSA of Cleavage Oligos 1 and 2. For example, a solution may include Trigger Probes 1 and 2 as well as Suppression Oligos 1 and 2. Hybridization of Suppression Oligo 1 to Trigger Probe 1 and/or hybridization of Suppression Oligo 2 to Trigger Probe 2 suppresses binding interactions between Trigger Probes 1 and 2 (e.g., hybridization between region b' of Trigger Probe 1 and region b of Trigger Probe 2, and hybridization between region b' of Trigger Probe 2 and region b of Trigger Probe 1), thereby preventing the formation of duplexes between copies of Trigger Probes 1 and 2 and subsequent DSN cleavage. This solution is accordingly substantially free of target-independent DSA. Any production of Cleavage Oligos 1 and 2 (e.g., detectable production of Cleavage Oligo 2) would be primarily due to interaction between Trigger Probe 1 and a target nucleic acid (e.g., a RNA molecule), for example, according to the exponential DSA method of Example 23.

Example 25. Exponential DSA of a DNA Target

Figure 69:
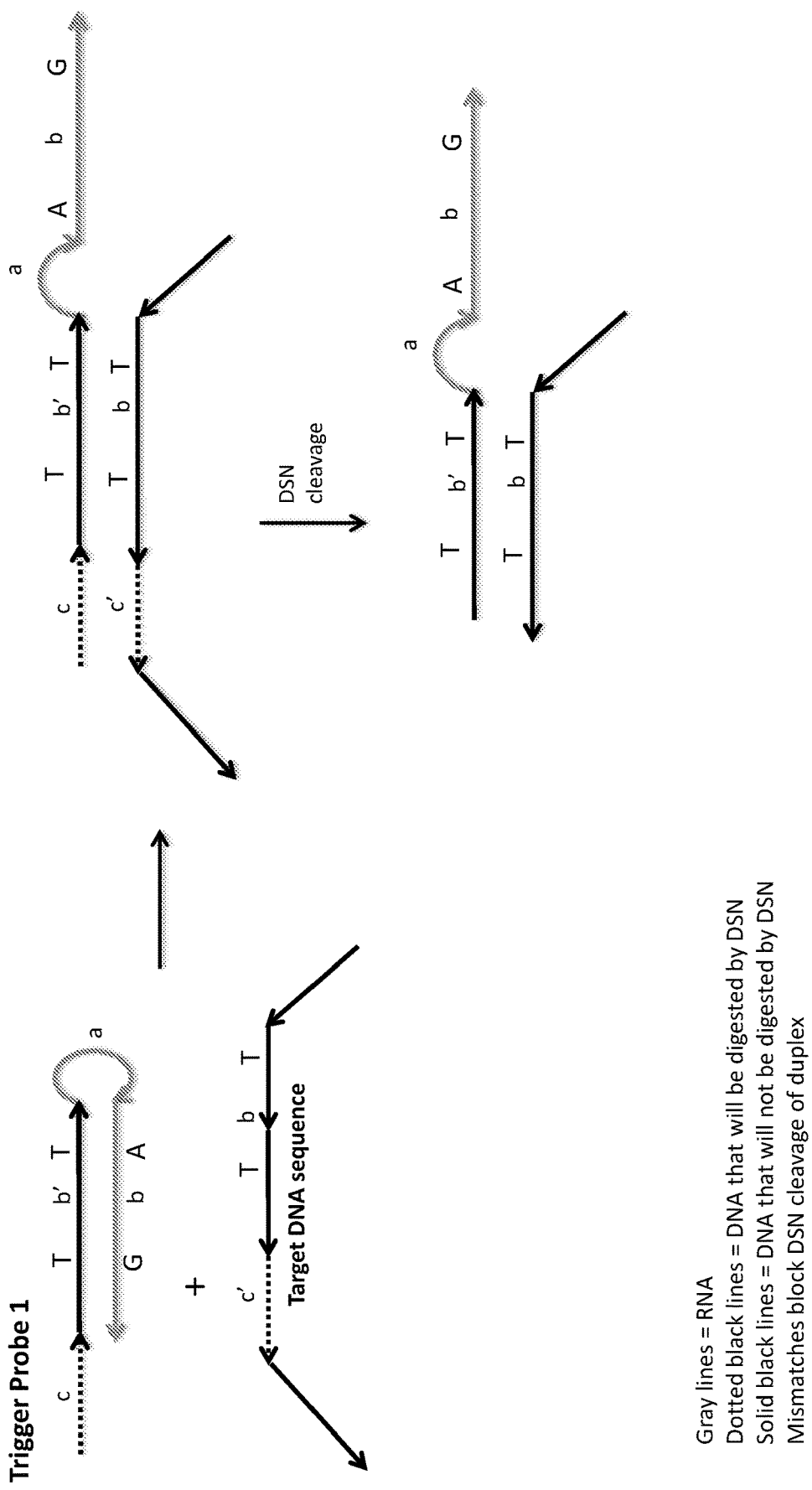
FIG. 69 shows probe designs and initial steps in a scheme for exponential DSA of a DNA target using multiple hairpin trigger probes.
Figure 70:
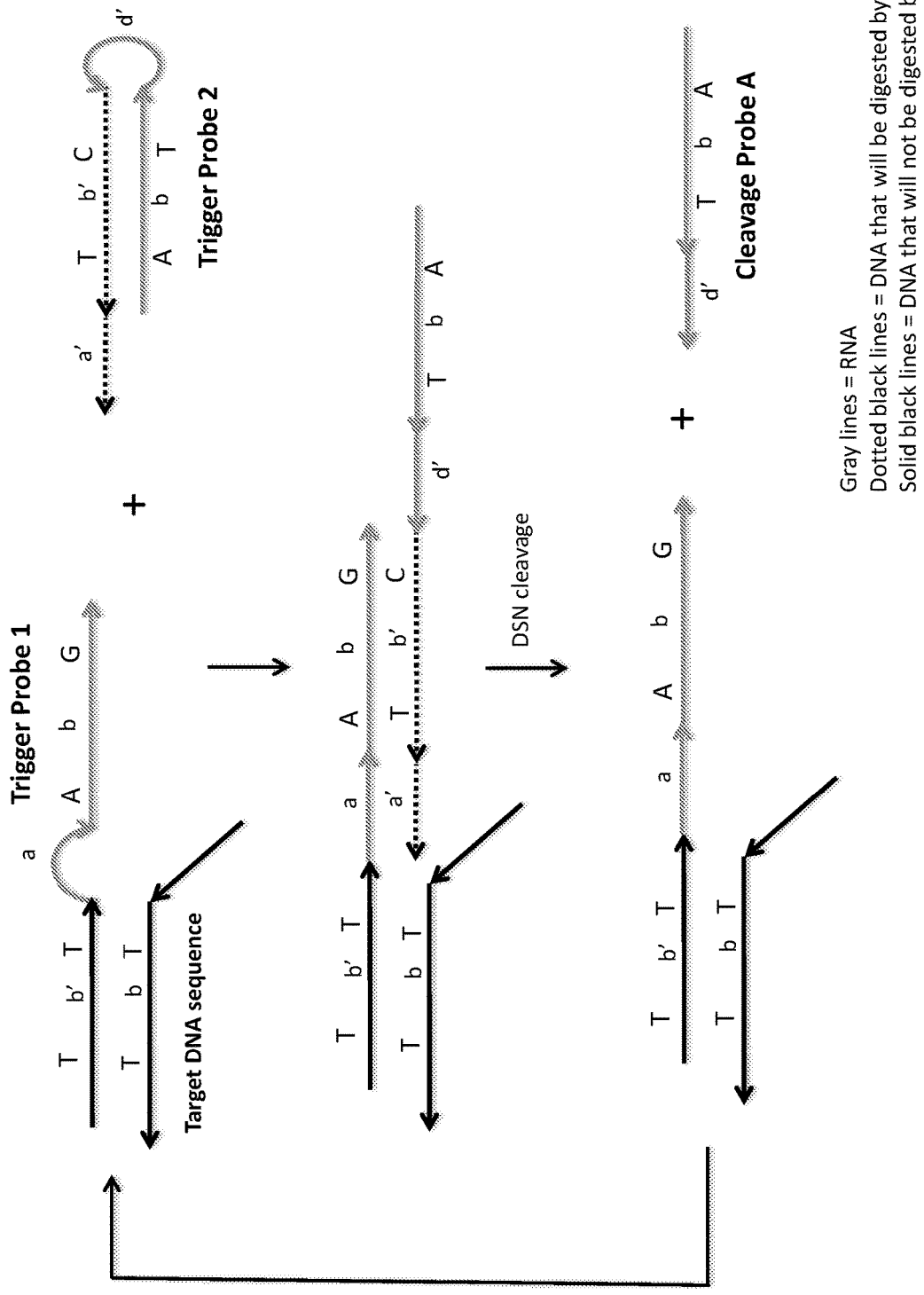
FIG. 70 shows further probe designs and steps in a scheme for exponential DSA of a DNA target using multiple hairpin trigger probes.

Referring to FIGS. 69-71, a DSA scheme is provided that utilizes at least three distinct trigger probes, shown as Trigger Probe 1 (FIG. 69), Trigger Probe 2 (FIG. 70), and Trigger Probe 3 (FIG. 71). Each of the trigger probes is capable of self-hybridizing to form a hairpin structure. Trigger Probes 2 and 3 each include a cleavage probe (respectively referred to herein as Cleavage Probe A and Cleavage Probe B), which may be released upon DSN cleavage of the trigger probe. Cleavage Probes A and B are exponentially produced in this DSA scheme.

In this example, as shown in FIG. 69, Trigger Probe 1 includes, in order, DNA regions c and b' and RNA regions a and b. Regions b' and b are capable of hybridizing to each other, but include at least one mismatch or bulge region, such that the two regions are not perfectly complementary. For example, region b' includes an thymine (T) nucleobase, while the corresponding position in region b includes a guanine (G) nucleobase, which cannot form a base-pair. Region b' may also include, for example, a second thymine nucleobase and the corresponding position in region b includes an adenine (A) nucleobase, such that this position forms a base-pair. Thus, the duplex formed by hybridization between regions b' and b is resistant to degradation by a DSN. Region c does not hybridize to another part of Trigger Probe 1 and thus forms an overhang. Region a also does not hybridize to any other part of Trigger Probe 1 and thus forms a loop of the hairpin structure. Regions c and b' of Trigger Probe 1 are capable of hybridizing to a target DNA molecule that includes regions c' and b. The target DNA molecule may include, in some instances, sequences that are not part of the reaction, as shown, for example, by the additional segment in region b in FIG. 69. In some instances, region c of Trigger Probe 1 is perfectly complementary to region c' of the target DNA molecule. In certain instances, region b' of Trigger Probe 1 includes a mismatch or bulge region relative to region b of the target DNA molecule, such that only regions c and c' may be degraded by the DSN.

Further in this example, as shown in FIG. 70, Trigger Probe 2 includes, in order, DNA regions a' and b' and RNA regions d' and b, of which Cleavage Probe A includes RNA regions d' and b. Region b is, in some instances, attached to a fluorophore (e.g., a quantum dot, fluorescent bead, or any other fluorophore described herein). Regions b' and b of Trigger Probe 2 may hybridize to each other, but include at least one mismatch or bulge region that prevents degradation of the resultant duplex by a DSN. For example, region b' may include a cytosine (C) nucleobase, while the corresponding position in region b has a thymine (T) nucleobase, which cannot form a base-pair. In certain instances, region b' includes a thymine (T) nucleobase and the corresponding position in region b includes an adenine (A) nucleobase, such that this position forms a base-pair. These C and T nucleobases of region b' of Trigger Probe 2, for example, hybridize to the corresponding A and G of region b of Trigger Probe 1 if Trigger Probe 1 is in an open state. Region a' of Trigger Probe 2 does not hybridize to any other portion of Trigger Probe 2 and thus forms an overhang. Region d' of Trigger Probe 2 also does not hybridize to any other part of Trigger Probe 2 and thus forms a loop of the hairpin structure. Region b' of Trigger Probe 2 is perfectly complementary to region b of Trigger Probe 1. In some instances, region a' is perfectly complementary to region a of Trigger Probe 1.

Further in this example, as shown in FIG. 71, Trigger Probe 3 includes, in order, DNA regions d' and b' and RNA regions a and b, of which Cleavage Probe B includes RNA regions a and b. Region b is, in some instances, attached to a fluorophore (e.g., a quantum dot, fluorescent bead, or any other fluorophore described herein). Regions b' and b of Trigger Probe 3 may hybridize to each other, but include at least one mismatch or bulge region that prevents degradation of the resultant duplex by a DSN. For example, region b' may include an adenine (A) nucleobase, while the corresponding position in region b has a guanine (G) nucleobase, which cannot form a base-pair. In certain instances, region b' includes a thymine (T) nucleobase and the corresponding position in region b includes an adenine (A) nucleobase, such that this position forms a base-pair. These A and T nucleobases of region b' of Trigger Probe 3, for example, hybridize to the corresponding T and A of region b of Cleavage Probe A. Region d of Trigger Probe 3 does not hybridize to any other portion of Trigger Probe 3 and accordingly forms an overhang. Region a of Trigger Probe 3 also does not hybridize to any other part of Trigger Probe 3 and accordingly forms a loop of the hairpin structure. Region b' of Trigger Probe 3 is perfectly complementary to region b of Cleavage Probe A. In some instances, region d of Trigger Probe 3 is perfectly complementary to region d' of Cleavage Probe A.

The initiation of this DSA scheme involves separation of the self-hybridized strands of Trigger Probe 1 and hybridization of the target DNA molecule to regions c and/or b' of Trigger Probe 1 (FIG. 69). This occurs, for example, by denaturation of Trigger Probe 1, followed by hybridization to the target DNA molecule. Alternatively, region c' of the target DNA molecule hybridizes to region c of Trigger Probe 1, followed by strand invasion (e.g., as described herein) of the target DNA molecule into region b' of Trigger Probe 1. This results in unzipping of the b'-b duplex of Trigger Probe 1 and hybridization of, for example, regions c' and b of the target DNA molecule to regions c and b' of Trigger Probe 1, thereby forming a duplex that is capable of being cleaved by a DSN. Cleavage by the DSN results in degradation of regions c and c'. Because regions b' and b include a mismatch or bulge region, the region b'-b duplex cannot be cleaved by the DSN. As a result, Trigger Probe 1 and the target DNA molecule remain attached to each other as a complex. This may, for example, block region b of Trigger Probe 1 from hybridizing to region b' of Trigger Probe 1, thus maintaining regions a and b of Trigger Probe 1 in an unhybridized state.

Turning to FIG. 70, the complex including Trigger Probe 1 and the target DNA molecule interacts with Trigger Probe 2. For example, RNA regions a and b of Trigger Probe 1 hybridizes to DNA regions a' and b' of Trigger Probe 2. This occurs, for example, by denaturation of the region b'-b duplex of Trigger Probe 2, followed by hybridization to Trigger Probe 1. Alternatively, region a of Trigger Probe 1 hybridizes to region a' of Trigger Probe 2, followed by strand invasion (e.g., as described herein) of region b of Trigger Probe 1 into region b' of Trigger Probe 2. This results in unzipping of the b'-b duplex of Trigger Probe 2 and hybridization of, for example, regions a and b of Trigger Probe 1 to regions a' and b' of Trigger Probe 2, thereby forming a duplex that is capable of being cleaved by a DSN. Cleavage by the DSN releases Cleavage Probe A. RNA regions a and b of Trigger Probe 1 are resistant to DSN cleavage. Thus, the complex including Trigger Probe 1 and the target DNA molecule are also released, and regions a and b of Trigger Probe 1 may subsequently hybridize to and induce cleavage of additional copies of Trigger Probe 2. It is possible, in some instances, for target-independent DSA to occur (e.g., if both Trigger Probe 1 and Trigger Probe 2 breathe into the open state simultaneously, then regions a and b of Trigger Probe 1 and regions a' and b' of Trigger Probe 2 may hybridize, thereby leading to DSN cleavage). However, as the trigger probes preferentially maintain the closed, hybridized state, the level of target-independent DSA should be minimal. In some instances, target-independent DSA may be minimized using one or more suppression oligos, for example, as described in Example 24.

Turning to FIG. 71, Cleavage Probe A, which includes RNA regions d' and b of Trigger Probe 2, hybridizes to DNA regions d and b' of Trigger Probe 3. This occurs, for example, by denaturation of Trigger Probe 3, followed by hybridization to Cleavage Probe A. Alternatively, region d' of Cleavage Probe A hybridizes to region d of Trigger Probe 3, followed by strand invasion (e.g., as described herein) of Cleavage Probe A into region b' of Trigger Probe 3. This results in unzipping of the b'-b duplex of Trigger Probe 3 and hybridization of, for example, regions d' and b of Cleavage Probe A to regions d and b' of Trigger Probe 3, thereby forming a duplex that is capable of being cleaved by a DSN. Cleavage of this duplex by the DSN results in the release of Cleavage Probe B from Trigger Probe 3, as well as release of Cleavage Probe A, which may subsequently hybridize to and induce cleavage of additional copies of Trigger Probe 3. As a result, copies of Cleavage Probe B are produced by DSA at an exponential rate.

Cleavage Probe B, which includes RNA regions a and b of Trigger Probe 3, hybridizes to DNA regions a' and b' of a further copy of Trigger Probe 2. This occurs, for example, by denaturation of the further copy of Trigger Probe 2, followed by hybridization to Cleavage Probe B. Alternatively, region a of Cleavage Probe B hybridizes to region a' of the further copy of Trigger Probe 2, followed by strand invasion (e.g., as described herein) of Cleavage Probe B into region b' of the further copy of Trigger Probe 2. This results in unzipping of the b'-b duplex of the further copy of Trigger Probe 2 and hybridization of, for example, regions a and b of Cleavage Probe B to regions a' and b' of the further copy of Trigger Probe 2, thereby forming a duplex that may be cleaved by a DSN. Cleavage of this duplex by the DSN results in the release of a further copy of Cleavage Probe A, as well as release of Cleavage Probe B, which may subsequently hybridize to and induce cleavage of additional copies of Trigger Probe 2. As a result, copies of Cleavage Probe A are produced by DSA at an exponential rate.

Example 26. Geometric DSA without Mismatches

Referring to FIGS. 72A-72B, a geometric DSA scheme is provided that utilizes a trigger probe capable of self-hybridizing to form a hairpin structure. In some instances, the duplex formed by the self-hybridizing regions of the trigger probe does not contain any mismatches or bulge regions. The scheme further includes a target displacing oligo and a reporter probe capable of self-hybridizing to form a hairpin structure, the loop of which may be degraded (e.g., by a DSN) to release a fragment attached to a fluorophore.

As shown in FIG. 72A, the trigger probe includes, in order, DNA regions c and e', and RNA regions b', a', f, a, b, e, and d. Regions e', b', and a' are capable of hybridizing to regions e, b, and a to form a duplex. Although regions e' and e hybridize to form a DNA-RNA duplex, this DNA-RNA duplex includes a stretch of nucleotides which are substantially incapable of being cleaved by a DSN. This DNA-RNA region, in general, is less than about 8 nucleotides in length (e.g., 1, 2, 3, 4, 5, 6, or 7 nucleotides in length). As such, in its hairpin form, the trigger probe is resistant to cleavage by a DSN. Regions c and d do not hybridize to any other part of the trigger probe. Region f also does not hybridize to any other part of the trigger probe and thus forms a loop of the hairpin structure. Regions c, e', b', and a' are capable of hybridizing to a target RNA molecule that includes, in order, regions c', e, b, and a. In some instances, regions c and e' of the trigger probe are perfectly complementary to regions c' and e of the target RNA molecule. The target displacing oligo includes, in order, RNA regions b, a, f', and a'.

The initiation of this DSA scheme involves separation of the self-hybridized strands of the trigger probe and hybridization of the target RNA molecule to regions c, e', b', and a' of the trigger probe (FIG. 72A). This occurs, for example, by denaturation of the trigger probe, followed by hybridization to the target RNA molecule. Alternatively, region c' of the target RNA molecule hybridizes to region c of the trigger probe, followed by strand invasion (e.g., as described herein) of the target RNA molecule into region e', followed by regions b' and a', of the trigger probe. This results in unzipping of the self-hybridized duplex of the trigger probe and hybridization of, for example, regions c', e, b, and a of the target RNA molecule to regions c, e', b', and a' of the trigger probe, thereby forming a duplex that is capable of being cleaved at regions c and e' by a DSN. DSN cleavage results in degradation of regions c and e'. The trigger probe and the target RNA molecule remain attached to each other at the remaining RNA-RNA duplex, as shown in FIG. 72A. This RNA-RNA duplex may be separated using the target displacing oligo. For example, regions f' and a' of the target displacing oligo may hybridize to regions f and a of the trigger probe, followed by strand invasion (e.g., as described herein) of the target displacing oligo into regions a' and b' of the trigger probe, thereby displacing the target RNA and freeing it to bind and induce the DSN cleavage of additional copies of the trigger probe in a first level of geometric amplification.

Turning to FIG. 72B, the complex formed between the cleaved trigger probe and the target displacing oligo is capable of interacting with the reporter probe. The reporter probe includes, in order, an RNA region attached to a fluorophore, DNA regions b', e', and d', and an RNA region attached to a quencher. The two RNA regions of the reporter probe are complementary and thus hybridize to form a duplex that maintains the fluorophore in close proximity to the quencher, thereby preventing the fluorophore from producing a fluorescent signal. Regions b, e, and d of the cleaved trigger probe may hybridize to regions b', e', and d' of the reporter probe, thereby forming a DNA-RNA duplex capable of being cleaved by a DSN. DSN cleavage of regions b', e', and d' results in the release of the RNA regions attached to the fluorophore and the quencher, and thus separates the fluorophore from the quencher. The resultant fluorescent signal may be detected using methods well known in the art. Each copy of the cleaved trigger probe may bind to and induce cleavage of multiple copies of the reporter probe in a second level of geometric amplification.

Example 27. Exponential DSA without Mismatches

Referring to FIGS. 73A-73B, an exponential DSA scheme is provided that utilizes two trigger probes (Trigger Probe 1 and Trigger Probe 2) capable of self-hybridizing to form a hairpin structure. In some instances, the duplex formed by the self-hybridizing regions of a particular trigger probe does not contain any mismatches or bulge regions. The scheme further includes a target displacing oligo and, optionally, a reporter probe capable of self-hybridizing to form a hairpin structure, the loop of which may be degraded (e.g., by a DSN) to release a fragment attached to a fluorophore.

As shown in FIG. 73A, Trigger Probe 1 includes, in order, DNA regions c and e', and RNA regions b', a', f, a, b, e, and d. Regions e', b', and a' are capable of hybridizing to regions e, b, and a to form a duplex. Although regions e' and e hybridize to form a DNA-RNA duplex, this DNA-RNA duplex includes a stretch of nucleotides which are substantially incapable of being cleaved by a DSN. This DNA-RNA region, in general, is less than about 8 nucleotides in length (e.g., 1, 2, 3, 4, 5, 6, or 7 nucleotides in length). As such, in its hairpin form, Trigger Probe 1 is resistant to cleavage by a DSN. Regions c and d do not hybridize to any other part of Trigger Probe 1. Region f also does not hybridize to any other part of the trigger probe and thus forms a loop of the hairpin structure. Regions c, e', b', and a' are capable of hybridizing to a target RNA molecule that includes, in order, regions c', e, b, and a. In some instances, regions c and e' of Trigger Probe 1 are perfectly complementary to regions c' and e of the target RNA molecule.

As shown in FIG. 73B, Trigger Probe 2 includes, in order, DNA regions d' and e', RNA region b', DNA regions a' and f, and RNA regions a, b, e, and c'. Regions e', b', and a' are capable of hybridizing to regions e, b, and a to form a duplex. Although regions e' and e hybridize to form a DNA-RNA duplex, this DNA-RNA duplex includes a stretch of nucleotides which are substantially incapable of being cleaved by a DSN. This DNA-RNA region, in general, is less than about 8 nucleotides in length (e.g., 1, 2, 3, 4, 5, 6, or 7 nucleotides in length). As such, in its hairpin form, Trigger Probe 2 is resistant to cleavage by a DSN. Regions d' and c' do not hybridize to any other parts of Trigger Probe 2. Region f also does not hybridize to any other part of the trigger probe and thus forms a loop of the hairpin structure. Regions d', e', and b' are capable of hybridizing to regions d, e, and b of Trigger Probe 1. In some instances, regions d', e', and b' of Trigger Probe 2 are perfectly complementary to regions d, e, and b of Trigger Probe 1.

The initiation of this DSA scheme involves separation of the self-hybridized strands of the trigger probe and hybridization of the target RNA molecule to regions c, e', b', and a' of the trigger probe (FIG. 73A). This occurs, for example, by denaturation of the trigger probe, followed by hybridization to the target RNA molecule. Alternatively, region c' of the target RNA molecule hybridizes to region c of the trigger probe, followed by strand invasion (e.g., as described herein) of the target RNA molecule into region e', followed by regions b' and a', of the trigger probe. This results in unzipping of the self-hybridized duplex of the trigger probe and hybridization of, for example, regions c', e, b, and a of the target RNA molecule to regions c, e', b', and a' of the trigger probe, thereby forming a duplex that is capable of being cleaved at regions c and e' by a DSN. DSN cleavage results in degradation of regions c and e'. The trigger probe and the target RNA molecule remain attached to each other at the remaining RNA-RNA duplex, as shown in FIG. 73A. This RNA-RNA duplex may be separated using the target displacing oligo. The target displacing oligo includes, in order, RNA regions b, a, f', and a'. Thus, regions f' and a' of the target displacing oligo may hybridize to regions f and a of the trigger probe, followed by strand invasion (e.g., as described herein) of the target displacing oligo into regions a' and b' of the trigger probe, thereby displacing the target RNA and freeing it to bind and induce the DSN cleavage of additional copies of the trigger probe in a first level of amplification.

Turning to FIG. 73B, the complex formed between cleaved Trigger Probe 1 and the target displacing oligo is capable of interacting with Trigger Probe 2. For example, region d of cleaved Trigger Probe 1 may hybridize to region d' of Trigger Probe 2, followed by strand invasion (e.g., as described herein) of regions e and b of Trigger Probe 1 into regions e' and b' of Trigger Probe 2. This forms a DNA-RNA duplex between regions d and e of Trigger Probe 1 and regions d' and e' of Trigger Probe 2, which is long enough to be cleaved by a DSN. In some instances, a further copy of the target displacing oligo may hybridize to regions a' and f of Trigger Probe 2, thereby forming a DNA-RNA duplex long enough to be cleaved by a DSN. DSN cleavage of regions a' and f of Trigger Probe 2 results in the release of RNA regions c', e, b, and a of Trigger Probe 2, which effectively results in the formation of an additional copy of the RNA target. As such, progression of this DSA scheme results in the production of RNA targets that may hybridize to and induce DSN cleavage of further copies of Trigger Probe 1, thereby resulting in exponential amplification.

In some instances, the further copy of the target displacing oligo hybridizes to Trigger Probe 2 concurrently with hybridization between Trigger Probe 1 and Trigger Probe 2. In other instances, the further copy of the target displacing oligo hybridizes to Trigger Probe 2 prior to or after hybridization between Trigger Probe 1 and Trigger Probe 2. In particular instances, the DNA-RNA duplex between Trigger Probe 1 and Trigger Probe 2 is cleaved by a DSN prior to hybridization of the further copy of the target displacing oligo to Trigger Probe 2. In alternate instances, the DNA-RNA duplex between the target displacing oligo and Trigger Probe 2 is cleaved by a DSN prior to hybridization of the further copy of Trigger Probe 1 to Trigger Probe 2.

In some instances, cleaved copies of Trigger Probe 1 and/or Trigger Probe 2 are capable of hybridizing with a reporter probe including a fluorophore and a quencher, thereby inducing DSN cleavage of the reporter probe and activation of fluorophore signal (e.g., as described herein).

Example 28. Geometric DSA without Mismatches

Referring to FIGS. 74A-74B, a geometric DSA scheme is provided that utilizes a trigger probe capable of self-hybridizing to form a hairpin structure. In some instances, the duplex formed by the self-hybridizing regions of the trigger probe does not contain any mismatches or bulge regions. The scheme further includes a target displacing oligo and a reporter probe capable of self-hybridizing to form a hairpin structure, the loop of which may be degraded (e.g., by a DSN) to release a fragment attached to a fluorophore.

As shown in FIG. 74A, the trigger probe includes, in order, DNA region c and RNA regions e', b', a', f, a, b, e, and d. Regions e', b', and a' are capable of hybridizing to regions e, b, and a to form an RNA-RNA duplex resistant to cleavage by a DSN. Regions c and d do not hybridize to any other part of the trigger probe. Region f also does not hybridize to any other part of the trigger probe and thus forms a loop of the hairpin structure. Regions c, e', b', and a' are capable of hybridizing to a target RNA molecule that includes, in order, regions c', e, b, and a. In some instances, region c of the trigger probe is perfectly complementary to region c' of the target RNA molecule. The target displacing oligo includes, in order, RNA regions e, b, a, f', and a'.

The initiation of this DSA scheme involves separation of the self-hybridized strands of the trigger probe and hybridization of the target RNA molecule to regions c, e', b', and a' of the trigger probe (FIG. 74A). This occurs, for example, by denaturation of the trigger probe, followed by hybridization to the target RNA molecule. Alternatively, region c' of the target RNA molecule hybridizes to region c of the trigger probe, followed by strand invasion (e.g., as described herein) of the target RNA molecule into region e', followed by regions b' and a', of the trigger probe. This results in unzipping of the self-hybridized duplex of the trigger probe and hybridization of, for example, regions c', e, b, and a of the target RNA molecule to regions c, e', b', and a' of the trigger probe, thereby forming a duplex that is capable of being cleaved by a DSN. DSN cleavage results in degradation of region c. The trigger probe and the target RNA molecule remain attached to each other at the remaining RNA-RNA duplex, as shown in FIG. 74A. This RNA-RNA duplex may be separated using the target displacing oligo. For example, regions f' and a' of the target displacing oligo may hybridize to regions f and a of the trigger probe, followed by strand invasion (e.g., as described herein) of the target displacing oligo into regions a', b', and e' of the trigger probe, thereby displacing the target RNA and freeing it to bind and induce the DSN cleavage of additional copies of the trigger probe in a first level of geometric amplification.

Turning to FIG. 74B, the complex formed between the cleaved trigger probe and the target displacing oligo is capable of interacting with the reporter probe. The reporter probe includes, in order, an RNA region attached to a fluorophore, DNA regions b', e', and d', and an RNA region attached to a quencher. The two RNA regions of the reporter probe are complementary and thus hybridize to form a duplex that maintains the fluorophore in close proximity to the quencher, thereby preventing the fluorophore from producing a fluorescent signal. Regions b, e, and d of the cleaved trigger probe may hybridize to regions b', e', and d' of the reporter probe, thereby forming a DNA-RNA duplex capable of being cleaved by a DSN. DSN cleavage of regions b', e', and d' results in the release of the RNA regions attached to the fluorophore and the quencher, and thus separates the fluorophore from the quencher. The resultant fluorescent signal may be detected using methods well known in the art. Each copy of the cleaved trigger probe may bind to and induce cleavage of multiple copies of the reporter probe in a second level of geometric amplification.

Example 29. Geometric DSA without Mismatches

Referring to FIGS. 75A-75B, a geometric DSA scheme is provided that utilizes a trigger probe capable of self-hybridizing to form a hairpin structure. In some instances, the duplex formed by the self-hybridizing regions of the trigger probe does not contain any mismatches or bulge regions. The scheme further includes a reporter probe capable of self-hybridizing to form a hairpin structure, the loop of which may be degraded (e.g., by a DSN) to release a fragment attached to a fluorophore. Unlike the schemes described in Examples 26-28, this scheme does not require a target displacing oligo.

As shown in FIG. 75A, the trigger probe includes, in order, DNA regions c and e', and RNA regions b', a', f, a, b, e, and d. Regions e', b', and a' are capable of hybridizing to regions e, b, and a to form a duplex. Although regions e' and e hybridize to form a DNA-RNA duplex, this DNA-RNA duplex includes a stretch of nucleotides which are substantially incapable of being cleaved by a DSN. This DNA-RNA region, in general, is less than about 8 nucleotides in length (e.g., 1, 2, 3, 4, 5, 6, or 7 nucleotides in length). As such, in its hairpin form, the trigger probe is resistant to cleavage by a DSN. Regions c and d do not hybridize to any other part of the trigger probe. Region f also does not hybridize to any other part of the trigger probe and thus forms a loop of the hairpin structure. Regions c, e', b', and a' are capable of hybridizing to a target RNA molecule that includes, in order, regions c', e, b, and a. In some instances, regions c and e' of the trigger probe are perfectly complementary to regions c' and e of the target RNA molecule.

The initiation of this DSA scheme involves separation of the self-hybridized strands of the trigger probe and hybridization of the target RNA molecule to regions c, e', b', and a' of the trigger probe (FIG. 75A). This occurs, for example, by denaturation of the trigger probe, followed by hybridization to the target RNA molecule. Alternatively, region c' of the target RNA molecule hybridizes to region c of the trigger probe, followed by strand invasion (e.g., as described herein) of the target RNA molecule into region e', followed by regions b' and a', of the trigger probe. This results in unzipping of the self-hybridized duplex of the trigger probe and hybridization of, for example, regions c', e, b, and a of the target RNA molecule to regions c, e', b', and a' of the trigger probe, thereby forming a duplex that is capable of being cleaved, at regions c and e', by a DSN. DSN cleavage results in degradation of regions c and e'. The trigger probe and the target RNA molecule remain attached to each other at the remaining RNA-RNA duplex, as shown in FIG. 75A. This RNA-RNA duplex may be separated by hybridization of regions a and b of the trigger probe to regions b' and a' of the trigger form to form a new hairpin structure. This results in displacement of the target RNA from regions b' and a' of the trigger probe by regions a and b of the trigger probe, thereby freeing the target RNA to bind and induce the DSN cleavage of additional copies of the trigger probe in a first level of geometric amplification.

Turning to FIG. 75B, the cleaved trigger probe, which has formed the new hairpin structure, is capable of interacting with the reporter probe. The reporter probe includes, in order, an RNA region attached to a fluorophore, DNA regions e' and d', and an RNA region attached to a quencher. The two RNA regions of the reporter probe are complementary and thus hybridize to form a duplex that maintains the fluorophore in close proximity to the quencher, thereby preventing the fluorophore from producing a fluorescent signal. Regions e and d of the cleaved trigger probe may hybridize to regions e' and d' of the reporter probe, thereby forming a DNA-RNA duplex capable of being cleaved by a DSN. DSN cleavage of regions e' and d' results in the release of the RNA regions attached to the fluorophore and the quencher, and thus separates the fluorophore from the quencher. The resultant fluorescent signal may be detected using methods well known in the art. Each copy of the cleaved trigger probe may bind to and induce cleavage of multiple copies of the reporter probe in a second level of geometric amplification.

Example 30. Geometric DSA with Beacon Detection

Referring to FIG. 76, a geometric DSA scheme is provided that utilizes a pair of hairpin probes capable of self-hybridization (Hairpin Probe 1 and Hairpin Probe 2). In some instances, the duplexes formed by the self-hybridizing regions of the hairpin probes do not contain any mismatches or bulge regions.

As shown in FIG. 76, Hairpin Probe 1 includes, in order, RNA region a, DNA region b', and RNA region a'. Region a is capable of hybridizing to region a' to form an RNA-RNA duplex resistant to DSN cleavage. In some instances, region a is complementary to region a'. Region b' is capable of hybridizing to a target RNA molecule that includes region b. In some instances, region b' of Hairpin Probe 1 is perfectly complementary to region b of the target RNA molecule.

As shown in FIG. 76, Hairpin Probe 2 includes, in order, a fluorophore, RNA region c, DNA region a', RNA region c', and a quencher. Region c is capable of hybridizing to region c' to form an RNA-RNA duplex resistant to DSN cleavage. In some instances, region c is complementary to region c'. Region a' is capable of hybridizing to region a of Hairpin Probe 1. In some instances, region a' of Hairpin Probe 1 is perfectly complementary to region a of Hairpin Probe 1. When region c is hybridized to region c', the fluorophore and quencher are placed in close physical proximity, resulting in quenching of the fluorescent signal. Hairpin Probe 2 may be referred to as a beacon. In some instances, the portion of Hairpin Probe 2 that includes the fluorophore may be referred to as a beacon.

The initiation of this DSA scheme involves hybridization of the target RNA molecule to region b' of Hairpin Probe 1 (FIG. 76, step 1). This may result in denaturation of the RNA-RNA duplex of Hairpin Probe 1, resulting in separation of region a from region a'. The DNA-RNA duplex formed by hybridization of the target RNA molecule to region b' is cleaved by a DSN, thereby releasing region a and region a'. The target RNA molecule is not degraded by the DSN and is freed to bind and induce cleavage of further copies of Hairpin Probe 1, thereby resulting in a first level of amplification.

The released region a may hybridize to region a' of Hairpin Probe 2 (FIG. 76, step 2). This may result in denaturation of the RNA-RNA duplex of Hairpin Probe 2, resulting in separation of region c from region c'. The DNA-RNA duplex formed by hybridization of released region a to region a' is cleaved by a DSN, thereby releasing region c and region c'. The released region a originating from Hairpin 1 is not degraded by the DSN and is freed to bind and induce cleavage of further copies of Hairpin Probe 2, thereby resulting in a second level of amplification. Separation of region c from region c', whether by the initial hybridization of region a to Hairpin Probe 2 or by degradation of region a' by the DSN, leads to separation of the fluorophore and quencher, thereby permitting fluorescence to occur. In this way, the released region c acts as a detectable beacon.

Example 31. Geometric DSA with Surface Detection

Referring to FIGS. 77-78, a geometric DSA scheme is provided that utilizes a pair of hairpin probes capable of self-hybridization (Hairpin Probe 1 and Hairpin Probe 2). In some instances, the duplexes formed by the self-hybridizing regions of the hairpin probes do not contain any mismatches or bulge regions.

As shown in FIG. 77, Hairpin Probe 1 includes, in order, RNA region a, DNA region b', and RNA region a'. Region a is capable of hybridizing to region a' to form an RNA-RNA duplex resistant to DSN cleavage. In some instances, region a is complementary to region a'. Region b' is capable of hybridizing to a target RNA molecule that includes region b. In some instances, region b' of Hairpin Probe 1 is perfectly complementary to region b of the target RNA molecule.

As shown in FIG. 77, Hairpin Probe 2 includes, in order, a fluorophore, RNA region c, DNA region a', and RNA region c'. Region c is capable of hybridizing to region c' to form an RNA-RNA duplex resistant to DSN cleavage. In some instances, region c is complementary to region c'. Region a' is capable of hybridizing to region a of Hairpin Probe 1. In some instances, region a' of Hairpin Probe 1 is perfectly complementary to region a of Hairpin Probe 1.

The initiation of this DSA scheme involves hybridization of the target RNA molecule to region b' of Hairpin Probe 1 (FIG. 77, step 1). This may result in denaturation of the RNA-RNA duplex of Hairpin Probe 1, resulting in separation of region a from region a'. The DNA-RNA duplex formed by hybridization of the target RNA molecule to region b' is cleaved by a DSN, thereby releasing region a and region a'. The target RNA molecule is not degraded by the DSN and is freed to bind and induce cleavage of further copies of Hairpin Probe 1, thereby resulting in a first level of amplification.

The released region a may hybridize to region a' of Hairpin Probe 2 (FIG. 77, step 2). This may result in denaturation of the RNA-RNA duplex of Hairpin Probe 2, resulting in separation of region c from region c'. The DNA-RNA duplex formed by hybridization of released region a to region a' is cleaved by a DSN, thereby releasing region c and region c'. The released region a originating from Hairpin 1 is not degraded by the DSN and is freed to bind and induce cleavage of further copies of Hairpin Probe 2, thereby resulting in a second level of amplification. The released region c remains attached to the fluorophore. Copies of released region c may be captured from the solution using any nucleic acid capture method, as well known in the art. For example, as shown in FIG. 78, a surface may be provided, to which may be immobilized nucleic acid capture probes. Any or all of the nucleic acid capture probes may include a sequence capable of hybridizing to region c (i.e., region c'). The copies of released region c may, for example, be flowed along the surface. The copies of released region c may then hybridize to the nucleic acid capture probe and be immobilized on the surface. The captured copies of released region c may be analyzed while immobilized on the detection surface using, for example, any standard imaging device. Alternatively, the captured copies of released region c may be subsequently detached from the nucleic acid capture probes, or the hybridization region c-nucleic acid capture probe complexes may be detached from the surface, and the solution containing the copies of released region c may be analyzed at a later time point.

Example 32. Exponential DSA with Beacon Detection

Referring to FIGS. 79A-79B, an exponential DSA scheme is provided that utilizes a pair of hairpin probes capable of self-hybridization (Hairpin Probe 1 and Hairpin Probe 2). In some instances, the duplexes formed by the self-hybridizing regions of the hairpin probes do not contain any mismatches or bulge regions.

As shown in FIG. 79A, Hairpin Probe 1 includes, in order, RNA region a, DNA region b', and RNA region a'. Region a is capable of hybridizing to region a' to form an RNA-RNA duplex resistant to DSN cleavage. In some instances, region a is complementary to region a'. Region b' is capable of hybridizing to a target RNA molecule that includes region b. In some instances, region b' of Hairpin Probe 1 is perfectly complementary to region b of the target RNA molecule.

As shown in FIG. 79A, Hairpin Probe 2 includes, in order, a fluorophore, RNA region b, DNA region a', RNA region b', and a quencher. Region b is capable of hybridizing to region b' to form an RNA-RNA duplex resistant to DSN cleavage. In some instances, region b is complementary to region b'. Region a' is capable of hybridizing to region a of Hairpin Probe 1. In some instances, region a' of Hairpin Probe 1 is perfectly complementary to region a of Hairpin Probe 1. When region b is hybridized to region b', the fluorophore and quencher are placed in close physical proximity, resulting in quenching of the fluorescent signal. In addition, region b is capable of hybridizing to region b' of Hairpin Probe 1. In some instances, region b of Hairpin Probe 2 is complementary to region b' of Hairpin Probe 1. Hairpin Probe 2 may be referred to as a beacon. In some instances, the portion of Hairpin Probe 2 that includes the fluorophore may be referred to as a beacon.

The initiation of this DSA scheme involves hybridization of the target RNA molecule to region b' of Hairpin Probe 1 (FIG. 79A, step 1). This may result in denaturation of the RNA-RNA duplex of Hairpin Probe 1, resulting in separation of region a from region a'. The DNA-RNA duplex formed by hybridization of the target RNA molecule to region b' is cleaved by a DSN, thereby releasing region a and region a'. The target RNA molecule is not degraded by the DSN and is freed to bind and induce cleavage of further copies of Hairpin Probe 1, thereby resulting in a first level of amplification.

The released region a may hybridize to region a' of Hairpin Probe 2 (FIG. 79A, step 2). This may result in denaturation of the RNA-RNA duplex of Hairpin Probe 2, resulting in separation of region b from region b'. The DNA-RNA duplex formed by hybridization of released region a to region a' is cleaved by a DSN, thereby releasing region b and region b'. The released region a originating from Hairpin 1 is not degraded by the DSN and is freed to bind and induce cleavage of further copies of Hairpin Probe 2, thereby resulting in a second level of amplification. Separation of region b from region b', whether by the initial hybridization of region a to Hairpin Probe 2, or by degradation of region a' by the DSN, leads to separation of the fluorophore and quencher, thereby permitting fluorescence to occur. In this way, the released region b acts as a detectable beacon.

Turning to FIG. 79B, the released region b may also hybridize to DNA region b' of a further copy of Hairpin Probe 1, in a manner similar to the target RNA molecule. This results in DSN cleavage of the region b'-region b duplex, thereby releasing further copies of region a and region a'. The released region b is not degraded and is freed to bind and induce cleavage of additional copies of Hairpin Probe 1, thereby resulting in a third level of amplification (FIG. 79B, step 3). The further copy of released region a may, in turn, hybridize to region a' of a further copy of Hairpin Probe 2, leading to DSN cleavage and release of further copies of region b and region b' of Hairpin Probe 2. The further copy of released region a is not degraded and is freed to bind and induce cleavage of additional copies of Hairpin Probe 2, thereby resulting in a fourth level of amplification (FIG. 79B, step 4).

Example 33. Exponential DSA with Surface Detection

Figure 80B:
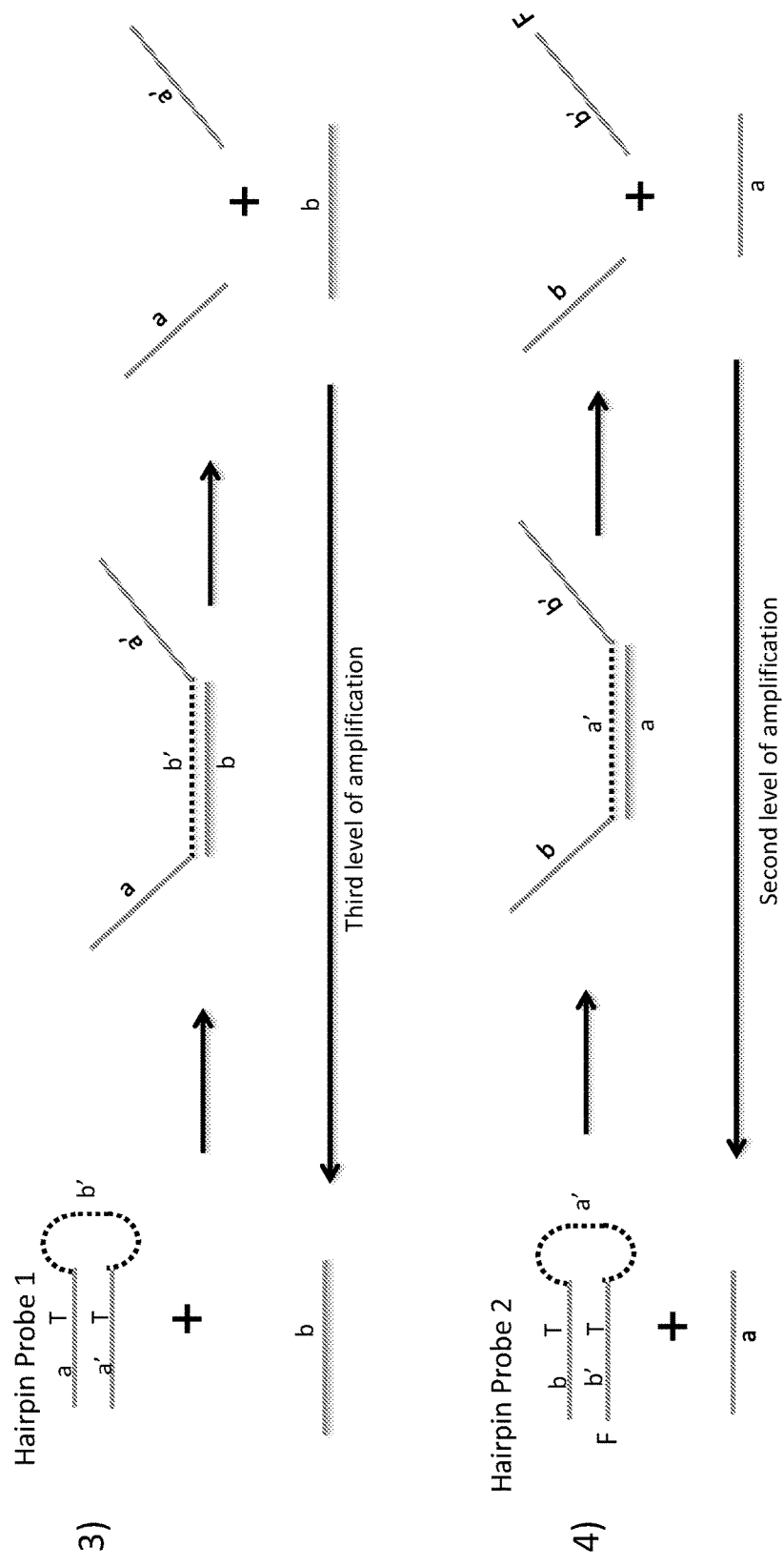
Figure 81:
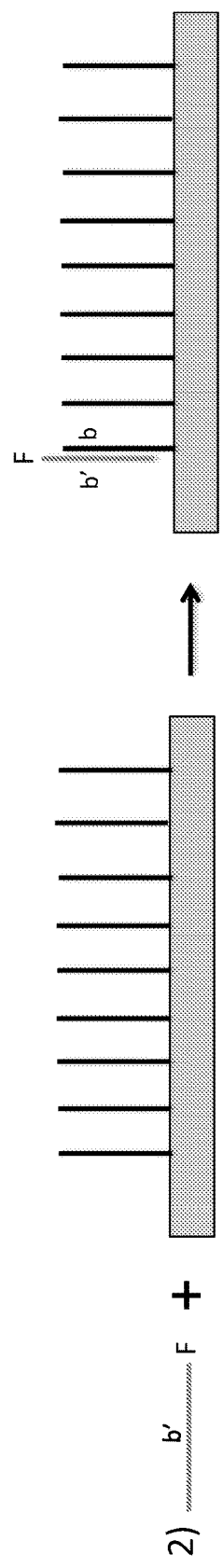
FIG. 81 shows a scheme for detection of a fluorescent probe generated according to the schemes shown in FIGS. 79 and 80.

Referring to FIGS. 80-81, an exponential DSA scheme is provided that utilizes a pair of hairpin probes capable of self-hybridization (Hairpin Probe 1 and Hairpin Probe 2). In some instances, the duplexes formed by the self-hybridizing regions of the hairpin probes do not contain any mismatches or bulge regions.

As shown in FIG. 80A, Hairpin Probe 1 includes, in order, RNA region a, DNA region b', and RNA region a'. Region a is capable of hybridizing to region a' to form an RNA-RNA duplex resistant to DSN cleavage. In some instances, region a is complementary to region a'. Region b' is capable of hybridizing to a target RNA molecule that includes region b. In some instances, region b' of Hairpin Probe 1 is perfectly complementary to region b of the target RNA molecule.

As shown in FIG. 80A, Hairpin Probe 2 includes, in order, RNA region b, DNA region a', RNA region b', and a fluorophore. Region b is capable of hybridizing to region b' to form an RNA-RNA duplex resistant to DSN cleavage. In some instances, region b is complementary to region b'. Region a' is capable of hybridizing to region a of Hairpin Probe 1. In some instances, region a' of Hairpin Probe 1 is perfectly complementary to region a of Hairpin Probe 1. In addition, region b is capable of hybridizing to region b' of Hairpin Probe 1. In some instances, region b of Hairpin Probe 2 is complementary to region b' of Hairpin Probe 1.

The initiation of this DSA scheme involves hybridization of the target RNA molecule to region b' of Hairpin Probe 1 (FIG. 80A, step 1). This may result in denaturation of the RNA-RNA duplex of Hairpin Probe 1, resulting in separation of region a from region a'. The DNA-RNA duplex formed by hybridization of the target RNA molecule to region b' is cleaved by a DSN, thereby releasing region a and region a'. The target RNA molecule is not degraded by the DSN and is freed to bind and induce cleavage of further copies of Hairpin Probe 1, thereby resulting in a first level of amplification.

The released region a may hybridize to region a' of Hairpin Probe 2 (FIG. 80A, step 2). This may result in denaturation of the RNA-RNA duplex of Hairpin Probe 2, resulting in separation of region b from region b'. The DNA-RNA duplex formed by hybridization of released region a to region a' is cleaved by a DSN, thereby releasing region b and region b'. The released region a originating from Hairpin 1 is not degraded by the DSN and is freed to bind and induce cleavage of further copies of Hairpin Probe 2, thereby resulting in a second level of amplification.

Turning to FIG. 80B, the released region b may also hybridize to DNA region b' of a further copy of Hairpin Probe 1, in a manner similar to the target RNA molecule. This results in DSN cleavage of the region b'-region b duplex, thereby releasing further copies of region a and region a'. The released region b is not degraded and is freed to bind and induce cleavage of additional copies of Hairpin Probe 1, thereby resulting in a third level of amplification (FIG. 80B, step 3). The further copy of released region a may, in turn, hybridize to region a' of a further copy of Hairpin Probe 2, leading to DSN cleavage and release of further copies of region b and region b' of Hairpin Probe 2. The further copy of released region a is not degraded and is freed to bind and induce cleavage of additional copies of Hairpin Probe 2, thereby resulting in a fourth level of amplification (FIG. 80B, step 4).

Released copies of region b' remain attached to fluorophores. As such, copies of released region b' may be captured from the solution using any nucleic acid capture method, as well known in the art. For example, as shown in FIG. 81, a surface may be provided, to which may be immobilized nucleic acid capture probes. Any or all of the nucleic acid capture probes may include a sequence capable of hybridizing to region b' (i.e., region b). The copies of released region b' may, for example, be flowed along the surface. The copies of released region b' may then hybridize to the nucleic acid capture probe and be immobilized on the surface. The captured copies of released region b' may be analyzed while immobilized on the detection surface using, for example, any standard imaging device. Alternatively, the captured copies of released region b' may be subsequently detached from the nucleic acid capture probes, or the hybridization region b'-nucleic acid capture probe complexes may be detached from the surface, and the solution containing the copies of released region b' may be analyzed at a later time point.

Example 34. Linear DSA with Surface Detection

Figure 82:
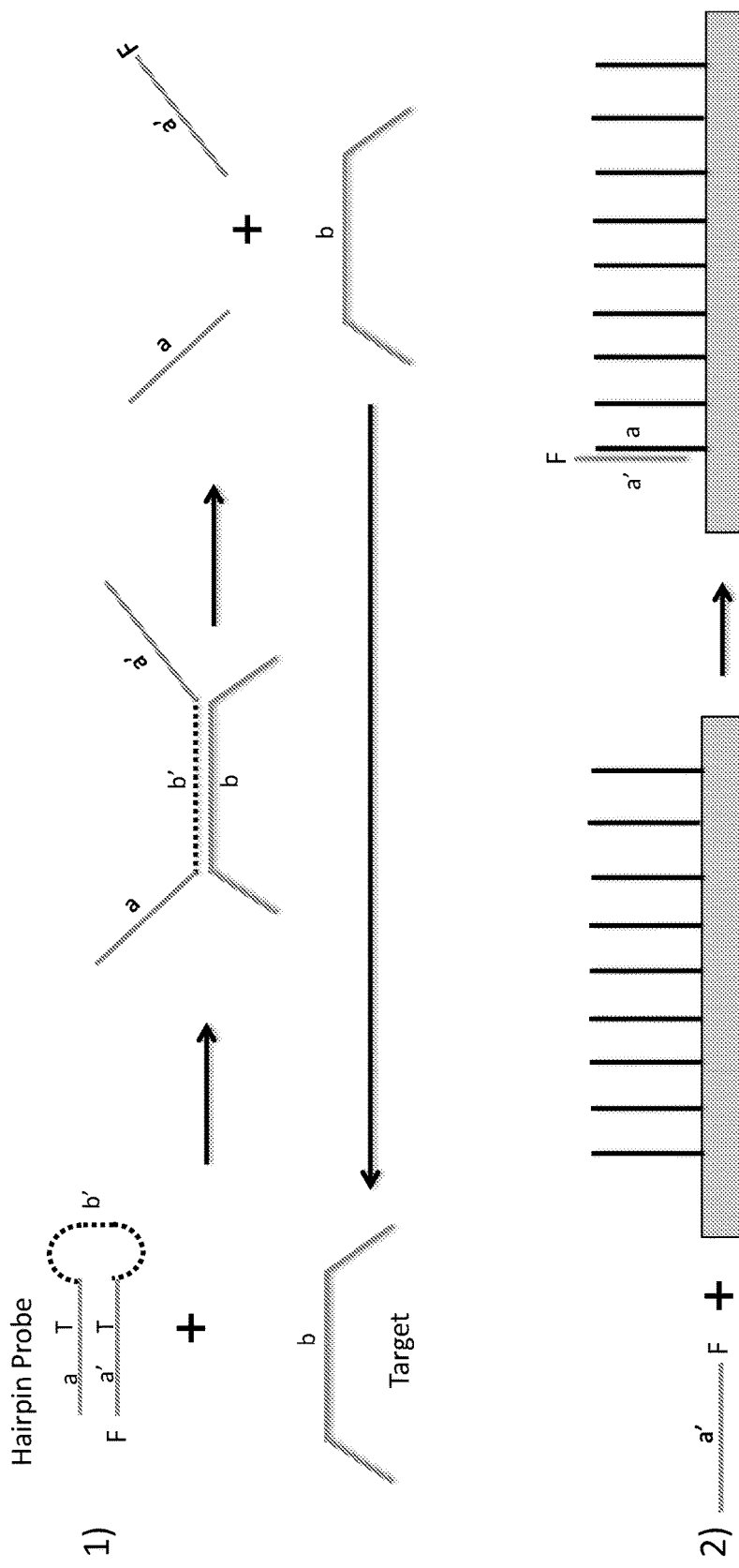
FIG. 82 shows probe designs and a scheme for linear DSA with surface detection.

Referring to FIG. 82, a linear DSA scheme is provided that utilizes a hairpin probe capable of self-hybridization. In some instances, the duplex formed by the self-hybridizing regions of the hairpin probe does not contain any mismatches or bulge regions.

As shown in FIG. 82, the Hairpin Probe includes, in order, RNA region a, DNA region b', RNA region a', and a fluorophore. Region a is capable of hybridizing to region a' to form an RNA-RNA duplex resistant to DSN cleavage. In some instances, region a is complementary to region a'. Region b' is capable of hybridizing to a target RNA molecule that includes region b. In some instances, region b' of the Hairpin Probe is perfectly complementary to region b of the target RNA molecule.

The initiation of this DSA scheme involves hybridization of the target RNA molecule to region b' of the Hairpin Probe (FIG. 82, step 1). This may result in denaturation of the RNA-RNA duplex of the Hairpin Probe, resulting in separation of region a' from region a'. The DNA-RNA duplex formed by hybridization of the target RNA molecule to region b' is cleaved by a DSN, thereby releasing region a and region a'. The target RNA molecule is not degraded by the DSN and is freed to bind and induce cleavage of further copies of Hairpin Probe 1, thereby resulting in linear amplification.

Copies of released region a' may be captured from the solution using any nucleic acid capture method, as well known in the art. For example, as shown in FIG. 82, step 2, a surface may be provided, to which may be immobilized nucleic acid capture probes. Any or all of the nucleic acid capture probes may include a sequence capable of hybridizing to region a' (i.e., region a). The copies of released region a' may, for example, be flowed along the surface. The copies of released region a' may then hybridize to the nucleic acid capture probe and be immobilized on the surface. The captured copies of released region a' may be analyzed while immobilized on the detection surface using, for example, any standard imaging device. Alternatively, the captured copies of released region a' may be subsequently detached from the nucleic acid capture probes, or the hybridization region a'-nucleic acid capture probe complexes may be detached from the surface, and the solution containing the copies of released region a' may be analyzed at a later time point.

Example 35. DSA in Clinical Specimens

The methods of the invention can be used to detect nucleic acids in directly in complex samples that have not been otherwise purified or amplified. In some instances, the complex sample is a biological sample (e.g., a clinical sample). In one example, cleavable hairpin probes, also referred to as beacons, which included a fluorophore attached to one end and a quencher attached to the opposite end, as well as a region complementary to at least a portion of a target nucleic acid located in the loop region, were used for quantifiable detection of the target nucleic acid in complex samples. In addition, different buffer formulations were also tested. Cleavage of the hairpin probes may be monitored in real time, e.g., independently of target binding. In this example, the fluorescent signal detected in controls when the beacon as fully cleaved averaged approximately 4,000 relative fluorescence units. For real-time monitoring of DSN cleavage, the enzyme levels needed to be reduced from 0.5 units/reaction to 0.05 units per reaction.

Figure 83:
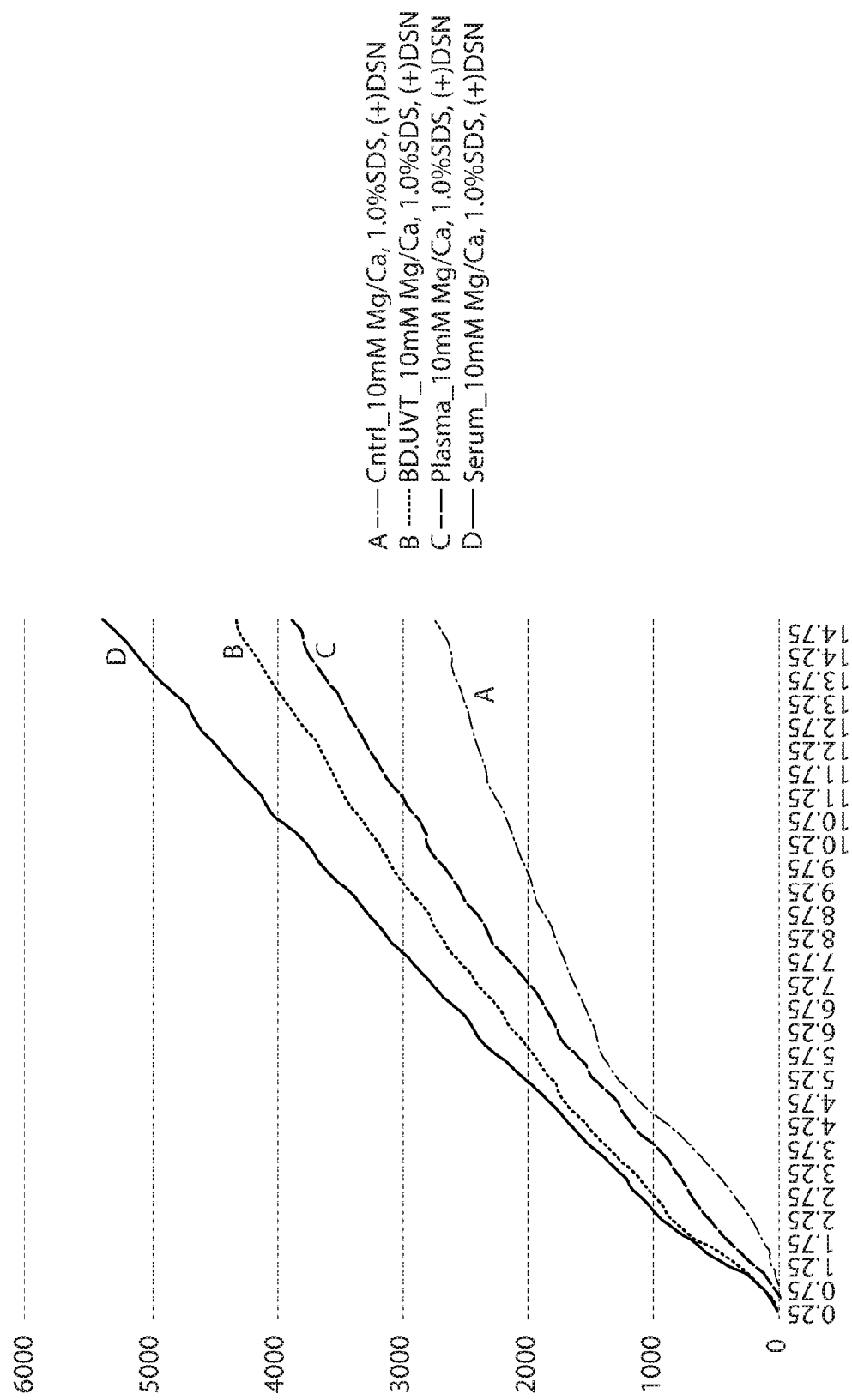
FIG. 83 is a graph showing the results of DSN cleavage reactions in plasma, serum, and a pathogen buffer.
Figure 84:
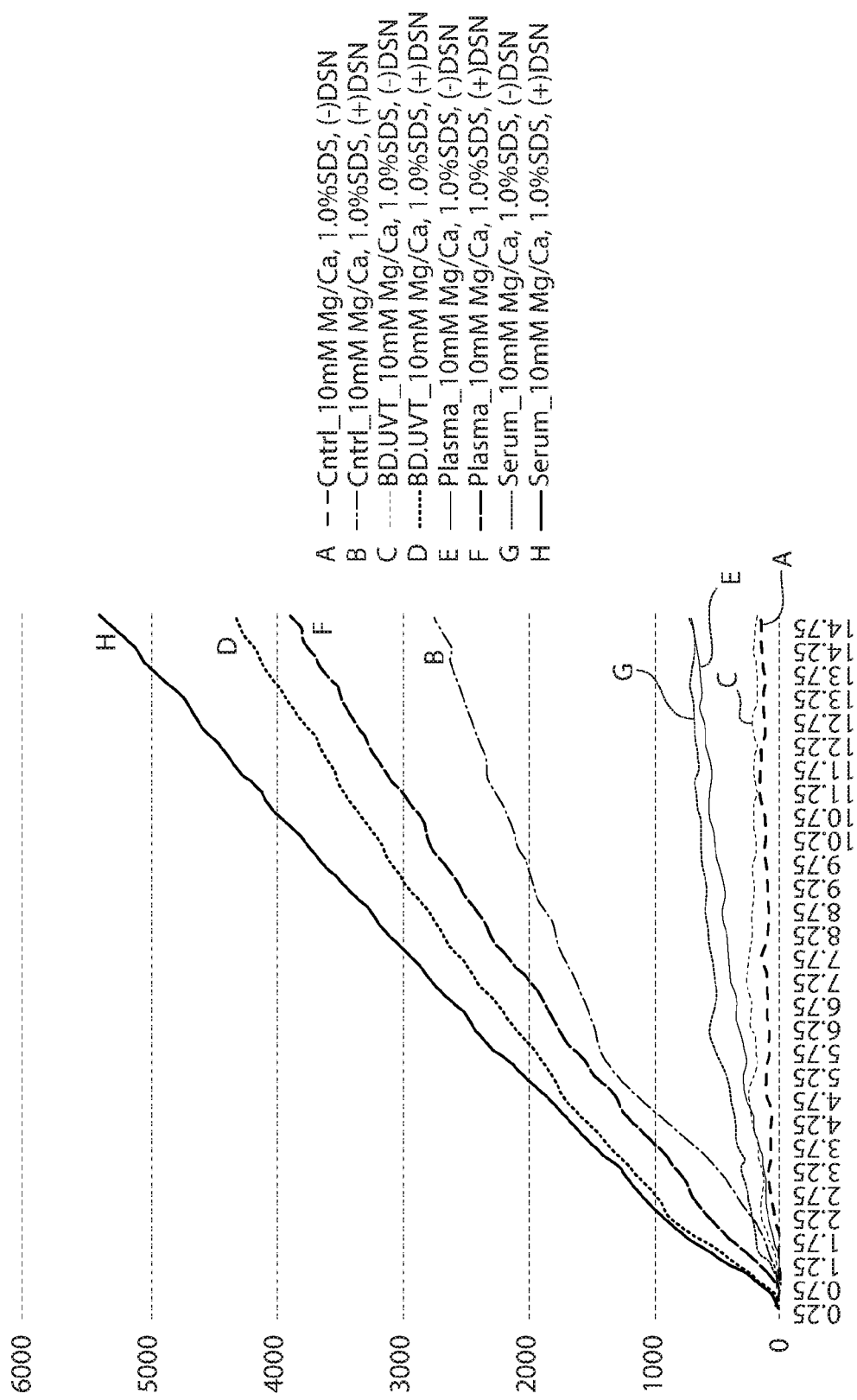
FIG. 84 is a graph showing the results of cleavage reactions in plasma, serum, and a pathogen buffer with or without a DSN present.

DSN Chemistry Conditions
    1× Buffer (Working Concentration)
        50 mM Tris pH 8.0
        1 mM DTT
        10 mM $MgCl_2$
        10 mM $CaCl_2$
        SDS (0-1.0%)
        10 pmol Beacon
    Reaction Volume
        100 ul Total Volume
        50 ul of clinical sample added
Temperature of Reactions: 42° C.
Length of Reactions: 30 min Results DSN cleavage reactions using Kamchatka crab nuclease were performed using the chemistry conditions described above. In a first experiment, DSN cleavage was assayed in a variety of sample types (i.e., plasma, serum, Becton Dickinson Universal Viral Transport Solution (UVT solution), and control), each in the presence of 1.0% SDS and the DSN. It was shown that DSN cleavage proceeded successfully in plasma, serum, and the UVT solution (FIG. 83). Further, when a similar experiment was performed in the presence or absence of DSN, it was shown that all four sample types showed significantly greater fluorescent signal with the DSN present, indicating that the DSN is responsible for the bulk of observed cleavage (FIG. 84).

Figure 85:
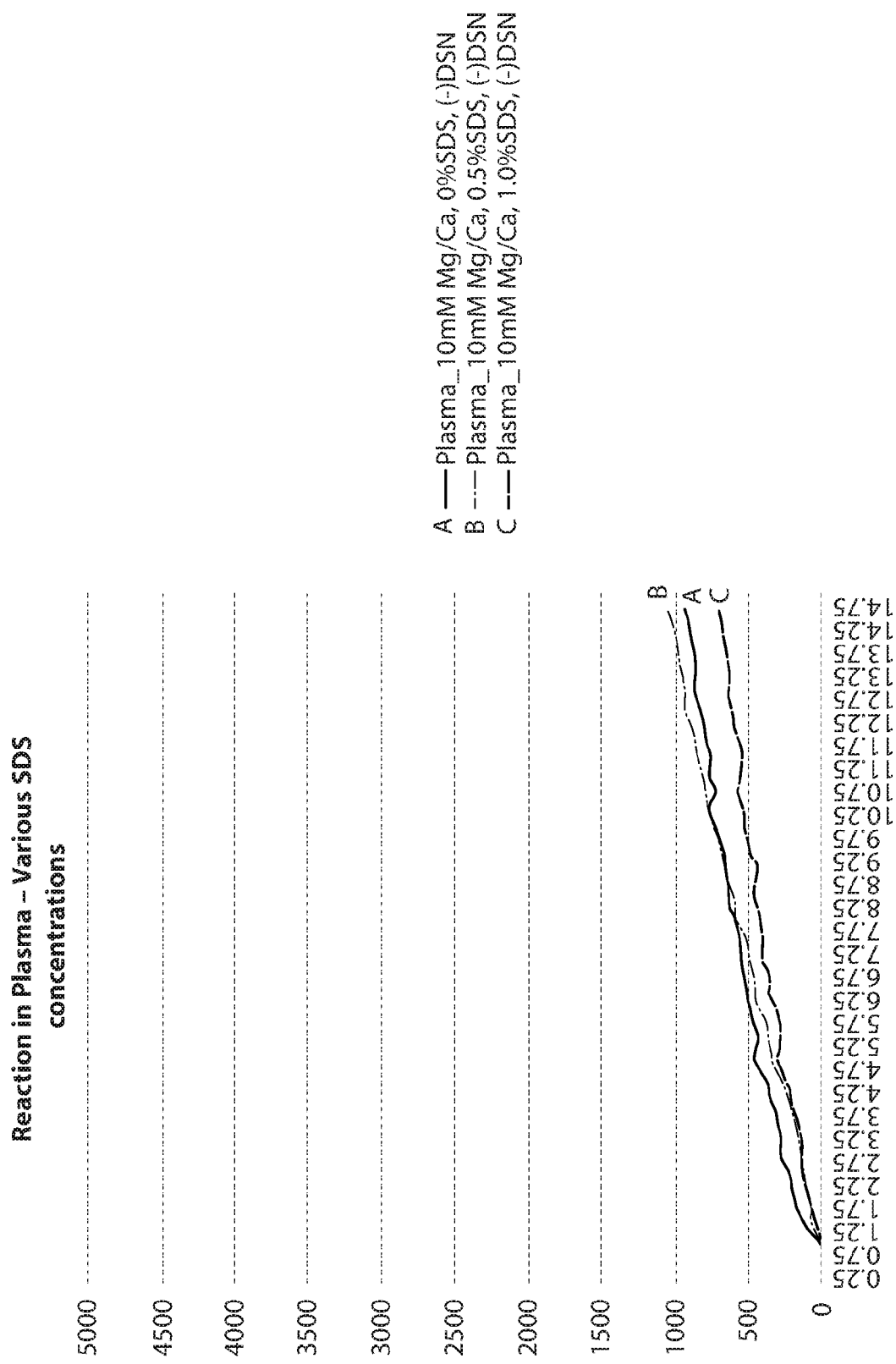
FIG. 85 is a graph showing the results of cleavage reactions in plasma with various SDS concentrations.
Figure 86:
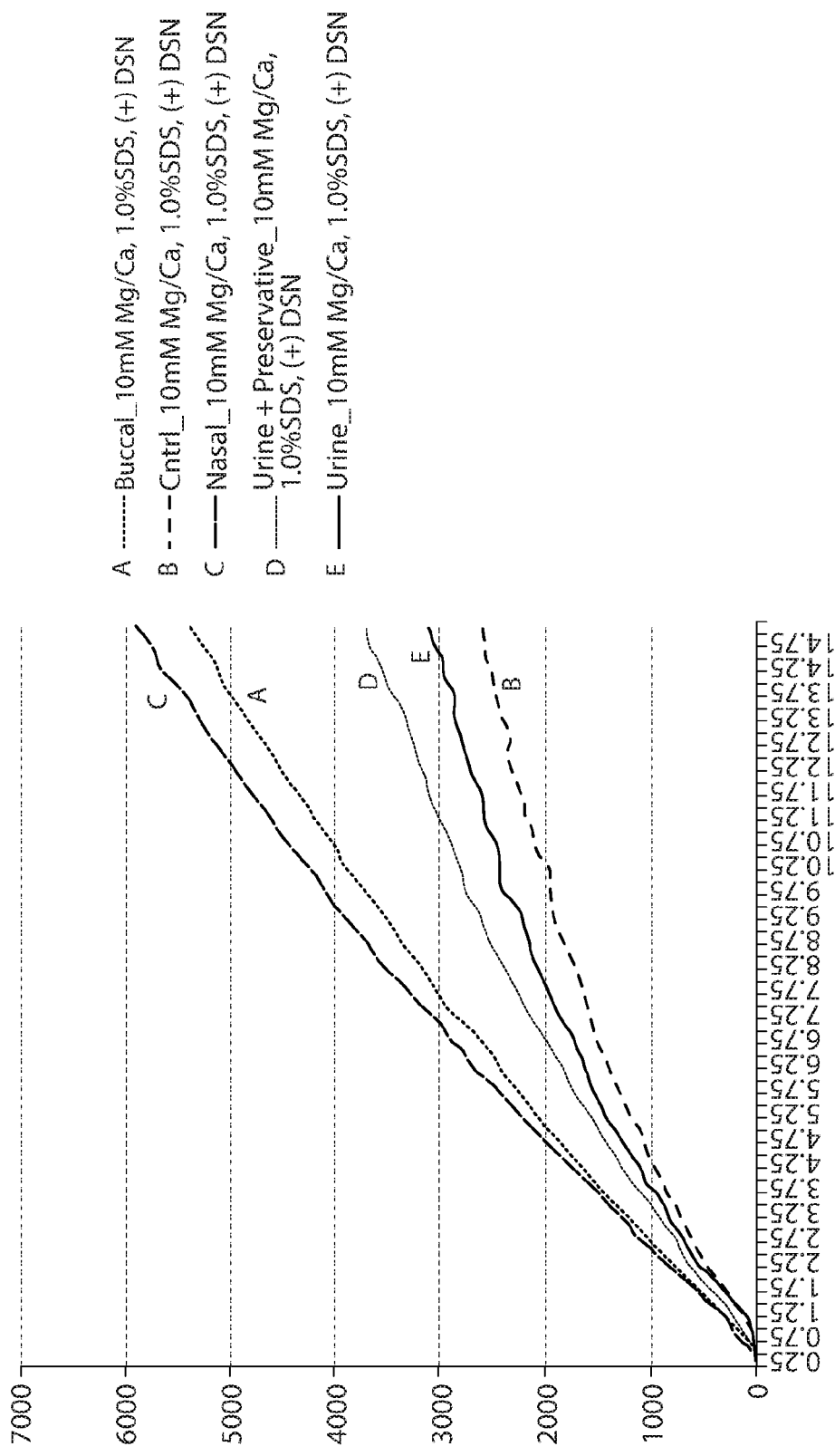
FIG. 86 is a graph showing the results of DSN cleavage reactions in buccal swabs, nasal swabs, and urine samples.
Figure 87:
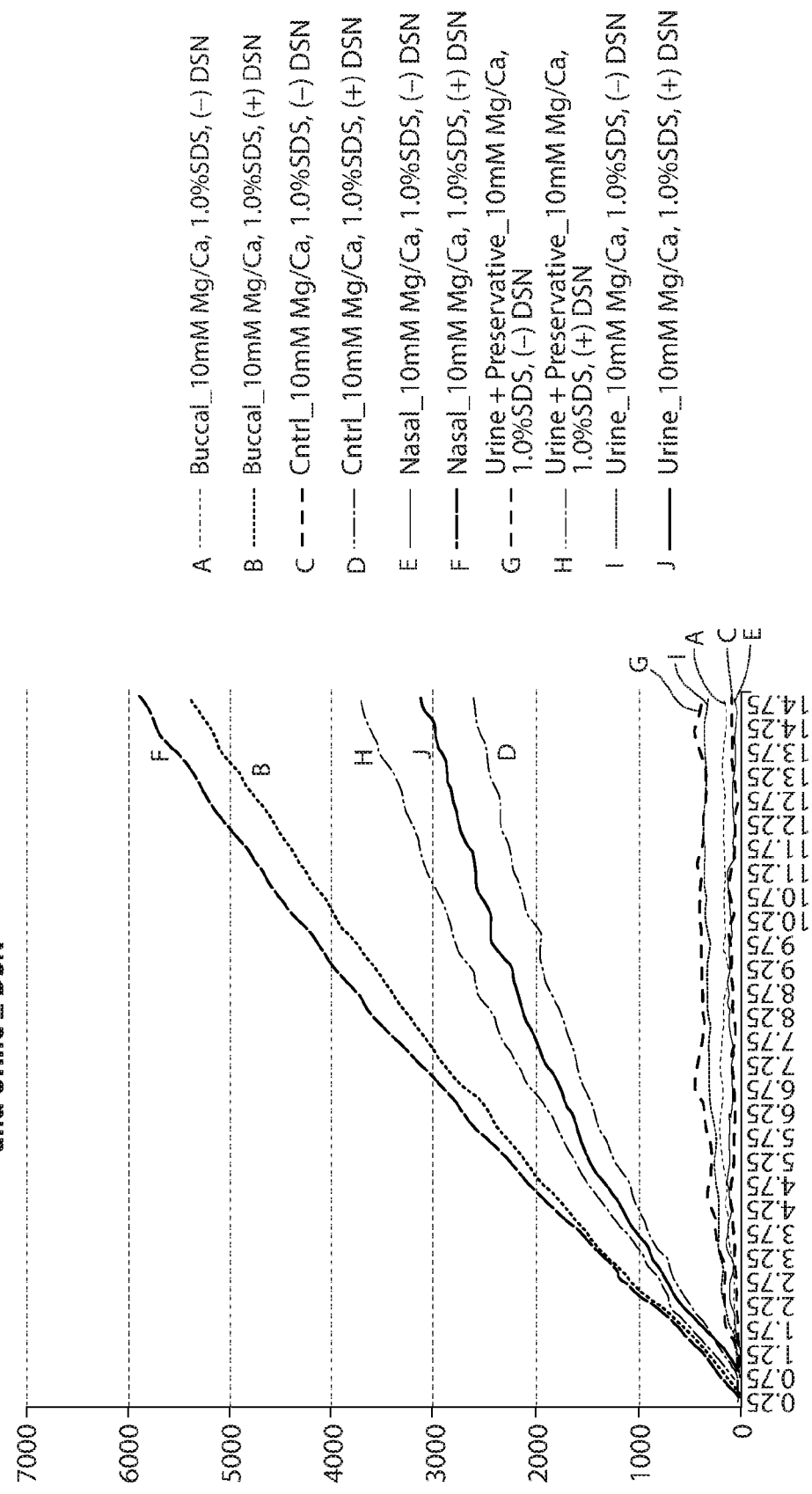
FIG. 87 is a graph showing the results of cleavage reactions in buccal swabs, nasal swabs, and urine samples with or without a DSN present.

In order to examine whether varying SDS concentration would affect cleavage efficiency, plasma samples were assayed for cleavage in the absence of DSN at three SDS concentrations (0%, 0.5%, and 1.0% SDS; FIG. 85). Similar levels of cleavage were observed at all three SDS concentrations. Further tests were run on additional types of biological samples (i.e., buccal swabs, nasal swabs, and urine samples). In the presence of DSN, buccal swab and nasal swab samples showed the strongest levels of DSN cleavage, while urine samples (with or without preservative) showed similar DSN cleavage results to the control (FIG. 86). All sample types showed substantially greater cleavage in the presence of DSNs than in the absence of DSNs (FIG. 87). These data show that DSNs are capable of inducing duplex-specific cleavage of target nucleic acids in complex samples, such as unprocessed biological samples.

Other Embodiments

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of amplifying a nucleic acid region, said method comprising:
   (a) providing a mixture in a clinical sample comprising:
      a target nucleic acid,
      a plurality of nucleic acid probes each comprising a first region, a second region, and a third region, wherein said second region comprises a nucleic acid sequence complementary to at least a portion of said target nucleic acid,
      a DSN, and
      a lysis buffer;
   (b) incubating said mixture under conditions to hybridize said second region to said target nucleic acid, thereby forming a nucleic acid probe-target nucleic acid complex comprising a double-stranded nucleic acid region, and to digest said double-stranded nucleic acid region with said DSN, thereby releasing said first region and said third region, and
   (c) repeating step (b) with additional copies of said nucleic acid probe, thereby amplifying said first region and/or said third region.

2. The method of claim 1, wherein said DSN is a Kamchatka crab DSN.

3. The solution of claim 1, wherein said probes are each attached to a surface.

4. A method of activating a nucleic acid probe, said method comprising:
   (a) providing a mixture in a clinical sample comprising:
      a target nucleic acid,
      a nucleic acid probe comprising a first region, a second region, a third region, and a fourth, wherein said first region and said second region form a nucleic acid sequence complementary to at least a portion of said target nucleic acid,
      an enzyme capable of selectively digesting double-stranded nucleic acids; and
      a lysis buffer,
   (b) incubating said mixture under conditions to hybridize said first region and said second region to said target nucleic acid, thereby forming a nucleic acid probe-target nucleic acid complex comprising a double-stranded nucleic acid region, and to digest at least a portion of said double-stranded nucleic acid region with said enzyme, thereby releasing an end region comprising said third region and said fourth region, thereby activating said nucleic acid probe.

5. The method of claim 4, wherein said clinical sample comprises blood, peripheral blood, a blood component, serum, isolated blood cells, plasma, buccal samples, buccal swabs, nasal samples, nasal swabs, urine, fecal material, saliva, amniotic fluid, cerebrospinal fluid (CSF), synovial fluid, tissue, a biopsy, pancreatic fluid, chorionic villus sample, cells, extracellular matrix, cultured cells, cellular organelles, cancerous cells, or any combination or derivative thereof.

6. A method of activating a nucleic acid probe, said method comprising:
   (a) providing a mixture in a clinical sample comprising:
      a target nucleic acid,
      a nucleic acid probe comprising a first region, a second region, and a third region, wherein said second region comprises a nucleic acid sequence complementary to at least a portion of said target nucleic acid,
      an enzyme capable of selectively digesting double-stranded nucleic acids, and
      a lysis buffer;
   (b) incubating said mixture under conditions to hybridize said second region to said target nucleic acid, thereby forming a nucleic acid probe-target nucleic acid complex comprising a double-stranded nucleic acid region, and to digest said double-stranded nucleic acid region with said enzyme, thereby releasing said first region and said third region,
   thereby activating said nucleic acid probe.

7. The method of claim 6, wherein said first region comprises a portion complementary to at least a portion of said target nucleic acid, and said incubating step further comprises hybridizing said portion of said first region to said target nucleic acid.

8. The method of claim 6, wherein said third region comprises a portion complementary to at least a portion of said target nucleic acid, and said incubating step further comprises hybridizing said portion of said third region to said target nucleic acid.

9. The method of claim 6, wherein said target nucleic acid comprises RNA.

10. The method of claim 6, wherein said target nucleic acid comprises DNA.

11. The method of claim 6, wherein said clinical sample comprises blood, peripheral blood, a blood component, serum, isolated blood cells, plasma, buccal samples, buccal swabs, nasal samples, nasal swabs, urine, fecal material, saliva, amniotic fluid, cerebrospinal fluid (CSF), synovial fluid, tissue, a biopsy, pancreatic fluid, chorionic villus sample, cells, extracellular matrix, cultured cells, cellular organelles, cancerous cells, or any combination or derivative thereof.

* * * * *

SEQUENCE LISTING

<160> NUMBER OF SEQ ID NOS: 2

<210> SEQ ID NO 1
<211> LENGTH: 11

```
<212> TYPE: DNA
<213> ORGANISM: Artificial Sequence
<220> FEATURE:
<223> OTHER INFORMATION: Synthetic Construct

<400> SEQUENCE: 1
tttttttttt t                                                          11

<210> SEQ ID NO 2
<211> LENGTH: 11
<212> TYPE: DNA
<213> ORGANISM: Artificial Sequence
<220> FEATURE:
<223> OTHER INFORMATION: Synthetic Construct

<400> SEQUENCE: 2
aaaaaaaaaa a                                                          11
```